(12) United States Patent
Zhang et al.

(10) Patent No.: US 9,974,785 B2
(45) Date of Patent: May 22, 2018

(54) AROMATIC HETEROCYCLIC DERIVATIVES AND PHARMACEUTICAL APPLICATIONS THEREOF

(71) Applicant: SUNSHINE LAKE PHARMA CO., LTD., Dongguan, Guangdong (CN)

(72) Inventors: Yingjun Zhang, Dongguan (CN); Chuanfei Jin, Dongguan (CN); Wenhe Zhong, Dongguan (CN); Kangzhi Chen, Dongguan (CN); Li Gao, Dongguan (CN); Runzhi Liu, Dongguan (CN); Ji Zhang, Dongguan (CN)

(73) Assignee: Sunshine Lake Pharma Co., Ltd., Dongguan, Guangdong (CN)

(*) Notice: Subject to any disclaimer, the term of this patent is extended or adjusted under 35 U.S.C. 154(b) by 0 days. days.

(21) Appl. No.: 15/314,932

(22) PCT Filed: Jul. 8, 2015

(86) PCT No.: PCT/CN2015/083605
§ 371 (c)(1),
(2) Date: Nov. 29, 2016

(87) PCT Pub. No.: WO2016/004882
PCT Pub. Date: Jan. 14, 2016

(65) Prior Publication Data
US 2017/0096392 A1    Apr. 6, 2017

(30) Foreign Application Priority Data

Jul. 8, 2014 (CN) .......................... 2014 1 0324179

(51) Int. Cl.
| | |
|---|---|
| *A61K 31/496* | (2006.01) |
| *A61K 31/454* | (2006.01) |
| *C07D 401/04* | (2006.01) |
| *C07D 401/12* | (2006.01) |
| *C07D 405/12* | (2006.01) |
| *C07D 209/10* | (2006.01) |
| *C07D 209/42* | (2006.01) |
| *A61K 45/06* | (2006.01) |

(52) U.S. Cl.
CPC .......... *A61K 31/496* (2013.01); *A61K 31/454* (2013.01); *A61K 45/06* (2013.01); *C07D 209/10* (2013.01); *C07D 209/42* (2013.01); *C07D 401/04* (2013.01); *C07D 401/12* (2013.01); *C07D 405/12* (2013.01)

(58) Field of Classification Search
CPC ..... A61K 31/454; A61K 31/496; A61K 45/06
USPC ....................................... 514/214
See application file for complete search history.

(56) References Cited

U.S. PATENT DOCUMENTS

| | | | |
|---|---|---|---|
| 6,100,291 A | 8/2000 | Slassi et al. | |
| 6,509,357 B1 | 1/2003 | Zhou et al. | |
| 6,613,781 B2 | 9/2003 | Zhou et al. | |
| 6,767,912 B2 | 7/2004 | Zhou et al. | |
| 6,774,241 B2 | 8/2004 | Clark et al. | |
| 6,787,535 B2 | 9/2004 | Beard | |
| 6,790,848 B2 | 9/2004 | Briggs | |
| 6,800,640 B2 | 10/2004 | Bernotas et al. | |
| 6,815,456 B2 | 11/2004 | Zhou et al. | |
| 6,831,094 B2 | 12/2004 | Li et al. | |
| 6,897,215 B1 | 5/2005 | Xin et al. | |
| 7,022,708 B2 | 4/2006 | Clark | |
| 7,034,029 B2 | 4/2006 | Kelly et al. | |
| 7,084,169 B2 | 8/2006 | Zhao | |
| 7,087,750 B2 | 8/2006 | Caldirola | |
| 7,202,241 B2 | 4/2007 | Berger | |
| 7,230,011 B2 | 6/2007 | Filla | |
| 7,238,696 B2 | 7/2007 | Bernotas et al. | |
| 7,247,651 B2 | 7/2007 | Madera et al. | |
| 7,259,165 B2 | 8/2007 | Bernotas et al. | |
| 7,271,180 B2 | 9/2007 | Zhou et al. | |
| 7,288,561 B2 | 10/2007 | Cole et al. | |
| 7,378,415 B2 | 5/2008 | Sethofer et al. | |
| 7,381,739 B2 | 6/2008 | Madera et al. | |
| 7,501,421 B2 | 3/2009 | Liu et al. | |
| 7,557,108 B2 | 7/2009 | Nettekoven et al. | |

(Continued)

FOREIGN PATENT DOCUMENTS

| | | |
|---|---|---|
| CN | 104276993 A | 1/2015 |
| CN | 104557726 A | 4/2015 |

(Continued)

OTHER PUBLICATIONS

Ahmed et al, Bioorganic & Med Chem Letters (2005), vol. 15, pp. 4867-4871.*
Zajdel et al, ACS Med Chem Letters (2016), vol. 7, pp. 618-622. (Year: 2016).*
Nirogi et al., Design, synthesis and pharmacological evaluation of 4-(piperazin-1-ylmethyl)-N1-arylsulfonyl indole derivates as 5-HT6 receptor ligands, Bioorganic & Medicinal Chemistry Letters, 2012, 22(24): 7431-7435.
Nirogi et al., Indole-3-piperazinyl derivatives: Novel chemical class of 5-HT6 receptor antagonists, Bioorganic & Medicinal Chemistry Letters, 2011, 21(1): 346-349.
Nirogi et al., Novel and Potent 5-Piperazinyl Methyl-N1-aryl Sulfonyl Indole Derivatives as 5-HT6 Receptor Ligands, ACS Medicinal Chemistry Letters, 2010, 1(7): 340-344.
Ahmed et al., Bicyclic heteroarylpiperazines as selective brain penetrant 5-HT6 receptor antagonists, Bioorganic & Medicinal Chemistry Letters, 2005, 15(21): 4867-4871.

(Continued)

*Primary Examiner* — Craig D Ricci
*Assistant Examiner* — Janet L. Coppins
(74) *Attorney, Agent, or Firm* — Squire Patton Boggs (US) LLP

(57) ABSTRACT

Provided herein are aromatic heterocyclic derivatives or a stereoisomer, a tautomer, an N-oxide, a solvate, a metabolite, a pharmaceutically acceptable salt or a prodrug thereof used for treating Alzheimer's disease. Also provided herein are pharmaceutical compositions containing such compounds, and use of such compounds or pharmaceutical compositions thereof for managing or treating 5-HT$_6$ receptor-mediated diseases, especially in the manufacture of a medicament for managing or treating Alzheimer's disease.

16 Claims, No Drawings

(56) References Cited

U.S. PATENT DOCUMENTS

| | | |
|---|---|---|
| 7,582,760 B2 | 9/2009 | Owens et al. |
| 7,645,752 B2 | 1/2010 | McDevitt et al. |
| 7,655,690 B2 | 2/2010 | Merce Vidal et al. |
| 7,678,800 B2 | 3/2010 | Kehler et al. |
| 7,696,229 B2 | 4/2010 | Dunn et al. |
| 7,713,954 B2 | 5/2010 | Bonhaus et al. |
| 7,741,326 B2 | 6/2010 | Bamberg et al. |
| 7,812,017 B2 | 10/2010 | Angbrant et al. |
| 7,838,518 B2 | 11/2010 | Spinks |
| 7,875,605 B2 | 1/2011 | Ramakrishna et al. |
| 7,939,520 B2 | 5/2011 | Haydar et al. |
| 7,943,639 B2 | 5/2011 | Johansson |
| 7,964,603 B2 | 6/2011 | Diaz-Fernandez et al. |
| 7,998,981 B2 | 8/2011 | Ramakrishna et al. |
| 8,003,670 B2 | 8/2011 | Nirogi et al. |
| 8,063,053 B2 | 11/2011 | Haydar et al. |
| 8,153,680 B2 | 4/2012 | Chen et al. |
| 8,318,725 B2 | 11/2012 | Nirogi |
| 8,453,188 B2 | 5/2013 | Campagna et al. |
| 8,470,830 B2 | 6/2013 | Ramakrishna |
| 8,507,469 B2 | 8/2013 | Schultz et al. |
| 8,552,017 B2 | 10/2013 | Ivashchenko |
| 8,618,114 B2 | 12/2013 | Ivashchenko |
| 8,829,199 B2 | 9/2014 | Taka |
| 9,018,231 B2 | 4/2015 | Nirogi |
| 2004/0242589 A1 | 12/2004 | Bromidge |
| 2005/0090496 A1 | 4/2005 | Ahmed |
| 2005/0124626 A1 | 6/2005 | Johnson |
| 2005/0176705 A1 | 8/2005 | Bromidge |
| 2006/0148818 A1 | 7/2006 | Johansson et al. |
| 2008/0200471 A1 | 8/2008 | Dunn et al. |
| 2008/0275040 A1 | 11/2008 | Johnson et al. |
| 2008/0318933 A1 | 12/2008 | Ahmed et al. |
| 2008/0318941 A1 | 12/2008 | Dunn et al. |
| 2009/0005417 A1 | 1/2009 | Merce Vidal et al. |
| 2009/0069337 A1 | 3/2009 | Dunn et al. |
| 2009/0318470 A1 | 12/2009 | Liu et al. |
| 2010/0016297 A1 | 1/2010 | Conticello et al. |
| 2010/0022581 A1 | 1/2010 | Danca et al. |
| 2010/0029629 A1 | 2/2010 | Conticello et al. |
| 2010/0041669 A1 | 2/2010 | Ramakrishna et al. |
| 2010/0056491 A1 | 3/2010 | Schumacher et al. |
| 2010/0075963 A1 | 3/2010 | Lehr et al. |
| 2012/0230965 A1 | 9/2012 | Sung |
| 2015/0044293 A1 | 2/2015 | Rosen et al. |
| 2016/0159790 A1 | 6/2016 | Zajdel et al. |
| 2016/0251339 A1 | 9/2016 | Zhang et al. |

FOREIGN PATENT DOCUMENTS

| | | | |
|---|---|---|---|
| EP | 1947085 | 7/2008 | |
| WO | 0063203 A1 | 10/2000 | |
| WO | 2001012629 A1 | 2/2001 | |
| WO | 2004108671 A1 | 12/2004 | |
| WO | 2005066157 A1 | 7/2005 | |
| WO | 2007020653 A1 | 2/2007 | |
| WO | 2007138611 A1 | 12/2007 | |
| WO | WO 2008101247 A2 * | 8/2008 | ........... C07D 209/08 |
| WO | WO-2008101247 A2 * | 8/2008 | ........... C07D 209/08 |
| WO | 2009034581 A1 | 3/2009 | |
| WO | 2009093934 A2 | 7/2009 | |
| WO | 2011088836 A1 | 7/2011 | |
| WO | 2014065710 A1 | 5/2014 | |

OTHER PUBLICATIONS

Liu, Kevin G. et al. 5-Piperazinyl-3-sulfonylindazoles as Potent and Selective 5-Hydroxytryptamine-6 Antagonists, Journal of Medicinal Chemistry, 2010, 53(21): 7639-7646.

Glennon et al., Higher-end serotonin receptors: 5-HT5, 5-HT6, and 5-HT7, Journal of Medicinal Chemistry, 2003, 46(14): 2795-2812.

Doddareddy et al., Hologram quantitative structure activity relationship studies on 5-HT6 antagonists, Bioorganic and Medicinal Chemistry, 2004, 12(14): 3815-3824.

* cited by examiner

AROMATIC HETEROCYCLIC DERIVATIVES AND PHARMACEUTICAL APPLICATIONS THEREOF

CROSS-REFERENCE TO RELATED APPLICATIONS

This is a U.S. national stage application of the International Patent Application No. PCT/CN2015/083605, filed Jul. 8, 2015, which claims priorities to Chinese Patent Application No. 201410324179.6, filed Jul. 8, 2014, both of which are incorporated herein by reference in their entirety.

FIELD

The invention belongs to the pharmaceutical field, and it relates to the compounds used for treating Alzheimer's disease, and to the pharmaceutical compositions containing such compounds and their uses. Especially, these compounds of the invention are aromatic heterocyclic derivatives used as $5\text{-}HT_6$ receptor antagonists.

BACKGROUND

Various central nervous system disorders such as anxiety, depression etc., are believed to involve a disturbance of the neurotransmitter 5-hydroxytryptamine (5-HT) or serotonin. The actions of the neurotransmitter 5-hydroxytryptamine (5-HT) as a major modulatory neurotransmitter in the brain, are mediated through a number of receptor families termed as $5\text{-}HT_1$, $5\text{-}HT_2$, $5\text{-}HT_3$, $5\text{-}HT_4$, $5\text{-}HT_5$, $5\text{-}HT_6$ and $5\text{-}HT_7$. Based on a high level of $5\text{-}HT_6$ receptor mRNA in the brain, it has been stated that the $5\text{-}HT_6$ receptor may play a role in the pathology and treatment of central nervous system disorders. In particular, $5\text{-}HT_6$-selective ligands have been identified as potentially useful in the treatment of certain central nervous system (CNS) disorders such as Parkinson's disease, Huntington's disease, anxiety, depression, manic depression, psychoses, epilepsy, obsessive compulsive disorders, migraine, Alzheimer's disease (enhancement of cognitive memory), sleep disorders, feeding disorders such as anorexia and bulimia, panic attacks, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. Such $5\text{-}HT_6$-selective ligands are also expected to be useful in the treatment of certain gastrointestinal (GI) disorders such as functional bowel disorder. (See for example, B. L. Roth et al., *J. Pharmacol. Exp. Ther,* 1994, 268, 1403-14120; D. R. Sibley et al., *Mol. Pharmacol,* 1993, 43, 320-327; A. J. Sleight et al., *Neurotransmission,* 1995, 11, 1-5; and A. J. Sleight et al., *Serotonin ID Research Alert.,* 1997, 2 (3), 115-118, all of which are incorporated herein by reference).

Studies have shown that a known selective $5\text{-}HT_6$ receptor antagonist may significantly increase glutamate and aspartate levels in the frontal cortex without elevating levels of noradrenaline, dopamine or 5-HT. This selective elevation of certain neurochemicals is noted during memory and cognition, strongly suggests a role for $5\text{-}HT_6$ ligands in cognition (Dawson, L. A.; Nguyen, H. Q.; Li, P., *British Journal of Pharmacology,* 2000, 130 (1), 23-26). Animal studies of memory and learning with a known selective $5\text{-}HT_6$ receptor antagonist has some positive effects (Rogers, D. C.; Hatcher, P. D.; Hagan, J. J., *Society of Neuroscience, Abstracts,* 2000, 26, 680, all of which are incorporated herein by reference). A related potential therapeutic use for $5\text{-}HT_6$ ligands is the treatment of attention deficit disorders (ADD, also known as Attention Deficit Hyperactivity Disorder or ADHD) in children as well as adults. As $5\text{-}HT_6$ receptor antagonists appear to enhance the activity of the nigrostriatal dopamine pathway and ADHD has been linked to abnormalities in the caudate nuclei (Ernst, M.; Zametkin, A. J.; Matochik, J. H.; Jons, P. A.; Cohen, R. M., *Journal of Neuroscience,* 1998, 18 (15), 5901-5907), $5\text{-}HT_6$ receptor antagonists may attenuate attention deficit disorders. $5\text{-}HT_6$ receptor antagonists have also been identified as potentially useful compounds for treatment of obesity. See for example, Bentley et al., *Br. J. Pharmac.* 1999, Suppl 126; Bently et al., *J. Psychopharmacol.* 1997, Suppl A64, 255; Wooley et al., *Neuropharmacology* 2001, 41, 210-129; and WO02098878, all of which are incorporated herein by reference.

SUMMARY

The invention provides aromatic heterocyclic derivatives having $5\text{-}HT_6$ receptor antagonist activity and good properties for clinical use. Compared with existing compounds, the compounds disclosed herein have high affinities for $5\text{-}HT_6$ receptor, and exhibit high selectivity and antagonistic activities for $5\text{-}HT_6$ receptor, which also have better efficacies, pharmacokinetic properties and/or toxicological properties, e.g., a good brain plasma ratio, a good bioavailability, a good metabolic stability, or a decreased inhibition of the mitochondrial respiration.

The compounds of the invention have excellent properties, such as, half-life, clearance, selectivity, bioavailability, chemical stability, metabolic stability, membrane permeability, solubility, which may lead to improvements such as, reduced side effects, enlarged therapeutic index or improved compliance.

The invention relates to novel aromatic heterocyclic derivatives used for treating Alzheimer's disease and methods of treating Alzheimer's disease. The compounds and their pharmaceutical compositions provided herein have good affinities for $5\text{-}HT_6$ receptor, especially have good therapeutic effect on Alzheimer's disease.

In one aspect, provided herein are compounds having Formula (I), or a stereoisomer, a tautomer, an N-oxide, a solvate, a metabolite, a pharmaceutically acceptable salt or a prodrug thereof,

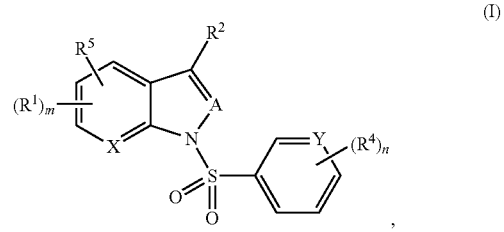

wherein
m is 0, 1 or 2;
n is 0, 1, 2, 3 or 4;
A is $CR^3$ or N;
X is $CR^1$;
Y is $CR^4$ or N;

each $R^1$ is independently H, D, F, Cl, Br, I, —CN, —NO$_2$, —OH, —NH$_2$, C$_{1-6}$ alkyl, C$_{2-6}$ alkenyl, C$_{2-6}$ alkynyl, C$_{1-6}$ haloalkyl, C$_{1-6}$ alkoxy, C$_{1-6}$ haloalkoxy, C$_{1-6}$ alkylthio, —C(=O)NR$^6$R$^{6a}$, —C(=O)R$^{6b}$, —C(=O)OR$^{6c}$, R$^6$R$^{6a}$N—S(=O)$_2$—, R$^{6b}$S(=O)$_2$—, C$_{3-8}$ cycloalkyl, 3- to 12-membered heterocyclyl, C$_{6-10}$ aryl or 5- to 12-membered heteroaryl;

$R^2$ is D, —CN, —OH, —NR$^6$R$^{6a}$, —C(=O)—(C$_{1-6}$ alkyl), —C(=O)NR$^6$R$^{6a}$, R$^6$R$^{6a}$N—S(=O)$_2$—, C$_{3-6}$ alkyl, hydroxy-substituted C$_{1-6}$ alkyl, C$_{1-6}$ haloalkyl, C$_{2-6}$ alkoxy or (C$_{6-10}$ aryl)-(C$_{1-6}$ alkylene)-;

$R^3$ is H, D, F, Cl, Br, I, —CN, —NO$_2$, —OH, —NH$_2$, C$_{1-6}$ alkyl, C$_{2-6}$ alkenyl, C$_{2-6}$ alkynyl, carboxy-substituted C$_{1-6}$ alkyl, C$_{1-6}$ haloalkyl, C$_{1-6}$ haloalkoxy, —C(=O)NR$^6$R$^{6a}$, —C(=O)R$^{6b}$, C$_{3-8}$ cycloalkyl or C$_{6-10}$ aryl;

each $R^4$ is independently H, D, F, Cl, Br, I, —CN, C$_{1-6}$ alkyl, C$_{2-6}$ alkenyl, C$_{2-6}$ alkynyl, C$_{1-6}$ haloalkyl, C$_{1-6}$ alkoxy, C$_{1-6}$ haloalkoxy, C$_{3-8}$ cycloalkyl or C$_{6-10}$ aryl; or two $R^4$, together with the adjacent ring carbon atoms to which they are attached, form a substituted or unsubstituted 5- to 7-membered carbocyclic ring, 5- to 7-membered heterocyclic ring, benzene ring or 5- to 6-membered heteroaromatic ring;

$R^5$ is 3- to 12-membered heterocyclyl, C$_{5-8}$ cycloalkyl, 5- to 12-membered heteroaryl, (3- to 12-membered heterocyclyl)-NH—, (3- to 12-membered heterocyclyl)-(C$_{1-3}$ alkylene)-, (3- to 12-membered heterocyclyl)-O— or (3- to 12-membered heterocyclyl)-S—, and wherein optionally each of 3- to 12-membered heterocyclyl, C$_{5-8}$ cycloalkyl, 5- to 12-membered heteroaryl, (3- to 12-membered heterocyclyl)-NH—, (3- to 12-membered heterocyclyl)-(C$_{1-3}$ alkylene)-, (3- to 12-membered heterocyclyl)-O— and (3- to 12-membered heterocyclyl)-S— is independently substituted with 1, 2, 3 or 4 $R^7$;

each $R^6$, $R^{6a}$, $R^{6b}$ and $R^{6c}$ is independently H, D, —OH, C$_{1-6}$ alkyl, C$_{1-6}$ haloalkyl, C$_{1-6}$ alkoxy, C$_{3-8}$ cycloalkyl, 3- to 12-membered heterocyclyl, C$_{6-10}$ aryl or 5- to 12-membered heteroaryl; or $R^6$ and $R^{6a}$, together with the nitrogen atom to which they are attached, form a substituted or unsubstituted 3- to 8-membered ring; and each $R^7$ is independently H, D, F, Cl, Br, I, —CN, —C(=O)NR$^6$R$^{6a}$, —C(O)R$^{6b}$, —C(=O)OR$^{6c}$, C$_{1-6}$ alkyl, C$_{1-6}$ haloalkyl, C$_{1-6}$ alkoxy, C$_{1-6}$ haloalkoxy, C$_{3-8}$ cycloalkyl, 3- to 12-membered heterocyclyl or (5- to 12-membered heteroaryl)-(C$_{1-6}$ alkylene)-.

In certain embodiments, $R^5$ is 5- to 6-membered heterocyclyl, (5- to 6-membered heterocyclyl)-NH—, (5- to 6-membered heterocyclyl)-CH$_2$—, (5- to 6-membered heterocyclyl)-CH(CH$_3$)—, (5- to 6-membered heterocyclyl)-O— or (5- to 6-membered heterocyclyl)-S—, and wherein optionally each of 5- to 6-membered heterocyclyl, (5- to 6-membered heterocyclyl)-NH—, (5- to 6-membered heterocyclyl)-CH$_2$—, (5- to 6-membered heterocyclyl)-CH(CH$_3$)—, (5- to 6-membered heterocyclyl)-O— and (5- to 6-membered heterocyclyl)-S— is independently substituted with 1, 2, 3 or 4 $R^7$; and each $R^7$ is as defined herein.

In certain embodiments, provided herein are compounds having Formula (II), or a stereoisomer, a tautomer, an N-oxide, a solvate, a metabolite, a pharmaceutically acceptable salt or a prodrug thereof,

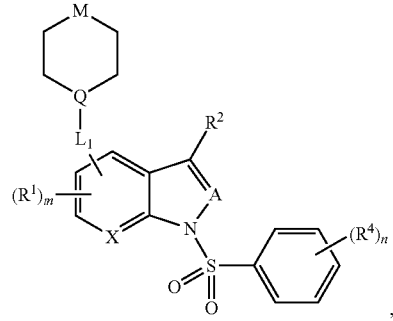

(II)

wherein
Q is CH or N;
M is —NR$^7$— or —O—;
L$_1$ is a bond, —NH—, —CH$_2$—, —O— or —S—; and
each $R^1$, $R^2$, $R^4$, $R^7$, X, A, m and n is as defined herein.

In certain embodiments, each $R^1$ is independently H, D, F, Cl, Br, I, —CN, —NO$_2$, —OH, —NH$_2$, methyl, ethyl, —CHF$_2$ or —CF$_3$.

In certain embodiments, $R^2$ is D, —CN, —OH, —NH$_2$, —C(=O)—(C$_{1-4}$ alkyl), C$_{3-4}$ alkyl, hydroxy-substituted C$_{1-4}$ alkyl, C$_{1-4}$ haloalkyl, C$_{2-4}$ alkoxy or phenyl-(C$_{1-4}$ alkylene)-.

In other embodiments, $R^2$ is D, —CN, —OH, —NH$_2$, —C(=O)CH$_3$, —C(=O)CH$_2$CH$_3$, —C(=O)CH$_2$CH$_2$CH$_3$, —C(=O)CH$_2$(CH$_3$)$_2$, n-propyl, i-propyl, n-butyl, i-butyl, t-butyl, —CH$_2$F, —CHF$_2$, —CF$_3$, —CH$_2$Cl, —CHCl$_2$, —CCl$_3$, —CH$_2$Br, —CHBr$_2$, —CBr$_3$, —CH$_2$CHF$_2$, —CH$_2$CF$_3$, —CHFCF$_3$, —CF$_2$CHF$_2$, —CF$_2$CF$_3$, —CH$_2$CH$_2$CF$_3$, —CH$_2$CF$_2$CHF$_2$ or ethoxy.

In certain embodiments, each $R^4$ is independently H, D, F, Cl, Br, I, —CN, C$_{1-4}$ alkyl, C$_{2-4}$ alkenyl, C$_{2-4}$ alkynyl, C$_{1-4}$ haloalkyl, C$_{1-4}$ alkoxy, C$_{1-4}$ haloalkoxy, C$_{3-6}$ cycloalkyl or C$_{6-10}$ aryl; or two $R^4$, together with the adjacent ring carbon atoms to which they are attached, form a substituted or unsubstituted benzene ring.

In other embodiments, each $R^4$ is independently H, D, F, Cl, Br, I, —CN, methyl, ethyl, n-propyl, i-propyl, n-butyl, i-butyl, t-butyl, —CH$_2$F, —CHF$_2$, —CF$_3$, —CH$_2$CHF$_2$, —CH$_2$CF$_3$, —CHFCF$_3$, —CF$_2$CHF$_2$, —CF$_2$CF$_3$, methoxy, ethoxy, n-propoxy, i-propoxy, n-butoxy, i-butoxy, t-butoxy, —OCHF$_2$, —OCF$_3$ or —OCH$_2$CF$_3$; or two $R^4$, together with the adjacent ring carbon atoms to which they are attached, form a substituted or unsubstituted benzene ring.

In certain embodiments, each $R^7$ is independently H, D, F, Cl, Br, I, —CN, C$_{1-4}$ alkyl, C$_{1-4}$ haloalkyl, C$_{3-6}$ cycloalkyl or 3- to 6-membered heterocyclyl.

In other embodiments, each $R^7$ is independently H, D, methyl, ethyl, n-propyl, i-propyl, n-butyl, i-butyl, t-butyl, cyclopropyl, cyclobutyl, cyclopentyl, azetidinyl, oxetanyl, thietanyl, pyrrolidyl or tetrahydrofuryl.

In another aspect, provided herein is a pharmaceutical composition comprising the compound disclosed herein.

In certain embodiments, the pharmaceutical composition disclosed herein further comprising a pharmaceutically acceptable carrier, excipient, diluent, adjuvant, vehicle or a combination thereof.

In other embodiments, the pharmaceutical composition disclosed herein further comprising an additional therapeutic agent used for treating Alzheimer's disease, neuropathy or a combination thereof.

In still other embodiments, the additional therapeutic agent disclosed herein is donepezil, nalmefene, risperidone, Vitamin E, SAM-760, AVN-211, AVN-101, RP-5063, tozadenant, PRX-3140, PRX-8066, RVT-101, naluzaton, idalopirdine, tacrine, rivastigmine, galantamine, memantine, mirtazapine, venlafaxine, desipramine, nortriptyline, zolpidem, zopiclone, nicergoline, piracetam, selegiline, pentoxifylline or a combination thereof.

In another aspect, provided herein is the use of the compound or the pharmaceutical composition disclosed herein in the manufacture of a medicament for preventing, treating or lessening a 5-HT$_6$ receptor-mediated disease.

In certain embodiments, the 5-HT$_6$ receptor-mediated disease disclosed herein is a central nervous system (CNS) disorder, a gastrointestinal disorder or obesity.

In other embodiments, the central nervous system (CNS) disorder is an attention deficit hyperactivity disorder (ADHD), anxiety, a stress-related disorder, schizophrenia, an obsessive-compulsive disorder, manic depression, a neurological disorder, a memory disorder, an attention deficit disorder, Parkinson's disease, amyotrophic lateral sclerosis, Alzheimer's disease or Huntington's chorea.

In another aspect, provided herein is a method for preventing, treating or lessening a 5-HT$_6$ receptor-mediated disease, comprising administering to a subject in need of such treatment a therapeutically effective amount of the compound or the pharmaceutical composition disclosed herein.

In certain embodiments, the 5-HT$_6$ receptor-mediated disease is a central nervous system (CNS) disorder, a gastrointestinal disorder or obesity.

In other embodiments, the central nervous system (CNS) disorder is an attention deficit hyperactivity disorder (ADHD), anxiety, a stress-related disorder, schizophrenia, an obsessive-compulsive disorder, manic depression, a neurological disorder, a memory disorder, an attention deficit disorder, Parkinson's disease, amyotrophic lateral sclerosis, Alzheimer's disease or Huntington's chorea.

In another aspect, provided herein is the compound or the pharmaceutical composition disclosed herein for use in preventing, treating or lessening a 5-HT$_6$ receptor-mediated disease in a subject.

In certain embodiments, the 5-HT$_6$ receptor-mediated disease is a central nervous system (CNS) disorder, a gastrointestinal disorder or obesity.

In other embodiments, the central nervous system (CNS) disorder is an attention deficit hyperactivity disorder (ADHD), anxiety, a stress-related disorder, schizophrenia, an obsessive-compulsive disorder, manic depression, a neurological disorder, a memory disorder, an attention deficit disorder, Parkinson's disease, amyotrophic lateral sclerosis, Alzheimer's disease or Huntington's chorea.

In another aspect, provided herein are methods for preparing, separating, and purifying of the compounds represented by Formula (I) or (II).

Any embodiment disclosed herein can be combined with other embodiments as long as they are not contradictory to one another, even though the embodiments are described under different aspects of the invention. In addition, any technical feature in one embodiment can be applied to the corresponding technical feature in other embodiments as long as they are not contradictory to one another, even though the embodiments are described under different aspects of the invention.

The foregoing merely summarizes certain aspects disclosed herein and is not intended to be limiting in nature. These aspects and other aspects and embodiments are described more fully below. All references of this specification are incorporated herein by reference in their entirety.

DETAILED DESCRIPTION

Definitions and General Terminology

Reference will now be made in detail to certain embodiments disclosed herein, examples of which are illustrated in the accompanying structures and formulas. The invention is intended to cover all alternatives, modifications, and equivalents that may be included within the scope disclosed herein as defined by the claims. One skilled in the art will recognize many methods and materials similar or equivalent to those described herein, which could be used in the practice disclosed herein. Described herein is in no way limited to the methods and materials. In the event that one or more of the incorporated literature, patents, and similar materials differ from or contradict this application, including but not limited to defined terms, term usage, described techniques, or the like, this application controls.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

Unless otherwise defined, all technical and scientific terms used herein have the same meaning as is commonly understood by one skilled in the art to which this invention belongs. All patents and publications referred to herein are incorporated by reference in their entirety.

As used herein, the following definitions shall be applied unless otherwise indicated. For purposes disclosed herein, the chemical elements are identified in accordance with the Periodic Table of the Elements, CAS version, and *the Handbook of Chemistry and Physics*, 75$^{th}$ Ed. 1994. Additionally, general principles of organic chemistry are described in Sorrell et al., "*Organic Chemistry*", University Science Books, Sausalito: 1999, and Smith et al., "*March's Advanced Organic Chemistry*", John Wiley & Sons, New York: 2007, all of which are incorporated herein by reference in their entireties.

The grammatical articles "a", "an" and "the", as used herein, are intended to include "at least one" or "one or more" unless otherwise indicated herein or clearly contradicted by the context. Thus, the articles are used herein to refer to one or more than one (i.e. at least one) of the grammatical objects of the article. By way of example, "a component" means one or more components, and thus, possibly, more than one component is contemplated and may be employed or used in an implementation of the described embodiments.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, "patient" refers to a human (including adults and children) or other animal. In one embodiment, "patient" refers to a human.

"Stereoisomers" refers to compounds which have identical chemical constitution, but differ with regard to the arrangement of the atoms or groups in space. Stereoisomers include enantiomer, diastereomers, conformer (rotamer), geometric (cis/trans) isomer, atropisomer, etc.

"Chiral" refers to molecules which have the property of non-superimposability of the mirror image partner, while the term "achiral" refers to molecules which are superimposable on their mirror image partner.

"Enantiomers" refer to two stereoisomers of a compound which are non-superimposable mirror images of one another.

"Racemate" or "racemic mixture" refers to a 50:50 mixture of enantiomers which lacks optical activity.

"Diastereomer" refers to a stereoisomer with two or more centers of chirality and whose molecules are not mirror images of one another. Diastereomers have different physical properties, e.g. melting points, boiling points, spectral properties or biological activities. Mixture of diastereomers may separate under high resolution analytical procedures such as electrophoresis and chromatography such as HPLC.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "*Stereochemistry of Organic Compounds*", John Wiley & Sons, Inc., New York, 1994, all of which are incorporated herein by reference. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. A specific stereoisomer may be referred to as an enantiomer, and a mixture of such stereoisomers is called an enantiomeric mixture. A 50:50 mixture of enantiomers is referred to as a racemic mixture or a racemate, which may occur when there has been no stereoselection or stereospecificity in a chemical reaction or process.

Any asymmetric atom (e.g., carbon or the like) of the compound(s) disclosed herein can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration.

Depending on the choice of the starting materials and procedures, the compounds can be present in the form of one of the possible stereoisomers or as mixtures thereof, such as racemates and diastereoisomer mixtures, depending on the number of asymmetric carbon atoms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration.

Any resulting mixtures of stereoisomers can be separated on the basis of the physicochemical differences of the constituents, into the pure or substantially pure geometric isomers, enantiomers, diastereomers, for example, by chromatography and/or fractional crystallization.

Any resulting racemates of final products or intermediates can be resolved into the optical antipodes by methods known to those skilled in the art, e.g., by separation of the diastereomeric salts thereof. Racemic products can also be resolved by chiral chromatography, e.g., high performance liquid chromatography (HPLC) using a chiral adsorbent. Preferred enantiomers can also be prepared by asymmetric syntheses. See, for example, Jacques, et al., *Enantiomers, Racemates and Resolutions* (Wiley Interscience, New York, 1981); Principles of *Asymmetric Synthesis* (2$^{nd}$ Ed. Robert E. Gawley, Jeffrey Aubé, Elsevier, Oxford, U K, 2012); Eliel, E. L. *Stereochemistry of Carbon Compounds* (McGraw-Hill, N Y, 1962); Wilen, S. H. *Tables of Resolving Agents and Optical Resolutions* p. 268 (E. L. Eliel, Ed., Univ. of Notre Dame Press, Notre Dame, Ind. 1972); *Chiral Separation Techniques: A Practical Approach* (Subramanian, G Ed., Wiley-VCH Verlag GmbH & Co. KGaA, Weinheim, Germany, 2007), all of which are incorporated herein by reference.

The term "tautomer" or "tautomeric form" refers to structural isomers of different energies which are interconvertible via a low energy barrier. Where tautomerization is possible (e.g. in solution), a chemical equilibrium of tautomers can be reached. For example, proton tautomers (also known as prototropic tautomers) include interconversions via migration of a proton, such as keto-enol and imine-enamine isomerizations. Valence tautomers include interconversions by reorganization of some of the bonding electrons. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers. Unless otherwise stated, all tautomeric forms of the compounds disclosed herein are within the scope of the invention.

The term "optional" or "optionally" refers to that a subsequently described event or circumstance may but need not occur, and that the description includes instances where the event or circumstance occurs and instances in which it does not. For example, "optional bond" means that the bond may or may not be present, and that the description includes single, double or triple bonds.

The term "comprising" or "comprise" is meant to be open ended, including the indicated component but not excluding other elements.

The term "unsaturated" refers to a moiety having one or more units of unsaturation.

As described herein, compounds disclosed herein may optionally be substituted with one or more substituents, such as the compound(s) illustrated by general formula above, or as exemplified by particular classes, subclasses, and species of the invention. It will be appreciated that the phrase "optionally substituted" is used interchangeably with the phrase "substituted or unsubstituted". In general, the term "substituted" refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position. Substituents described herein include, but are not limited to, deuterium, hydroxy, amino, F, Cl, Br, I, cyano, azido, aryl, heteroaryl, alkoxy, alkylamino, alkylthio, alkyl, alkenyl, alkynyl, cycloalkyl, heterocyclyl, mercapto, nitro, aryloxy, heteroaryloxy, oxo (=O), carboxy, haloalkyl, haloalkoxy, hydroxy-substituted alkyl, hydroxy-substituted haloalkyl, hydroxy-substituted alkoxy, hydroxy-substituted alkyl-C(=O)—, alkyl-C(=O)—, alkyl-S(=O)—, alkyl-S(=O)$_2$—, hydroxy-substituted alkyl-S(=O)—, hydroxy-substituted S(=O)$_2$—, carboxyalkoxy, and the like.

Unless otherwise defined herein, for a variable that occurs more than one time in any substituent or in the compound of the invention or any other formulae herein, its definition on each occurrence is independent of its definition at every other occurrence. Combinations of substituents are permissible only if such combinations result in stable compound. Stable compounds are compounds which can be isolated in a useful degree of purity from a reaction mixture.

In addition, the description of "each . . . is independently", "each (of) . . . and . . . is independently" and " . . . is independently" in the invention can be used interchangeably herein, unless otherwise specified. It should have a general understanding that it can be expressed both in different groups in which same symbols expressed specific options do not affect each other and the same groups in which same symbols expressed specific options do not affect each other. For example, the specific options of $R^6$ and $R^{6a}$ in Formula "—C(=O)NR$^6$R$^{6a}$" and Formula "R$^6$R$^{6a}$N—S(=O)$_2$—" are not affected with each other.

At various places in the present specification, substituents of compounds disclosed herein are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At various places in the present specification, linking substituents are described. Where the structure clearly requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "alkyl" or "alkyl group" refers to a saturated linear or branched-chain monovalent hydrocarbon radical of 1 to 20 carbon atoms, wherein the alkyl radical may be optionally substituted with one or more substituents described herein. In some embodiments, the alkyl group contains 1-12 carbon atoms. In other embodiments, the alkyl group contains 1-6 carbon atoms. In still other embodiments, the alkyl group contains 1-4 carbon atoms, and in yet other embodiments, the alkyl group contains 1-3 carbon atoms. In some specific structures, the alkyl group acts as a linking group, it should be understood that the alkyl group represents a linking alkylene group. For example, the $C_{1-6}$ alkyl group in ($C_{6-10}$ aryl)-($C_{1-6}$ alkyl)- should be understood as $C_{1-6}$ alkylene.

Some non-limiting examples of the alkyl group include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), 1-heptyl, 1-octyl, and the like.

The term "alkylene" refers to a saturated divalent hydrocarbon group derived from a straight or branched chain saturated hydrocarbon by the removal of two hydrogen atoms. Unless otherwise specified, the alkylene group contains 1-12 carbon atoms. In some embodiments, the alkylene group contains 1-6 carbon atoms. In other embodiments, the alkylene group contains 1-4 carbon atoms. In other embodiments, the alkylene group contains 1-3 carbon atoms. In still other embodiments, the alkylene group contains 1-2 carbon atoms. And alkylene group is exemplified by methylene (—CH$_2$—), ethylene (—CH$_2$CH$_2$—), isopropylene (—CH(CH$_3$)CH$_2$—), and the like. Wherein the alkylene group is optionally substituted with one or more substitutents described herein.

The term "alkenyl" refers to a linear or branched-chain monovalent hydrocarbon radical of 2 to 12 carbon atoms with at least one site of unsaturation, i.e., a carbon-carbon, sp$^2$ double bond, wherein the alkenyl radical may be optionally substituted with one or more substituents described herein, and includes radicals having "cis" and "trans" orientations, or alternatively, "E" and "Z" orientations. In some embodiments, the alkenyl group contains 2 to 8 carbon atoms. In other embodiments, the alkenyl group contains 2 to 6 carbon atoms, and in still other embodiments, the alkenyl group contains 2 to 4 carbon atoms. Examples of alkenyl groups include, but are not limited to, ethylenyl or vinyl (—CH=CH$_2$), allyl (—CH$_2$CH=CH$_2$), and the like.

The term "alkynyl" refers to a linear or branched monovalent hydrocarbon radical of 2 to 12 carbon atoms with at least one site of unsaturation, i.e., a carbon-carbon, sp triple bond, wherein the alkynyl radical may be optionally substituted with one or more substituents described herein. In some embodiments, the alkynyl group contains 2 to 8 carbon atoms; in other embodiments, the alkynyl group contains 2 to 6 carbon atoms; and in still other embodiments, the alkynyl group contains 2 to 4 carbon atoms. Examples of such groups include, but are not limited to, ethynyl (—C≡CH), propargyl (—CH$_2$C≡CH), 1-propynyl (—C≡C—CH$_3$), and the like.

The term "D" or "$^2$H" refers to a single deuterium atom.

The term "heteroatom" refers to one or more of oxygen (O), sulfur (S), nitrogen (N), phosphorus (P), or silicon (Si), including any oxidized form of nitrogen (N), sulfur (S), or phosphorus (P); the quaternized form of any basic nitrogen; or a substitutable nitrogen of a heterocyclic ring, for example N (as in 3,4-dihydro-2H-pyrrolyl), NH (as in pyrrolidinyl) or NR (as in N-substituted pyrrolidinyl).

The term "halogen" or "halo" refers to fluorine (F), chlorine (Cl), bromine (Br), or iodine (I).

The term "haloalkyl" refers to an alkyl substituted with one or more halogen atoms independently selected from fluorine (F), chlorine (Cl) or bromine (Br), and wherein the alkyl group is as defined herein. Examples of haloalkyl group include, but are not limited to, difluoromethyl, trifluoromethyl, 2,2,2-trifluoroethyl, 2,2,3,3-tetrafluoropropyl, and the like. In some embodiments, "haloalkyl" is a lower $C_{1-4}$ haloalkyl, and wherein the "$C_{1-4}$ haloalkyl" includes $C_{1-2}$ alkyl substituted with F, $C_{3-4}$ alkyl substituted with F, $C_{1-2}$ alkyl substituted with Cl, $C_{3-4}$ alkyl substituted with Cl, $C_{1-2}$ alkyl substituted with Br, $C_{3-4}$ alkyl substituted with Br, and the like. Specifically, wherein the "$C_{1-4}$ haloalkyl" includes —$CH_2F$, —$CHF_2$, —$CF_3$, —$CH_2Cl$, —$CHCl_2$, —$CCl_3$, —$CH_2Br$, —$CHBr_2$, —$CBr_3$, —$CH_2CH_2F$, —$CH_2CHF_2$, —$CH_2CF_3$, —$CF_2CH_2F$, —$CF_2CHF_2$, —$CF_2CF_3$, —$CHFCF_3$, —$CHFCHF_2$, —$CHFCH_2F$, —$CH_2CH_2CF_3$, —$CH_2CF_2CHF_2$, —$CHBrCH_2CF_3$, —$CHBrCF_2CHF_2$, and the like. And wherein the haloalkyl group may be optionally substituted with one or more substituents described herein.

The term "alkoxy" refers to an alkyl group, as previously defined, attached to the parent molecular moiety via an oxygen atom. Unless otherwise specified, the alkoxy group contains 1-12 carbon atoms. In some embodiments, the alkoxy group contains 1-6 carbon atoms. In other embodiments, the alkoxy group contains 1-4 carbon atoms. In still other embodiments, the alkoxy group contains 1-3 carbon atoms. The alkoxy radicals are optionally substituted with one or more substituents described herein.

Some non-limiting examples of alkoxy group include, methoxy (MeO, —$OCH_3$), ethoxy (EtO, —$OCH_2CH_3$), 1-propoxy (n-PrO, n-propoxy, —$OCH_2CH_2CH_3$), 2-propoxy (i-PrO, i-propoxy, —$OCH(CH_3)_2$), 1-butoxy (n-BuO, n-butoxy, —$OCH_2CH_2CH_2CH_3$), 2-methyl-1-propoxy (i-BuO, i-butoxy, —$OCH_2CH(CH_3)_2$), 2-butoxy (s-BuO, s-butoxy, —$OCH(CH_3)CH_2CH_3$), 2-methyl-2-propoxy (t-BuO, t-butoxy, —$OC(CH_3)_3$), 1-pentoxy (n-pentoxy, —$OCH_2CH_2CH_2CH_2CH_3$), 2-pentoxy (—$OCH(CH_3)CH_2CH_2CH_3$), 3-pentoxy (—$OCH(CH_2CH_3)_2$), 2-methyl-2-butoxy (—$OC(CH_3)_2CH_2CH_3$), 3-methyl-2-butoxy (—$OCH(CH_3)CH(CH_3)_2$), 3-methyl-1-butoxy (—$OCH_2CH_2CH(CH_3)_2$), 2-methyl-1-butoxy (—$OCH_2CH(CH_3)CH_2CH_3$), and the like.

The term "haloalkoxy" refers to an alkoxy group substituted with one or more halogen atoms, and wherein the alkoxy group is as defined herein. Examples of such group include, but are not limited to, trifluoromethoxy, 2,2,2-trifluoroethoxy, 2,2,3,3-tetrafluoropropoxy, and the like. Wherein the haloalkoxy group is optionally substituted with one or more substitutents described herein.

The term "alkylthio" refers to a linear or branched-alkyl radical attached to the rest of the molecular via a divalent sulfur atom, and wherein the alkyl group is as defined herein. In some embodiments, the alkylthio radical is a lower alkylthio radical having one to four carbon atoms. Some non-limiting examples of "alkylthio" include methylthio ($CH_3S$—). Wherein the alkylthio radical is optionally substituted with one or more substitutents described herein.

The term "alkylamino" embraces "N-alkylamino" and "N,N-dialkylamino", that is an amino group independently substituted with one or two alkyl radicals and wherein the alkyl group is as defined herein. Suitable alkylamino radical may be monoalkylamino or dialkylamino. Examples of the alkylamino radical include, but are not limited to, N-methylamino, N-ethylamino, N,N-dimethylamino, N,N-diethylamino, and the like. And wherein the alkylamino radical is optionally substituted with one or more substituents described herein.

The term "ring" refers to "carbocyclic", "heterocyclic", "aromatic", "heteroaromatic", and the like, and wherein "carbocyclic", "heterocyclic", "aromatic" and "heteroaromatic" are defined as described herein.

The term "carbocycle", "carbocyclyl", or "carbocyclic ring" refers to a monovalent or multivalent ring having 3 to 12 ring carbon atoms as a monocyclic, bicyclic or tricyclic ring system, which is saturated or contains one or more units of unsaturation, but an aromatic ring can not exist in the carbocyclyl group. Suitable carbocyclyl groups include, but are not limited to, cycloalkyl, cycloalkenyl and cycloalkynyl. Further examples of carbocyclyl group include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, and the like, and wherein the carbocyclyl group is optionally substituted with one or more substituents described herein.

The term "cycloalkyl" refers to a monovalent or multivalent saturated ring having 3 to 12 ring carbon atoms as a monocyclic, bicyclic, or tricyclic ring system, and wherein the bicyclic or tricyclic ring system may include fused ring, bridged ring and spiro ring. In some embodiments, the cycloalkyl group is $C_{3-10}$ cycloalkyl which contains 3 to 10 ring carbon atoms. In other embodiments, the cycloalkyl group is $C_{3-8}$ cycloalkyl which contains 3 to 8 ring carbon atoms. In still other embodiments, the cycloalkyl group is $C_{3-6}$ cycloalkyl which contains 3 to 6 ring carbon atoms. Examples of cycloalkyl group include, but are not limited to, cyclopropyl, cyclobutyl, cyclopentyl, cyclohexyl, and the like. Specifically, the $C_{3-6}$ cycloalkyl includes cyclopropyl, cyclobutyl, cyclopentyl and cyclohexyl. The cycloalkyl radical is optionally substituted with one or more substituents described herein.

The term "heterocyclic", "heterocyclyl", or "heterocyclic ring" as used interchangeably herein refers to a monovalent or multivalent ring having 3 to 12 ring atoms as a monocyclic, bicyclic or tricyclic ring system, of which one or more ring atoms are selected from nitrogen, sulfur and oxygen, and which is completely saturated or contains one or more units of unsaturation, but an aromatic ring can not exist in the heterocyclyl group. The heterocyclyl group may be a carbon radical or a heteroatom radical, of which a —$CH_2$— group can optionally be replaced by a —$C(=O)$— group. Ring sulfur atoms may be optionally oxidized to form S-oxides, and ring nitrogen atoms may be optionally oxidized to form N-oxides. Some non-limiting examples of the heterocyclyl group include oxiranyl, azetidinyl, oxetanyl (oxetan-2-yl, oxetan-3-yl), thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl, thioxanyl, homopiperazinyl, homopiperidinyl, oxepanyl, thiepanyl, oxazepinyl, diazepinyl, thiazepinyl, 2-oxa-5-azabicyclo[2.2.1]hept-5-yl, and the like. Some non-limiting examples of the heterocyclyl group of which the —$CH_2$— group is replaced by —$C(=O)$— moiety include 2-oxopyrrolidinyl, oxo-1,3-thiazolidinyl, 2-piperidonyl, 3,5-dioxopiperidinyl, pyrimidinedionyl, and the like. Some non-limiting examples of the heterocyclyl group of which the ring sulfur atom is oxidized include sulfolanyl, 1,1-dioxo-thiomorpholinyl, and the like. The heterocyclyl group is optionally substituted with one or more substituents described herein.

In one embodiment, the heterocyclyl group may be a 4- to 7-membered heterocyclyl, which refers to a saturated or partially unsaturated monocyclic ring containing 4 to 7 ring atoms, of which at least one ring atom is selected from nitrogen, sulfur and oxygen. Some non-limiting examples of the 4- to 7-membered heterocyclyl group include azetidinyl, oxetanyl (oxetan-2-yl, oxetan-3-yl), thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl, thioxanyl, homopiperazinyl, homopiperidinyl, oxepanyl, thiepanyl, oxazepinyl, diazepinyl, thiazepinyl, and the like. Some non-limiting examples of the heterocyclyl group of which the —CH$_2$— group is replaced by —C(=O)— moiety include 2-oxopyrrolidinyl, oxo-1,3-thiazolidinyl, 2-piperidonyl, 3,5-dioxopiperidinyl, pyrimidinedionyl, and the like. Some non-limiting examples of the heterocyclyl group of which the ring sulfur atom is oxidized include sulfolanyl, 1,1-dioxo-thiomorpholinyl, and the like. The 4- to 7-membered heterocyclyl group is optionally substituted with one or more substituents described herein.

In another embodiment, the heterocyclyl group may be a 3- to 6-membered heterocyclyl, and wherein the 3- to 6-membered heterocyclyl includes 3-membered heterocyclyl, 4-membered heterocyclyl, 5-membered heterocyclyl and 6-membered heterocyclyl.

In another embodiment, the heterocyclyl group may be a 5- to 6-membered heterocyclyl, and wherein the 5- to 6-membered heterocyclyl includes 5-membered heterocyclyl and 6-membered heterocyclyl.

In another embodiment, the heterocyclyl group may be a 4-membered heterocyclyl, which refers to a saturated or partially unsaturated monocyclic ring containing 4 ring atoms, of which at least one ring atom is selected from nitrogen, sulfur and oxygen. Examples of 4-membered heterocyclyl include, but are not limited to, azetidinyl, oxetanyl (oxetan-2-yl, oxetan-3-yl), thietanyl, and the like. The 4-membered heterocyclyl group is optionally substituted with one or more substituents described herein.

In another embodiment, heterocyclyl may be a 5-membered heterocyclyl, which refers to a saturated or partially unsaturated monocyclic ring containing 5 ring atoms, of which at least one ring atom is selected from nitrogen, sulfur and oxygen. Examples of 5-membered heterocyclyl include, but are not limited to, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, and the like. Some non-limiting examples of heterocyclyl wherein —CH$_2$— group is replaced by —C(=O)— moiety are 2-oxopyrrolidinyl, oxo-1,3-thiazolidinyl, and the like. A non-limiting example of heterocyclyl wherein the ring sulfur atom is oxidized is sulfolanyl, and the like. The 5-membered heterocyclyl group is optionally substituted with one or more substituents described herein.

In still another embodiment, heterocyclyl may be a 6-membered heterocyclyl, which refers to a saturated or partially unsaturated monocyclic ring containing 6 ring atoms, of which at least one ring atom is selected from nitrogen, sulfur and oxygen. Examples of 6-membered heterocyclyl include, but are not limited to, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl, thioxanyl, and the like. Some non-limiting examples of heterocyclyl wherein —CH$_2$— group is replaced by —C(=O)— moiety are 2-piperidinonyl, 3,5-dioxopiperidinyl, pyrimidinedionyl, and the like. A non-limiting example of heterocyclyl wherein the ring sulfur atom is oxidized is 1,1-dioxo-thiomorpholinyl, and the like. The 6-membered heterocyclyl group is optionally substituted with one or more substituents described herein.

The term "aryl" refers to a monocyclic, bicyclic, or tricyclic carbocyclic ring system having a total of 6 to 14 ring members, preferably, 6 to 12 ring members, and more preferably 6 to 10 ring members, and wherein at least one ring in the system is aromatic. The aryl group is generally, but not necessarily bonded to the parent molecule through an aromatic ring of the aryl group. The term "aryl" may be used interchangeably with the term "aryl ring" or "aromatic". Examples of aryl ring may include phenyl, naphthyl and anthracene. The aryl radical is optionally substituted with one or more substituents described herein.

The term "heteroaryl" refers to a monocyclic, bicyclic or tricyclic ring system having a total of 5 to 12 ring members, preferably, 5 to 10 ring members, and more preferably 5 to 6 ring members, wherein at least one ring in the system is aromatic, and at least one ring in the system contains one or more heteroatoms. The heteroaryl group is generally, but not necessarily bonded to the parent molecule through an aromatic ring of the heteroaryl group. The term "heteroaryl" may be used interchangeably with the term "heteroaryl ring", "aromatic heterocyclic" or the term "heteroaromatic compound". The heteroaryl radical is optionally substituted with one or more substituents described herein.

Some non-limiting examples of heteroaryl rings include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles, but are not limited to: benzimidazolyl, benzofuryl, benzothienyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl or 4-isoquinolinyl), imidazo[1,2-a]pyridyl, pyrazolo[1,5-a]pyridyl, pyrazolo[1,5-a]pyrimidyl, imidazo[1,2-b]pyridazinyl, [1,2,4]triazolo[4,3-b]pyridazinyl, [1,2,4]triazolo[1,5-a]pyrimidinyl, or [1,2,4]triazolo[1,5-a]pyridyl, and the like.

As described herein, a bond drawn from a substituent R to the center of one ring within a ring system (as shown in Figure f) represents substitution of the substituent R at any substitutable or reasonable position on the ring (such as ring A of Figure f). For example, Figure f represents the substituent R at any of the substitutable positions on the A ring, as shown in Figure f$^1$-f$^4$:

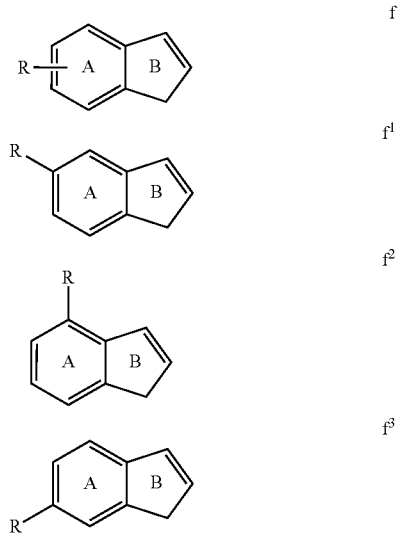

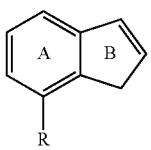

As described herein, the substituent on the ring can attach to the rest of the molecule at any attachable position on the rings, unless otherwise specified. For example, oxetanyl includes oxetan-2-yl, oxetan-3-yl, and the like; piperidyl includes piperid-1-yl, piperid-2-yl, piperid-3-yl, piperid-4-yl, and the like; piperazinyl includes piperazin-1-yl, piperazin-2-yl, piperazin-3-yl, piperazin-4-yl, and the like.

The term "prodrug" refers to a compound that is transformed in vivo into a compound of Formula (I) to Formula (V). Such a transformation can be affected, for example, by hydrolysis in blood or enzymatic transformation of the prodrug form to the parent form in blood or tissue. Prodrugs of the compounds disclosed herein may be, for example, esters. Esters that may be utilized as prodrugs in the present invention are phenyl esters, aliphatic ($C_1$-$C_{24}$) esters, acyloxymethyl esters, carbonates, carbamates, and amino acid esters. For example, a compound disclosed herein that contains a hydroxy group may be acylated at this position to form its prodrug. Other prodrug forms include phosphates, such as, those phosphates resulting from the phosphonation of a hydroxy group on the parent compound. A thorough discussion of prodrugs is provided in T. Higuchi and V. Stella, Pro-drugs as Novel Delivery Systems, Vol. 14 of *the A.C.S. Symposium Series*, Edward B. Roche, ed., *Bioreversible Carriers in Drug Design*, American Pharmaceutical Association and Pergamon Press, 1987, J. Rautio et al., Prodrugs: Design and Clinical Applications, *Nature Review Drug Discovery*, 2008, 7, 255-270, and S. J. Hecker et al., Prodrugs of Phosphates and Phosphonates, *Journal of Medicinal Chemistry*, 2008, 51, 2328-2345, each of which is incorporated herein by reference.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzyme cleavage, and the like, of the administered compound. Accordingly, the invention includes metabolites of compounds disclosed herein, including compounds produced by a process comprising contacting a compound disclosed herein with a mammal for a period of time sufficient to yield a metabolic product thereof.

A "pharmaceutically acceptable salts" refers to organic or inorganic salts of a compound disclosed herein. Pharmaceutically acceptable salts are well known in the art. For example, S. M. Berge et al., describe pharmaceutically acceptable salts in detail in *J. Pharmacol Sci*, 1977, 66, 1-19, which is incorporated herein by reference. Some non-limiting examples of pharmaceutically acceptable salts include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphanic acid salt, camphorsulfonate, cyclopentanepropionate, digluconate, dodecyl sulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, malonate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oilsoluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate or aryl sulfonate.

A "solvate" refers to an association or complex of one or more solvent molecules and a compound disclosed herein. Some non-limiting examples of solvents that form solvates include water, isopropanol, ethanol, methanol, dimethylsulfoxide, ethyl acetate, acetic acid and ethanolamine. The term "hydrate" refers to the complex where the solvent molecule is water.

The term "hydrate" can be used when said solvent is water. In one embodiment, one solvent molecule is associated with one molecule of the compounds disclosed herein, such as a hydrate. In another embodiment, more than one solvent molecule may be associated with one molecule of the compounds disclosed herein, such as a dihydrate. In still another embodiment, less than one solvent molecule may be associated with one molecule of the compounds disclosed herein, such as a hemihydrate. Furthermore, all the solvates of the invention retain the biological effectiveness of the non-hydrate form of the compounds disclosed herein.

The term "protecting group" or "PG" refers to a substituent that is commonly employed to block or protect a particular functionality while reacting with other functional groups on the compound. For example, an "amino-protecting group" is a substituent attached to an amino group that blocks or protects the amino functionality in the compound. Some non-limiting examples of suitable amino-protecting groups include acetyl, trifluoroacetyl, t-butoxycarbonyl (BOC, Boc), benzyloxycarbonyl (CBZ, Cbz) and 9-fluorenylmethyloxycarbonyl (Fmoc). Similarly, a "hydroxy-protecting group" refers to a substituent of a hydroxy group that blocks or protects the hydroxy functionality. Some non-limiting examples of suitable hydroxy-protecting groups include trialkylsilyl, acetyl, benzoyl, and benzyl. A "carboxy-protecting group" refers to a substituent of the carboxy group that blocks or protects the carboxy functionality. Some non-limiting examples of common carboxy-protecting groups include —$CH_2CH_2SO_2Ph$, cyanoethyl, 2-(trimethylsilyl)ethyl, 2-(trimethylsilyl)ethoxymethyl, 2-(p-toluenesulfonyl)ethyl, 2-(p-nitrophenylsulfonyl)ethyl, 2-(diphenylphosphino)ethyl, nitroethyl, and the like. For a general description of protecting groups and their use, see Greene et al., *Protective Groups in Organic Synthesis*, John Wiley & Sons, New York, 1991 and Kocienski et al., *Protecting Groups*, Thieme, Stuttgart, 2005.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment, "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

The term "preventing" or "prevention" refers to a reduction in risk of acquiring a disease or disorder (i.e., causing at least one of the clinical symptoms of the disease not to develop in a subject that may be exposed to or predisposed to the disease but does not yet experience or display symptoms of the disease).

The term "ADHD" is an abbreviation of "Attention-deficit hyperactivity disorder", which is a mental disorder commonly appeared in childhood. This disease is called "Hyperkinetic Disorder" according to the World Health Organization's "*The General Classification of Disease Manual*" 10$^{th}$ edit (ICD-10, WHO, 1992), and classification number is F90. "ADHD" is also commonly known as "hyperactive child".

The term "schizophrenia" is refers to Schizophrenia, Schizophrenia disorders, schizoaffective disorders and psychiatric disorders. Wherein the term "psychosis" refers to the action of delusions, obvious hallucinations, disorganized language or behavior, or stiff behavior, according to "*Diagnostic and Statistical Manual of Mental Disorder*" 4$^{th}$ edit, American Psychiatric Association, Washington, D.C., all of which are incorporated herein by reference.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlorotheophyllinate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, p-toluenesulfonic acid, sulfosalicylic acid, and the like.

Pharmaceutically acceptable base addition salts can be formed with inorganic or organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "*Remington's Pharmaceutical Sciences*", 20th ed., Mack Publishing Company, Easton, Pa., (1985); and in "*Handbook of Pharmaceutical Salts: Properties, Selection, and Use*" by Stahl and Wermuth (Wiley-VCH, Weinheim, Germany, 2002), all of which are incorporated herein by reference.

Furthermore, the compounds disclosed herein, including their salts, can also be obtained in the form of their hydrates, or include other solvents such as ethanol, DMSO, and the like, used for their crystallization. The compounds of the present invention may inherently or by design form solvates with pharmaceutically acceptable solvents (including water); therefore, it is intended that the invention embrace both solvated and unsolvated forms.

Any formula given herein is also intended to represent isotopically unenriched forms as well as isotopically enriched forms of the compounds. Isotopically enriched compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, sulfur, fluorine, and chlorine, such as $^{2}$H (deuterium, D), $^{3}$H, $^{11}$C, $^{13}$C, $^{14}$C, $^{15}$N, $^{17}$O, $^{18}$O, $^{18}$F, $^{31}$P, $^{32}$P, $^{35}$S, $^{36}$Cl, $^{125}$I, respectively.

In another aspect, the compounds of the invention include isotopically enriched compounds as defined herein, for example those into which radioactive isotopes, such as $^{3}$H, $^{14}$C and $^{18}$F, or those into which non-radioactive isotopes, such as $^{2}$H and $^{13}$C are present. Such isotopically enriched compounds are useful in metabolic studies (with $^{14}$C), reaction kinetic studies (with, for example $^{2}$H or $^{3}$H), detection or imaging techniques, such as positron emission tomography (PET) or single-photon emission computed tomography (SPECT) including drug or substrate tissue distribution assays, or in radioactive treatment of patients. In particular, an $^{18}$F-enriched compound may be particularly desirable for PET or SPECT studies. Isotopically-enriched compounds of Formula (I) to Formula (V) can generally be prepared by conventional techniques known to those skilled in the art or by processes analogous to those described in the accompanying examples and preparations using an appropriate isotopically-labeled reagent in place of the non-labeled reagent previously employed.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of Formula (I) to Formula (V). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). Pharmaceutically acceptable solvates in accordance with the invention include those wherein the solvent of crystallization may be isotopically substituted, e.g. $D_2O$, acetone-$d_6$, DMSO-$d_6$.

DESCRIPTION OF COMPOUNDS OF THE INVENTION

Provided herein are aromatic heterocyclic derivatives, pharmaceutically acceptable salts, pharmaceutical preparations and pharmaceutical compositions thereof, which have 5-$HT_6$ receptor antagonist activities, especially have potential effects on the treatment of Alzheimer's disease.

In one aspect, provided herein are compounds having Formula (I), or a stereoisomer, a tautomer, an N-oxide, a solvate, a metabolite, a pharmaceutically acceptable salt or a prodrug thereof,

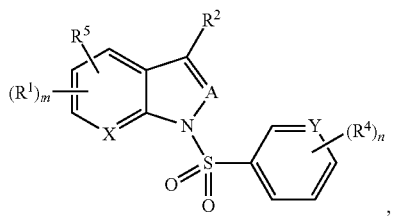

(I)

wherein, each $R^1$, $R^2$, $R^4$, $R^5$, X, A, Y, m and n is as defined herein.

In certain embodiments, m is 0, 1 or 2.

In certain embodiments, n is 0, 1, 2, 3 or 4.

In certain embodiments, A is $CR^3$ or N; and $R^3$ is as defined herein.

In certain embodiments, X is $CR^1$; and $R^1$ is as defined herein.

In certain embodiments, Y is $CR^4$ or N; and $R^4$ is as defined herein.

In certain embodiments, each $R^1$ is independently H, D, F, Cl, Br, I, —CN, —$NO_2$, —OH, —$NH_2$, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$ alkylthio, —C(=O)$NR^6R^{6a}$, —C(O)$R^{6b}$, —C(=O)$OR^{6c}$, $R^6R^{6a}N$—S(=O)$_2$—, $R^{6b}S(=O)_2$—, $C_{3-8}$ cycloalkyl, 3- to 12-membered heterocyclyl, $C_{6-10}$ aryl or 5- to 12-membered heteroaryl; and each $R^6$, $R^{6a}$, $R^{6b}$ and $R^{6c}$ is as defined herein.

In certain embodiments, $R^2$ is D, —CN, —OH, —$NR^6R^{6a}$, —C(=O)—($C_{1-6}$ alkyl), —C(=O)$NR^6R^{6a}$, $R^6R^{6a}N$—S(=O)$_2$—, $C_{3-6}$ alkyl, hydroxy-substituted $C_{1-6}$ alkyl, $C_{1-6}$ haloalkyl, $C_{2-6}$ alkoxy or ($C_{6-10}$ aryl)-($C_{1-6}$ alkylene)-; and each $R^6$ and $R^{6a}$ is as defined herein.

In certain embodiments, $R^3$ is H, D, F, Cl, Br, I, —CN, —$NO_2$, —OH, —$NH_2$, $C_{1-6}$ alkyl, $C_{2-6}$ alkenyl, $C_{2-6}$ alkynyl, carboxy-substituted $C_{1-6}$ alkyl, $C_{1-6}$ haloalkyl, $C_{1-6}$ haloalkoxy, —C(=O)$NR^6R^{6a}$, —C(O)$R^{6b}$, $C_{3-8}$ cycloalkyl or $C_{6-10}$ aryl; and each $R^6$, $R^{6a}$ and $R^{6b}$ is as defined herein.

In certain embodiments, each $R^4$ is independently H, D, F, Cl, Br, I, —CN, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{3-8}$ cycloalkyl or $C_{6-10}$ aryl; or two $R^4$, together with the adjacent ring carbon atoms to which they are attached, form a substituted or unsubstituted 5- to 7-membered carbocyclic ring, 5- to 7-membered heterocyclic ring, benzene ring or 5- to 6-membered heteroaromatic ring.

In certain embodiments, $R^5$ is 3- to 12-membered heterocyclyl, $C_{5-8}$ cycloalkyl, 5- to 12-membered heteroaryl, (3- to 12-membered heterocyclyl)-NH—, (3- to 12-membered heterocyclyl)-($C_{1-3}$ alkylene)-, (3- to 12-membered heterocyclyl)-O— or (3- to 12-membered heterocyclyl)-S—, and wherein optionally each of 3- to 12-membered heterocyclyl, $C_{5-8}$ cycloalkyl, 5- to 12-membered heteroaryl, (3- to 12-membered heterocyclyl)-NH—, (3- to 12-membered heterocyclyl)-($C_{1-3}$ alkylene)-, (3- to 12-membered heterocyclyl)-O— and (3- to 12-membered heterocyclyl)-S— is independently substituted with 1, 2, 3 or 4 $R^7$; and each $R^7$ is as defined herein.

In certain embodiments, each $R^6$, $R^{6a}$, $R^{6b}$ and $R^{6c}$ is independently H, D, —OH, $C_{1-6}$ alkyl, $C_{1-6}$ haloalkyl, $C_{1-6}$ alkoxy, $C_{3-8}$ cycloalkyl, 3- to 12-membered heterocyclyl, $C_{6-10}$ aryl or 5- to 12-membered heteroaryl; or $R^6$ and $R^{6a}$, together with the nitrogen atom to which they are attached, form a substituted or unsubstituted 3- to 8-membered ring.

In certain embodiments, each $R^7$ is independently H, D, F, Cl, Br, I, —CN, oxo (=O), —C(=O)$NR^6R^{6a}$, —C(O)$R^{6b}$, —C(=O)$OR^{6c}$, $C_{1-6}$ alkyl, $C_{1-6}$ haloalkyl, $C_{1-6}$ alkoxy, $C_{1-6}$ haloalkoxy, $C_{3-8}$ cycloalkyl, 3- to 12-membered heterocyclyl or (5- to 12-membered heteroaryl)-($C_{1-6}$ alkylene)-; and each $R^6$, $R^{6a}$, $R^{6b}$ and $R^{6c}$ is as defined herein.

In certain embodiments, $R^5$ is 5- to 6-membered heterocyclyl, (5- to 6-membered heterocyclyl)-NH—, (5- to 6-membered heterocyclyl)-$CH_2$—, (5- to 6-membered heterocyclyl)-CH($CH_3$)—, (5- to 6-membered heterocyclyl)-O— or (5- to 6-membered heterocyclyl)-S—, and wherein optionally each of 5- to 6-membered heterocyclyl, (5- to 6-membered heterocyclyl)-NH—, (5- to 6-membered heterocyclyl)-$CH_2$—, (5- to 6-membered heterocyclyl)-CH($CH_3$)—, (5- to 6-membered heterocyclyl)-O— and (5- to 6-membered heterocyclyl)-S— is independently substituted with 1, 2, 3 or 4 $R^7$; and each $R^7$ is as defined herein.

In certain embodiments, provided herein are compounds having Formula (II), or a stereoisomer, a tautomer, an N-oxide, a solvate, a metabolite, a pharmaceutically acceptable salt or a prodrug thereof,

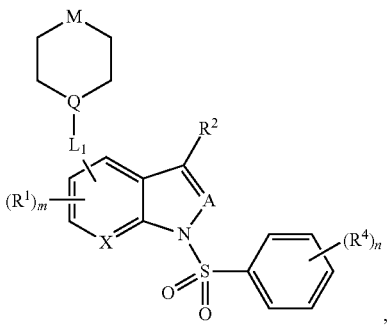

(II)

wherein
Q is CH or N;
M is —NR$^7$— or —O—;
L$_1$ is a bond, —NH—, —CH$_2$—, —O— or —S—; and
each R$^1$, R$^2$, R$^4$, R$^7$, X, A, m and n is as defined herein.

In other embodiments, provided herein are compounds having Formula (III), or a stereoisomer, a tautomer, an N-oxide, a solvate, a metabolite, a pharmaceutically acceptable salt or a prodrug thereof,

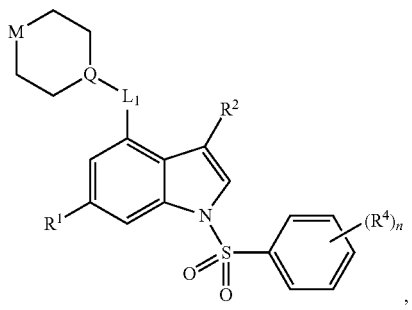

(III)

wherein
Q is CH or N;
M is —NR$^7$— or —O—;
L$_1$ is a bond, —NH—, —CH$_2$—, —O— or —S—; and
each R$^1$, R$^2$, R$^4$, R$^7$ and n is as defined herein.

In other embodiments, provided herein are compounds having Formula (IV), or a stereoisomer, a tautomer, an N-oxide, a solvate, a metabolite, a pharmaceutically acceptable salt or a prodrug thereof,

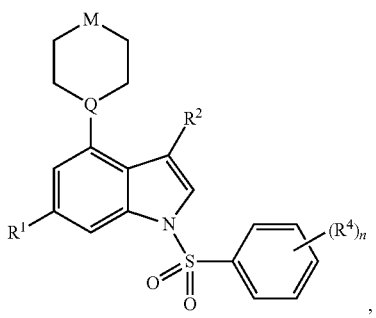

(IV)

wherein
Q is CH or N;
M is —NR$^7$— or —O—; and
each R$^1$, R$^2$, R$^4$, R$^7$ and n is as defined herein.

In other embodiments, provided herein are compounds having Formula (V), or a stereoisomer, a tautomer, an N-oxide, a solvate, a metabolite, a pharmaceutically acceptable salt or a prodrug thereof,

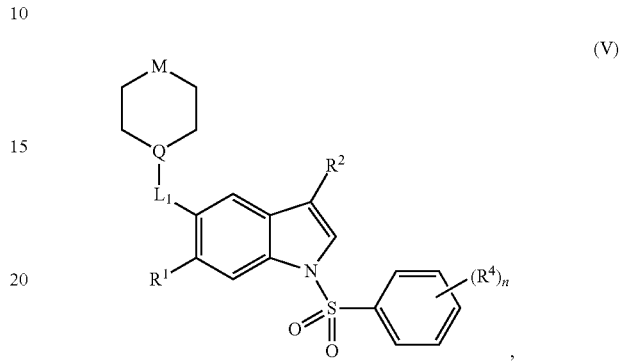

(V)

wherein
Q is CH or N;
M is —NR$^7$— or —O—;
L$_1$ is a bond, —NH—, —CH$_2$—, —O— or —S—; and
each R$^1$, R$^2$, R$^4$, R$^7$ and n is as defined herein.

In certain embodiments, each R$^1$ is independently H, D, F, Cl, Br, I, —CN, —NO$_2$, —OH, —NH$_2$, methyl, ethyl, —CHF$_2$ or —CF$_3$.

In certain embodiments, R$^2$ is D, —CN, —OH, —NH$_2$, —C(=O)—(C$_{1-4}$ alkyl), C$_{3-4}$ alkyl, hydroxy-substituted C$_{1-4}$ alkyl, C$_{1-4}$ haloalkyl, C$_{2-4}$ alkoxy or phenyl-(C$_{1-4}$ alkylene)-.

In other embodiments, R$^2$ is D, —CN, —OH, —NH$_2$, —C(=O)CH$_3$, —C(=O)CH$_2$CH$_3$, —C(=O)CH$_2$CH$_2$CH$_3$, —C(=O)CH$_2$(CH$_3$)$_2$, n-propyl, i-propyl, n-butyl, i-butyl, t-butyl, —CH$_2$F, —CHF$_2$, —CF$_3$, —CH$_2$Cl, —CHCl$_2$, —CCl$_3$, —CH$_2$Br, —CHBr$_2$, —CBr$_3$, —CH$_2$CHF$_2$, —CH$_2$CF$_3$, —CHFCF$_3$, —CF$_2$CHF$_2$, —CF$_2$CF$_3$, —CH$_2$CH$_2$CF$_3$, —CH$_2$CF$_2$CHF$_2$ or ethoxy.

In certain embodiments, each R$^4$ is independently H, D, F, Cl, Br, I, —CN, C$_{1-4}$ alkyl, C$_{2-4}$ alkenyl, C$_{2-4}$ alkynyl, C$_{1-4}$ haloalkyl, C$_{1-4}$ alkoxy, C$_{1-4}$ haloalkoxy, C$_{3-6}$ cycloalkyl or C$_{6-10}$ aryl; or two R$^4$, together with the adjacent ring carbon atoms to which they are attached, form a substituted or unsubstituted benzene ring.

In other embodiments, each R$^4$ is independently H, D, F, Cl, Br, I, —CN, methyl, ethyl, n-propyl, i-propyl, n-butyl, i-butyl, t-butyl, —CH$_2$F, —CHF$_2$, —CF$_3$, —CH$_2$CHF$_2$, —CH$_2$CF$_3$, —CHFCF$_3$, —CF$_2$CHF$_2$, —CF$_2$CF$_3$, methoxy, ethoxy, n-propoxy, i-propoxy, n-butoxy, i-butoxy, t-butoxy, —OCHF$_2$, —OCF$_3$ or —OCH$_2$CF$_3$; or two R$^4$, together with the adjacent ring carbon atoms to which they are attached, form a substituted or unsubstituted benzene ring.

In certain embodiments, each R$^7$ is independently H, D, F, Cl, Br, I, —CN, oxo (=O), C$_{1-4}$ alkyl, C$_{1-4}$ haloalkyl, C$_{3-6}$ cycloalkyl or 3- to 6-membered heterocyclyl.

In other embodiments, each R$^7$ is independently H, D, methyl, ethyl, n-propyl, i-propyl, n-butyl, i-butyl, t-butyl, cyclopropyl, cyclobutyl, cyclopentyl, azetidinyl, oxetanyl, thietanyl, pyrrolidyl or tetrahydrofuryl.

In certain embodiments, provided herein is the compound having one of the following structures, or a stereoisomer, a tautomer, an N-oxide, a solvate, a metabolite, a pharmaceutically acceptable salt or a prodrug thereof,
(1)
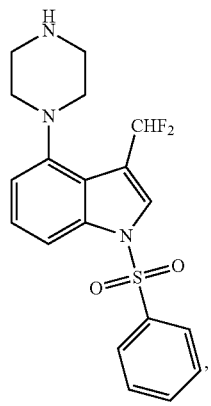
(2)
(3)
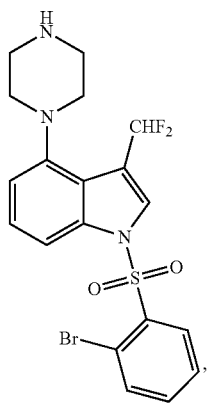
(4)
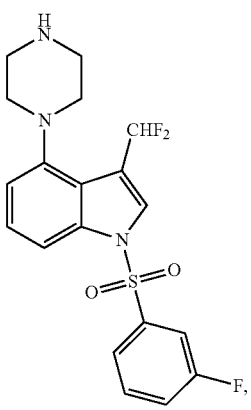
(5)
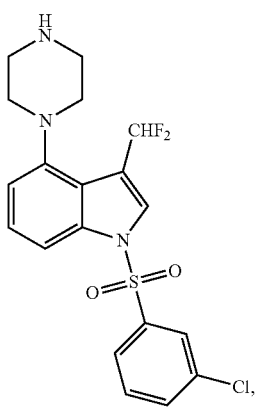
(6)
(7)
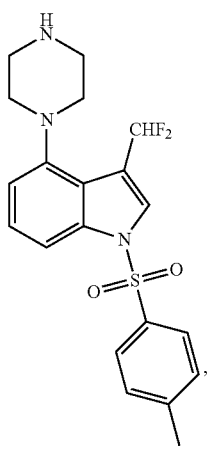

(8)
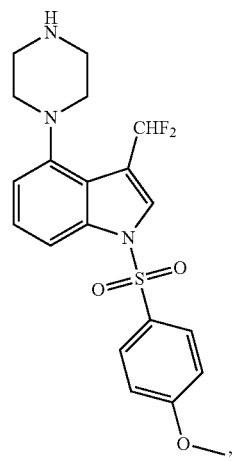
(9)
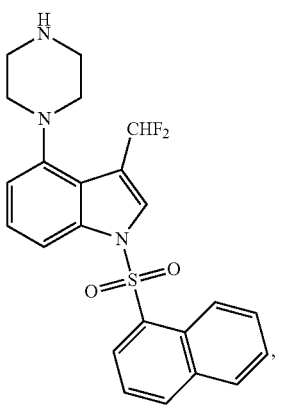
(10)
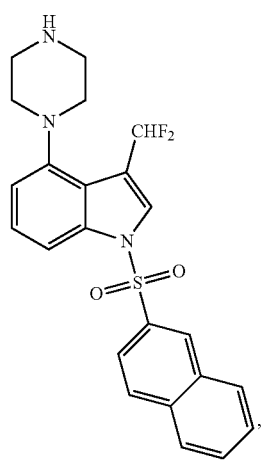
(11)
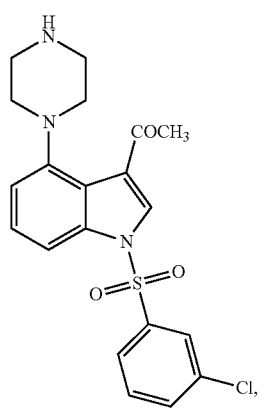
(12)
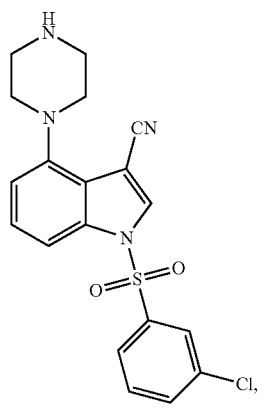
(13)
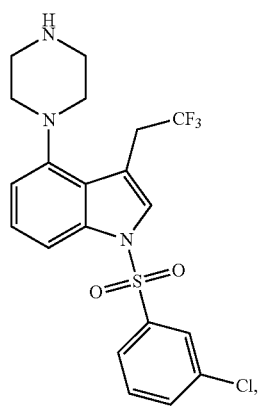
(14)
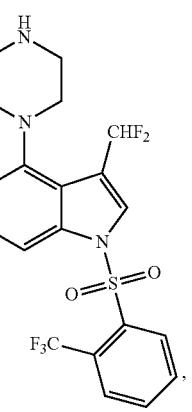

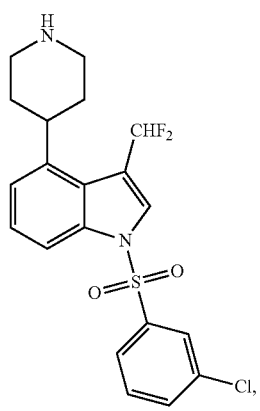(15)
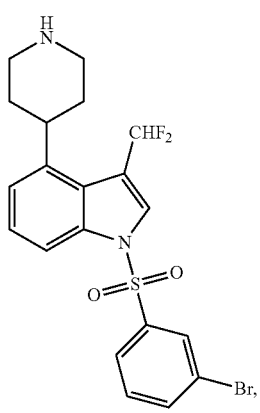(16)
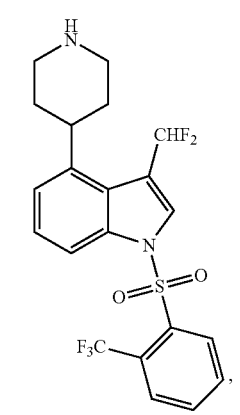(17)
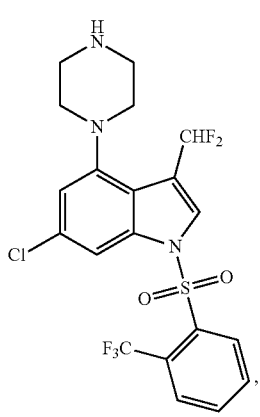(18)
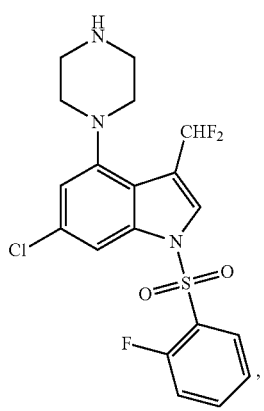(19)
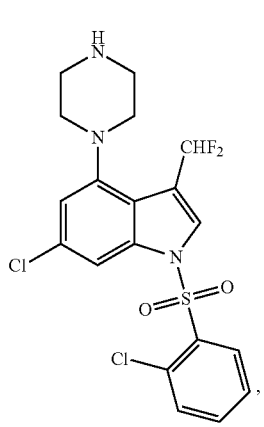(20)
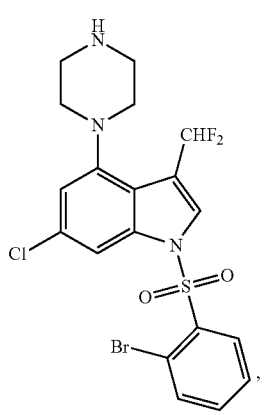(21)
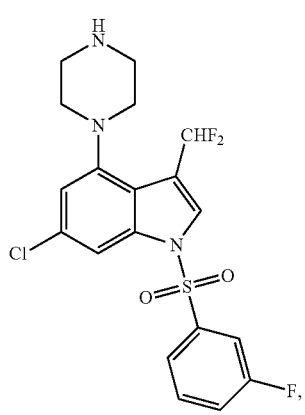(22)

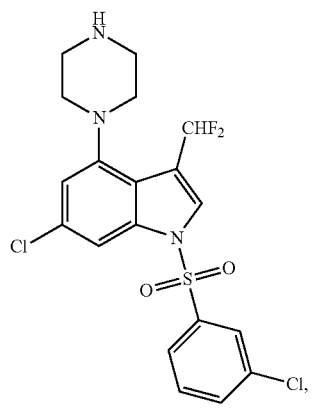
(23)
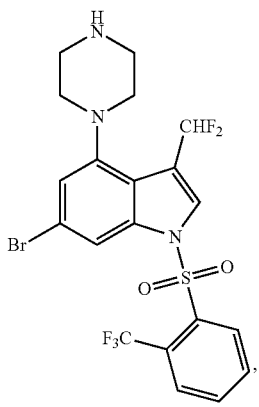
(26)
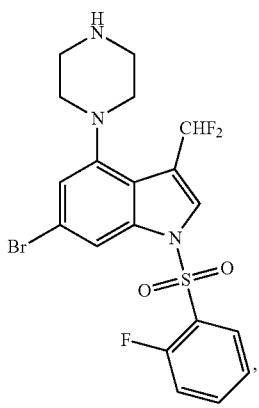
(27)
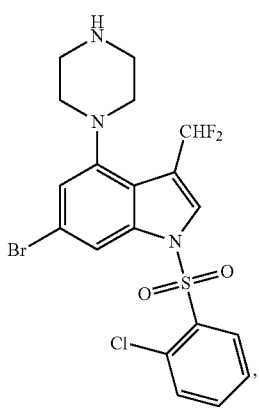
(28)
(24)
(25)
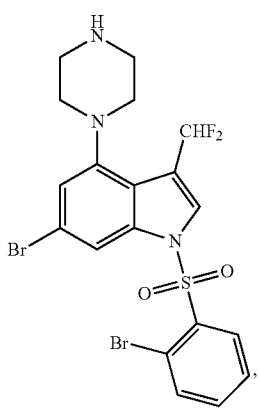
(29)

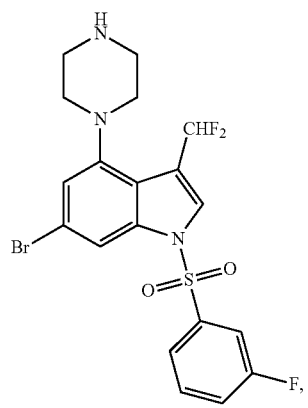
(30)
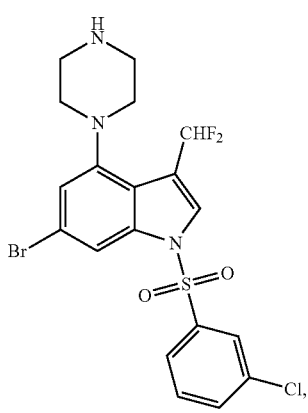
(31)
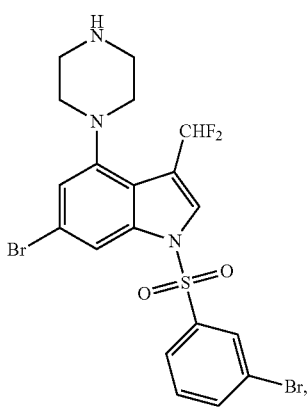
(32)
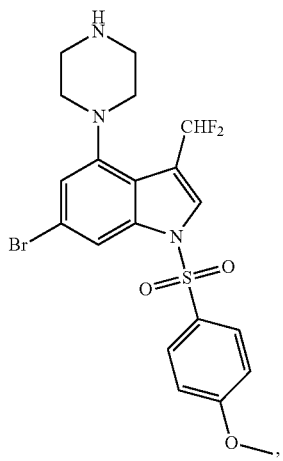
(33)
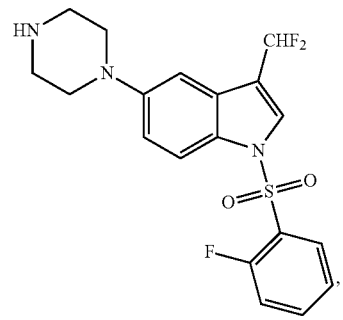
(34)
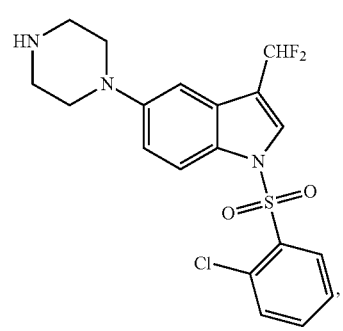
(35)
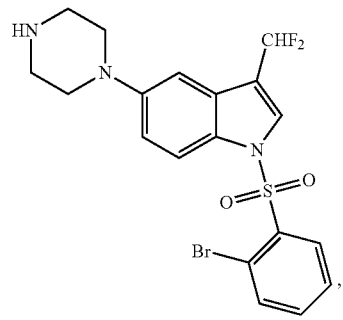
(36)

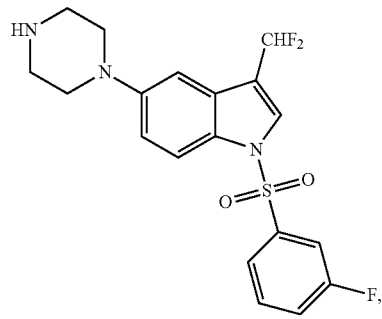
(37)
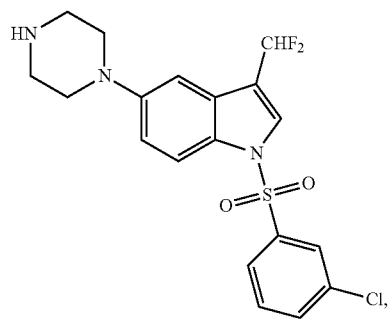
(38)
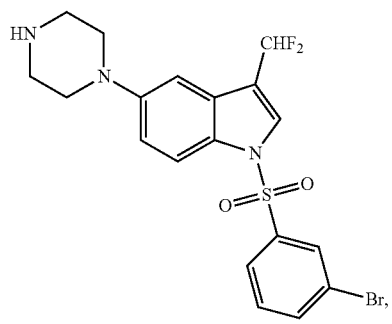
(39)
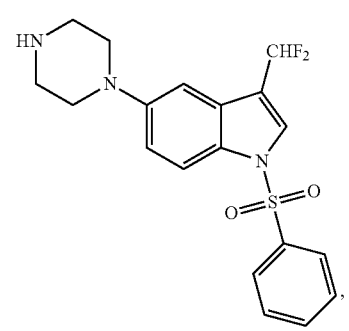
(40)
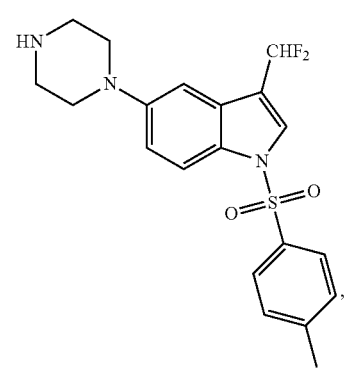
(41)
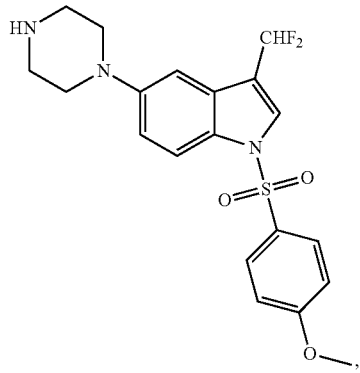
(42)
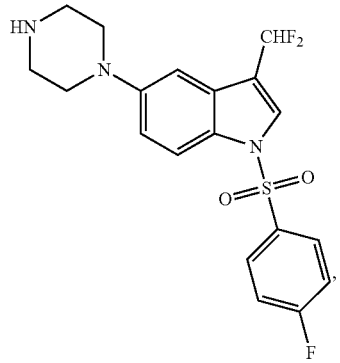
(43)
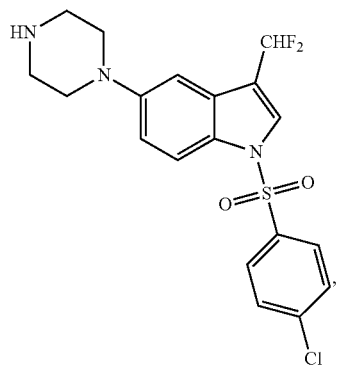
(44)
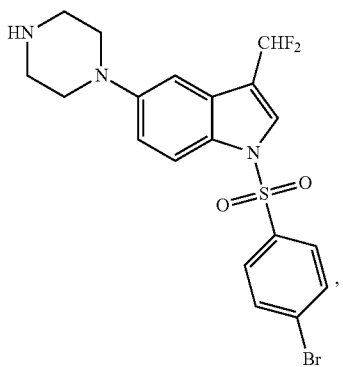
(45)

-continued
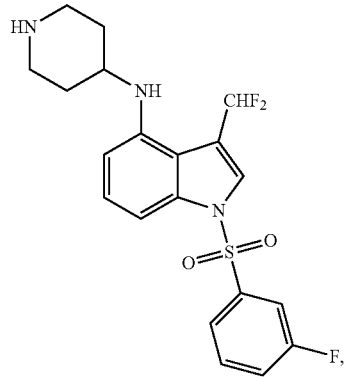
(46)
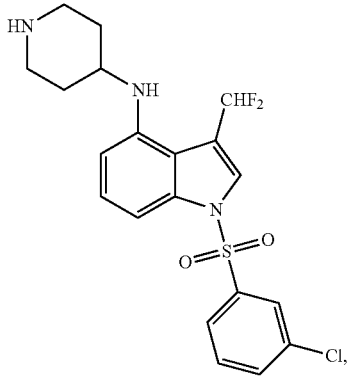
(47)
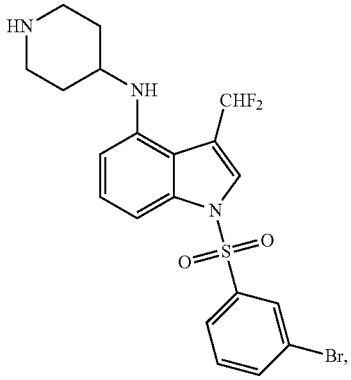
(48)
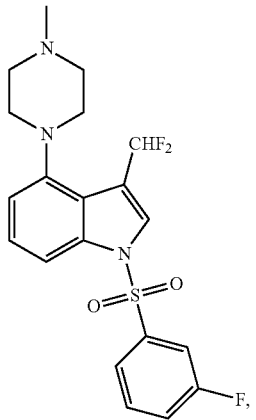
(49)
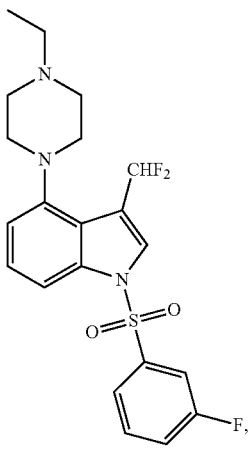
(50)
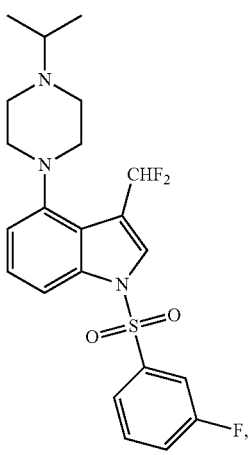
(51)
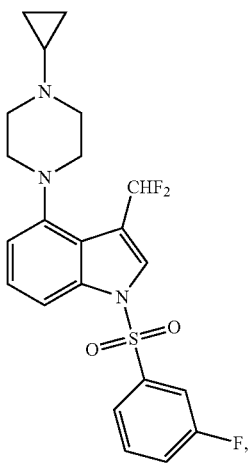
(52)

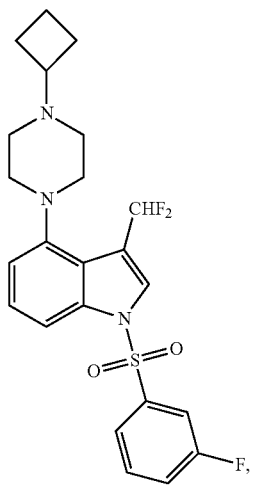
(53)
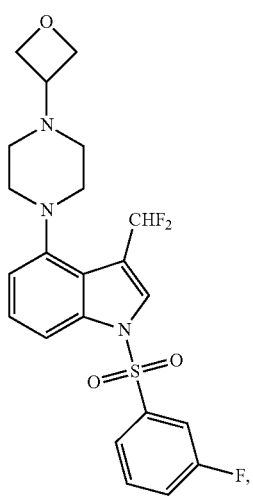
(54)
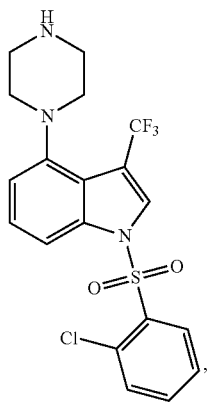
(56)
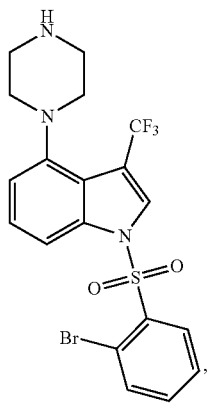
(57)
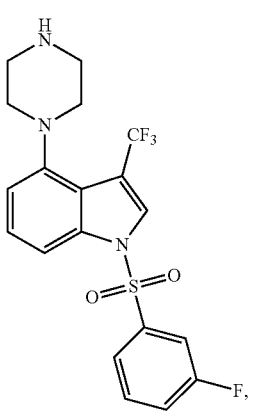
(58)
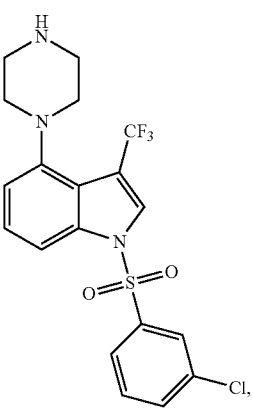
(59)

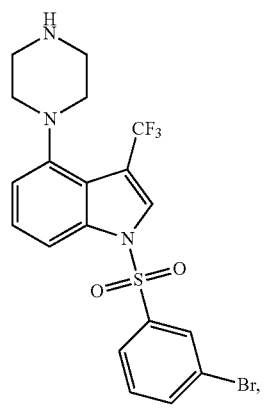
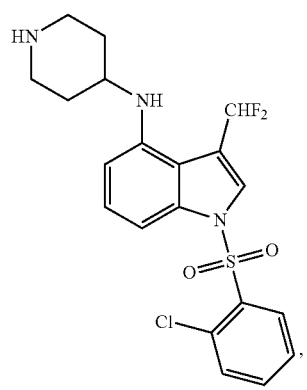
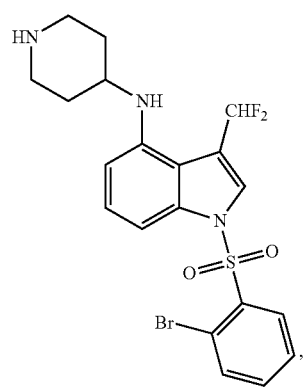
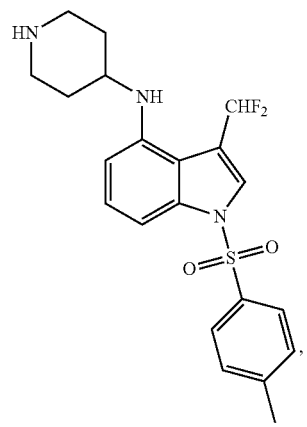
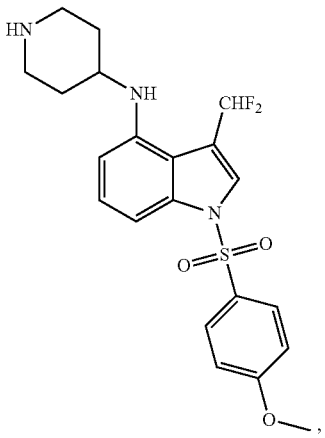

-continued (68), (69), (70), (71), (72), (73), (74), (75)

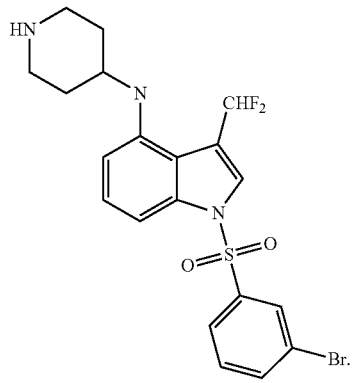

(76)

Also provided herein is the use of a compound disclosed herein, or a pharmaceutically acceptable salt thereof, in the manufacture of a medicament for treating Alzheimer's disease, and those diseases described herein. The compounds disclosed herein are also useful in the manufacture of a medicament to lessen, prevent, manage or treat $5\text{-}HT_6$ receptor-mediated disease in a patient, especially Alzheimer's disease. Also provided herein is a pharmaceutical composition comprising a therapeutically effective amount of a compound of Formula (I) to Formula (V) in association with at least one pharmaceutically acceptable carrier, adjuvant or diluent.

Unless otherwise stated, all suitable isotopic variations, all stereoisomers, tautomers, N-oxides, hydrates, solvates, metabolites, salts, and pharmaceutically acceptable prodrugs of the compounds disclosed herein are within the scope of the invention.

Unless otherwise stated, structures depicted herein are also meant to include all isomeric (e.g., enantiomeric, diastereomeric, and geometric (or conformational) forms of the structure; for example, the R and S configurations for each asymmetric center, (Z) and (E) double bond isomers, and (Z) and (E) conformational isomers. Therefore, single stereochemical isomers as well as enantiomeric, diastereomeric, or geometric (or conformational) mixtures of the present compounds are within the scope disclosed herein.

Unless otherwise stated, all tautomeric forms of the compounds disclosed herein are within the scope of the invention. Additionally, unless otherwise stated, structures depicted herein are also meant to include compounds that differ only in the presence of one or more isotopically enriched atoms.

The compounds disclosed herein may contain asymmetric or chiral centers, and therefore exist in different stereoisomeric forms. It is intended that all stereoisomeric forms of the compounds of Formula (I) to Formula (V), including but not limited to, diastereomers, enantiomers, atropisomers and geometric (conformational) isomers as well as mixtures thereof such as racemic mixtures, form part of the present invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

N-oxides of the compounds disclosed herein are also within the scope of the invention and may be prepared by oxidation of the corresponding nitrogen base using a conventional oxidizing agent such as hydrogen peroxide in the presence of an acid such as acetic acid at an elevated temperature, or by reaction with a peracid such as peracetic acid in a suitable solvent, e.g. dichloromethane, ethyl acetate or methyl acetate, or in chloroform or dichloromethane with 3-chloroperoxybenzoic acid.

In other aspect, provided herein are intermediates for preparation of the compounds represented by Formula (I) to Formula (V).

In other aspect, provided herein are methods for preparation, separation and purification of the compounds represented by Formula (I) to Formula (V).

In one embodiment, the salt is a pharmaceutically acceptable salt. The phrase "pharmaceutically acceptable" refers to that the substance or composition must be chemically and/or toxicologically compatible with the other ingredients comprising a formulation, and/or the mammal being treated therewith.

In another embodiment, the salts are not necessarily pharmaceutically acceptable salts, and which may be useful as intermediates for preparing and/or purifying compounds of Formula (I) to Formula (V) and/or for separating enantiomers of compounds of Formula (I) to Formula (V).

If the compound disclosed herein is a base, the desired salt may be prepared by any suitable method available in the art, for example, treatment of the free base with an inorganic acid, such as hydrochloric acid, hydrobromic acid, sulfuric acid, nitric acid, phosphoric acid, and the like. Or with an organic acid, such as acetic acid, maleic acid, succinic acid, mandelic acid, fumaric acid, malonic acid, pyruvic acid, oxalic acid, glycolic acid, salicylic acid; a pyranosidyl acid, such as glucuronic acid or galacturonic acid; an alpha hydroxy acid, such as citric acid or tartaric acid; an amino acid, such as aspartic acid or glutamic acid; an aromatic acid, such as benzoic acid or cinnamic acid; a sulfonic acid, such as p-toluenesulfonic acid, ethanesulfonic acid, and the like.

If the compound disclosed herein is an acid, the desired salt may be prepared by any suitable method, for example, treatment of the free acid with an inorganic or organic base, such as an amine (primary, secondary or tertiary), an alkali metal hydroxide or an alkaline earth metal hydroxide, and the like. Some non-limiting examples of suitable salts include organic salts derived from amino acids, such as glycine and arginine, ammonia (primary, secondary, and tertiary amines), and cyclic amines, such as piperidine, morpholine and piperazine, and inorganic salts derived from sodium, calcium, potassium, magnesium, manganese, iron, copper, zinc, aluminum, lithium, and the like.

Compounds, Pharmaceutical Compositions, Pharmaceutical Preparations and Administration A therapeutically effective amount of the compounds having Formula (I) to Formula (V) and their pharmaceutically acceptable salts can be administered to patients as chemical raw drugs, and also can be provided as active ingredients in pharmaceutical compositions. Therefore, also provided herein is a pharmaceutical composition containing the compound having Formula (I) to Formula (V), or a stereoisomer, or a racemic mixture or non-racemic mixture, or a pharmaceutically acceptable salt, or a solvate thereof. In one embodiment, the pharmaceutical composition further comprises at least one pharmaceutically acceptable carriers, adjuvants or excipients, and optionally other treating and/or preventing ingredients.

Appropriate carriers, adjuvants and excepients are well known to those of skill in the art and described in, for example, Ansel et al., *Ansel's Pharmaceutical Dosage Forms and Drug Delivery Systems,* 2004, Lippincott, Williams & Wilkins, Philadelphia; Gennaro et al., *Remington: The Science and Practice of Pharmacy,* 2000, Lippincott, Williams & Wilkins, Philadelphia; and Rowe et al., *Handbook of Pharmaceutical Excipients,* 2005, Pharmaceutical Press, Chicago.

Provide herein is the therapeutic method comprising administering the compound or the pharmaceutical composition described herein to a patient, further comprising administering an additional anti-Alzheimer's disease drug (combination therapy). And in some embodiments, the additional anti-Alzheimer's disease drug is donepezil, nalmefene, risperidone, Vitamin E, SAM-760, AVN-211, AVN-101, RP-5063, tozadenant, PRX-3140, PRX-8066, RVT-101, naluzaton, idalopirdine, tacrine, rivastigmine, galantamine, memantine, mirtazapine, venlafaxine, desipramine, nortriptyline, zolpidem, zopiclone, nicergoline, piracetam, selegiline, pentoxifylline or a combination thereof.

The term "therapeutically effective amount" means a total amount of active components which is sufficiently effective for treating the disease. When administering a single active component to a patient, term "therapeutically effective amount" means the amount of this active component. When administering the combination agents, term "therapeutically effective amount" means the total amount of active compositions, which is sufficient to bring the therapeutic effect of given disease, no matter that the dose of active composition is combinated, administered simultaneously or sequentially. Compounds having Formula (I) to Formula (V) or pharmaceutically acceptable salts thereof are described above. Considering the compatible with other ingredients and harmless to subjects, the carrier, diluent, or excipient must be acceptable. According to another aspect described herein, also provided herein is a method for preparing the pharmaceutical preparation, comprising mixing the compound having formula (I) to Formula (V) or a pharmaceutically acceptable salt thereof with one or more pharmaceutically acceptable carriers, diluents or excipients uniformly. The term "pharmaceutically acceptable" refers to a compound, material, composition and/or dose form, which are in the reasonable scope of medical judgment, must be compatible with the tissue of patent, and without excessive toxicity, irritation, allergic reaction, or other problems related to reasonable benefit/risk and complications, and effectively used in the intended application.

In general, the compounds of the present invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this application, to ascertain a therapeutically effective amount of the compounds of the present invention for a given disease.

In general, compounds of the present invention will be administered as pharmaceutical formulations including those suitable for oral (including buccal and sublingual), rectal, nasal, topical, pulmonary, vaginal, or parenteral (including intramuscular, intraarterial, intrathecal, subcutaneous, and intravenous) administration or in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or ingredients, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one milligram of active ingredient or, more broadly, about 0.01 to about one hundred milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, favouring agents, solubilizers, lubricants, suspending agents, binders, preservatives, tablet disintegrating agents, or an encapsulating material. In powders, the carrier generally is a finely divided solid which is mixed with finely divided active component to form a mixture. In tablets, the active component is generally mixed with the carrier having the necessary binding capacity in suitable proportions and compacted in the shape and size desired. The powders and tablets preferably contain the active compound about one to seventy percent. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, such as lecithin, sorbitan monooleate, or acacia. Aqueous solutions can be prepared by dissolving the active component in water and adding suitable colorants, flavors, stabilizing and thickening agents. Aqueous suspensions can be prepared by dispersing the finely divided active component in water with viscous material, such as natural or synthetic gums, resins, methylcellulose, sodium carboxymethylcellulose, and other well-known suspending agents. Liquid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous injection) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilising and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or colouring agents. Formulations suitable for topical administration in the mouth include lozenges comprising active agents in a flavoured base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomising spray pump.

The compounds of the present invention may be formulated for aerosol administration, particularly to the respiratory tract and including intranasal administration. The compound will generally have a small particle size for example of the order of five microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to a skin adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or can be the appropriate number of any of these in packaged form.

Other suitable pharmaceutical carriers and their formulations are described in *Remington: The Science and Practice of Pharmacy* 1995, edited by E. W. Martin, Mack Publishing Company, 19$^{th}$ edition, Easton, Pa., incorporated herein by reference.

Uses of the Compounds and Pharmaceutical Compositions

Compounds and pharmaceutical compositions provided herein are used for manufacture of a medicament for preventing, treating or lessening Alzheimer's disease, and also used for manufacture of a medicament for preventing, treating or lessening a 5-HT$_6$ receptor-mediated disease.

Provided herein are pharmaceutical compositions containing compounds described herein, especially compounds represented by Formula (I) to Formula (V), and a pharmaceutically acceptable carrier, excipient, or adjuvant. The amount of compound in the composition described herein is an effective and detectable amount for treating a CNS disorder, a gastrointestinal disease and obesity by antagonizing 5-$HT_6$ receptor, wherein the CNS disorder is ADHD, anxiety, a stress-related disorder, schizophrenia, an obsessive-compulsive disorder, manic depression, a neurological disorder, a memory disorder, an attention deficit disorder, Parkinson's disease, amyotrophic lateral sclerosis, Alzheimer's disease, Huntington's chorea, and the like.

An "effective amount" or "effective dose" of the compound or pharmaceutically acceptable composition is an amount that is effective in treating or lessening the severity of one or more of the aforementioned disorders or diseases. According to the method of the invention, any dose and any route of administering the compound or composition to a subject are effective for treating or lessening the severity of the disorder or disease. The accurate dose varies with the the relative health of a subject, which depending upon numerous factors such as the race, the age, the general condition of the patient, the severity of the infection, the special factor, the route of the administration, and the like. The compound or composition described herein can be administered with one or more additional therapeutic agents to a subject, as the invention discussed.

Besides being useful for human treatment, these compounds and compositions are also useful for veterinary treatment of companion animals, exotic animals and mammals of farm animals. In other embodiments, animals include horses, dogs and cats. As used herein, the compounds disclosed herein include the pharmaceutically acceptable derivatives thereof.

General Synthetic Procedures

In order to describe the invention, the following examples are set forth. It is to be understood that the invention is not limited to these embodiments, but only provides the methods to practice the invention.

Generally, the compounds disclosed herein may be prepared by methods described herein, wherein the substituents are as defined for Formulas (I) to Formula (V), above, except where further noted. The following non-limiting schemes and examples are presented to further exemplify the invention.

Persons skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds disclosed herein.

In the examples described below, unless otherwise indicated, all temperatures are set forth in degrees Celsius (° C.). Reagents were purchased from commercial suppliers such as Shanghai LinkChem Co., Ltd, Aldrich Chemical Company, Inc., Arco Chemical Company and Alfa Chemical Company, and were used without further purification unless otherwise indicated. Common solvents were purchased from commercial suppliers such as Shantou XiLong Chemical Factory, Guangdong Guanghua Reagent Chemical Factory Co. Ltd., Guangzhou Reagent Chemical Factory, Tianjin YuYu Fine Chemical Ltd., Qingdao Tenglong Reagent Chemical Ltd., and Qingdao Ocean Chemical Factory.

Anhydrous tertrahydrofuran was obtained by drying tertrahydrofuran in the refluxing condition with sodium added. Anhydrous dichloromethane and anhydrous chloroform were obtained by drying dichloromethane and chloroform independently in the refluxing condition equipped with hydride calcium. Ethyl acetate, N,N-dimethylacetamide and petroleum ether were dried over anhydrous sodium sulfate before use.

Generally, the following reactions were occurred in nitrogen atmosphere or argon atmosphere or anhydrous solvents equipped with drying tubes (Unless otherwise specified), and reaction flasks were plugged with suitable rubber plugs, substrates were added via syringes. All glassware was dried before use.

Column chromatography was conducted using a silica gel column. Silica gel (300-400 mesh) was purchased from Qingdao Ocean Chemical Factory. NMR spectra were obtained using $CDCl_3$, DMSO-$d_6$, $CD_3OD$ or acetone-$d_6$ as solvents (reported in ppm) and TMS (0 ppm) or chloroform (7.25 ppm) as the reference standard. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Low-resolution mass spectral (MS) data were determined on an Agilent 6320 Series LC-MS spectrometer equipped with G1312A binary pumps and a G1316A TCC (Temperature Control of Column, maintained at 30° C.). A G1329A autosampler and a G1315B DAD detector were used in the analysis, and an ESI source was used on the LC-MS spectrometer.

Low-resolution mass spectral (MS) data were determined on an Agilent 6120 Series LC-MS spectrometer equipped with G1311A quaternary pump and a G1316A TCC (Temperature Control of Column, maintained at 30° C.). A G1329A autosampler and a G1315D DAD detector were used in the analysis, and an ESI source was used on the LC-MS spectrometer.

Both Spectrographs were equipped with an Agilent Zorbax SB-C18 (2.1×30 mm, 5 µm). Injection volume was decided by the sample concentration. The flow rate was 0.6 mL/min. HPLC chromatogram was recorded using a UV-Vis wavelength detector at 210/254 nm. The mobile phase was (0.1% formic acid in $CH_3CN$ as mobile phase A) in (0.1% formic acid in ultrapure water as mobile phase B). The conditions of gradient elution were listed in Table 1:

TABLE 1

| Time (min) | A ($CH_3CN$, 0.1% HCOOH) | B ($H_2O$, 0.1% HCOOH) |
|---|---|---|
| 0-3 | 5-100 | 95-0 |
| 3-6 | 100 | 0 |
| 6-6.1 | 100-5 | 0-95 |
| 6.1-8 | 5 | 95 |

Purities of compounds were assessed by Agilent 1100 Series high performance liquid chromatography (HPLC) with UV detection at 210 nm and 254 nm (Zorbax SB-C18, 2.1×30 mm, 4 µm), 10 min, 0.6 mL/min flow rate, 5 to 95% (0.1% formic acid in $CH_3CN$) in (0.1% formic acid in $H_2O$). Column was operated at 40° C.

The following abbreviations are used throughout the specification:
HOAc acetic acid
MeCN, CH$_3$CN acetonitrile
CHCl$_3$ chloroform
CDCl$_3$ chloroform-d, deuterated chloroform
DMSO dimethylsulfoxide
DMSO-d$_6$ deuterated dimethylsulfoxide
DMF N,N-dimethylformamide
POCl$_3$ phosphoryl chloride
EtOAc, EA ethyl acetate
HCl hydrochloric acid
MgSO$_4$ magnesium sulfate
MgCl$_2$ magnesium chloride
MeOH, CH$_3$OH methanol
HCHO formaldehyde
CH$_2$Cl$_2$, DCM dichloromethane
mL, ml milliliter
M mol/L
PE petroleum ether (60-90° C.)
Na$_2$CO$_3$ sodium carbonate
NaHCO$_3$ sodium bicarbonate
K$_2$CO$_3$ potassium carbonate
KOH potassium hydroxide
RT room temperature
Rt retention time
h, hr hour(s)
min minute(s)
NaBH$_3$CN sodium cyanoborohydride
NaCl sodium chloride
NaH sodium hydride
Na$_2$SO$_4$ sodium sulfate
THF tetrahydrofuran
Et$_3$N, TEA triethylamine
H$_2$O water
EDTA ethylenediaminetetraacetic acid
PEI polyethyleneimine
Tris-HCl Tris(hydroxymethyl)aminomethane-hydrochloric acid
PdCl$_2$(dppf) [1,1'-bis(diphenylphosphino)ferrocene]dichloropalladium(II)
Pd/C palladium on carbon
Boc$_2$O di-tert-butyl dicarbonate
p-TsCl p-toluenesulfonyl chloride The following schemes describe the preparation of the compounds disclosed herein, unless otherwise indicated, each R$^1$, R$^4$, R$^7$, m and n is as defined herein.

Scheme 1

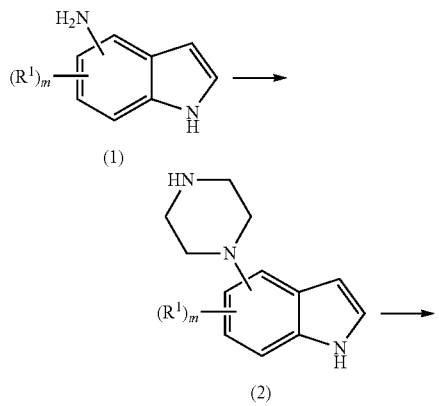

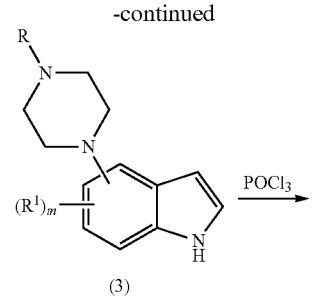

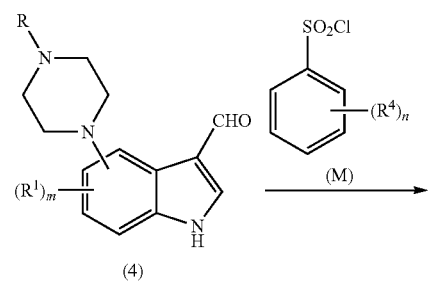

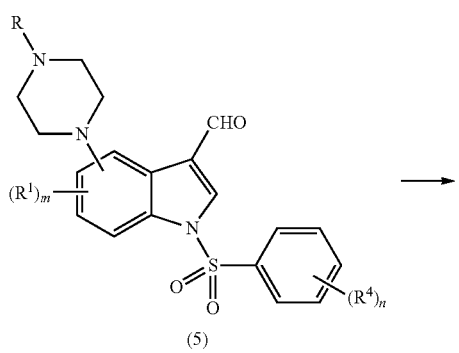

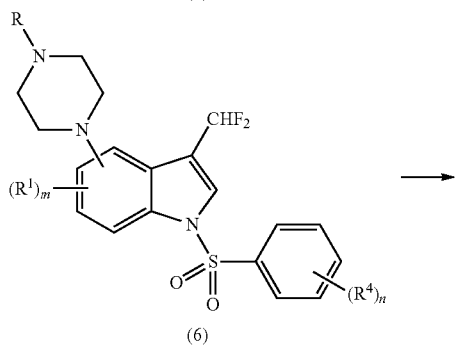

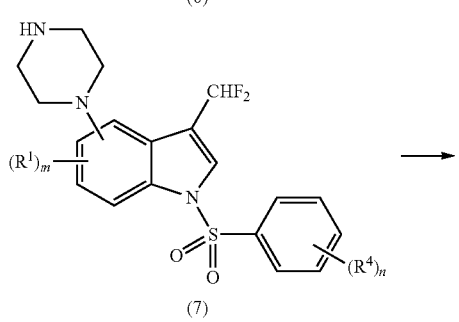

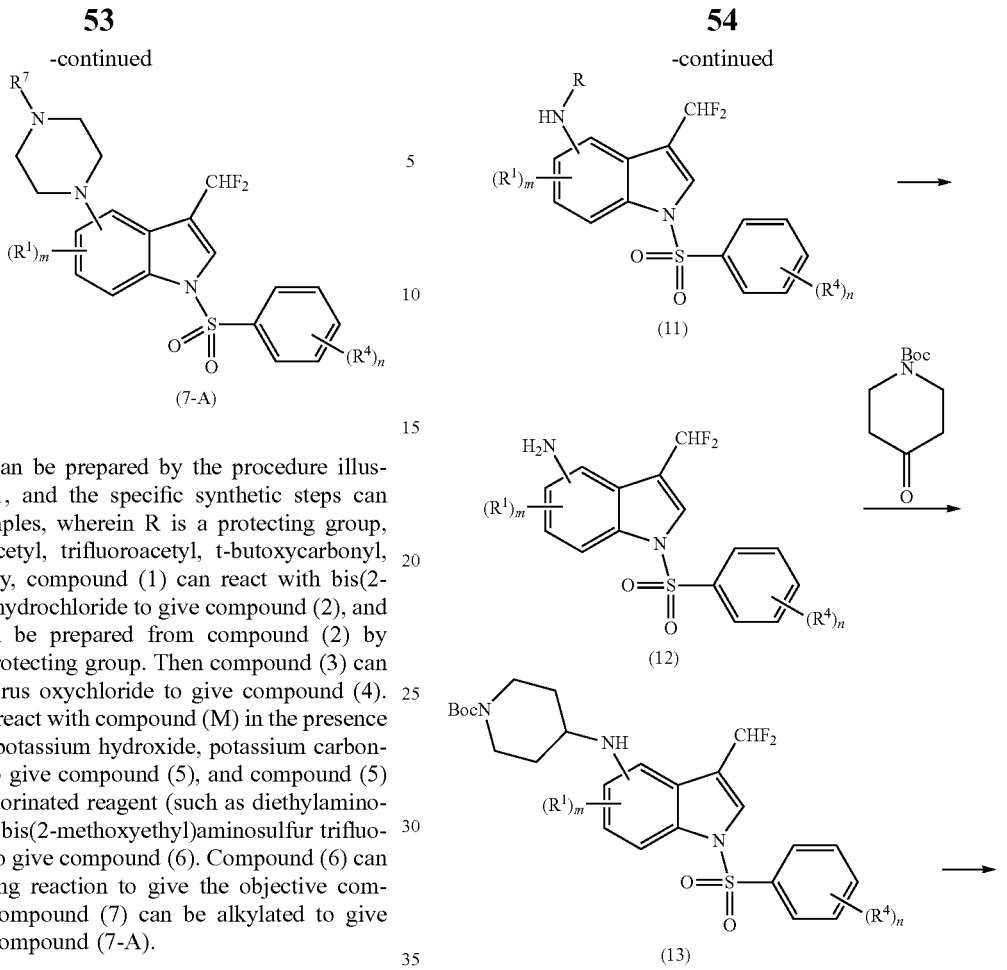

(7-A)

Compound (7) can be prepared by the procedure illustrated in scheme 1, and the specific synthetic steps can reference the examples, wherein R is a protecting group, such as trichloroacetyl, trifluoroacetyl, t-butoxycarbonyl, and the like. Firstly, compound (1) can react with bis(2-chloroethyl)amine hydrochloride to give compound (2), and compound (3) can be prepared from compound (2) by introduction of a protecting group. Then compound (3) can react with phosphorus oxychloride to give compound (4). Compound (4) can react with compound (M) in the presence of a base (such as potassium hydroxide, potassium carbonate, and the like) to give compound (5), and compound (5) can react with a fluorinated reagent (such as diethylaminosulphur trifluoride, bis(2-methoxyethyl)aminosulfur trifluoride, and the like) to give compound (6). Compound (6) can undergo deprotecting reaction to give the objective compound (7). Then compound (7) can be alkylated to give another objective compound (7-A).

Scheme 2

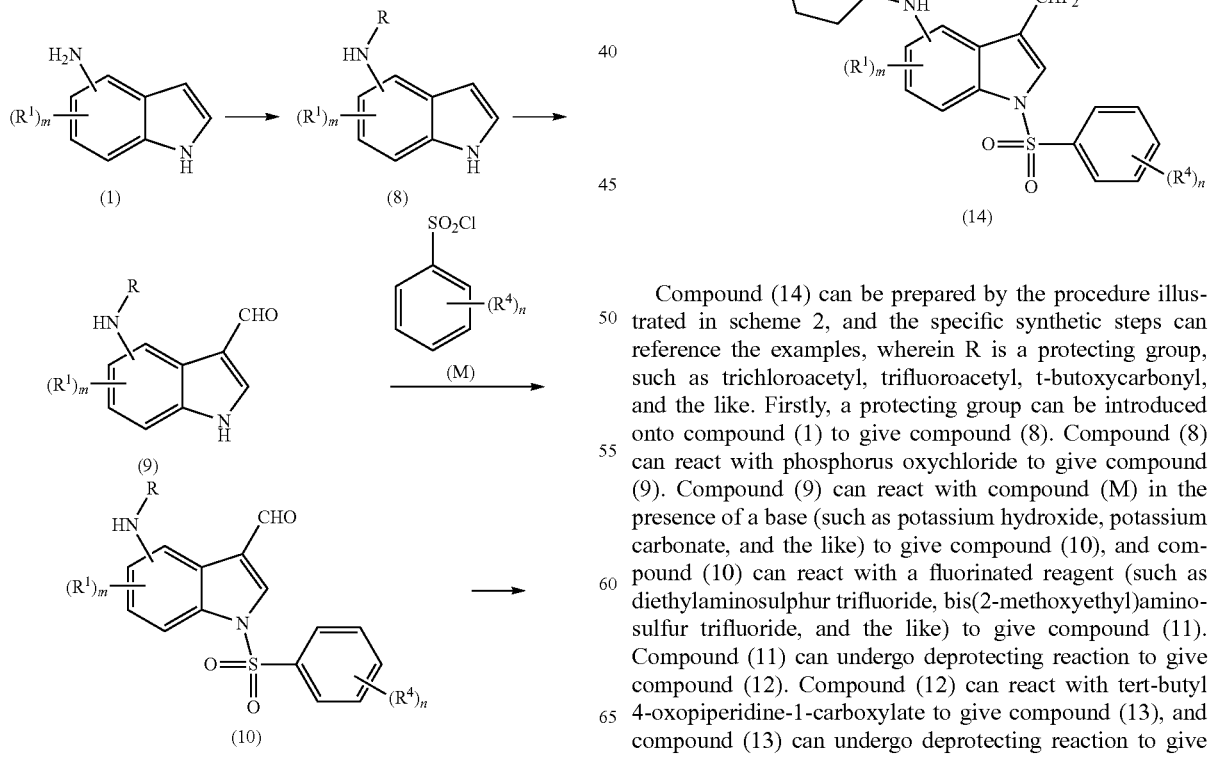

Compound (14) can be prepared by the procedure illustrated in scheme 2, and the specific synthetic steps can reference the examples, wherein R is a protecting group, such as trichloroacetyl, trifluoroacetyl, t-butoxycarbonyl, and the like. Firstly, a protecting group can be introduced onto compound (1) to give compound (8). Compound (8) can react with phosphorus oxychloride to give compound (9). Compound (9) can react with compound (M) in the presence of a base (such as potassium hydroxide, potassium carbonate, and the like) to give compound (10), and compound (10) can react with a fluorinated reagent (such as diethylaminosulphur trifluoride, bis(2-methoxyethyl)aminosulfur trifluoride, and the like) to give compound (11). Compound (11) can undergo deprotecting reaction to give compound (12). Compound (12) can react with tert-butyl 4-oxopiperidine-1-carboxylate to give compound (13), and compound (13) can undergo deprotecting reaction to give the objective compound (14).

Scheme 3

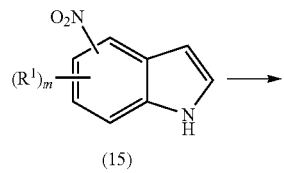
(15)

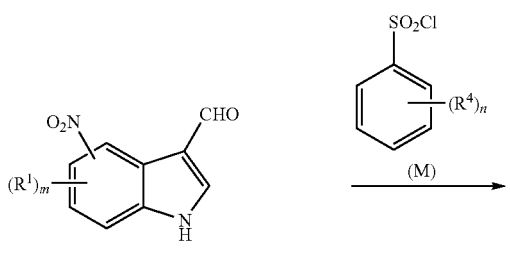
(16) → (17)

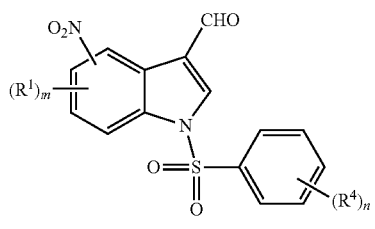
(17)

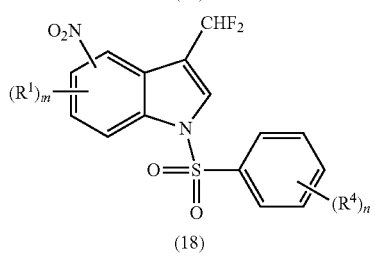
(18)

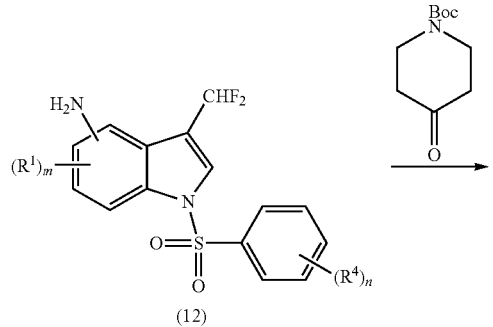
(12)

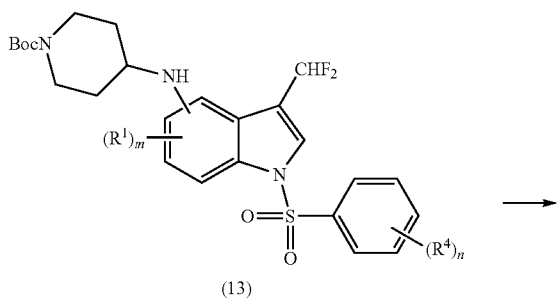
(13)

-continued

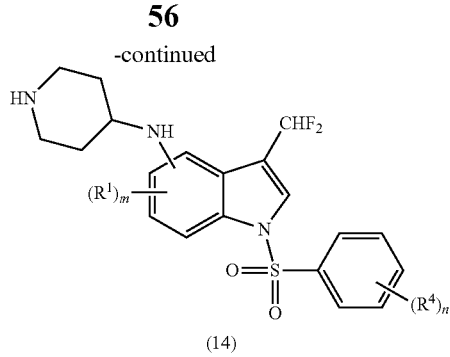
(14)

Compound (14) can be prepared by the procedure illustrated in scheme 3, and the specific synthetic steps can reference the examples. Firstly, compound (15) can react with phosphorus oxychloride to give compound (16). Compound (16) can react with compound (M) in the presence of a base (such as potassium hydroxide, potassium carbonate, and the like) to give compound (17), and compound (17) can react with a fluorinated reagent (such as diethylaminosulphur trifluoride, bis(2-methoxyethyl)aminosulfur trifluoride, and the like) to give compound (18). Compound (18) can undergo reduction reaction to give compound (12). Compound (12) can react with tert-butyl 4-oxopiperidine-1-carboxylate to give compound (13), and compound (13) can undergo deprotecting reaction to give the objective compound (14).

Scheme 4

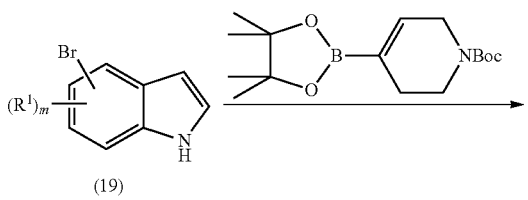
(19)

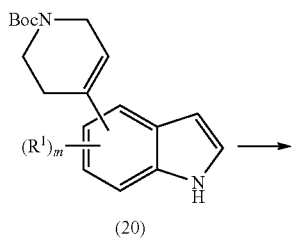
(20)

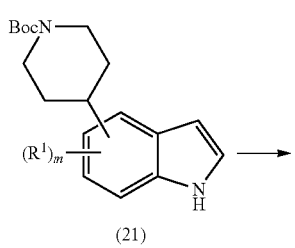
(21)

57
-continued

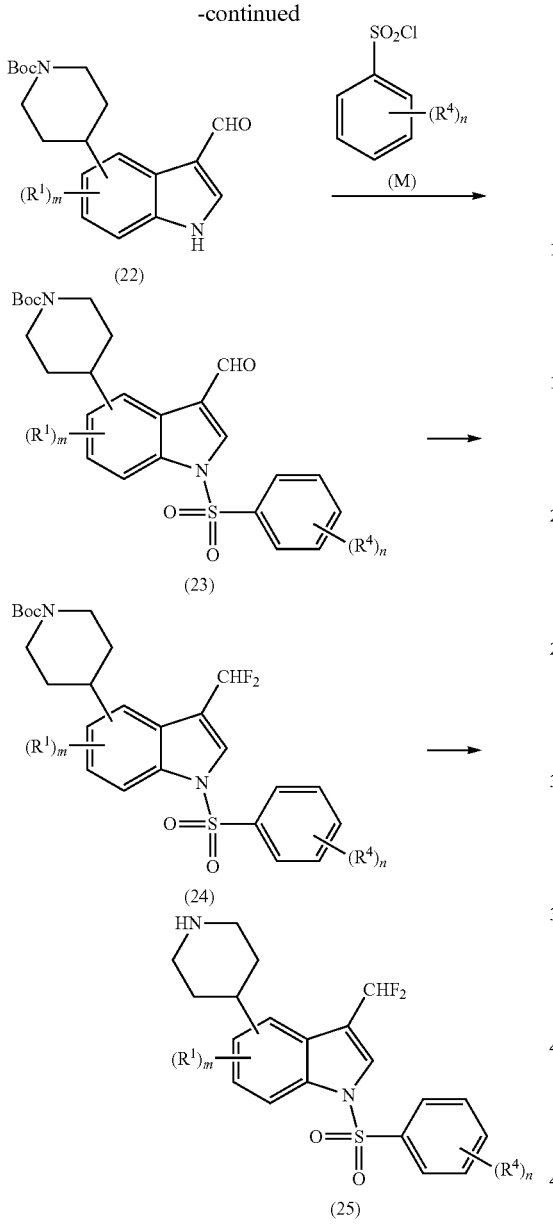

Compound (25) can be prepared by the procedure illustrated in scheme 4, and the specific synthetic steps can reference the examples. Firstly, compound (19) can undergo coupling reaction with N-Boc-1,2,5,6-tetrahydropyridine-4-boronic acid pinacol ester to give compound (20). Compound (20) can be reduced to give compound (21). Then compound (21) can react with phosphorus oxychloride to give compound (22). Compound (22) can react with compound (M) in the presence of a base (such as potassium hydroxide, potassium carbonate, and the like) to give compound (23), and compound (23) can react with a fluorinated reagent (such as diethylaminosulphur trifluoride, bis(2-methoxyethyl)aminosulfur trifluoride, and the like) to give compound (24). Compound (24) can undergo deprotecting reaction to give compound (25).

Compounds, pharmaceutical compositions and applications thereof described herein are further illustrated by the following examples.

58
EXAMPLES

Example 1 3-(difluoromethyl)-1-(phenylsulfonyl)-4-(piperazin-1-yl)-1H-indole

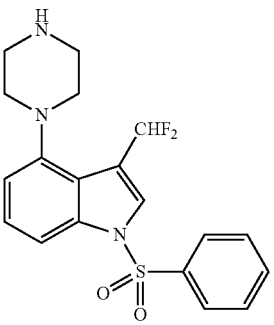 [SMILES: O=S(=O)(c1ccccc1)n1cc(C(F)F)c2c(N3CCNCC3)cccc21]

Step 1) 4-(piperazin-1-yl)-1H-indole

To 30 mL of i-propanol were added 4-aminoindole (2 g, 15.2 mmol), bis(2-chloroethyl)amine hydrochloride (3.2 g, 18.2 mmol) and potassium carbonate (4.2 g, 30.4 mmol). The mixture was stirred at 90° C. for 48 hours. To the reaction mixture were added dichlormethane (50 mL) and methanol (50 mL), and the mixture was filtered. The filtrate was concentrated in vacuo and the residue was purified by silica gel column chromatography eluted with DCM/MeOH (v/v=10/1) to give the title compound as a brown solid (2.78 g, 90.8%). The compound was characterized by the following spectroscopic data: MS (ESI, pos. ion) m/z: 202.1 [M+H]$^+$; and $^1$H NMR (600 MHz, DMSO-d$_6$) δ (ppm): 11.17 (s, 1H), 7.29-7.25 (m, 1H), 7.09 (d, J=8.1 Hz, 1H), 6.98 (t, J=7.8 Hz, 1H), 6.49 (d, J=7.5 Hz, 1H), 6.46 (s, 1H), 3.32-3.28 (m, 8H).

Step 2) 1-(4-(1H-indol-4-yl)piperazin-1-yl)-2,2,2-trichloroethanone

To a mixture of 4-(piperazin-1-yl)-1H-indole (2.75 g, 13.7 mmol) and triethylamine (5.66 mL, 41.0 mmol) in dichloromethane (20 mL) was added dropwise slowly a solution of trichloroacetyl chloride (2.28 mL, 20.5 mmol) in dichloromethane (20 mL) at 0° C. The resulting mixture was stirred at rt for 4 hours. To the reaction mixture was added 50 mL of dichloromethane, and the resulting mixture was washed with saturated aqueous sodium bicarbonate (60 mL). The organic layer was dried over anhydrous sodium sulfate and filtered. The filtrate was concentrated in vacuo and the residue was purified by silica gel column chromatography eluted with PE/EtOAc (v/v=10/1) to give the title compound as a brown solid (1.37 g, 28.8%). The compound was characterized by the following spectroscopic data: MS (ESI, pos. ion) m/z: 346.1 [M+H]$^+$; and $^1$H NMR (600 MHz, DMSO-d$_6$) δ (ppm): 11.08 (s, 1H), 7.27 (t, J=2.6 Hz, 1H), 7.07 (d, J=8.1 Hz, 1H), 6.98 (t, J=7.8 Hz, 1H), 6.49-6.46 (m, 2H), 4.10-3.84 (m, 4H), 3.22 (brs, 4H).

Step 3) 4-(4-(2,2,2-trichloroacetyl)piperazin-1-yl)-1H-indole-3-carbaldehyde

To 15 mL of DMF was added 1-(4-(1H-indol-4-yl)piperazin-1-yl)-2,2,2-trichloroethanone (1.02 g, 2.94 mmol) at 0°

C., and then phosphorus oxychloride (540 mg, 3.52 mmol) was added dropwise slowly to the solution. The resulting mixture was warmed to 25° C. and stirred for 24 hours. The reaction mixture was quenched with 30 mL of water and then the resulting mixture was neutralized with sodium carbonate solid to pH about 8~9. The mixture was filtered and the filter cake was dried in vacuo to give the title compound as a claybank solid (729 mg, 66.2%). The compound was characterized by the following spectroscopic data: MS (ESI, pos. ion) m/z: 374.0 [M+H]$^+$; and $^1$H NMR (600 MHz, DMSO-d$_6$) δ (ppm): 12.28 (s, 1H), 10.28 (s, 1H), 8.16 (d, J=2.9 Hz, 1H), 7.25 (d, J=8.0 Hz, 1H), 7.17 (t, J=7.8 Hz, 1H), 6.89 (d, J=7.6 Hz, 1H), 4.05-4.01 (m, 4H), 3.12 (brs, 4H).

Step 4) 1-(phenylsulfonyl)-4-(4-(2,2,2-trichloro-acetyl)piperazin-1-yl)-1H-indole-3-carbaldehyde To 8 mL of dichloromethane were added 4-(4-(2,2,2-trichloroacetyl)piperazin-1-yl)-1H-indole-3-carbaldehyde (187 mg, 0.5 mmol), tetrabutylammonium hydrogen sulfate (17 mg, 0.05 mmol), potassium hydroxide (56 mg, 1.0 mmol) and benzenesulfonyl chloride (106 mg, 0.6 mmol) in turn. The mixture was stirred at 25° C. for 6 hours. The reaction mixture was diluted with 30 mL of DCM and washed with saturated aqueous sodium bicarbonate (40 mL). The organic layer was dried over anhydrous sodium sulfate and filtered. The filtrate was concentrated in vacuo and the residue was purified by silica gel column chromatography eluted with PE/EtOAc (v/v=2/1) to give the title compound as a gray solid (219 mg, 85%). The compound was characterized by the following spectroscopic data: MS (ESI, pos. ion) m/z: 514.0 [M+H]$^+$; and $^1$H NMR (600 MHz, CDCl$_3$) δ (ppm): 10.54 (s, 1H), 8.37 (s, 1H), 8.00 (d, J=7.9 Hz, 2H), 7.83 (d, J=8.1 Hz, 1H), 7.66 (t, J=7.3 Hz, 1H), 7.55 (t, J=7.6 Hz, 2H), 7.39 (t, J=7.9 Hz, 1H), 7.08 (d, J=7.4 Hz, 1H), 3.19 (brs, 4H), 1.83 (brs, 4H).

Step 5) 2,2,2-trichloro-1-(4-(3-(difluoromethyl)-1-(phenylsulfonyl)-1H-indol-4-yl)piperazin-1-yl)etha-none To a solution of 1-(phenylsulfonyl)-4-(4-(2,2,2-trichloro-acetyl)piperazin-1-yl)-1H-indole-3-carbaldehyde (206 mg, 0.4 mmol) in DCM (8 mL) was added diethylaminosulphur trifluoride (0.194 mL, 1.2 mmol). The mixture was stirred at rt for 24 hours. The reaction mixture was diluted with 30 mL of DCM and the resulting mixture was washed with saturated aqueous sodium bicarbonate (40 mL). The organic layer was dried over anhydrous sodium sulfate and filtered. The filtrate was concentrated in vacuo and the residue was purified by silica gel column chromatography eluted with PE/EtOAc (v/v=2/1) to give the title compound as a gray solid (176 mg, 82%). The compound was characterized by the following spectroscopic data: MS (ESI, pos. ion) m/z: 535.9 [M+H]$^+$; and $^1$H NMR (600 MHz, CDCl$_3$) δ (ppm): 7.97 (d, J=7.7 Hz, 2H), 7.93 (s, 1H), 7.85 (d, J=8.3 Hz, 1H), 7.63 (t, J=7.5 Hz, 1H), 7.53 (t, J=7.9 Hz, 2H), 7.40 (t, J=55.2 Hz, 1H), 7.36 (t, J=8.1 Hz, 1H), 7.11 (d, J=7.8 Hz, 1H), 4.62 (brs, 2H), 3.12 (brs, 6H).

Step 6) 3-(difluoromethyl)-1-(phenylsulfonyl)-4-(piperazin-1-yl)-1H-indole

To a solution of 2,2,2-trichloro-1-(4-(3-(difluoromethyl)-1-(phenylsulfonyl)-1H-indol-4-yl)piperazin-1-yl)ethanone (161 mg, 0.3 mmol) in THF (10 mL) was added slowly potassium hydroxide (0.9 mL, 0.9 mmol, 1 mmol/mL in water) at 25° C. The mixture was stirred for 24 hours. To the reaction mixture was added 30 mL of DCM and the resulting mixture was partitioned. The organic layer was washed with saturated aqueous sodium chloride (30 mL), dried over anhydrous sodium sulfate and filtered. The filtrate was concentrated in vacuo and the residue was purified by silica gel column chromatography eluted with DCM/MeOH (v/v=30/1) to give the title compound as a light yellow solid (83 mg, 71%). The compound was characterized by the following spectroscopic data: MS (ESI, pos. ion) m/z: 392.1 [M+H]$^+$; $^1$H NMR (600 MHz, DMSO-d$_6$) δ (ppm): 8.15-8.09 (m, 3H), 7.75 (t, J=7.5 Hz, 2H), 7.65 (t, J=7.8 Hz, 2H), 7.46 (t, J=55.2 Hz, 1H), 7.39-7.34 (m, 1H), 7.14 (d, J=7.8 Hz, 1H), 2.85-2.84 (m, 4H), 2.79 (brs, 4H); and $^{13}$C NMR (150 MHz, DMSO-d$_6$) δ (ppm): 147.8, 137.1, 135.7, 135.6, 130.6, 127.6, 127.1, 126.1 (t, J=8.3 Hz), 123.4 (t, J=3.8 Hz), 116.8, 111.9 (t, J=232.1 Hz), 110.4, 52.8, 45.1.

Example 2 3-(difluoromethyl)-1-((2-fluorophenyl)sulfonyl)-4-(piperazin-1-yl)-1H-indole

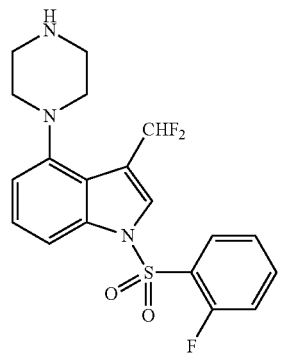 [SMILES: O=S(=O)(c1ccccc1F)n1cc(C(F)F)c2c(N3CCNCC3)cccc21]

Step 1) 1-((2-fluorophenyl)sulfonyl)-4-(4-(2,2,2-trichloroacetyl)piperazin-1-yl)-1H-indole-3-carbaldehyde 4-(4-(2,2,2-trichloroacetyl)piperazin-1-yl)-1H-indole-3-carbaldehyde (187 mg, 0.5 mmol) was reacted with tetrabutylammonium hydrogen sulfate (17 mg, 0.05 mmol), potassium hydroxide (56 mg, 1.0 mmol) and 2-fluorobenzenesulfonyl chloride (106 mg, 0.6 mmol) in DCM (10 mL) according to the procedure as described in step 4 of example 1, and the crude product was purified by silica gel column chromatography eluted with PE/EtOAc (v/v=2/1) to give the title compound as a brown solid (267 mg, 99%). The compound was characterized by the following spectroscopic data: MS (ESI, pos. ion) m/z: 532.1 [M+H]$^+$; and $^1$H NMR (600 MHz, CDCl$_3$) δ (ppm): 10.52 (s, 1H), 8.41 (s, 1H), 8.16 (t, J=7.0 Hz, 1H), 7.67-7.59 (m, 2H), 7.44-7.35 (m, 2H), 7.20-7.17 (m, 2H), 3.37-3.21 (m, 8H).

Step 2) 2,2,2-trichloro-1-(4-(3-(difluoromethyl)-1-((2-fluorophenyl)sulfonyl)-1H-indol-4-yl) piperazin-1-yl)ethanone 1-((2-Fluorophenyl)sulfonyl)-4-(4-(2,2,2-trichloroacetyl) piperazin-1-yl)-1H-indole-3-carbaldehyde (213 mg, 0.4 mmol) was reacted with diethylaminosulphur trifluoride (0.194 mL, 1.2 mmol) in DCM (10 mL) according to the procedure as described in step 5 of example 1, and the crude product was purified by silica gel column chromatography eluted with PE/EtOAc (v/v=2/1) to give the title compound as a yellow solid (131 mg, 59%). The compound was characterized by the following spectroscopic data: MS (ESI, pos. ion) m/z: 554.0 [M+H]$^+$; and $^1$H NMR (600 MHz, CDCl$_3$) δ (ppm): 8.13 (t, J=7.1 Hz, 1H), 7.99 (s, 1H), 7.65-7.53 (m, 2H), 7.41 (t, J=55.2 Hz, 1H), 7.36-7.27 (m, 1H), 7.20-7.11 (m, 2H), 7.09 (d, J=7.9 Hz, 1H), 4.63 (brs, 2H), 3.08 (brs, 6H).

Step 3) 3-(difluoromethyl)-1-((2-fluorophenyl)sulfonyl)-4-(piperazin-1-yl)-1H-indole 2,2,2-Trichloro-1-(4-(3-(difluoromethyl)-1-((2-fluorophenyl)sulfonyl)-1H-indol-4-yl) piperazin-1-yl)ethanone (130 mg, 0.24 mmol) was reacted with potassium hydroxide (0.72 mL, 0.72 mmol, 1 mmol/mL in water) in THF (10 mL) according to the procedure as described in step 6 of example 1, and the crude product was purified by silica gel column chromatography eluted with DCM/MeOH (v/v=30/1) to give the title compound as a claybank solid (78 mg, 79.1%). The compound was characterized by the following spectroscopic data: MS (ESI, pos. ion) m/z: 410.1 [M+H]$^+$; $^1$H NMR (600 MHz, CDCl$_3$) δ (ppm): 8.15-8.13 (m, 1H), 7.99 (s, 1H), 7.67-7.60 (m, 2H), 7.41 (t, J=55.8 Hz, 1H), 7.36 (t, J=7.7 Hz, 1H), 7.31 (d, J=7.9 Hz, 1H), 7.17-7.13 (m, 2H), 3.19 (brs, 4H), 3.08 (brs, 4H); and $^{13}$C NMR (150 MHz, CDCl$_3$) δ (ppm): 159.2 (d, J=258 Hz), 147.1, 136.9 (d, J=8.7 Hz), 135.8, 130.4, 126.1, 125.8 (d, J=13.2 Hz), 124.8 (d, J=3.8 Hz), 123.8 (t, J=4.1 Hz), 117.8 (d, J=20.5 Hz), 116.5, 116.1 (t, J=24.3 Hz), 111.3 (t, J=233.5 Hz), 110.6, 53.0, 45.5.

Example 3 1-((2-chlorophenyl)sulfonyl)-3-(difluoromethyl)-4-(piperazin-1-yl)-1H-indole

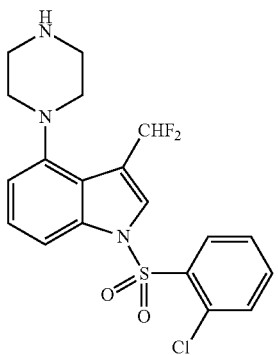 [SMILES: O=S(=O)(c1ccccc1Cl)n1cc(C(F)F)c2c(N3CCNCC3)cccc21]

Step 1) 1-((2-chlorophenyl)sulfonyl)-4-(4-(2,2,2-trichloroacetyl)piperazin-1-yl)-1H-indole-3-carbaldehyde 4-(4-(2,2,2-Trichloroacetyl)piperazin-1-yl)-1H-indole-3-carbaldehyde (187 mg, 0.5 mmol) was reacted with tetrabutylammonium hydrogen sulfate (17 mg, 0.05 mmol), potassium hydroxide (56 mg, 1.0 mmol) and 2-chlorobenzenesulfonyl chloride (127 mg, 0.6 mmol) in DCM (10 mL) according to the procedure as described in step 4 of example 1, and the crude product was purified by silica gel column chromatography eluted with PE/EtOAc (v/v=2/1) to give the title compound as a brown solid (199 mg, 72.5%). The compound was characterized by the following spectroscopic data: MS (ESI, pos. ion) m/z: 548.0 [M+H]$^+$; and $^1$H NMR (600 MHz, CDCl$_3$) δ (ppm): 10.55 (s, 1H), 8.61 (s, 1H), 8.43 (d, J=7.5 Hz, 1H), 7.73 (d, J=7.9 Hz, 1H), 7.65 (t, J=7.4 Hz, 1H), 7.54 (t, J=7.2 Hz, 1H), 7.43 (d, J=7.1 Hz, 1H), 7.32 (s, 1H), 7.05 (s, 1H), 3.25 (brs, 4H), 1.85 (brs, 4H).

Step 2) 2,2,2-trichloro-1-(4-(1-((2-chlorophenyl)sulfonyl)-3-(difluoromethyl)-1H-indol-4-yl) piperazin-1-yl) ethanone 1-((2-Chlorophenyl)sulfonyl)-4-(4-(2,2,2-trichloroacetyl)piperazin-1-yl)-1H-indole-3-carbaldehyde (199 mg, 0.36 mmol) was reacted with diethylaminosulphur trifluoride (0.194 mL, 1.2 mmol) in DCM (10 mL) according to the procedure as described in step 5 of example 1, and the crude product was purified by silica gel column chromatography eluted with PE/EtOAc (v/v=2/1) to give the title compound as a yellow solid (132 mg, 63.7%). The compound was characterized by the following spectroscopic data: $^1$H NMR (400 MHz, CDCl$_3$) δ (ppm): 8.31 (d, J=7.8 Hz, 1H), 8.08 (s, 1H), 7.61-7.48 (m, 4H), 7.41 (t, J=55.2 Hz, 1H), 7.26 (d, J=8.0 Hz, 1H), 7.07 (d, J=7.8 Hz, 1H), 4.59 (brs, 2H), 3.06 (brs, 6H).

Step 3) 1-((2-chlorophenyl)sulfonyl)-3-(difluoromethyl)-4-(piperazin-1-yl)-1H-indole 2,2,2-Trichloro-1-(4-(1-((2-chlorophenyl)sulfonyl)-3-(difluoromethyl)-1H-indol-4-yl) piperazin-1-yl) ethanone (132 mg, 0.23 mmol) was reacted with potassium hydroxide (0.72 mL, 0.72 mmol, 1 mmol/mL in water) in THF (10 mL) according to the procedure as described in step 6 of example 1, and the crude product was purified by silica gel column chromatography eluted with DCM/MeOH (v/v=30/1) to give the title compound as a claybank solid (78 mg, 79.3%). The compound was characterized by the following spectroscopic data: MS (ESI, pos. ion) m/z: 426.1 [M+H]$^+$; and $^1$H NMR (600 MHz, CDCl$_3$) δ (ppm): 8.31 (dd, J=7.9, 1.4 Hz, 1H), 8.09 (s, 1H), 7.59-7.54 (m, 1H), 7.52-7.45 (m, 3H), 7.38 (t, J=55.8 Hz, 1H), 7.25 (t, J=8.1 Hz, 1H), 7.10 (d, J=7.8 Hz, 1H), 3.09 (brs, 4H), 3.00 (brs, 4H).

Example 4 1-((2-bromophenyl)sulfonyl)-3-(difluoromethyl)-4-(piperazin-1-yl)-1H-indole

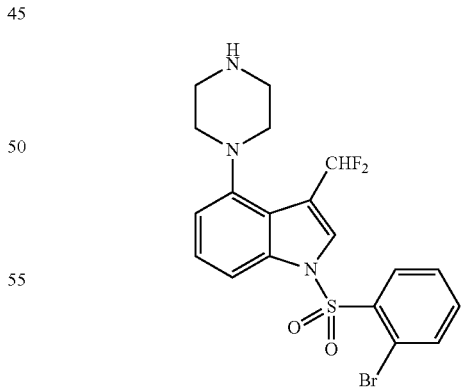

Step 1) 1-((2-bromophenyl)sulfonyl)-4-(4-(2,2,2-trichloroacetyl)piperazin-1-yl)-1H-indole-3-carbaldehyde 4-(4-(2,2,2-Trichloroacetyl)piperazin-1-yl)-1H-indole-3-carbaldehyde (187 mg, 0.5 mmol) was reacted with tetrabutylammonium hydrogen sulfate (17 mg, 0.05 mmol), potassium hydroxide (56 mg, 1.0 mmol) and 2-bromobenzenesulfonyl chloride (154 mg, 0.6 mmol) in DCM (10 mL) according to the procedure as described in step 4 of example 1, and the crude product was purified by silica gel column chromatography eluted with PE/EtOAc (v/v=2/1) to give the title compound as a brown solid (244 mg, 82%). The compound was characterized by the following spectroscopic data: MS (ESI, pos. ion) m/z: 591.8 [M+H]+; and ¹H NMR (600 MHz, CDCl₃) δ (ppm): 10.55 (s, 1H), 8.60 (s, 1H), 8.44 (d, J=7.5 Hz, 1H), 7.73 (d, J=7.7 Hz, 1H), 7.63 (t, J=7.4 Hz, 1H), 7.53 (t, J=7.4 Hz, 1H), 7.44 (d, J=7.1 Hz, 1H), 7.30 (s, 1H), 7.08 (s, 1H), 3.24 (brs, 4H), 1.85 (brs, 4H).

Step 2) 1-(4-(1-((2-bromophenyl)sulfonyl)-3-(difluoromethyl)-1H-indol-4-yl)piperazin-1-yl)-2,2,2-trichloroethanone 1-((2-Bromophenyl)sulfonyl)-4-(4-(2,2,2-trichloroacetyl)piperazin-1-yl)-1H-indole-3-carbaldehyde (244 mg, 0.41 mmol) was reacted with diethylaminosulphur trifluoride (0.194 mL, 1.2 mmol) in DCM (10 mL) according to the procedure as described in step 5 of example 1, and the crude product was purified by silica gel column chromatography eluted with PE/EtOAc (v/v=2/1) to give the title compound as a yellow solid (189 mg, 75%). The compound was characterized by the following spectroscopic data: MS (ESI, pos. ion) m/z: 613.9 [M+H]+; and ¹H NMR (600 MHz, CDCl₃) δ (ppm): 8.34 (dd, J=8.0, 1.4 Hz, 1H), 8.15 (s, 1H), 7.72 (d, J=7.9 Hz, 1H), 7.58 (t, J=7.7 Hz, 1H), 7.50-7.47 (m, 2H), 7.44 (t, J=55.8 Hz, 1H), 7.27 (t, J=8.1 Hz, 1H), 7.10 (d, J=7.8 Hz, 1H), 4.62 (brs, 2H), 3.08 (brs, 6H).

Step 3) 1-((2-bromophenyl)sulfonyl)-3-(difluoromethyl)-4-(piperazin-1-yl)-1H-indole 1-(4-(1-((2-Bromophenyl)sulfonyl)-3-(difluoromethyl)-1H-indol-4-yl)piperazin-1-yl)-2,2,2-trichloroethanone (189 mg, 0.31 mmol) was reacted with potassium hydroxide (0.93 mL, 0.93 mmol, 1 mmol/mL in water) in THF (10 mL) according to the procedure as described in step 6 of example 1, and the crude product was purified by silica gel column chromatography eluted with DCM/MeOH (v/v)=30/1 to give the title compound as a claybank solid (118 mg, 81%). The compound was characterized by the following spectroscopic data: MS (ESI, pos. ion) m/z: 470.0 [M+H]+; ¹H NMR (600 MHz, DMSO-d₆) δ (ppm): 8.39 (d, J=8.0 Hz, 1H), 8.16 (s, 1H), 7.89 (d, J=7.8 Hz, 1H), 7.74 (t, J=7.7 Hz, 1H), 7.69-7.66 (m, 1H), 7.51 (t, J=55.2 Hz, 1H), 7.40 (d, J=8.4 Hz, 1H), 7.31 (t, J=8.1 Hz, 1H), 7.14 (d, J=7.8 Hz, 1H), 2.89 (brs, 4H), 2.83 (brs, 4H); and ¹³C NMR (150 MHz, DMSO-d₆) δ (ppm): 148.7, 137.2, 136.8, 136.2, 135.4, 132.9, 129.5, 127.5 (t, J=8.0 Hz), 126.9, 123.1, 120.2, 116.6, 115.4 (t, J=24.0 Hz), 111.8 (t, J=232.1 Hz), 109.6, 54.4, 46.1.

Example 5 3-(difluoromethyl)-1-((3-fluorophenyl)sulfonyl)-4-(piperazin-1-yl)-1H-indole

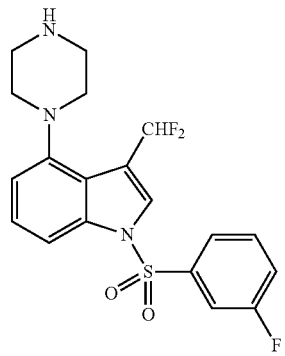 [SMILES: O=S(=O)(c1cccc(F)c1)n1cc(C(F)F)c2c(N3CCNCC3)cccc21]

Step 1) 1-((3-fluorophenyl)sulfonyl)-4-(4-(2,2,2-trichloroacetyl)piperazin-1-yl)-1H-indole-3-carbaldehyde 4-(4-(2,2,2-Trichloroacetyl)piperazin-1-yl)-1H-indole-3-carbaldehyde (187 mg, 0.5 mmol) was reacted with tetrabutylammonium hydrogen sulfate (17 mg, 0.05 mmol), potassium hydroxide (56 mg, 1.0 mmol) and 3-fluorobenzenesulfonyl chloride (116 mg, 0.6 mmol) in DCM (10 mL) according to the procedure as described in step 4 of example 1, and the crude product was purified by silica gel column chromatography eluted with PE/EtOAc (v/v=2/1) to give the title compound as a brown solid (213 mg, 80%). The compound was characterized by the following spectroscopic data: MS (ESI, pos. ion) m/z: 532.0 [M+H]+; and ¹H NMR (400 MHz, DMSO-d₆) δ (ppm): 10.43 (s, 1H), 8.58 (s, 1H), 8.17 (d, J=8.2 Hz, 1H), 8.04 (d, J=7.8 Hz, 1H), 7.77 (d, J=8.3 Hz, 1H), 7.75-7.62 (m, 2H), 7.40 (t, J=8.1 Hz, 1H), 7.14 (d, J=7.9 Hz, 1H), 4.26-3.61 (m, 4H), 3.08 (brs, 4H).

Step 2) 2,2,2-trichloro-1-(4-(3-(difluoromethyl)-1-((3-fluorophenyl)sulfonyl)-1H-indol-4-yl) piperazin-1-yl) ethanone 1-((3-Fluorophenyl)sulfonyl)-4-(4-(2,2,2-trichloroacetyl)piperazin-1-yl)-1H-indole-3-carbaldehyde (210 mg, 0.39 mmol) was reacted with diethylaminosulphur trifluoride (0.194 mL, 1.2 mmol) in DCM (10 mL) according to the procedure as described in step 5 of example 1, and the crude product was purified by silica gel column chromatography eluted with PE/EtOAc (v/v=2/1) to give the title compound as a yellow solid (175 mg, 81%). The compound was characterized by the following spectroscopic data: MS (ESI, pos. ion) m/z: 553.9 [M+H]+; and ¹H NMR (400 MHz, DMSO-d₆) δ (ppm): 8.20 (s, 1H), 8.11 (dt, J=8.2, 2.0 Hz, 1H), 7.98 (d, J=7.8 Hz, 1H), 7.85 (d, J=8.3 Hz, 1H), 7.73-7.68 (m, 1H), 7.65-7.61 (m, 1H), 7.55 (t, J=54.4 Hz, 1H), 7.41 (t, J=8.1 Hz, 1H), 7.26 (d, J=7.8 Hz, 1H), 4.05-4.0 (m, 4H), 2.97 (brs, 4H).

Step 3) 3-(difluoromethyl)-1-((3-fluorophenyl)sulfonyl)-4-(piperazin-1-yl)-1H-indole 2,2,2-Trichloro-1-(4-(3-(difluoromethyl)-1-((3-fluorophenyl)sulfonyl)-1H-indol-4-yl) piperazin-1-yl) ethanone (170 mg, 0.31 mmol) was reacted with potassium hydroxide (0.93 mL, 0.93 mmol, 1 mmol/mL in water) in THF (10 mL) according to the procedure as described in step 6 of example 1, and the crude product was purified by silica gel column chromatography eluted with DCM/MeOH (v/v=30/1) to give the title compound as a light yellow solid (71 mg, 56%). The compound was characterized by the following spectroscopic data: MS (ESI, pos. ion) m/z: 410.1 [M+H]$^+$; $^1$H NMR (600 MHz, DMSO-d$_6$) δ (ppm): 8.18 (s, 1H), 8.10 (dt, J=8.3, 2.0 Hz, 1H), 7.97 (dd, J=7.9, 0.6 Hz, 1H), 7.78 (d, J=8.3 Hz, 1H), 7.69 (td, J=8.1, 5.4 Hz, 1H), 7.62 (td, J=8.5, 2.3 Hz, 1H), 7.47 (t, J=55.2 Hz, 1H), 7.40-7.36 (m, 1H), 7.14 (d, J=7.8 Hz, 1H), 2.87-2.80 (m, 4H), 2.77 (brs, 4H); and $^{13}$C NMR (150 MHz, DMSO-d$_6$) δ (ppm): 162.3 (d, J=250.7 Hz), 148.7, 138.8 (d, J=7.6 Hz), 135.6, 133.0 (d, J=9.1 Hz), 127.2, 126.0 (t, J=9.1 Hz), 124.0 (d, J=3.0 Hz), 123.3 (t, J=4.5 Hz), 123.0 (d, J=21.1 Hz), 117.3 (t, J=24.2 Hz), 116.7, 115.0 (d, J=25.7 Hz), 111.8 (t, J=234.1 Hz), 110.0, 54.7, 46.2.

Example 6 1-((3-chlorophenyl)sulfonyl)-3-(difluoromethyl)-4-(piperazin-1-yl)-1H-indole

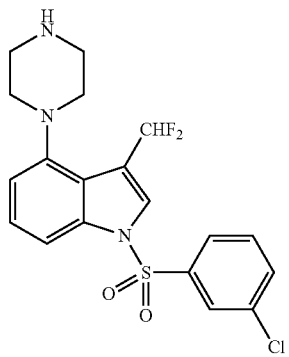 [SMILES: O=S(=O)(c1cccc(Cl)c1)n1cc(C(F)F)c2c(N3CCNCC3)cccc21]

Step 1) 1-((3-chlorophenyl)sulfonyl)-4-(4-(2,2,2-trichloroacetyl)piperazin-1-yl)-1H-indole-3-carbaldehyde 4-(4-(2,2,2-Trichloroacetyl)piperazin-1-yl)-1H-indole-3-carbaldehyde (187 mg, 0.5 mmol) was reacted with tetrabutylammonium hydrogen sulfate (17 mg, 0.05 mmol), potassium hydroxide (56 mg, 1.0 mmol) and 3-chlorobenzenesulfonyl chloride (127 mg, 0.6 mmol) in DCM (10 mL) according to the procedure as described in step 4 of example 1, and the crude product was purified by silica gel column chromatography eluted with PE/EtOAc (v/v=2/1) to give the title compound as a brown solid (214 mg, 78%). The compound was characterized by the following spectroscopic data: MS (ESI, pos. ion) m/z: 547.9 [M+H]$^+$; and $^1$H NMR (400 MHz, DMSO-d$_6$) δ (ppm): 10.42 (s, 1H), 8.60 (s, 1H), 8.32 (s, 1H), 8.15 (d, J=8.0 Hz, 1H), 7.84 (d, J=8.1 Hz, 1H), 7.76 (d, J=8.4 Hz, 1H), 7.67 (t, J=8.0 Hz, 1H), 7.40 (t, J=8.1 Hz, 1H), 7.13 (d, J=7.9 Hz, 1H), 4.15-3.70 (m, 4H), 3.07 (brs, 4H).

Step 2) 2,2,2-trichloro-1-(4-(1-((3-chlorophenyl)sulfonyl)-3-(difluoromethyl)-1H-indol-4-yl) piperazin-1-yl) ethanone 1-((3-Chlorophenyl)sulfonyl)-4-(4-(2,2,2-trichloroacetyl)piperazin-1-yl)-1H-indole-3-carbaldehyde (210 mg, 0.39 mmol) was reacted with diethylaminosulphur trifluoride (0.194 mL, 1.2 mmol) in DCM (10 mL) according to the procedure as described in step 5 of example 1, and the crude product was purified by silica gel column chromatography eluted with PE/EtOAc (v/v=2/1) to give the title compound as a yellow solid (188 mg, 89%). The compound was characterized by the following spectroscopic data: MS (ESI, pos. ion) m/z: 570.0 [M+H]$^+$; and $^1$H NMR (400 MHz, CDCl$_3$) δ (ppm): 8.01 (s, 1H), 7.87 (s, 1H), 7.81 (d, J=7.7 Hz, 1H), 7.80 (d, J=8.3 Hz, 1H), 7.57 (d, J=8.1 Hz, 1H), 7.47 (t, J=8.0 Hz, 1H), 7.43 (t, J=58.9 Hz, 1H), 7.36 (t, J=8.2 Hz, 1H), 7.12 (d, J=7.8 Hz, 1H), 3.48-3.41 (m, 4H), 3.19-3.05 (m, 4H).

Step 3) 1-((3-chlorophenyl)sulfonyl)-3-(difluoromethyl)-4-(piperazin-1-yl)-1H-indole 2,2,2-Trichloro-1-(4-(1-((3-chlorophenyl)sulfonyl)-3-(difluoromethyl)-1H-indol-4-yl) piperazin-1-yl) ethanone (180 mg, 0.32 mmol) was reacted with potassium hydroxide (0.93 mL, 0.93 mmol, 1 mmol/mL in water) in THF (10 mL) according to the procedure as described in step 6 of example 1, and the crude product was purified by silica gel column chromatography eluted with DCM/MeOH (v/v=30/1) to give the title compound as a brown solid (67 mg, 49%). The compound was characterized by the following spectroscopic data: MS (ESI, pos. ion) m/z: 426.0 [M+H]$^+$; $^1$H NMR (600 MHz, DMSO-d$_6$) δ (ppm): 8.25 (t, J=1.9 Hz, 1H), 8.21 (s, 1H), 8.10 (dd, J=8.0, 0.8 Hz, 1H), 7.81 (dd, J=8.0, 1.2 Hz, 1H), 7.79 (d, J=8.3 Hz, 1H), 7.66 (t, J=8.1 Hz, 1H), 7.46 (t, J=55.2 Hz, 1H), 7.40 (t, J=8.1 Hz, 1H), 7.15 (d, J=7.7 Hz, 1H), 2.88-2.81 (m, 4H), 2.78 (brs, 4H); and $^{13}$C NMR (150 MHz, DMSO-d$_6$) δ (ppm): 148.6, 138.8, 135.7, 135.6, 135.1, 132.5, 127.2, 127.1, 126.4, 126.1 (t, J=7.5 Hz), 123.3 (t, J=4.5 Hz), 117.3 (t, J=24.6 Hz), 116.8, 111.8 (t, J=234.1 Hz), 110.0, 54.6, 46.1.

Example 7 3-(difluoromethyl)-4-(piperazin-1-yl)-1-tosyl-1H-indole

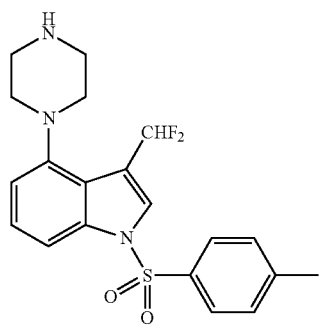 [SMILES: Cc1ccc(S(=O)(=O)n2cc(C(F)F)c3c(N4CCNCC4)cccc32)cc1]

Step 1) 1-tosyl-4-(4-(2,2,2-trichloroacetyl)piperazin-1-yl)-1H-indole-3-carbaldehyde 4-(4-(2,2,2-Trichloroacetyl)piperazin-1-yl)-1H-indole-3-carbaldehyde (187 mg, 0.5 mmol) was reacted with tetrabutylammonium hydrogen sulfate (17 mg, 0.05 mmol), potassium hydroxide (56 mg, 1.0 mmol) and p-methylbenzenesulfonyl chloride (114 mg, 0.6 mmol) in DCM (10 mL) according to the procedure as described in step 4 of example 1, and the crude product was purified by silica gel column chromatography eluted with PE/EtOAc (v/v=2/1) to give the title compound as a brown solid (206 mg, 78%). The compound was characterized by the following spectroscopic data: MS (ESI, pos. ion) m/z: 528.0 [M+H]$^+$; and $^1$H NMR (400 MHz, CDCl$_3$) δ (ppm): 10.50 (s, 1H), 8.34 (s, 1H), 7.86 (s, 1H), 7.84 (s, 1H), 7.80 (d, J=8.4 Hz, 1H), 7.36 (t, J=7.6 Hz, 1H), 7.32 (s, 1H), 7.30 (s, 1H), 7.07 (s, 1H), 3.19 (brs, 4H), 2.48 (s, 3H), 1.82 (brs, 4H).

Step 2) 2,2,2-trichloro-1-(4-(3-(difluoromethyl)-1-tosyl-1H-indol-4-yl)piperazin-1-yl)ethanone 1-Tosyl-4-(4-(2,2,2-trichloroacetyl)piperazin-1-yl)-1H-indole-3-carbaldehyde (200 mg, 0.38 mmol) was reacted with diethylaminosulphur trifluoride (0.194 mL, 1.2 mmol) in DCM (10 mL) according to the procedure as described in step 5 of example 1, and the crude product was purified by silica gel column chromatography eluted with PE/EtOAc (v/v=2/1) to give the title compound as a yellow solid (132 mg, 63.2%). The compound was characterized by the following spectroscopic data: MS (ESI, pos. ion) m/z: 550.0 [M+H]$^+$; and $^1$H NMR (400 MHz, CDCl$_3$) δ (ppm): 7.90 (s, 1H), 7.85-7.80 (m, 3H), 7.40 (t, J=55.7 Hz, 1H), 7.36 (d, J=8.1 Hz, 1H), 7.35-7.32 (m, 2H), 7.07 (d, J=7.6 Hz, 1H), 3.04 (brs, 4H), 2.38 (s, 3H), 1.60 (brs, 4H).

Step 3) 3-(difluoromethyl)-4-(piperazin-1-yl)-1-tosyl-1H-indole 2,2,2-Trichloro-1-(4-(3-(difluoromethyl)-1-tosyl-1H-indol-4-yl)piperazin-1-yl)ethanone (125 mg, 0.23 mmol) was reacted with potassium hydroxide (0.70 mL, 0.70 mmol, 1 mmol/mL in water) in THF (10 mL) according to the procedure as described in step 6 of example 1, and the crude product was purified by silica gel column chromatography eluted with DCM/MeOH (v/v=30/1) to give the title compound as a claybank solid (75 mg, 80%). The compound was characterized by the following spectroscopic data: MS (ESI, pos. ion) m/z: 406.1 [M+H]$^+$; $^1$H NMR (600 MHz, CDCl$_3$) δ (ppm): 7.91 (s, 1H), 7.83 (d, J=8.3 Hz, 2H), 7.79 (d, J=8.3 Hz, 1H), 7.43 (t, J=55.6 Hz, 1H), 7.33 (dd, J=10.3, 5.8 Hz, 1H), 7.30-7.25 (m, 2H), 7.10 (d, J=7.8 Hz, 1H), 3.08 (brs, 4H), 2.59 (brs, 4H), 2.36 (s, 3H); and $^{13}$C NMR (150 MHz, CDCl$_3$) δ (ppm): 147.6, 145.7, 136.0, 134.8, 130.2, 127.2, 126.2, 125.4 (t, J=7.7 Hz), 123.8 (d, J=4.4 Hz), 116.7 (t, J=24.0 Hz), 116.1, 111.4 (t, J=233.1 Hz), 110.5, 54.0, 46.1, 21.8.

Example 8 3-(difluoromethyl)-1-((4-methoxyphenyl)sulfonyl)-4-(piperazin-1-yl)-1H-indole

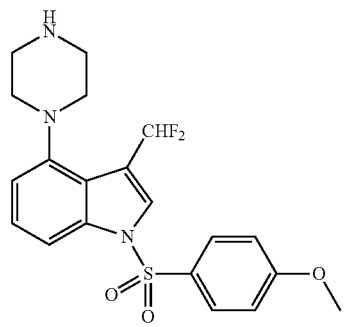 [SMILES: COc1ccc(S(=O)(=O)n2cc(C(F)F)c3c(N4CCNCC4)cccc32)cc1]

Step 1) 1-((4-methoxyphenyl)sulfonyl)-4-(4-(2,2,2-trichloroacetyl)piperazin-1-yl)-1H-indole-3-carbaldehyde 4-(4-(2,2,2-Trichloroacetyl)piperazin-1-yl)-1H-indole-3-carbaldehyde (187 mg, 0.5 mmol) was reacted with tetrabutylammonium hydrogen sulfate (17 mg, 0.05 mmol), potassium hydroxide (56 mg, 1.0 mmol) and p-methoxybenzenesulfonyl chloride (124 mg, 0.6 mmol) in DCM (10 mL) according to the procedure as described in step 4 of example 1, and the crude product was purified by silica gel column chromatography eluted with PE/EtOAc (v/v=2/1) to give the title compound as a brown solid (164 mg, 60%). The compound was characterized by the following spectroscopic data: MS (ESI, pos. ion) m/z: 544.0 [M+H]$^+$; and $^1$H NMR (400 MHz, CDCl$_3$) δ (ppm): 10.51 (s, 1H), 8.33 (s, 1H), 7.92 (s, 1H), 7.90 (s, 1H), 7.78 (d, J=8.0 Hz, 1H), 7.35 (t, J=8.0 Hz, 1H), 7.05 (d, J=8.4 Hz, 1H), 6.96 (s, 1H), 6.94 (s, 1H), 3.83 (s, 3H), 3.17 (brs, 4H), 1.77 (brs, 4H).

Step 2) 2,2,2-trichloro-1-(4-(3-(difluoromethyl)-1-((4-methoxyphenyl)sulfonyl)-1H-indol-4-yl) piperazin-1-yl) ethanone 1-((4-Methoxyphenyl)sulfonyl)-4-(4-(2,2,2-trichloroacetyl)piperazin-1-yl)-1H-indole-3-carbaldehyde (160 mg, 0.29 mmol) was reacted with diethylaminosulphur trifluoride (0.15 mL, 0.9 mmol) in DCM (10 mL) according to the procedure as described in step 5 of example 1, and the crude product was purified by silica gel column chromatography eluted with PE/EtOAc (v/v=2/1) to give the title compound as a yellow solid (107 mg, 65%). The compound was characterized by the following spectroscopic data: MS (ESI, pos. ion) m/z: 566.0 [M+H]$^+$; and $^1$H NMR (400 MHz, CDCl$_3$) δ (ppm): 7.92-7.89 (m, 3H), 7.84 (d, J=8.4 Hz, 1H), 7.40 (d, J=55.8 Hz, 1H), 7.35 (t, J=8.1 Hz, 1H), 7.10 (d, J=7.8 Hz, 1H), 6.96 (d, J=8.8 Hz, 2H), 4.62 (brs, 2H), 3.82 (s, 3H), 3.04 (brs, 6H).

Step 3) 3-(difluoromethyl)-1-((4-methoxyphenyl)sulfonyl)-4-(piperazin-1-yl)-1H-indole 2,2,2-Trichloro-1-(4-(3-(difluoromethyl)-1-((4-methoxyphenyl)sulfonyl)-1H-indol-4-yl)piperazin-1-yl) ethanone (107 mg, 0.19 mmol) was reacted with potassium hydroxide (0.60 mL, 0.60 mmol, 1 mmol/mL in water) in THF (10 mL) according to the procedure as described in step 6 of example 1, and the crude product was purified by silica gel column chromatography eluted with DCM/MeOH (v/v=30/1) to give the title compound as a claybank solid (76 mg, 95%). The compound was characterized by the following spectroscopic data: MS (ESI, pos. ion) m/z: 422.1 [M+H]$^+$; $^1$H NMR (600 MHz, CDCl$_3$) δ (ppm): 7.93-7.87 (m, 3H), 7.79 (d, J=8.3 Hz, 1H), 7.42 (t, J=55.7 Hz, 1H), 7.33 (t, J=8.1 Hz, 1H), 7.11 (d, J=7.8 Hz, 1H), 6.94 (d, J=9.0 Hz, 2H), 3.81 (s, 3H), 3.09 (brs, 4H), 2.55 (brs, 4H); and $^{13}$C NMR (150 MHz, CDCl$_3$) δ (ppm): 164.3, 147.5, 136.0, 129.5, 129.2, 126.1, 125.4 (t, J=7.5 Hz), 123.8, 116.5 (t, J=24.2 Hz), 116.0, 114.8, 111.4 (t, J=233.1 Hz), 110.6, 55.8, 46.04, 22.8.

Example 9 3-(difluoromethyl)-1-(naphthalen-1-yl-sulfonyl)-4-(piperazin-1-yl)-1H-indole

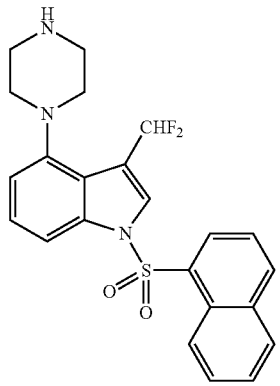 [SMILES: O=S(=O)(c1cccc2ccccc12)n1cc(C(F)F)c2c(N3CCNCC3)cccc21]

Step 1) 1-(naphthalen-1-ylsulfonyl)-4-(4-(2,2,2-trichloroacetyl)piperazin-1-yl)-1H-indole-3-carbaldehyde 4-(4-(2,2,2-Trichloroacetyl)piperazin-1-yl)-1H-indole-3-carbaldehyde (187 mg, 0.5 mmol) was reacted with tetrabutylammonium hydrogen sulfate (17 mg, 0.05 mmol), potassium hydroxide (56 mg, 1.0 mmol) and 1-naphthalenesulfonyl chloride (136 mg, 0.6 mmol) in DCM (10 mL) according to the procedure as described in step 4 of example 1, and the crude product was purified by silica gel column chromatography eluted with PE/EtOAc (v/v=2/1) to give the title compound as a brown solid (240 mg, 85%). The compound was characterized by the following spectroscopic data: MS (ESI, pos. ion) m/z: 564.1 [M+H]$^+$; and $^1$H NMR (400 MHz, DMSO-d$_6$) δ (ppm): 10.39 (s, 1H), 8.87 (s, 1H), 8.69 (d, J=7.5 Hz, 1H), 8.60 (d, J=8.6 Hz, 1H), 8.41 (d, J=8.3 Hz, 1H), 8.13 (d, J=8.0 Hz, 1H), 7.79 (dd, J=16.0, 8.3 Hz, 2H), 7.68 (t, J=7.5 Hz, 1H), 7.52 (d, J=8.3 Hz, 1H), 7.30 (t, J=8.1 Hz, 1H), 7.04 (d, J=7.8 Hz, 1H), 4.10-3.76 (m, 4H), 3.02 (brs, 4H).

Step 2) 2,2,2-trichloro-1-(4-(3-(difluoromethyl)-1-(naphthalen-1-ylsulfonyl)-1H-indol-4-yl) piperazin-1-yl) ethanone 1-(Naphthalen-1-ylsulfonyl)-4-(4-(2,2,2-trichloroacetyl)piperazin-1-yl)-1H-indole-3-carbaldehyde (240 mg, 0.43 mmol) was reacted with diethylaminosulphur trifluoride (0.194 mL, 1.2 mmol) in DCM (10 mL) according to the procedure as described in step 5 of example 1, and the crude product was purified by silica gel column chromatography eluted with PE/EtOAc (v/v=2/1) to give the title compound as a yellow solid (182 mg, 72%). The compound was characterized by the following spectroscopic data: MS (ESI, pos. ion) m/z: 586.0 [M+H]$^+$; and $^1$H NMR (400 MHz, DMSO-d$_6$) δ (ppm): 8.66-8.57 (m, 2H), 8.45 (s, 1H), 8.37 (d, J=8.3 Hz, 1H), 8.11 (d, J=8.0 Hz, 1H), 7.77 (t, J=7.9 Hz, 2H), 7.67 (t, J=7.3 Hz, 1H), 7.61 (d, J=8.3 Hz, 1H), 7.54 (t, J=54.9 Hz, 1H), 7.31 (t, J=8.1 Hz, 1H), 7.16 (d, J=7.7 Hz, 1H), 4.51-3.52 (m, 4H), 2.92 (brs, 4H).

Step 3) 3-(difluoromethyl)-1-(naphthalen-1-ylsulfonyl)-4-(piperazin-1-yl)-1H-indole 2,2,2-Trichloro-1-(4-(3-(difluoromethyl)-1-(naphthalen-1-ylsulfonyl)-1H-indol-4-yl) piperazin-1-yl) ethanone (182 mg, 0.31 mmol) was reacted with potassium hydroxide (0.93 mL, 0.93 mmol, 1 mmol/mL in water) in THF (10 mL) according to the procedure as described in step 6 of example 1, and the crude product was purified by silica gel column chromatography eluted with DCM/MeOH (v/v=30/1) to give the title compound as a claybank solid (71 mg, 52%). The compound was characterized by the following spectroscopic data: MS (ESI, pos. ion) m/z: 442.1 [M+H]$^+$; $^1$H NMR (600 MHz, DMSO-d$_6$) δ (ppm): 8.63 (d, J=8.7 Hz, 1H), 8.60 (d, J=7.0 Hz, 1H), 8.44 (s, 1H), 8.37 (d, J=8.2 Hz, 1H), 8.10 (d, J=8.1 Hz, 1H), 7.78-7.75 (m, 2H), 7.67 (t, J=7.4 Hz, 1H), 7.56 (d, J=8.2 Hz, 1H), 7.47 (t, J=55.2 Hz, 1H), 7.30 (t, J=8.1 Hz, 1H), 7.08 (d, J=7.8 Hz, 1H), 2.96-2.89 (m, 4H), 2.78 (brs, 4H); and $^{13}$C NMR (150 MHz, DMSO-d$_6$) δ (ppm): 148.3, 137.3, 135.4, 134.3, 131.9, 131.8, 130.2, 129.9, 128.1, 127.4, 126.9, 126.5 (t, J=7.5 Hz), 125.3, 123.4, 123.1 (t, J=3.0 Hz), 116.5, 116.0 (t, J=24.2 Hz), 111.8 (t, J=234.1 Hz), 109.9, 53.8, 45.7.

Example 10 3-(difluoromethyl)-1-(naphthalen-2-ylsulfonyl)-4-(piperazin-1-yl)-1H-indole

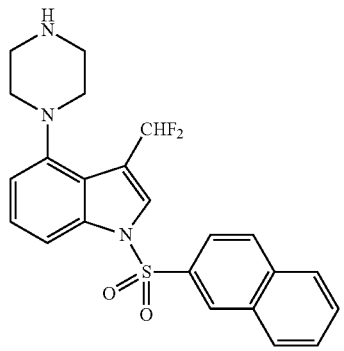 [SMILES: O=S(=O)(c1ccc2ccccc2c1)n1cc(C(F)F)c2c(N3CCNCC3)cccc21]

Step 1) 1-(naphthalen-2-ylsulfonyl)-4-(4-(2,2,2-trichloroacetyl)piperazin-1-yl)-1H-indole-3-carbaldehyde 4-(4-(2,2,2-Trichloroacetyl)piperazin-1-yl)-1H-indole-3-carbaldehyde (187 mg, 0.5 mmol) was reacted with tetrabutylammonium hydrogen sulfate (17 mg, 0.05 mmol), potassium hydroxide (56 mg, 1.0 mmol) and 2-naphthalenesulfonyl chloride (136 mg, 0.6 mmol) in DCM (10 mL) according to the procedure as described in step 4 of example 1, and the crude product was purified by silica gel column chromatography eluted with PE/EtOAc (v/v=2/1) to give the title compound as a brown solid (195 mg, 69%). The compound was characterized by the following spectroscopic data: MS (ESI, pos. ion) m/z: 563.9 [M+H]$^+$; and $^1$H NMR (400 MHz, DMSO-d$_6$) δ (ppm): 10.42 (s, 1H), 9.03 (d, J=1.4 Hz, 1H), 8.60 (s, 1H), 8.26 (d, J=7.9 Hz, 1H), 8.14 (d, J=8.9 Hz, 1H), 8.04-8.00 (m, 2H), 7.81 (d, J=8.3 Hz, 1H), 7.79-7.68 (m, 2H), 7.37 (t, J=8.1 Hz, 1H), 7.08 (d, J=7.9 Hz, 1H), 4.05-3.96 (m, 4H), 3.03 (brs, 4H).

Step 2) 2,2,2-trichloro-1-(4-(3-(difluoromethyl)-1-(naphthalen-2-ylsulfonyl)-1H-indol-4-yl) piperazin-1-yl) ethanone 1-(Naphthalen-2-ylsulfonyl)-4-(4-(2,2,2-trichloroacetyl)piperazin-1-yl)-1H-indole-3-carbaldehyde (190 mg, 0.34 mmol) was reacted with diethylaminosulphur trifluoride (0.16 mL, 1.01 mmol) in DCM (10 mL) according to the procedure as described in step 5 of example 1, and the crude product was purified by silica gel column chromatography eluted with PE/EtOAc (v/v=2/1) to give the title compound as a yellow solid (162 mg, 81%). The compound was characterized by the following spectroscopic data: MS (ESI, pos. ion) m/z: 585.9 [M+H]$^+$; and $^1$H NMR (400 MHz, DMSO-d$_6$) δ (ppm): 8.97 (s, 1H), 8.25 (d, J=7.9 Hz, 1H), 8.21 (s, 1H), 8.13 (d, J=8.8 Hz, 1H), 8.02 (d, J=7.9 Hz, 1H), 7.98 (dd, J=8.8, 1.8 Hz, 1H), 7.89 (d, J=8.4 Hz, 1H), 7.77-7.66 (m, 2H), 7.54 (t, J=55.2 Hz, 1H), 7.37 (d, J=8.2 Hz, 1H), 7.20 (d, J=7.8 Hz, 1H), 4.05-4.00 (m, 4H), 2.93 (brs, 4H).

Step 3) 3-(difluoromethyl)-1-(naphthalen-2-ylsulfonyl)-4-(piperazin-1-yl)-1H-indole 2,2,2-Trichloro-1-(4-(3-(difluoromethyl)-1-(naphthalen-2-ylsulfonyl)-1H-indol-4-yl) piperazin-1-yl) ethanone (162 mg, 0.28 mmol) was reacted with potassium hydroxide (0.93 mL, 0.93 mmol, 1 mmol/mL in water) in THF (10 mL) according to the procedure as described in step 6 of example 1, and the crude product was purified by silica gel column chromatography eluted with DCM/MeOH (v/v=30/1) to give the title compound as a claybank solid (88 mg, 71%). The compound was characterized by the following spectroscopic data: MS (ESI, pos. ion) m/z: 442.1 [M+H]$^+$; $^1$H NMR (600 MHz, DMSO-d$_6$) δ (ppm): 9.00-8.94 (m, 1H), 8.25 (d, J=8.1 Hz, 1H), 8.20 (s, 1H), 8.13 (d, J=8.8 Hz, 1H), 8.02 (d, J=8.0 Hz, 1H), 7.98 (dd, J=8.8, 2.0 Hz, 1H), 7.86 (d, J=8.4 Hz, 1H), 7.76-7.73 (m, 1H), 7.72-7.70 (m, 1H), 7.49 (t, J=55.1 Hz, 1H), 7.39 (t, J=8.1 Hz, 1H), 7.12 (d, J=7.8 Hz, 1H), 2.97-2.94 (m, 4H), 2.83 (brs, 4H); and $^{13}$C NMR (150 MHz, DMSO-d$_6$) δ (ppm): 148.0, 135.7, 135.5, 133.9, 132.0, 130.8, 130.6, 130.2, 129.9, 128.7, 128.4, 127.0, 126.1 (t, J=7.5 Hz), 123.4 (t, J=3.8 Hz), 121.8, 116.7, 111.9 (t, J=233.7 Hz), 110.4, 53.3, 45.4.

Example 11 3-(difluoromethyl)-1-(phenylsulfonyl)-5-(piperazin-1-yl)-1H-indole

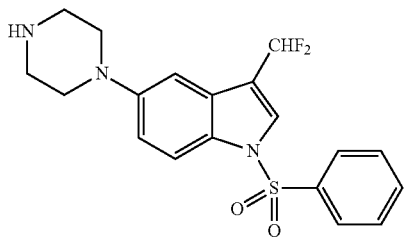 [SMILES: O=S(=O)(c1ccccc1)n1cc(C(F)F)c2cc(N3CCNCC3)ccc21]

Step 1) 1-(phenylsulfonyl)-5-(4-(2,2,2-trichloroacetyl)piperazin-1-yl)-1H-indole-3-carbaldehyde 5-(4-(2,2,2-Trichloroacetyl)piperazin-1-yl)-1H-indole-3-carbaldehyde (500 mg, 1.33 mmol) was reacted with tetrabutylammonium hydrogen sulfate (45 mg, 0.13 mmol), potassium hydroxide (150 mg, 2.67 mmol) and benzenesulfonyl chloride (283 mg, 1.6 mmol) in DCM (15 mL) according to the procedure as described in step 4 of example 1, and the crude product was purified by silica gel column chromatography eluted with PE/EtOAc (v/v=2/1) to give the title compound as a brown solid (570 mg, 83%). The compound was characterized by the following spectroscopic data: MS (ESI, pos. ion) m/z: 514.0 [M+H]$^+$; and $^1$H NMR (600 MHz, DMSO-d$_6$) δ (ppm): 10.05 (s, 1H), 8.82 (s, 1H), 8.10 (d, J=7.6 Hz, 1H), 7.85 (d, J=9.2 Hz, 1H), 7.69-7.62 (m, 2H), 7.35-7.29 (m, 4H), 3.64 (brs, 4H), 3.19-3.15 (m, 4H).

Step 2) 2,2,2-trichloro-1-(4-(3-(difluoromethyl)-1-(phenylsulfonyl)-1H-indol-5-yl)piperazin-1-yl)ethanone 1-(Phenylsulfonyl)-5-(4-(2,2,2-trichloroacetyl)piperazin-1-yl)-1H-indole-3-carbaldehyde (570 mg, 1.11 mmol) was reacted with diethylaminosulphur trifluoride (0.44 mL, 3.32 mmol) in DCM (10 mL) according to the procedure as described in step 5 of example 1, and the crude product was purified by silica gel column chromatography eluted with PE/EtOAc (v/v=2/1) to give the title compound as a yellow solid (352 mg, 59.3%). The compound was characterized by the following spectroscopic data: MS (ESI, pos. ion) m/z: 536.0 [M+H]$^+$; and $^1$H NMR (600 MHz, CDCl$_3$) δ (ppm): 7.91-7.89 (m, 3H), 7.73 (s, 1H), 7.58 (t, J=7.5 Hz, 1H), 7.48 (t, J=7.9 Hz, 2H), 7.12 (s, 1H), 7.07 (dd, J=9.1, 2.1 Hz, 1H), 6.82 (t, J=55.4 Hz, 1H), 4.16-3.79 (m, 4H), 3.35-3.12 (m, 4H).

Step 3) 3-(difluoromethyl)-1-(phenylsulfonyl)-5-(piperazin-1-yl)-1H-indole 2,2,2-Trichloro-1-(4-(3-(difluoromethyl)-1-(phenylsulfonyl)-1H-indol-5-yl)piperazin-1-yl)ethanone (400 mg, 0.65 mmol) was reacted with potassium hydroxide (1.95 mL, 1.95 mmol, 1 mmol/mL in water) in THF (10 mL) according to the procedure as described in step 6 of example 1, and the crude product was purified by silica gel column chromatography eluted with DCM/MeOH (v/v=30/1) to give the title compound as a yellow solid (220 mg, 72%). The compound was characterized by the following spectroscopic data: MS (ESI, pos. ion) m/z: 392.1 [M+H]$^+$; $^1$H NMR (600 MHz, DMSO-d$_6$) δ (ppm): 8.12 (s, 1H), 8.01 (d, J=7.8 Hz, 2H), 7.82 (d, J=9.2 Hz, 1H), 7.73 (t, J=7.4 Hz, 1H), 7.63 (t, J=7.8 Hz, 2H), 7.25 (t, J=54.8 Hz, 1H), 7.14 (dd, J=9.2, 2.0 Hz, 1H), 7.03 (d, J=1.4 Hz, 1H), 3.06-2.96 (m, 4H), 2.89-2.78 (m, 4H); and $^{13}$C NMR (150 MHz, DMSO-d$_6$) δ (ppm): 149.7, 137.2, 135.40, 130.5, 128.6, 127.8 (t, J=10.2 Hz), 127.6, 127.3, 117.0, 116.8 (t, J=25.5 Hz), 114.3, 112.8 (t, J=229.4 Hz), 105.5, 50.7, 46.0.

Example 12 3-(difluoromethyl)-1-((2-fluorophenyl)sulfonyl)-5-(piperazin-1-yl)-1H-indole

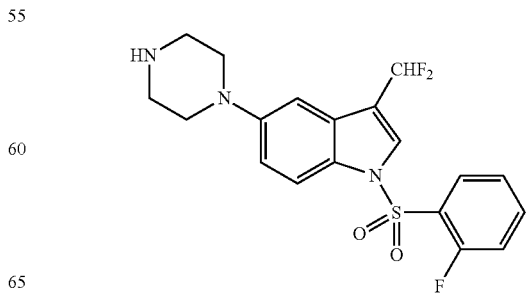

Step 1) 1-((2-fluorophenyl)sulfonyl)-5-(4-(2,2,2-trichloroacetyl)piperazin-1-yl)-1H-indole-3-carbaldehyde 5-(4-(2,2,2-Trichloroacetyl)piperazin-1-yl)-1H-indole-3-carbaldehyde (300 mg, 0.80 mmol) was reacted with tetrabutylammonium hydrogen sulfate (27 mg, 0.08 mmol), potassium hydroxide (90 mg, 1.6 mmol) and 2-fluorobenzenesulfonyl chloride (283 mg, 1.6 mmol) in DCM (15 mL) according to the procedure as described in step 4 of example 1, and the crude product was purified by silica gel column chromatography eluted with PE/EtOAc (v/v=2/1) to give the title compound as a brown solid (310 mg, 72.7%). The compound was characterized by the following spectroscopic data: MS (ESI, pos. ion) m/z: 532.0 [M+H]$^+$; and $^1$H NMR (400 MHz, CDCl$_3$) δ (ppm): 10.11 (s, 1H), 8.29 (d, J=2.3 Hz, 1H), 8.16 (t, J=6.9 Hz, 1H), 7.81 (d, J=2.0 Hz, 1H), 7.70 (d, J=9.2 Hz, 2H), 7.38 (t, J=7.7 Hz, 1H), 7.17 (t, J=9.2 Hz, 1H), 7.04 (dd, J=9.1, 2.2 Hz, 1H), 3.35-3.23 (m, 4H), 2.19 (brs, 4H).

Step 2) 2,2,2-trichloro-1-(4-(3-(difluoromethyl)-1-fluorophenyl)sulfonyl)-1H-indol-5-yl) piperazin-1-yl) ethanone 1-((2-Fluorophenyl)sulfonyl)-5-(4-(2,2,2-trichloroacetyl) piperazin-1-yl)-1H-indole-3-carbaldehyde (610 mg, 1.14 mmol) was reacted with diethylaminosulphur trifluoride (0.45 mL, 3.43 mmol) in DCM (10 mL) according to the procedure as described in step 5 of example 1, and the crude product was purified by silica gel column chromatography eluted with PE/EtOAc (v/v=4/1) to give the title compound as a yellow solid (280 mg, 44.1%). The compound was characterized by the following spectroscopic data: MS (ESI, pos. ion) m/z: 554.1 [M+H]$^+$; and $^1$H NMR (400 MHz, CDCl$_3$) δ (ppm): 8.11-8.05 (m, 1H), 7.82 (d, J=2.4 Hz, 1H), 7.75 (d, J=9.1 Hz, 1H), 7.60 (ddd, J=8.2, 4.9, 1.7 Hz, 1H), 7.32 (t, J=7.8 Hz, 1H), 7.16 (d, J=2.4 Hz, 1H), 7.12 (d, J=8.9 Hz, 1H), 7.02 (dd, J=9.1, 2.4 Hz, 1H), 6.84 (t, J=55.3 Hz, 1H), 3.99-3.97 (m, 4H), 3.29-3.20 (m, 4H).

Step 3) 3-(difluoromethyl)-1-((2-fluorophenyl)sulfonyl)-5-(piperazin-1-yl)-1H-indole 2,2,2-Trichloro-1-(4-(3-(difluoromethyl)-1-((2-fluorophenyl)sulfonyl)-1H-indol-5-yl) piperazin-1-yl) ethanone (150 mg, 0.27 mmol) was reacted with potassium hydroxide (0.81 mL, 0.81 mmol, 1 mmol/mL in water) in THF (10 mL) according to the procedure as described in step 6 of example 1, and the crude product was purified by silica gel column chromatography eluted with DCM/MeOH (v/v=30/1) to give the title compound as a white solid (83 mg, 75.0%). The compound was characterized by the following spectroscopic data: MS (ESI, pos. ion) m/z: 410.1 [M+H]$^+$; $^1$H NMR (600 MHz, DMSO-d$_6$) δ (ppm): 8.18 (t, J=7.5 Hz, 1H), 8.10 (s, 1H), 7.82-7.80 (m, 1H), 7.64 (d, J=9.2 Hz, 1H), 7.50 (m, 2H), 7.25 (t, J=54.0 Hz, 1H), 7.12 (d, J=9.2 Hz, 1H), 7.08 (s, 1H), 3.06 (brs, 4H), 2.88 (brs, 4H); and $^{13}$C NMR (150 MHz, DMSO-d$_6$) δ (ppm): 158.6 (d, J=255.0 Hz), 149.6, 138.7 (d, J=9.0 Hz), 130.9, 130.1, 128.4, 127.4, 126.3, 124.9 (d, J=13.3 Hz), 118.5 (d, J=20.5 Hz), 116.9, 114.0, 112.8 (t, J=229.5 Hz), 105.8, 50.2, 45.6.

Example 13 1-((2-chlorophenyl)sulfonyl)-3-(difluoromethyl)-5-(piperazin-1-yl)-1H-indole

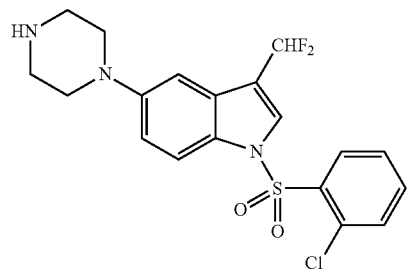 [SMILES: O=S(=O)(c1ccccc1Cl)n1cc(C(F)F)c2cc(N3CCNCC3)ccc21]

Step 1) 1-((2-chlorophenyl)sulfonyl)-5-(4-(2,2,2-trichloroacetyl)piperazin-1-yl)-1H-indole-3-carbaldehyde 5-(4-(2,2,2-Trichloroacetyl)piperazin-1-yl)-1H-indole-3-carbaldehyde (450 mg, 1.2 mmol) was reacted with tetrabutylammonium hydrogen sulfate (41 mg, 0.12 mmol), potassium hydroxide (135 mg, 2.4 mmol) and 2-chlorobenzenesulfonyl chloride (304 mg, 1.44 mmol) in DCM (15 mL) according to the procedure as described in step 4 of example 1, and the crude product was purified by silica gel column chromatography eluted with PE/EtOAc (v/v=2/1) to give the title compound as a brown solid (432 mg, 65.5%). The compound was characterized by the following spectroscopic data: MS (ESI, pos. ion) m/z: 548.0 [M+H]$^+$; and $^1$H NMR (600 MHz, CDCl$_3$) δ (ppm): 10.09 (s, 1H), 8.36 (s, 1H), 8.34 (d, J=8.0 Hz, 1H), 7.80 (s, 1H), 7.58 (t, J=7.6 Hz, 1H), 7.53-7.50 (m, 2H), 7.47 (d, J=7.9 Hz, 1H), 6.98 (d, J=9.1 Hz, 1H), 4.09-3.79 (m, 4H), 3.34-3.22 (m, 4H).

Step 2) 2,2,2-trichloro-1-(4-(1-((2-chlorophenyl)sulfonyl)-3-(difluoromethyl)-1H-indol-5-yl) piperazin-1-yl) ethanone 1-((2-Chlorophenyl)sulfonyl)-5-(4-(2,2,2-trichloroacetyl) piperazin-1-yl)-1H-indole-3-carbaldehyde (410 mg, 0.75 mmol) was reacted with diethylaminosulphur trifluoride (0.3 mL, 2.24 mmol) in DCM (10 mL) according to the procedure as described in step 5 of example 1, and the crude product was purified by silica gel column chromatography eluted with PE/EtOAc (v/v=4/1) to give the title compound as a yellow solid (250 mg, 58.6%). The compound was characterized by the following spectroscopic data: $^1$H NMR (600 MHz, CDCl$_3$) δ (ppm): 8.23 (dd, J=7.9, 1.4 Hz, 1H), 7.91 (s, 1H), 7.58 (d, J=9.1 Hz, 1H), 7.54 (dd, J=7.6, 1.5 Hz, 1H), 7.48-7.45 (m, 2H), 7.17 (s, 1H), 6.99 (dd, J=9.1, 2.1 Hz, 1H), 6.85 (t, J=55.4 Hz, 1H), 4.03 (brs, 4H), 3.25-3.23 (m, 4H).

Step 3) 1-((2-chlorophenyl)sulfonyl)-3-(difluoromethyl)-5-(piperazin-1-yl)-1H-indole 2,2,2-Trichloro-1-(4-(1-((2-chlorophenyl)sulfonyl)-3-(difluoromethyl)-1H-indol-5-yl) piperazin-1-yl) ethanone (350 mg, 0.61 mmol) was reacted with potassium hydroxide (1.84 mL, 1.84 mmol, 1 mmol/mL in water) in THF (10 mL) according to the procedure as described in step 6 of example 1, and the crude product was purified by silica gel column chromatography eluted with DCM/MeOH (v/v=30/1) to give the title compound as a white solid (198 mg, 75.9%). The compound was characterized by the following spectroscopic data: MS (ESI, pos. ion) m/z: 426.1 [M+H]⁺; ¹H NMR (600 MHz, DMSO-d₆) δ (ppm): 8.33 (dd, J=7.9, 1.3 Hz, 1H), 8.21 (s, 1H), 7.77 (t, J=7.5 Hz, 1H), 7.72-7.64 (m, 2H), 7.50 (d, J=9.0 Hz, 1H), 7.25 (t, J=54.7 Hz, 1H), 7.07 (dd, J=11.8, 2.4 Hz, 2H), 3.04-2.96 (m, 4H), 2.87-2.76 (m, 4H); and ¹³C NMR (150 MHz, DMSO-d₆) δ (ppm): 149.7, 137.1, 134.7, 133.2, 132.3, 131.7, 129.4 (t, J=10.6 Hz), 129.0, 128.2, 127.3, 116.8, 115.2 (t, J=25.5 Hz), 113.7, 112.9 (t, J=228.0 Hz), 105.7, 50.7, 46.1.

Example 14 1-((2-bromophenyl)sulfonyl)-3-(difluoromethyl)-5-(piperazin-1-yl)-1H-indole

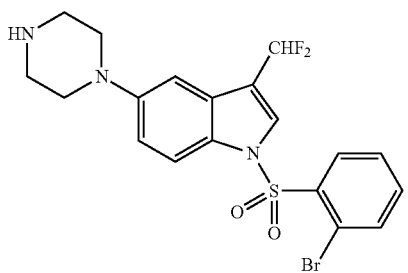 [SMILES: O=S(=O)(c1ccccc1Br)n1cc(C(F)F)c2cc(N3CCNCC3)ccc21]

Step 1) 1-((2-bromophenyl)sulfonyl)-5-(4-(2,2,2-trichloroacetyl)piperazin-1-yl)-1H-indole-3-carbaldehyde 5-(4-(2,2,2-Trichloroacetyl)piperazin-1-yl)-1H-indole-3-carbaldehyde (450 mg, 1.2 mmol) was reacted with tetrabutylammonium hydrogen sulfate (41 mg, 0.12 mmol), potassium hydroxide (135 mg, 2.4 mmol) and 2-bromobenzenesulfonyl chloride (368 mg, 1.44 mmol) in DCM (15 mL) according to the procedure as described in step 4 of example 1, and the crude product was purified by silica gel column chromatography eluted with PE/EtOAc (v/v=2/1) to give the title compound as a brown solid (692 mg, 97.0%). The compound was characterized by the following spectroscopic data: ¹H NMR (600 MHz, CDCl₃) δ (ppm): 10.10 (s, 1H), 8.41 (s, 1H), 8.35 (dd, J=8.0, 1.2 Hz, 1H), 7.80 (d, J=2.1 Hz, 1H), 7.70 (d, J=7.8 Hz, 1H), 7.58 (t, J=7.7 Hz, 1H), 7.51-7.45 (m, 2H), 6.98 (dd, J=9.1, 2.3 Hz, 1H), 4.10-3.85 (m, 4H), 3.32-3.20 (m, 4H).

Step 2) 1-(4-(1-((2-bromophenyl)sulfonyl)-3-(difluoromethyl)-1H-indol-5-yl)piperazin-1-yl)-2,2,2-trichloroethanone 1-((2-Bromophenyl)sulfonyl)-5-(4-(2,2,2-trichloroacetyl) piperazin-1-yl)-1H-indole-3-carbaldehyde (670 mg, 1.13 mmol) was reacted with diethylaminosulphur trifluoride (0.45 mL, 3.39 mmol) in DCM (10 mL) according to the procedure as described in step 5 of example 1, and the crude product was purified by silica gel column chromatography eluted with PE/EtOAc (v/v=4/1) to give the title compound as a yellow solid (410 mg, 59.0%). The compound was characterized by the following spectroscopic data: MS (ESI, pos. ion) m/z: 614.0 [M+H]⁺; and ¹H NMR (600 MHz, CDCl₃) δ (ppm): 8.21 (dd, J=8.0, 1.5 Hz, 1H), 7.96 (d, J=2.2 Hz, 1H), 7.69 (d, J=7.9 Hz, 1H), 7.56 (d, J=9.1 Hz, 1H), 7.54-7.50 (m, 1H), 7.44 (td, J=7.7, 1.6 Hz, 1H), 7.18 (s, 1H), 6.98 (dd, J=9.1, 2.2 Hz, 1H), 6.86 (t, J=55.4 Hz, 1H), 4.13-3.91 (m, 4H), 3.30-3.21 (m, 4H).

Step 3) 1-((2-bromophenyl)sulfonyl)-3-(difluoromethyl)-5-(piperazin-1-yl)-1H-indole 1-(4-(1-((2-Bromophenyl)sulfonyl)-3-(difluoromethyl)-1H-indol-5-yl)piperazin-1-yl)-2, 2,2-trichloroethanone (400 mg, 0.65 mmol) was reacted with potassium hydroxide (1.95 mL, 1.95 mmol, 1 mmol/mL in water) in THF (10 mL) according to the procedure as described in step 6 of example 1, and the crude product was purified by silica gel column chromatography eluted with DCM/MeOH (v/v=30/1) to give the title compound as a white solid (220 mg, 72.0%). The compound was characterized by the following spectroscopic data: MS (ESI, pos. ion) m/z: 470.1 [M+H]⁺; ¹H NMR (600 MHz, DMSO-d₆) δ (ppm): 8.29 (d, J=8.0 Hz, 1H), 8.23 (s, 1H), 7.91-7.85 (m, 1H), 7.72 (t, J=7.2 Hz, 1H), 7.67 (dd, J=9.3, 4.0 Hz, 1H), 7.49 (d, J=9.1 Hz, 1H), 7.26 (t, J=54.6 Hz, 1H), 7.11 (s, 1H), 7.07 (d, J=9.2 Hz, 1H), 3.08 (brs, 4H), 2.92-2.91 (m, 4H); and ¹³C NMR (150 MHz, DMSO-d₆) δ (ppm): 149.3, 136.9, 136.7, 136.5, 132.5, 129.6 (t, J=9.0 Hz), 129.5, 128.5, 127.3, 120.1, 116.8, 115.1 (t, J=25.5 Hz), 113.8, 112.9 (t, J=228.0 Hz), 105.98, 49.9, 45.4.

Example 15 3-(difluoromethyl)-5-(piperazin-1-yl)-1-tosyl-1H-indole

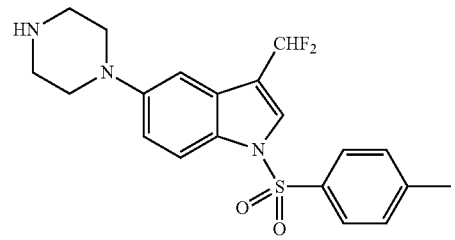 [SMILES: Cc1ccc(S(=O)(=O)n2cc(C(F)F)c3cc(N4CCNCC4)ccc32)cc1]

Step 1) 1-tosyl-5-(4-(2,2,2-trichloroacetyl)piperazin-1-yl)-1H-indole-3-carbaldehyde 5-(4-(2,2,2-Trichloroacetyl)piperazin-1-yl)-1H-indole-3-carbaldehyde (500 mg, 1.33 mmol) was reacted with tetrabutylammonium hydrogen sulfate (45 mg, 0.13 mmol), potassium hydroxide (150 mg, 2.67 mmol) and p-TsCl (305 mg, 1.6 mmol) in DCM (15 mL) according to the procedure as described in step 4 of example 1, and the crude product was purified by silica gel column chromatography eluted with PE/EtOAc (v/v=2/1) to give the title compound as a brown solid (593 mg, 84.0%). The compound was characterized by the following spectroscopic data: MS (ESI, pos. ion) m/z: 528.0 [M+H]⁺; and ¹H NMR (600 MHz, DMSO-d₆) δ (ppm): 10.04 (s, 1H), 8.78 (s, 1H), 7.97 (d, J=8.4 Hz, 2H), 7.83 (d, J=9.2 Hz, 1H), 7.59 (d, J=2.0 Hz, 1H), 7.45 (d, J=8.2 Hz, 2H), 7.20 (dd, J=9.2, 2.3 Hz, 1H), 4.09-3.71 (m, 6H), 3.19-3.15 (m, 2H), 2.35 (s, 3H).

Step 2) 2,2,2-trichloro-1-(4-(3-(difluoromethyl)-1-tosyl-1H-indol-5-yl)piperazin-1-yl)ethanone 1-Tosyl-5-(4-(2,2,2-trichloroacetyl)piperazin-1-yl)-1H-indole-3-carbaldehyde (590 mg, 1.12 mmol) was reacted with diethylaminosulphur trifluoride (0.44 mL, 3.35 mmol)

in DCM (10 mL) according to the procedure as described in step 5 of example 1, and the crude product was purified by silica gel column chromatography eluted with PE/EtOAc (v/v=4/1) to give the title compound as a yellow solid (363 mg, 59.1%). The compound was characterized by the following spectroscopic data: MS (ESI, pos. ion) m/z: 550.0 [M+H]$^+$; and $^1$H NMR (600 MHz, CDCl$_3$) δ (ppm): 7.89 (d, J=9.1 Hz, 1H), 7.77 (d, J=8.3 Hz, 2H), 7.72 (s, 1H), 7.25 (m, 2H), 7.12 (s, 1H), 7.07 (dd, J=9.1, 2.2 Hz, 1H), 6.81 (t, J=55.5 Hz, 1H), 4.02 (br, 4H), 3.30-3.17 (m, 4H), 2.36 (s, 3H).

Step 3 3-(difluoromethyl)-5-(piperazin-1-yl)-1-tosyl-1H-indole 2,2,2-Trichloro-1-(4-(3-(difluoromethyl)-1-tosyl-1H-indol-5-yl)piperazin-1-yl)ethanone (363 mg, 0.66 mmol) was reacted with potassium hydroxide (1.98 mL, 1.98 mmol, 1 mmol/mL in water) in THF (10 mL) according to the procedure as described in step 6 of example 1, and the crude product was purified by silica gel column chromatography eluted with DCM/MeOH (v/v=30/1) to give the title compound as a white solid (217 mg, 80.3%). The compound was characterized by the following spectroscopic data: MS (ESI, pos. ion) m/z: 406.1 [M+H]$^+$; $^1$H NMR (600 MHz, DMSO-d$_6$) δ (ppm): 8.10 (s, 1H), 7.88 (d, J=8.3 Hz, 2H), 7.81 (d, J=9.1 Hz, 1H), 7.40 (d, J=7.9 Hz, 2H), 7.20 (t, J=54.8 Hz, 1H), 7.14 (d, J=8.1 Hz, 1H), 7.03 (s, 1H), 3.03 (brs, 4H), 2.85 (brs, 4H), 2.32 (s, 3H); and $^{13}$C NMR (150 MHz, DMSO-d$_6$) δ (ppm): 146.3, 134.3, 130.9, 128.7, 127.9 (t, J=9.0 Hz), 127.5, 127.3, 116.9, 116.6 (t, J=25.5 Hz), 114.3, 112.8 (t, J=229.5 Hz), 105.6, 50.6, 45.9, 21.5.

Example 16 3-(difluoromethyl)-1-((4-methoxyphenyl)sulfonyl)-5-(piperazin-1-yl)-1H-indole

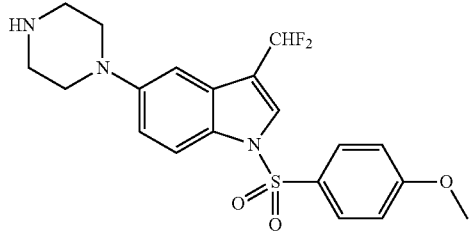 [SMILES: COc1ccc(S(=O)(=O)n2cc(C(F)F)c3cc(N4CCNCC4)ccc32)cc1]

Step 1) 1-((4-methoxyphenyl)sulfonyl)-5-(4-(2,2,2-trichloroacetyl)piperazin-1-yl)-1H-indole-3-carbaldehyde 5-(4-(2,2,2-Trichloroacetyl)piperazin-1-yl)-1H-indole-3-carbaldehyde (500 mg, 1.33 mmol) was reacted with tetrabutylammonium hydrogen sulfate (45 mg, 0.13 mmol), potassium hydroxide (150 mg, 2.67 mmol) and p-methoxybenzenesulfonyl chloride (331 mg, 1.6 mmol) in DCM (15 mL) according to the procedure as described in step 4 of example 1, and the crude product was purified by silica gel column chromatography eluted with PE/EtOAc (v/v=2/1) to give the title compound as a brown solid (618 mg, 85.0%). The compound was characterized by the following spectroscopic data: MS (ESI, pos. ion) m/z: 544.1 [M+H]$^+$; and $^1$H NMR (600 MHz, DMSO-d$_6$) δ (ppm): 10.04 (s, 1H), 8.77 (s, 1H), 8.03 (d, J=9.0 Hz, 2H), 7.83 (d, J=9.2 Hz, 1H), 7.59 (d, J=1.9 Hz, 1H), 7.20 (dd, J=9.2, 2.2 Hz, 1H), 7.14 (d, J=9.0 Hz, 2H), 4.02 (brs, 4H), 3.81 (s, 3H), 3.25 (brs, 4H).

Step 2) 2,2,2-trichloro-1-(4-(3-(difluoromethyl)-1-((4-methoxyphenyl)sulfonyl)-1H-indol-5-yl) piperazin-1-yl) ethanone 1-((4-Methoxyphenyl)sulfonyl)-5-(4-(2,2,2-trichloroacetyl)piperazin-1-yl)-1H-indole-3-carbaldehyde (618 mg, 1.33 mmol) was reacted with diethylaminosulphur trifluoride (0.45 mL, 3.40 mmol) in DCM (10 mL) according to the procedure as described in step 5 of example 1, and the crude product was purified by silica gel column chromatography eluted with PE/EtOAc (v/v=4/1) to give the title compound as a yellow solid (367 mg, 57.1%). The compound was characterized by the following spectroscopic data: MS (ESI, pos. ion) m/z: 566.0 [M+H]$^+$; and $^1$H NMR (400 MHz, CDCl$_3$) δ (ppm): 7.91 (d, J=9.1 Hz, 1H), 7.85 (d, J=9.0 Hz, 2H), 7.74 (t, J=2.3 Hz, 1H), 7.14 (d, J=1.9 Hz, 1H), 7.09 (dd, J=9.1, 2.3 Hz, 1H), 6.95-6.89 (m, 2H), 6.76 (t, J=55.5 Hz, 1H), 4.01 (brs, 4H), 3.83 (s, 3H), 3.30-3.22 (m, 4H).

Step 3) 3-(difluoromethyl)-1-((4-methoxyphenyl) sulfonyl)-5-(piperazin-1-yl)-1H-indole 2,2,2-Trichloro-1-(4-(3-(difluoromethyl)-1-((4-methoxyphenyl)sulfonyl)-1H-indol-5-yl)piperazin-1-yl) ethanone (367 mg, 0.65 mmol) was reacted with potassium hydroxide (1.94 mL, 1.94 mmol, 1 mmol/mL in water) in THF (10 mL) according to the procedure as described in step 6 of example 1, and the crude product was purified by silica gel column chromatography eluted with DCM/MeOH (v/v=30/1) to give the title compound as a white solid (211 mg, 77.3%). The compound was characterized by the following spectroscopic data: MS (ESI, pos. ion) m/z: 422.1 [M+H]$^+$; $^1$H NMR (600 MHz, DMSO-d$_6$) δ (ppm): 8.09 (s, 1H), 7.94 (d, J=9.0 Hz, 2H), 7.81 (d, J=9.2 Hz, 1H), 7.24 (t, J=54.8 Hz, 1H), 7.14 (dd, J=9.2, 2.2 Hz, 1H), 7.11 (d, J=9.0 Hz, 2H), 7.03 (s, 1H), 3.80 (s, 3H), 3.05-2.98 (m, 4H), 2.84 (br, 4H); and $^{13}$C NMR (150 MHz, DMSO-d$_6$) δ (ppm): 164.5 149.6, 129.8, 128.6, 128.5, 127.8 (t, J=10.5 Hz), 127.5, 116.9, 116.4 (t, J=25.5 Hz), 115.6, 114.3, 112.8 (t, J=229.5 Hz), 105.5, 56.4, 50.8, 46.0.

Example 17 3-(difluoromethyl)-1-((3-fluorophenyl)sulfonyl)-5-(piperazin-1-yl)-1H-indole

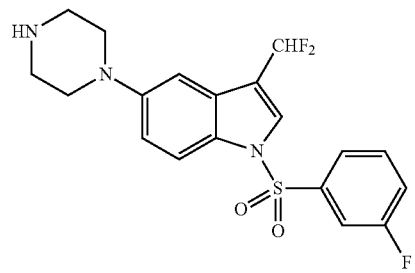 [SMILES: O=S(=O)(c1cccc(F)c1)n1cc(C(F)F)c2cc(N3CCNCC3)ccc21]

Step 1) tert-butyl 4-(1H-indol-5-yl)piperazine-1-carboxylate 5-(Piperazin-1-yl)-1H-indole (2.75 g, 13.7 mmol) was reacted with triethylamine (5.66 mL, 41.0 mmol) and di-tert-butyl dicarbonate (3.59 g, 16.4 mmol) in DCM (15 mL)

according to the procedure as described in step 2 of example 1, and the crude product was purified by silica gel column chromatography eluted with PE/EtOAc (v/v=5/1) to give the title compound as a brown solid (2.06 g, 50%). The compound was characterized by the following spectroscopic data: MS (ESI, pos. ion) m/z: 303.2 [M+H]$^+$; and $^1$H NMR (400 MHz, CDCl$_3$) δ (ppm): 8.11 (s, 1H), 7.31 (d, J=8.8 Hz, 1H), 7.18 (d, J=2.4 Hz, 2H), 6.97 (dd, J=8.8, 2.4 Hz, 1H), 6.47 (t, J=2.0 Hz, 1H), 3.62 (t, J=4.8 Hz, 4H), 3.07 (t, J=4.8 Hz, 4H), 1.50 (s, 9H).

Step 2) tert-butyl 4-(3-formyl-1H-indol-5-yl)piperazine-1-carboxylate tert-Butyl 4-(1H-indol-5-yl)piperazine-1-carboxylate (2.0 g, 6.64 mmol) was reacted with phosphorus oxychloride (1.08 g, 7.04 mmol) in DMF (15 mL) according to the procedure as described in step 3 of example 1 to give the title compound as a yellow solid (1.55 g, 71%). The compound was characterized by the following spectroscopic data: MS (ESI, pos. ion) m/z: 330.2 [M+H]$^+$; and $^1$H NMR (400 MHz, CDCl$_3$) δ (ppm): 10.00 (s, 1H), 9.17 (s, 1H), 7.85 (d, J=2.0 Hz, 1H), 7.78 (d, J=3.2 Hz, 1H), 7.34 (d, J=8.8 Hz, 1H), 7.05 (dd, J=8.8, 2.0 Hz, 1H), 3.61 (t, J=3.8 Hz, 4H), 3.14 (t, J=4.8 Hz, 4H), 1.50 (s, 9H).

Step 3) tert-butyl 4-(1-((3-fluorophenyl)sulfonyl)-3-formyl-1H-indol-5-yl)piperazine-1-carboxylate tert-Butyl 4-(3-formyl-1H-indol-5-yl)piperazine-1-carboxylate (264 mg, 0.80 mmol) was reacted with tetrabutylammonium hydrogen sulfate (27 mg, 0.08 mmol), potassium hydroxide (90 mg, 1.6 mmol) and 3-fluorobenzenesulfonyl chloride (283 mg, 1.6 mmol) in DCM (15 mL) according to the procedure as described in step 4 of example 1, and the crude product was purified by silica gel column chromatography eluted with PE/EtOAc (v/v=2/1) to give the title compound as a brown solid (340 mg, 87%). The compound was characterized by the following spectroscopic data: MS (ESI, pos. ion) m/z: 488.2 [M+H]$^+$; and $^1$H NMR (400 MHz, CDCl$_3$) δ (ppm): 10.06 (s, 1H), 8.11 (s, 1H), 7.82 (d, J=9.2 Hz, 1H), 7.75-7.72 (m, 2H), 7.67-7.63 (m, 1H), 7.50 (td, J=8.0, 5.2 Hz, 1H), 7.31 (td, J=8.0, 1.6 Hz, 1H), 7.09 (dd, J=9.2, 2.4 Hz, 1H), 3.59 (t, J=4.8 Hz, 4H), 3.15 (t, J=4.8 Hz, 4H), 1.48 (s, 9H).

Step 4) tert-butyl 4-(3-(difluoromethyl)-1-((3-fluorophenyl)sulfonyl)-1H-indol-5-yl)piperazine-1-carboxylate tert-Butyl 4-(1-((3-fluorophenyl)sulfonyl)-3-formyl-1H-indol-5-yl)piperazine-1-carboxylate (320 mg, 0.66 mmol) was reacted with diethylaminosulphur trifluoride (0.26 mL, 1.98 mmol) in DCM (10 mL) according to the procedure as described in step 5 of example 1, and the crude product was purified by silica gel column chromatography eluted with PE/EtOAc (v/v=4/1) to give the title compound as a yellow solid (236 mg, 70%). The compound was characterized by the following spectroscopic data: MS (ESI, pos. ion) m/z: 510.2 [M+H]$^+$; and $^1$H NMR (400 MHz, CDCl$_3$) δ (ppm): 7.89 (d, J=9.1 Hz, 1H), 7.70 (dd, J=5.6, 3.1 Hz, 2H), 7.63-7.58 (m, 1H), 7.49 (td, J=8.1, 5.2 Hz, 1H), 7.31 (dd, J=8.2, 2.0 Hz, 1H), 7.14-7.08 (m, 2H), 6.84 (t, J=55.4 Hz, 1H), 3.59 (t, J=5.2 Hz, 4H), 3.12 (t, J=5.2 Hz, 4H), 1.48 (s, 9H).

Step 5) 3-(difluoromethyl)-1-((3-fluorophenyl)sulfonyl)-5-(piperazin-1-yl)-1H-indole To a solution of tert-butyl 4-(3-(difluoromethyl)-1-((3-fluorophenyl)sulfonyl)-1H-indol-5-yl)piperazine-1-carboxylate (200 mg, 0.39 mmol) in dichloromethane (10 mL) was added a solution of hydrogen chloride in ethyl acetate (2 mL, 2 M). The mixture was stirred at rt for 2 hours and concentrated in vacuo. To the residue were added methanol (10 mL) and water (10 mL), then the mixture was neutralized with saturated aqueous sodium bicarbonate to pH about 8-9. The resulting mixture was extracted with dichloromethane (30 mL), then the organic layer was dried over anhydrous sodium sulfate and filtered. The filtrate was concentrated in vacuo to give the title compound as a yellow solid (155 mg, 97%). The compound was characterized by the following spectroscopic data: MS (ESI, pos. ion) m/z: 410.1 [M+H]$^+$; $^1$H NMR (600 MHz, DMSO-d$_6$) δ (ppm): 8.14 (s, 1H), 7.96 (d, J=8.4 Hz, 1H), 7.86 (d, J=7.8 Hz, 1H), 7.84 (d, J=9.6 Hz, 1H), 7.70-7.66 (m, 1H), 7.61 (t, J=7.2 Hz, 1H), 7.20 (t, J=55.2 Hz, 1H), 7.14 (d, J=9.0 Hz, 1H), 7.03 (s, 1H), 3.02 (br, 4H), 2.85 (br, 4H); and $^{13}$C NMR (150 MHz, DMSO-d$_6$) δ (ppm): 149.3, 138.4 (d, J=7.3 Hz), 132.5 (d, J=8.2 Hz), 131.6 (t, J=20.2 Hz), 127.9 (t, J=101.3 Hz), 127.4 (t, J=10.0 Hz), 123.2 (d, J=2.9 Hz), 122.3 (d, J=21.1 Hz), 116.6 (t, J=26.0 Hz), 116.5, 114.2, 114.1, 113.9, 112.2 (t, J=231.2 Hz), 105.1, 50.1, 45.5.

Example 18 1-((3-chlorophenyl)sulfonyl)-3-(difluoromethyl)-5-(piperazin-1-yl)-1H-indole

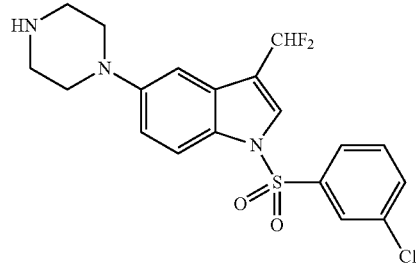 [SMILES: O=S(=O)(c1cccc(Br)c1)n1cc(C(F)F)c2cc(N3CCNCC3)ccc21]

Step 1) tert-butyl 4-(1-((3-chlorophenyl)sulfonyl)-3-formyl-1H-indol-5-yl)piperazine-1-carboxylate tert-Butyl 4-(3-formyl-1H-indol-5-yl)piperazine-1-carboxylate (264 mg, 0.80 mmol) was reacted with tetrabutylammonium hydrogen sulfate (27 mg, 0.08 mmol), potassium hydroxide (90 mg, 1.6 mmol) and 3-chlorobenzenesulfonyl chloride (338 mg, 1.6 mmol) in DCM (15 mL) according to the procedure as described in step 4 of example 1, and the crude product was purified by silica gel column chromatography eluted with PE/EtOAc (v/v=2/1) to give the title compound as a brown solid (375 mg, 93%). The compound was characterized by the following spectroscopic data: MS (ESI, pos. ion) m/z: 504.2 [M+H]$^+$; and $^1$H NMR (400 MHz, CDCl$_3$) δ (ppm): 10.06 (s, 1H), 8.12 (s, 1H), 7.92 (t, J=2.0 Hz, 1H), 7.83 (s, 1H), 7.80 (s, 1H), 7.74 (d, J=2.4 Hz, 1H), 7.57 (d, J=8.4 Hz, 1H), 7.44 (t, J=8.0 Hz, 1H), 7.09 (dd, J=9.2, 2.4 Hz, 1H), 3.58 (t, J=5.2 Hz, 4H), 3.15 (t, J=5.2 Hz, 4H), 1.48 (s, 9H).

Step 2 tert-butyl 4-(1-((3-chlorophenyl)sulfonyl)-3-(difluoromethyl)-1H-indol-5-yl)piperazine-1-carboxylate tert-Butyl 4-(1-((3-chlorophenyl)sulfonyl)-3-formyl-1H-indol-5-yl)piperazine-1-carboxylate (350 mg, 0.69 mmol) was reacted with diethylaminosulphur trifluoride (0.28 mL, 2.10 mmol) in DCM (10 mL) according to the procedure as described in step 5 of example 1, and the crude product was purified by silica gel column chromatography eluted with PE/EtOAc (v/v=4/1) to give the title compound as a yellow solid (236 mg, 65%). The compound was characterized by the following spectroscopic data: $^1$H NMR (400 MHz, CDCl$_3$) δ (ppm): 7.89-7.84 (m, 2H), 7.76 (d, J=8.0 Hz, 1H), 7.68 (t, J=2.4 Hz, 1H), 7.56-7.52 (m, 1H), 7.41 (t, J=8.0 Hz, 1H), 7.09 (m, 2H), 6.82 (t, J=55.6 Hz, 1H), 3.59 (t, J=5.2 Hz, 4H), 3.12 (t, J=5.2 Hz, 4H), 1.48 (s, 9H).

Step 3) 1-((3-chlorophenyl)sulfonyl)-3-(difluoromethyl)-5-(piperazin-1-yl)-1H-indole tert-Butyl 4-(1-((3-chlorophenyl)sulfonyl)-3-(difluoromethyl)-1H-indol-5-yl)piperazine-1-carboxylate (220 mg, 0.42 mmol) was reacted with a solution of hydrogen chloride in ethyl acetate (2 mL, 2 M) in dichloromethane (10 mL) according to the procedure as described in step 5 of example 17 to give the title compound as a yellow solid (143 mg, 80%). The compound was characterized by the following spectroscopic data: MS (ESI, pos. ion) m/z: 426.1 [M+H]$^+$; $^1$H NMR (600 MHz, DMSO-d$_6$) δ (ppm): 8.16 (s, 1H), 8.11 (s, 1H), 7.98 (d, J=7.8 Hz, 1H), 7.84 (d, J=9.6 Hz, 1H), 7.81 (d, J=8.4 Hz, 1H), 7.65 (t, J=8.4 Hz, 1H), 7.20 (t, J=54.6 Hz, 1H), 7.15 (dd, J=9.0, 1.8 Hz, 1H), 7.03 (s, 1H), 3.02 (t, J=4.2 Hz, 4H), 2.83 (t, J=4.2 Hz, 4H); and $^{13}$C NMR (150 MHz, DMSO-d$_6$) δ (ppm): 149.4, 138.4, 134.9, 134.5, 132.0, 131.6 (t, J=22.5 Hz), 127.9 (t, J=109.9 Hz), 127.4 (t, J=9.8 Hz), 126.3, 125.6, 116.7 (t, J=25.8 Hz), 116.5, 113.8, 112.2 (t, J=231.3 Hz), 105.0, 50.2, 45.6.

Example 19 1-((3-bromophenyl)sulfonyl)-3-(difluoromethyl)-5-(piperazin-1-yl)-1H-indole

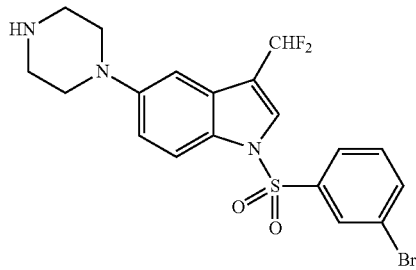

Step 1) tert-butyl 4-(1-((3-bromophenyl)sulfonyl)-3-formyl-1H-indol-5-yl)piperazine-1-carboxylate tert-Butyl 4-(3-formyl-1H-indol-5-yl)piperazine-1-carboxylate (264 mg, 0.80 mmol) was reacted with tetrabutylammonium hydrogen sulfate (27 mg, 0.08 mmol), potassium hydroxide (90 mg, 1.6 mmol) and 3-bromobenzenesulfonyl chloride (409 mg, 1.6 mmol) in DCM (15 mL) according to the procedure as described in step 4 of example 1, and the crude product was purified by silica gel column chromatography eluted with PE/EtOAc (v/v=2/1) to give the title compound as a brown solid (412 mg, 94%). The compound was characterized by the following spectroscopic data: MS (ESI, pos. ion) m/z: 548.1 [M+H]$^+$; and $^1$H NMR (400 MHz, CDCl$_3$) δ (ppm): 10.07 (s, 1H), 8.12 (s, 1H), 8.07 (t, J=2.0 Hz, 1H), 7.87-7.83 (m, 1H), 7.81 (d, J=9.2 Hz, 1H), 7.76-7.70 (m, 2H), 7.37 (t, J=8.0 Hz, 1H), 7.09 (dd, J=9.2, 2.4 Hz, 1H), 3.58 (t, J=5.2 Hz, 4H), 3.16 (t, J=5.2 Hz, 4H), 1.48 (s, 9H).

Step 2) tert-butyl 4-(1-((3-bromophenyl)sulfonyl)-3-(difluoromethyl)-1H-indol-5-yl)piperazine-1-carboxylate tert-Butyl 4-(1-((3-bromophenyl)sulfonyl)-3-formyl-1H-indol-5-yl)piperazine-1-carboxylate (400 mg, 0.73 mmol) was reacted with diethylaminosulphur trifluoride (0.29 mL, 2.19 mmol) in DCM (10 mL) according to the procedure as described in step 5 of example 1, and the crude product was purified by silica gel column chromatography eluted with PE/EtOAc (v/v=4/1) to give the title compound as a yellow solid (250 mg, 60%). The compound was characterized by the following spectroscopic data: MS (ESI, pos. ion) m/z: 570.1 [M+H]$^+$; and $^1$H NMR (400 MHz, CDCl$_3$) δ (ppm): 8.03 (t, J=1.6 Hz, 1H), 7.86 (d, J=9.2 Hz, 1H), 7.80 (d, J=8.0 Hz, 1H), 7.71-7.67 (m, 2H), 7.34 (t, J=8.0 Hz, 1H), 7.12-7.07 (m, 2H), 6.82 (d, J=55.6 Hz, 1H), 3.59 (t, J=5.2 Hz, 4H), 3.12 (t, J=5.2 Hz, 4H), 1.48 (s, 9H).

Step 3) 1-((3-bromophenyl)sulfonyl)-3-(difluoromethyl)-5-(piperazin-1-yl)-1H-indole tert-Butyl 4-(1-((3-bromophenyl)sulfonyl)-3-(difluoromethyl)-1H-indol-5-yl)piperazine-1-carboxylate (240 mg, 0.42 mmol) was reacted with a solution of hydrogen chloride in ethyl acetate (2 mL, 2 M) in dichloromethane (5 mL) according to the procedure as described in step 5 of example 17 to give the title compound as a yellow solid (188 mg, 95%). The compound was characterized by the following spectroscopic data: MS (ESI, pos. ion) m/z: 470.0 [M+H]$^+$; $^1$H NMR (600 MHz, DMSO-d$_6$) δ (ppm): 8.21 (s, 1H), 8.16 (s, 1H), 8.02 (d, J=8.4 Hz, 1H), 7.94 (d, J=7.8 Hz, 1H), 7.83 (d, J=9.0 Hz, 1H), 7.57 (t, J=8.4 Hz, 1H), 7.21 (t, J=54.6 Hz, 1H), 7.15 (dd, J=9.0, 1.8 Hz, 1H), 7.03 (s, 1H), 3.03 (t, J=4.2 Hz, 4H), 2.84 (t, J=4.2 Hz, 4H); and $^{13}$C NMR (150 MHz, DMSO-d$_6$) δ (ppm): 149.3, 138.5, 137.9, 132.2, 131.6 (t, J=19.8 Hz), 129.0, 127.9 (t, J=108.3 Hz), 127.4 (t, J=10.1 Hz), 125.9, 122.7, 116.7 (t, J=25.6 Hz), 116.5, 113.8, 112.2 (t, J=231.2 Hz), 105.1, 50.1, 45.5.

Example 20 1-((4-chlorophenyl)sulfonyl)-3-(difluoromethyl)-5-(piperazin-1-yl)-1H-indole

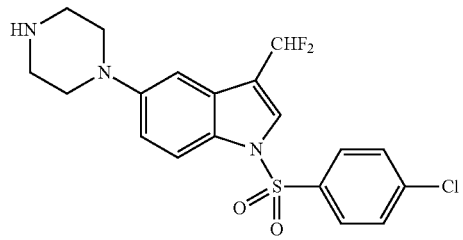 [SMILES: O=S(=O)(c1ccc(Br)cc1)n1cc(C(F)F)c2cc(N3CCNCC3)ccc21]

Step 1) tert-butyl 4-(1-((4-chlorophenyl)sulfonyl)-3-formyl-1H-indol-5-yl)piperazine-1-carboxylate tert-Butyl 4-(3-formyl-1H-indol-5-yl)piperazine-1-carboxylate (264 mg, 0.80 mmol) was reacted with tetrabutylammonium hydrogen sulfate (27 mg, 0.08 mmol), potassium hydroxide (90 mg, 1.6 mmol) and 4-chlorobenzenesulfonyl chloride (338 mg, 1.6 mmol) in DCM (15 mL) according to the procedure as described in step 4 of example 1, and the crude product was purified by silica gel column chromatography eluted with PE/EtOAc (v/v=2/1) to give the title compound as a brown solid (262 mg, 65%). The compound was characterized by the following spectroscopic data: MS (ESI, pos. ion) m/z: 504.1 [M+H]$^+$; and $^1$H NMR (400 MHz, CDCl$_3$) δ (ppm): 10.05 (s, 1H), 8.11 (s, 1H), 7.88 (s, 1H), 7.86 (s, 1H), 7.80 (d, J=9.2 Hz, 1H), 7.74 (d, J=2.4 Hz, 1H), 7.48 (s, 1H), 7.45 (s, 1H), 7.08 (dd, J=9.2, 2.4 Hz, 1H), 3.58 (t, J=5.2 Hz, 4H), 3.15 (t, J=5.2 Hz, 4H), 1.48 (s, 9H).

Step 2) tert-butyl 4-(1-((4-chlorophenyl)sulfonyl)-3-(difluoromethyl)-1H-indol-5-yl)piperazine-1-carboxylate tert-Butyl 4-(1-((4-chlorophenyl)sulfonyl)-3-formyl-1H-indol-5-yl)piperazine-1-carboxylate (250 mg, 0.50 mmol) was reacted with diethylaminosulphur trifluoride (0.20 mL, 1.50 mmol) in DCM (10 mL) according to the procedure as described in step 5 of example 1, and the crude product was purified by silica gel column chromatography eluted with PE/EtOAc (v/v=4/1) to give the title compound as a yellow solid (137 mg, 52%). The compound was characterized by the following spectroscopic data: MS (ESI, pos. ion) m/z: 526.1 [M+H]$^+$; and $^1$H NMR (400 MHz, CDCl$_3$) δ (ppm): 7.85 (d, J=9.2 Hz, 1H), 7.82 (s, 1H), 7.80 (s, 1H), 7.68 (t, J=2.4 Hz, 1H), 7.44 (s, 1H), 7.42 (s, 1H), 7.09 (s, 1H), 7.07 (d, J=9.2 Hz, 1H), 6.81 (t, J=55.4 Hz, 1H), 3.58 (t, J=5.2 Hz, 4H), 3.12 (t, J=5.2 Hz, 4H), 1.48 (s, 9H).

Step 3) 1-((4-chlorophenyl)sulfonyl)-3-(difluoromethyl)-5-(piperazin-1-yl)-1H-indole tert-Butyl 4-(1-((4-chlorophenyl)sulfonyl)-3-(difluoromethyl)-1H-indol-5-yl)piperazine-1-carboxylate (120 mg, 0.23 mmol) was reacted with a solution of hydrogen chloride in ethyl acetate (2 mL, 2 M) in dichloromethane (5 mL) according to the procedure as described in step 5 of example 17 to give the title compound as a yellow solid (82 mg, 84%). The compound was characterized by the following spectroscopic data: MS (ESI, pos. ion) m/z: 426.1 [M+H]$^+$; $^1$H NMR (600 MHz, DMSO-d$_6$) δ (ppm): 8.11 (s, 1H), 8.02 (s, 1H), 8.01 (s, 1H), 7.80 (d, J=9.0 Hz, 1H), 7.70 (s, 1H), 7.69 (s, 1H), 7.20 (t, J=54.6 Hz, 1H), 7.14 (d, J=9.0 Hz, 1H), 7.03 (s, 1H), 3.02 (brs, 4H), 2.84 (brs, 4H); and $^{13}$C NMR (150 MHz, DMSO-d$_6$) δ (ppm): 149.7, 140.6, 135.8, 132.1 (t, J=19.5 Hz), 130.7, 129.2, 128.5 (t, J=99.9 Hz), 127.8 (t, J=10.2 Hz), 117.1, 117.0, 114.3, 112.7 (t, J=28.9 Hz), 117.0, 114.3, 112.7 (t, J=189.9 Hz), 105.55. 50.1, 45.5.

Example 21 1-((4-bromophenyl)sulfonyl)-3-(difluoromethyl)-5-(piperazin-1-yl)-1H-indole

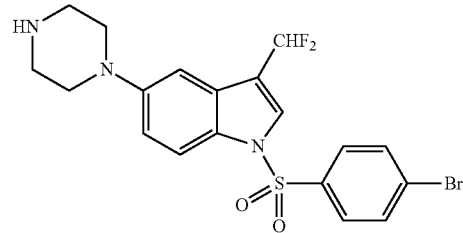

Step 1) tert-butyl 4-(1-((4-bromophenyl)sulfonyl)-3-formyl-1H-indol-5-yl)piperazine-1-carboxylate tert-Butyl 4-(3-formyl-1H-indol-5-yl)piperazine-1-carboxylate (264 mg, 0.80 mmol) was reacted with tetrabutylammonium hydrogen sulfate (27 mg, 0.08 mmol), potassium hydroxide (90 mg, 1.6 mmol) and 4-bromobenzenesulfonyl chloride (410 mg, 1.6 mmol) in DCM (15 mL) according to the procedure as described in step 4 of example 1, and the crude product was purified by silica gel column chromatography eluted with PE/EtOAc (v/v=2/1) to give the title compound as a brown solid (351 mg, 80%). The compound was characterized by the following spectroscopic data: MS (ESI, pos. ion) m/z: 548.1 [M+H]$^+$; and $^1$H NMR (600 MHz, CDCl$_3$) δ (ppm): 10.05 (s, 1H), 8.11 (s, 1H), 7.83-7.79 (m, 3H), 7.74 (d, J=1.8 Hz, 1H), 7.64 (s, 1H), 7.63 (s, 1H), 7.07 (dd, J=9.0, 1.8 Hz, 1H), 3.59 (t, J=4.2 Hz, 4H), 3.15 (brs, 4H), 1.48 (s, 9H).

Step 2) tert-butyl 4-(1-((4-bromophenyl)sulfonyl)-3-(difluoromethyl)-1H-indol-5-yl)piperazine-1-carboxylate tert-Butyl 4-(1-((4-bromophenyl)sulfonyl)-3-formyl-1H-indol-5-yl)piperazine-1-carboxylate (340 mg, 0.62 mmol) was reacted with diethylaminosulphur trifluoride (0.25 mL, 1.86 mmol) in DCM (10 mL) according to the procedure as described in step 5 of example 1, and the crude product was purified by silica gel column chromatography eluted with PE/EtOAc (v/v=4/1) to give the title compound as a yellow solid (177 mg, 50%). The compound was characterized by the following spectroscopic data: MS (ESI, pos. ion) m/z: 570.1 [M+H]$^+$; and $^1$H NMR (400 MHz, CDCl$_3$) δ (ppm): 7.84 (d, J=8.8 Hz, 1H), 7.74 (s, 1H), 7.72 (s, 1H), 7.67 (t, J=2.4 Hz, 1H), 7.60 (s, 1H), 7.58 (s, 1H), 7.09 (s, 1H), 7.07 (d, J=8.8 Hz, 1H), 6.80 (t, J=55.6 Hz, 1H), 3.58 (t, J=5.2 Hz, 4H), 3.12 (t, J=5.2 Hz, 4H), 1.48 (s, 9H).

Step 3) 1-((4-bromophenyl)sulfonyl)-3-(difluoromethyl)-5-(piperazin-1-yl)-1H-indole tert-Butyl 4-(1-((4-bromophenyl)sulfonyl)-3-(difluoromethyl)-1H-indol-5-yl)piperazine-1-carboxylate (150 mg, 0.26 mmol) was reacted with a solution of hydrogen chloride in ethyl acetate (2 mL, 2 M) in dichloromethane (5 mL) according to the procedure as described in step 5 of example 17 to give the title compound as a yellow solid (98 mg, 80%). The compound was characterized by the following spectroscopic data: MS (ESI, pos. ion) m/z: 470.0 [M+H]$^+$; $^1$H NMR (600 MHz, DMSO-d$_6$) δ (ppm): 8.12 (s, 1H), 7.94 (s, 1H), 7.92 (s, 1H), 7.84 (s, 1H), 7.83 (s, 1H), 7.80 (d, J=9.6

Hz, 1H), 7.21 (t, J=55.2 Hz, 1H), 7.15 (dd, J=9.6, 2.4 Hz, 1H), 7.06 (s, 1H), 3.10 (t, J=4.8 Hz, 4H), 2.93 (t, J=4.8 Hz, 4H); and $^{13}$C NMR (150 MHz, DMSO-$d_6$) δ (ppm): 148.9, 135.8, 133.1, 129.3, 128.7, 128.1, 127.4 (t, J=10.12 Hz), 127.2, 116.7, 113.8, 112.2 (t, J=229.4 Hz), 105.3, 49.3, 44.9.

Example 22 3-(difluoromethyl)-4-(piperazin-1-yl)-1-((2-(trifluoromethyl)phenyl)sulfonyl)-1H-indole

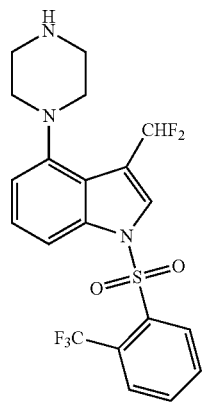 [SMILES: O=S(=O)(c1ccccc1C(F)(F)F)n1cc(C(F)F)c2c(N3CCNCC3)cccc21]

Step 1) 4-(4-(2,2,2-trifluoroacetyl)piperazin-1-yl)-1-((2-(trifluoromethyl)phenyl)sulfonyl)-1H-indole-3-carbaldehyde 4-(4-(2,2,2-Trifluoroacetyl)piperazin-1-yl)-1H-indole-3-carbaldehyde (500 mg, 1.54 mmol) was reacted with tetrabutylammonium hydrogen sulfate (27 mg, 0.08 mmol), potassium hydroxide (173 mg, 3.08 mmol) and 2-trifluoromethylbenzenesulfonyl chloride (488 mg, 1.99 mmol) in DCM (15 mL) according to the procedure as described in step 4 of example 1, and the crude product was purified by silica gel column chromatography eluted with DCM/PE (v/v=2/1) to give the title compound as a brown solid (780 mg, 95%). The compound was characterized by the following spectroscopic data: MS (ESI, pos. ion) m/z: 533.9 [M+H]$^+$; and $^1$H NMR (400 MHz, DMSO-$d_6$) δ (ppm): 10.42 (s, 1H), 8.40 (s, 1H), 8.10 (d, J=7.6 Hz, 1H), 7.98 (m, 2H), 7.90 (t, J=7.6 Hz, 1H), 7.41 (d, J=8.4 Hz, 1H), 7.32 (t, J=8.0 Hz, 1H), 7.10 (d, J=8.0 Hz, 1H), 3.75 (brs, 4H), 3.05 (brs, 4H).

Step 2) 1-(4-(3-(difluoromethyl)-1-((2-(trifluoromethyl)phenyl)sulfonyl)-1H-indol-4-yl) piperazin-1-yl)-2,2,2-trifluoroethanone 4-(4-(2,2,2-Trifluoroacetyl)piperazin-1-yl)-1-((2-(trifluoromethyl)phenyl)sulfonyl)-1H-indole-3-carbaldehyde (780 mg, 1.46 mmol) was reacted with diethylaminosulphur trifluoride (0.57 mL, 4.38 mmol) in DCM (10 mL) according to the procedure as described in step 5 of example 1, and the crude product was purified by silica gel column chromatography eluted with PE/EtOAc (v/v=4/1) to give the title compound as a yellow solid (750 mg, 92.3%). The compound was characterized by the following spectroscopic data: MS (ESI, pos. ion) m/z: 556.3 [M+H]$^+$; and $^1$H NMR (400 MHz, DMSO-$d_6$) δ (ppm): 8.09 (d, J=7.2 Hz, 1H), 8.01 (s, 1H), 7.99-7.88 (m, 3H), 7.55 (t, J=54.8 Hz, 1H), 7.52 (d, J=8.0 Hz, 1H), 7.34 (t, J=8.0 Hz, 1H), 7.25 (d, J=7.6 Hz, 1H), 3.73 (brs, 4H), 2.95 (brs, 4H).

Step 3) 3-(difluoromethyl)-4-(piperazin-1-yl)-1-((2-(trifluoromethyl)phenyl)sulfonyl)-1H-indole 1-(4-(3-(Difluoromethyl)-1-((2-(trifluoromethyl)phenyl)sulfonyl)-1H-indol-4-yl) piperazin-1-yl)-2,2,2-trifluoroethanone (750 mg, 1.35 mmol) was reacted with potassium hydroxide (151 mg, 2.7 mmol, dissolved in water (1 mL)) in THF (10 mL) according to the procedure as described in step 6 of example 1, and the crude product was purified by silica gel column chromatography eluted with DCM/MeOH (v/v=30/1) to give the title compound as a white solid (350 mg, 56.4%). The compound was characterized by the following spectroscopic data: MS (ESI, pos. ion) m/z: 460.2 [M+H]$^+$; $^1$H NMR (600 MHz, DMSO-$d_6$) δ (ppm): 8.07 (d, J=7.6 Hz, 1H), 7.98 (s, 1H), 7.96-7.92 (m, 1H), 7.90-7.89 (m, 2H), 7.47 (t, J=55.2 Hz, 1H), 7.44 (d, J=7.8 Hz, 1H), 7.31 (t, J=8.4 Hz, 1H), 7.13 (d, J=7.8 Hz, 1H), 2.82 (t, J=4.2 Hz, 4H), 2.78 (brs, 4H); and $^{13}$C NMR (150 MHz, DMSO-$d_6$) δ (ppm): 148.8, 136.1, 136.0, 135.9, 134.8, 131.3, 129.9 (q, J=6.15 Hz), 127.3, 126.7 (q, J=33.15 Hz), 126.4 (t, J=8.1 Hz), 123.1 (t, J=3.75 Hz), 122.8 (q, J=272.25 Hz), 116.8, 116.7 (t, J=24 Hz), 111.7 (t, J=232.35 Hz), 109.8, 54.8, 46.2.

Example 23 6-chloro-3-(difluoromethyl)-4-(piperazin-1-yl)-1-((2-(trifluoromethyl)phenyl) sulfonyl)-1H-indole

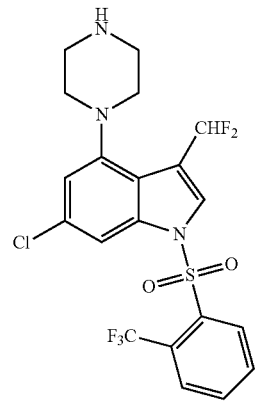 [SMILES: O=S(=O)(c1ccccc1C(F)(F)F)n1cc(C(F)F)c2c(N3CCNCC3)cc(Cl)cc21]

Step 1) 6-chloro-4-(piperazin-1-yl)-1H-indole

To 50 mL of isopropanol were added 4-amino-6-chloro indole (5 g, 30.0 mmol), bis(2-chloroethyl)amine hydrochloride (8.03 g, 45.0 mmol) and $K_2CO_3$ (9.12 g, 66.0 mmol). The mixture was stirred for 48 hours at 90° C., then to the reaction mixture were added dichloromethane (50 mL) and methanol (50 mL). The resulting mixture was filtered and the filtrate was concentrated in vacuo. The residue was purified by silica gel column chromatography eluted with DCM/MeOH (v/v=10/1) to give the title compound as a brown solid (3.4 g, 48.0%). The compound was characterized by the following spectroscopic data: MS (ESI, pos. ion) m/z: 236.2 [M+H]$^+$; and $^1$H NMR (400 MHz, CD$_3$OD) δ (ppm): 7.19 (d, J=3.2 Hz, 1H), 7.08 (dd, J=1.2, 0.8 Hz, 1H), 6.51 (d, J=1.6 Hz, 1H), 6.45 (dd, J=3.2, 0.8 Hz, 1H), 3.21-3.19 (m, 4H), 3.12-3.10 (m, 4H).

Step 2) 1-(4-(6-chloro-1H-indol-4-yl)piperazin-1-yl)-2,2,2-trifluoroethanone

To a solution of 6-chloro-4-(piperazin-1-yl)-1H-indole (3.4 g, 14.0 mmol) and triethylamine (5.9 mL, 43.0 mmol)

in dichloromethane (20 mL) was added dropwise slowly a solution of trifluoroacetic anhydride (3.1 mL, 22.0 mmol) in dichloromethane (20 mL) at 0° C. The mixture was stirred at rt for 4 hours, then diluted with 50 mL of dichloromethane. The resulting mixture was washed with saturated aqueous sodium bicarbonate (60 mL), then the organic layer was dried over anhydrous sodium sulfate and filtered. The filtrate was concentrated in vacuo and the residue was purified by silica gel column chromatography eluted with PE/EtOAc (v/v=10/1) to give the title compound as a yellow solid (3.2 g, 67.0%). The compound was characterized by the following spectroscopic data: MS (ESI, pos. ion) m/z: 332.0 [M+H]$^+$; and $^1$H NMR (400 MHz, CDCl$_3$) δ (ppm): 8.27 (s, 1H), 7.18 (t, J=2.8 Hz, 1H), 7.13 (s, 1H), 6.56 (d, J=1.6 Hz, 1H), 6.49 (t, J=2.0 Hz, 1H), 3.92 (t, J=4.8 Hz, 2H), 3.84 (t, J=4.8 Hz, 2H), 3.28 (t, J=4.8 Hz, 4H).

Step 3) 6-chloro-4-(4-(2,2,2-trifluoroacetyl)piperazin-1-yl)-1H-indole-3-carbaldehyde To a solution of 1-(4-(6-chloro-1H-indol-4-yl)piperazin-1-yl)-2,2,2-trifluoroethanone (3.2 g, 9.60 mmol) in DMF (15 mL) was added dropwise slowly phosphorus oxychloride (1.15 mL, 12.5 mmol) at 0° C. The mixture was warmed to 25° C. and stirred for 24 hours. The reaction mixture was quenched with water (30 mL) and the resulting mixture was neutralized with sodium carbonate solid to pH about 8-9, then filtered. The filter cake was dried in vacuo to give the title compound as a claybank solid (2.65 g, 76%). The compound was characterized by the following spectroscopic data: MS (ESI, pos. ion) m/z: 359.9 [M+H]$^+$; and $^1$H NMR (400 MHz, CDCl$_3$) δ (ppm): 10.32 (s, 1H), 9.35 (s, 1H), 7.95 (d, J=2.8 Hz, 1H), 7.23 (d, J=1.6 Hz, 1H), 6.86 (d, J=1.2 Hz, 1H), 3.88 (brs, 4H), 3.16 (brs, 4H).

Step 4) 6-chloro-4-(4-(2,2,2-trifluoroacetyl)piperazin-1-yl)-1-((2-(trifluoromethyl)phenyl) sulfonyl)-1H-indole-3-carbaldehyde 6-Chloro-4-(4-(2,2,2-trifluoroacetyl)piperazin-1-yl)-1H-indole-3-carbaldehyde (280 mg, 0.78 mmol) was reacted with tetrabutylammonium hydrogen sulfate (13 mg, 0.038 mmol), potassium hydroxide (87 mg, 1.56 mmol) and 2-trifluoromethylbenzenesulfonyl chloride (248 mg, 1.01 mmol) in DCM (15 mL) according to the procedure as described in step 4 of example 1, and the crude product was purified by silica gel column chromatography eluted with DCM/PE (v/v=2/1) to give the title compound as a white solid (355 mg, 80.3%). The compound was characterized by the following spectroscopic data: MS (ESI, pos. ion) m/z: 567.9 [M+H]$^+$; and $^1$H NMR (400 MHz, CDCl$_3$) δ (ppm): 10.44 (s, 1H), 8.32 (d, J=0.8 Hz, 1H), 8.15-8.09 (m, 1H), 8.01-7.95 (m, 1H), 7.90-7.78 (m, 2H), 7.56 (d, J=1.6 Hz, 1H), 7.00 (d, J=1.6 Hz, 1H), 3.87 (brs, 4H), 3.13 (brs, 4H).

Step 5) 1-(4-(6-chloro-3-(difluoromethyl)-1-((2-(trifluoromethyl)phenyl)sulfonyl)-1H-indol-4-yl)piperazin-1-yl)-2,2,2-trifluoroethanone 6-Chloro-4-(4-(2,2,2-trifluoroacetyl)piperazin-1-yl)-1-((2-(trifluoromethyl)phenyl) sulfonyl)-1H-indole-3-carbaldehyde (350 mg, 0.62 mmol) was reacted with diethylaminosulphur trifluoride (0.24 mL, 1.85 mmol) in DCM (10 mL) according to the procedure as described in step 5 of example 1, and the crude product was purified by silica gel column chromatography eluted with PE/EtOAc (v/v=4/1) to give the title compound as a yellow solid (340 mg, 93.5%). The compound was characterized by the following spectroscopic data: $^1$H NMR (400 MHz, CDCl$_3$) δ (ppm): 7.97-7.92 (m, 2H), 7.91 (s, 1H), 7.84-7.73 (m, 2H), 7.64 (d, J=1.6 Hz, 1H), 7.30 (t, J=55.2 Hz, 1H), 7.07 (d, J=1.6 Hz, 1H), 3.57-3.02 (m, 8H).

Step 6) 6-chloro-3-(difluoromethyl)-4-(piperazin-1-yl)-1-((2-(trifluoromethyl)phenyl)sulfonyl)-1H-indole 1-(4-(6-Chloro-3-(difluoromethyl)-1-((2-(trifluoromethyl)phenyl)sulfonyl)-1H-indol-4-yl)piperazin-1-yl)-2,2,2-trifluoroethanone (340 mg, 0.58 mmol) was reacted with potassium hydroxide (65 mg, 1.16 mmol, dissolved in water (1 mL)) in THF (10 mL) according to the procedure as described in step 6 of example 1, and the crude product was purified by silica gel column chromatography eluted with DCM/MeOH (v/v=30/1) to give the title compound as a white solid (140 mg, 49.2%). The compound was characterized by the following spectroscopic data: MS (ESI, pos. ion) m/z: 494.1 [M+H]$^+$; $^1$H NMR (600 MHz, CDCl$_3$) δ (ppm): 7.93 (d, J=7.8 Hz, 1H), 7.89 (s, 1H), 7.81 (d, J=8.4 Hz, 1H), 7.77 (t, J=7.2 Hz, 1H), 7.72 (t, J=7.8 Hz, 1H), 7.58 (d, J=1.8 Hz, 1H), 7.40 (t, J=55.2 Hz, 1H), 7.05 (d, J=1.8 Hz, 1H), 3.05 (brs, 4H), 2.94 (brs, 4H); and $^{13}$C NMR (150 MHz, CDCl$_3$) δ (ppm): 148.6, 137.0, 136.2, 134.4, 132.9, 132.1, 130.4, 129.1 (q, J=6.3 Hz), 128.5 (q, J=33.75 Hz), 126.6 (t, J=6.6 Hz), 122.1 (t, J=4.35 Hz), 122.0 (q, J=272.7 Hz), 117.4, 116.4 (t, J=24.45 Hz), 110.8 (t, J=233.85 Hz), 110.3, 54.6, 46.2.

Example 24 6-chloro-3-(difluoromethyl)-1-((2-fluorophenyl)sulfonyl)-4-(piperazin-1-yl)-1H-indole

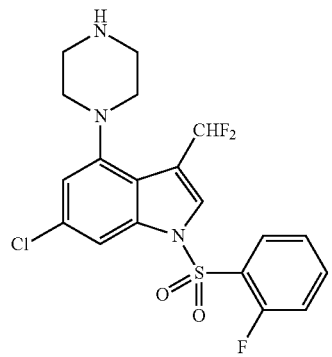 [SMILES: O=S(=O)(c1ccccc1F)n1cc(C(F)F)c2c(N3CCNCC3)cc(Cl)cc21]

Step 1) 6-chloro-1-((2-fluorophenyl)sulfonyl)-4-(4-(2,2,2-trifluoroacetyl)piperazin-1-yl)-1H-indole-3-carbaldehyde 6-Chloro-4-(4-(2,2,2-trifluoroacetyl)piperazin-1-yl)-1H-indole-3-carbaldehyde (300 mg, 0.83 mmol) was reacted with tetrabutylammonium hydrogen sulfate (15 mg, 0.043 mmol), potassium hydroxide (93 mg, 1.66 mmol) and 2-fluorobenzenesulfonyl chloride (212 mg, 1.09 mmol) in DCM (15 mL) according to the procedure as described in step 4 of example 1, and the crude product was purified by silica gel column chromatography eluted with DCM/PE (v/v=2/1) to give the title compound as a brown solid (415 mg, 96.1%). The compound was characterized by the following spectroscopic data: MS (ESI, pos. ion) m/z: 518.2

[M+H]⁺; and ¹H NMR (600 MHz, CDCl₃) δ (ppm): 10.41 (s, 1H), 8.36 (d, J=2.4 Hz, 1H), 8.17 (td, J=8.4, 1.8 Hz, 1H), 7.73-7.66 (m, 1H), 7.61 (d, J=1.8 Hz, 1H), 7.42 (td, J=8.4, 1.2 Hz, 1H), 7.20-7.17 (m, 1H), 6.96 (d, J=1.8 Hz, 1H), 3.84 (brs, 4H), 3.09 (brs, 4H).

Step 2) 1-(4-(6-chloro-3-(difluoromethyl)-1-fluorophenyl)sulfonyl)-1H-indol-4-yl) piperazin-1-yl)-2,2,2-trifluoroethanone 6-Chloro-1-((2-fluorophenyl)sulfonyl)-4-(4-(2,2,2-trifluoroacetyl)piperazin-1-yl)-1H-indole-3-carbaldehyde (415 mg, 0.80 mmol) was reacted with diethylaminosulphur trifluoride (0.32 mL, 2.40 mmol) in DCM (10 mL) according to the procedure as described in step 5 of example 1, and the crude product was purified by silica gel column chromatography eluted with PE/EtOAc (v/v=4/1) to give the title compound as a yellow solid (420 mg, 97.1%). The compound was characterized by the following spectroscopic data: MS (ESI, pos. ion) m/z: 539.8 [M+H]⁺; and ¹H NMR (600 MHz, CDCl₃) δ (ppm): 8.16-8.11 (m, 1H), 7.96 (d, J=1.8 Hz, 1H), 7.70 (d, J=1.2 Hz, 1H), 7.69-7.64 (m, 1H), 7.39 (t, J=7.2 Hz, 1H), 7.28 (t, J=55.2 Hz, 1H), 7.18 (t, J=9.0 Hz, 1H), 7.04 (d, J=1.8 Hz, 1H), 3.77-2.78 (m, 8H).

Step 3) 6-chloro-3-(difluoromethyl)-1-((2-fluorophenyl)sulfonyl)-4-(piperazin-1-yl)-1H-indole 1-(4-(6-Chloro-3-(difluoromethyl)-1-((2-fluorophenyl)sulfonyl)-1H-indol-4-yl) piperazin-1-yl)-2,2,2-trifluoroethanone (420 mg, 0.78 mmol) was reacted with potassium hydroxide (87 mg, 1.56 mmol, dissolved in water (1 mL)) in THF (10 mL) according to the procedure as described in step 6 of example 1, and the crude product was purified by silica gel column chromatography eluted with DCM/MeOH (v/v=30/1) to give the title compound as a white solid (200 mg, 57.9%). The compound was characterized by the following spectroscopic data: MS (ESI, pos. ion) m/z: 443.9 [M+H]⁺; ¹H NMR (600 MHz, CDCl₃) δ (ppm): 8.13-8.07 (m, 1H), 7.94 (d, J=1.2 Hz, 1H), 7.65-7.63 (m, 2H), 7.38 (t, J=7.8 Hz, 1H), 7.37 (t, J=55.2 Hz, 1H), 7.15 (t, J=9.0 Hz, 1H), 7.03 (d, J=1.2 Hz, 1H), 3.04 (brs, 4H), 2.92 (brs, 4H); and ¹³C NMR (150 MHz, CDCl₃) δ (ppm): 159.1 (d, J=258.3 Hz), 148.4, 137.2 (d, J=8.7 Hz), 135.8, 131.8, 130.4, 126.3 (td, J=7.7, 2.4 Hz), 125.7 (d, J=13.4 Hz), 125.0 (d, J=3.7 Hz), 122.2 (t, J=4.4 Hz), 117.8 (d, J=20.4 Hz), 117.3, 116.3 (t, J=24.3 Hz), 110.9 (t, J=233.7 Hz), 100.3, 54.4, 46.2.

Example 25 6-chloro-1-((2-chlorophenyl)sulfonyl)-3-(difluoromethyl)-4-(piperazin-1-yl)-1H-indole

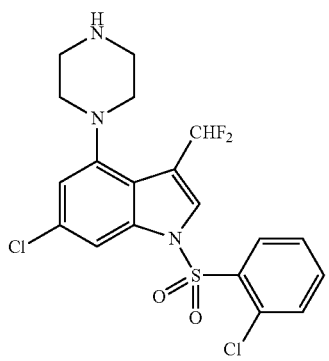

Step 1) 6-chloro-1-((2-chlorophenyl)sulfonyl)-4-(4-(2,2,2-trifluoroacetyl)piperazin-1-yl)-1H-indole-3-carbaldehyde 6-Chloro-4-(4-(2,2,2-trifluoroacetyl)piperazin-1-yl)-1H-indole-3-carbaldehyde (300 mg, 0.83 mmol) was reacted with tetrabutylammonium hydrogen sulfate (15 mg, 0.043 mmol), potassium hydroxide (93 mg, 1.66 mmol) and 2-chlorobenzenesulfonyl chloride (228 mg, 1.08 mmol) in DCM (15 mL) according to the procedure as described in step 4 of example 1, and the crude product was purified by silica gel column chromatography eluted with DCM/PE (v/v=2/1) to give the title compound as a brown solid (420 mg, 94.3%). The compound was characterized by the following spectroscopic data: MS (ESI, pos. ion) m/z: 534.2 [M+H]⁺; and ¹H NMR (400 MHz, CDCl₃) δ (ppm): 10.42 (s, 1H), 8.45 (s, 1H), 8.38 (dd, J=7.6, 1.6 Hz, 1H), 7.66-7.56 (m, 2H), 7.50 (dd, J=7.6, 1.2 Hz, 1H), 7.43 (d, J=1.6 Hz, 1H), 6.95 (d, J=1.6 Hz, 1H), 3.84 (brs, 4H), 3.10 (brs, 4H).

Step 2) 1-(4-(6-chloro-1-((2-chlorophenyl)sulfonyl)-3-(difluoromethyl)-1H-indol-4-yl) piperazin-1-yl)-2,2,2-trifluoroethanone 6-Chloro-1-((2-chlorophenyl)sulfonyl)-4-(4-(2,2,2-trifluoroacetyl)piperazin-1-yl)-1H-indole-3-carbaldehyde (420 mg, 0.79 mmol) was reacted with diethylaminosulphur trifluoride (0.31 mL, 2.37 mmol) in DCM (10 mL) according to the procedure as described in step 5 of example 1, and the crude product was purified by silica gel column chromatography eluted with PE/EtOAc (v/v=4/1) to give the title compound as a yellow solid (370 mg, 84.6%). The compound was characterized by the following spectroscopic data: MS (ESI, pos. ion) m/z: 556.2 [M+H]⁺; and ¹H NMR (400 MHz, CDCl₃) δ (ppm): 8.33 (dd, J=7.6, 1.6 Hz, 1H), 8.05 (t, J=1.6 Hz, 1H), 7.62-7.53 (m, 2H), 7.52 (d, J=1.6 Hz, 1H), 7.50 (dd, J=8.0, 1.6 Hz, 1H), 7.30 (t, J=55.2 Hz, 1H), 7.03 (d, J=1.6 Hz, 1H), 4.02-2.75 (m, 8H).

Step 3) 6-chloro-1-((2-chlorophenyl)sulfonyl)-3-(difluoromethyl)-4-(piperazin-1-yl)-1H-indole 1-(4-(6-Chloro-1-((2-chlorophenyl)sulfonyl)-3-(difluoromethyl)-1H-indol-4-yl) piperazin-1-yl)-2,2,2-trifluoroethanone (370 mg, 0.67 mmol) was reacted with potassium hydroxide (74 mg, 1.32 mmol, dissolved in water (1 mL)) in THF (10 mL) according to the procedure as described in step 6 of example 1, and the crude product was purified by silica gel column chromatography eluted with DCM/MeOH (v/v=30/1) to give the title compound as a white solid (120 mg, 39.2%). The compound was characterized by the following spectroscopic data: MS (ESI, pos. ion) m/z: 459.8 [M+H]⁺; ¹H NMR (600 MHz, CDCl₃) δ (ppm): 8.28 (dd, J=8.4, 1.8 Hz, 1H), 8.03 (t, J=1.8 Hz, 1H), 7.58 (td, J=7.8, 1.8 Hz, 1H), 7.53 (td, J=7.8, 1.2 Hz, 1H), 7.48 (dd, J=7.8, 1.2 Hz, 1H), 7.45 (d, J=1.8 Hz, 1H), 7.39 (t, J=55.2 Hz, 1H), 7.01 (d, J=1.8 Hz, 1H), 3.04 (t, J=4.2 Hz, 4H), 2.92 (brs, 4H); and ¹³C NMR (100 MHz, CDCl₃) δ (ppm): 148.6, 135.7, 135.8, 135.3, 133.1, 132.7, 131.7, 127.6, 127.4 (t, J=7.8 Hz), 122.2 (t, J=4.6 Hz), 117.1, 115.5 (t, J=24.2 Hz), 110.9 (t, J=233.6 Hz), 110.0, 54.6, 46.3.

Example 26 1-((2-bromophenyl)sulfonyl)-6-chloro-3-(difluoromethyl)-4-(piperazin-1-yl)-1H-indole

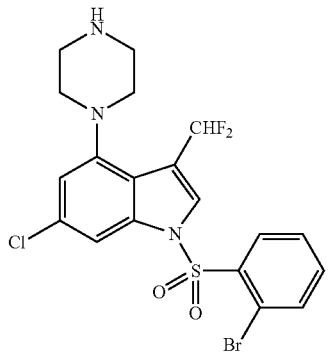 [SMILES: O=S(=O)(c1ccccc1Br)n1cc(C(F)F)c2c(N3CCNCC3)cc(Cl)cc21]

Step 1) 1-((2-bromophenyl)sulfonyl)-6-chloro-4-(4-(2,2,2-trifluoroacetyl)piperazin-1-yl)-1H-indole-3-carbaldehyde 6-Chloro-4-(4-(2,2,2-trifluoroacetyl)piperazin-1-yl)-1H-indole-3-carbaldehyde (280 mg, 0.78 mmol) was reacted with tetrabutylammonium hydrogen sulfate (13 mg, 0.039 mmol), potassium hydroxide (89 mg, 1.58 mmol) and 2-bromobenzenesulfonyl chloride (258 mg, 1.01 mmol) in DCM (15 mL) according to the procedure as described in step 4 of example 1, and the crude product was purified by silica gel column chromatography eluted with DCM/PE (v/v=2/1) to give the title compound as a brown solid (400 mg, 88.8%). The compound was characterized by the following spectroscopic data: MS (ESI, pos. ion) m/z: 578.1 [M+H]$^+$; and $^1$H NMR (400 MHz, CDCl$_3$) δ (ppm): 10.43 (s, 1H), 8.50 (s, 1H), 8.41 (dd, J=8.0, 1.6 Hz, 1H), 7.73 (dd, J=8.0, 0.8 Hz, 1H), 7.64 (td, J=8.0, 1.2 Hz, 1H), 7.53 (td, J=8.0, 1.6 Hz, 1H), 7.40 (d, J=1.6 Hz, 1H), 6.95 (d, J=1.6 Hz, 1H), 3.84 (brs, 4H), 3.10 (brs, 4H).

Step 2) 1-(4-(1-((2-bromophenyl)sulfonyl)-6-chloro-3-(difluoromethyl)-1H-indol-4-yl) piperazin-1-yl)-2,2,2-trifluoroethanone 1-((2-Bromophenyl)sulfonyl)-6-chloro-4-(4-(2,2,2-trifluoroacetyl)piperazin-1-yl)-1H-indole-3-carbaldehyde (400 mg, 0.69 mmol) was reacted with diethylaminosulphur trifluoride (0.28 mL, 2.14 mmol) in DCM (10 mL) according to the procedure as described in step 5 of example 1, and the crude product was purified by silica gel column chromatography eluted with PE/EtOAc (v/v=4/1) to give the title compound as a yellow solid (325 mg, 78.3%). The compound was characterized by the following spectroscopic data: MS (ESI, pos. ion) m/z: 599.7 [M+H]$^+$; and $^1$H NMR (400 MHz, CDCl$_3$) δ (ppm): 8.32 (dd, J=8.0, 1.6 Hz, 1H), 8.09 (s, 1H), 7.72 (dd, J=7.6, 0.8 Hz, 1H), 7.60 (td, J=7.6, 0.8 Hz, 1H), 7.53-7.47 (m, 2H), 7.31 (t, J=55.2 Hz, 1H), 7.03 (d, J=1.6 Hz, 1H), 3.63-2.76 (m, 8H).

Step 3) 1-((2-bromophenyl)sulfonyl)-6-chloro-3-(difluoromethyl)-4-(piperazin-1-yl)-1H-indole 1-(4-(1-((2-Bromophenyl)sulfonyl)-6-chloro-3-(difluoromethyl)-1H-indol-4-yl) piperazin-1-yl)-2,2,2-trifluoroethanone (325 mg, 0.54 mmol) was reacted with potassium hydroxide (62 mg, 1.1 mmol, dissolved in water (1 mL)) in THF (10 mL) according to the procedure as described in step 6 of example 1, and the crude product was purified by silica gel column chromatography eluted with DCM/MeOH (v/v=30/1) to give the title compound as a white solid (100 mg, 37.0%). The compound was characterized by the following spectroscopic data: MS (ESI, pos. ion) m/z: 504.1 [M+H]$^+$; $^1$H NMR (600 MHz, CDCl$_3$) δ (ppm): 8.28 (dd, J=7.8, 1.2 Hz, 1H), 8.08 (t, J=1.8 Hz, 1H), 7.71 (dd, J=7.8, 1.2 Hz, 1H), 7.58 (td, J=7.8, 1.2 Hz, 1H), 7.48 (td, J=7.8, 1.2 Hz, 1H), 7.43 (d, J=1.8 Hz, 1H), 7.40 (t, J=55.2 Hz, 1H), 7.02 (d, J=1.8 Hz, 1H), 3.04 (t, J=4.2 Hz, 4H), 2.93 (brs, 4H); and $^{13}$C NMR (150 MHz, CDCl$_3$) δ (ppm): 148.6, 137.0, 136.3, 135.8, 135.5, 131.9, 131.6, 128.6, 127.8 (t, J=7.65 Hz), 122.2 (t, J=4.5 Hz), 121.0, 117.1, 115.4 (t, J=24.3 Hz), 110.9 (t, J=233.4 Hz), 110.0, 54.5, 46.3.

Example 27 6-chloro-3-(difluoromethyl)-1-((3-fluorophenyl)sulfonyl)-4-(piperazin-1-yl)-1H-indole

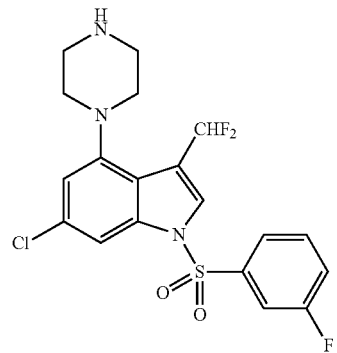 [SMILES: O=S(=O)(c1cccc(F)c1)n1cc(C(F)F)c2c(N3CCNCC3)cc(Cl)cc21]

Step 1) 6-chloro-1-((3-fluorophenyl)sulfonyl)-4-(4-(2,2,2-trifluoroacetyl)piperazin-1-yl)-1H-indole-3-carbaldehyde 6-Chloro-4-(4-(2,2,2-trifluoroacetyl)piperazin-1-yl)-1H-indole-3-carbaldehyde (300 mg, 0.83 mmol) was reacted with tetrabutylammonium hydrogen sulfate (15 mg, 0.043 mmol), potassium hydroxide (93 mg, 1.66 mmol) and 3-fluorobenzenesulfonyl chloride (212 mg, 1.09 mmol) in DCM (15 mL) according to the procedure as described in step 4 of example 1, and the crude product was purified by silica gel column chromatography eluted with DCM/PE (v/v=2/1) to give the title compound as a brown solid (380 mg, 88.0%). The compound was characterized by the following spectroscopic data: MS (ESI, pos. ion) m/z: 517.8 [M+H]$^+$; and $^1$H NMR (600 MHz, CDCl$_3$) δ (ppm): 10.46 (s, 1H), 8.28 (s, 1H), 7.82-7.79 (m, 2H), 7.67 (td, J=7.2, 1.8 Hz, 1H), 7.59 (dt, J=8.4, 5.4 Hz, 1H), 7.40-7.38 (m, 1H), 7.02 (d, J=1.8 Hz, 1H), 3.84 (brs, 4H), 3.11 (brs, 4H).

Step 2) 1-(4-(6-chloro-3-(difluoromethyl)-1-((3-fluorophenyl)sulfonyl)-1H-indol-4-yl) piperazin-1-yl)-2,2,2-trifluoroethanone 6-Chloro-1-((3-fluorophenyl)sulfonyl)-4-(4-(2,2,2-trifluoroacetyl)piperazin-1-yl)-1H-indole-3-carbaldehyde (380 mg, 0.73 mmol) was reacted with diethylaminosulphur trifluoride (0.29 mL, 2.21 mmol) in DCM (10 mL) according to the procedure as described in step 5 of example 1, and the crude product was purified by silica gel column chromatography eluted with PE/EtOAc (v/v=4/1) to give the title compound as a yellow solid (350 mg, 88.4%). The compound was characterized by the following spectroscopic data: MS (ESI, pos. ion) m/z: 540.2 [M+H]$^+$; $^1$H NMR (600 MHz, CDCl$_3$) δ (ppm): 7.85 (d, J=1.2 Hz, 2H), 7.75 (d, J=7.8 Hz, 1H), 7.62 (dt, J=7.8, 1.8 Hz, 1H), 7.54 (td, J=8.4, 4.2 Hz, 1H), 7.36-7.32 (m, 1H), 7.27 (t, J=55.2 Hz, 1H), 7.06 (d, J=1.8 Hz, 1H), 3.52-2.90 (m, 8H).

Step 3) 6-chloro-3-(difluoromethyl)-1-((3-fluorophenyl)sulfonyl)-4-(piperazin-1-yl)-1H-indole 1-(4-(6-Chloro-3-(difluoromethyl)-1-((3-fluorophenyl)sulfonyl)-1H-indol-4-yl) piperazin-1-yl)-2,2,2-trifluoroethanone (350 mg, 0.65 mmol) was reacted with potassium hydroxide (73 mg, 1.3 mmol, dissolved in water (1 mL)) in THF (10 mL) according to the procedure as described in step 6 of example 1, and the crude product was purified by silica gel column chromatography eluted with DCM/MeOH (v/v=30/1) to give the title compound as a white solid (102 mg, 34.8%). The compound was characterized by the following spectroscopic data: MS (ESI, pos. ion) m/z: 443.9 [M+H]$^+$; $^1$H NMR (600 MHz, CDCl$_3$) δ (ppm): 7.94 (d, J=1.2 Hz, 1H), 7.82 (s, 1H), 7.73 (d, J=8.4 Hz, 1H), 7.60 (dt, J=7.8, 1.8 Hz, 1H), 7.52 (td, J=7.8, 5.4 Hz, 1H), 7.35 (t, J=55.2 Hz, 1H), 7.32 (td, J=8.4, 1.8 Hz, 1H), 7.18 (d, J=1.8 Hz, 1H), 3.02 (brs, 4H), 2.91 (brs, 4H); and $^{13}$C NMR (100 MHz, CDCl$_3$) δ (ppm): 162.4 (d, J=252.3 Hz), 148.8, 139.4 (d, J=6.9 Hz), 136.4, 131.6 (d, J=7.8 Hz), 125.3 (t, J=7.7 Hz), 122.9 (d, J=3.5 Hz), 122.8 (t, J=4.6 Hz), 121.9 (d, J=21 Hz), 120.2, 119.8, 117.5 (t, J=24.4 Hz), 114.4 (d, J=24.8 Hz), 113.2, 110.7 (d, J=233.9 Hz), 54.6, 46.2.

Example 28 6-chloro-1-((3-chlorophenyl)sulfonyl)-3-(difluoromethyl)-4-(piperazin-1-yl)-1H-indole

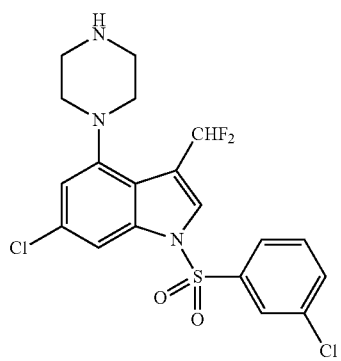 [SMILES: O=S(=O)(c1cccc(Cl)c1)n1cc(C(F)F)c2c(N3CCNCC3)cc(Cl)cc21]

Step 1) 6-chloro-1-((3-chlorophenyl)sulfonyl)-4-(4-(2,2,2-trifluoroacetyl)piperazin-1-yl)-1H-indole-3-carbaldehyde 6-Chloro-4-(4-(2,2,2-trifluoroacetyl)piperazin-1-yl)-1H-indole-3-carbaldehyde (300 mg, 0.83 mmol) was reacted with tetrabutylammonium hydrogen sulfate (15 mg, 0.043 mmol), potassium hydroxide (93 mg, 1.66 mmol) and 3-chlorobenzenesulfonyl chloride (228 mg, 1.08 mmol) in DCM (15 mL) according to the procedure as described in step 4 of example 1, and the crude product was purified by silica gel column chromatography eluted with DCM/PE (v/v=2/1) to give the title compound as a brown solid (420 mg, 94.3%). The compound was characterized by the following spectroscopic data: MS (ESI, pos. ion) m/z: 533.8 [M+H]$^+$; and $^1$H NMR (400 MHz, CDCl$_3$) δ (ppm): 10.43 (s, 1H), 8.25 (s, 1H), 7.92 (t, J=1.6 Hz, 1H), 7.86 (d, J=8.0 Hz, 1H), 7.78 (d, J=1.6 Hz, 1H), 7.65-7.61 (m, 1H), 7.51 (t, J=8.0 Hz, 1H), 7.00 (d, J=1.2 Hz, 1H), 3.82 (brs, 4H), 3.09 (brs, 4H).

Step 2) 1-(4-(6-chloro-1-((3-chlorophenyl)sulfonyl)-3-(difluoromethyl)-1H-indol-4-yl) piperazin-1-yl)-2,2,2-trifluoroethanone 6-Chloro-1-((3-chlorophenyl)sulfonyl)-4-(4-(2,2,2-trifluoroacetyl)piperazin-1-yl)-1H-indole-3-carbaldehyde (420 mg, 0.79 mmol) was reacted with diethylaminosulphur trifluoride (0.31 mL, 2.37 mmol) in DCM (10 mL) according to the procedure as described in step 5 of example 1, and the crude product was purified by silica gel column chromatography eluted with PE/EtOAc (v/v=4/1) to give the title compound as a yellow solid (400 mg, 91.5%). The compound was characterized by the following spectroscopic data: MS (ESI, pos. ion) m/z: 555.7 [M+H]$^+$; and $^1$H NMR (400 MHz, CDCl$_3$) δ (ppm): 7.90 (t, J=1.6 Hz, 1H), 7.86-7.81 (m, 3H), 7.63-7.59 (m, 1H), 7.49 (t, J=8.0 Hz, 1H), 7.27 (t, J=55.2 Hz, 1H), 7.07 (d, J=1.6 Hz, 1H), 4.02-2.85 (m, 8H).

Step 3) 6-chloro-1-((3-chlorophenyl)sulfonyl)-3-(difluoromethyl)-4-(piperazin-1-yl)-1H-indole 1-(4-(6-Chloro-1-((3-chlorophenyl)sulfonyl)-3-(difluoromethyl)-1H-indol-4-yl) piperazin-1-yl)-2,2,2-trifluoroethanone (400 mg, 0.72 mmol) was reacted with potassium hydroxide (84 mg, 1.50 mmol, dissolved in water (1 mL)) in THF (10 mL) according to the procedure as described in step 6 of example 1, and the crude product was purified by silica gel column chromatography eluted with DCM/MeOH (v/v=30/1) to give the title compound as a white solid (130 mg, 39.3%). The compound was characterized by the following spectroscopic data: MS (ESI, pos. ion) m/z: 459.9 [M+H]$^+$; $^1$H NMR (600 MHz, CDCl$_3$) δ (ppm): 7.90 (t, J=1.8 Hz, 1H), 7.83 (s, 1H), 7.81 (d, J=8.4 Hz, 1H), 7.77 (d, J=1.2 Hz, 1H), 7.58 (dd, J=7.8, 1.2 Hz, 1H), 7.47 (t, J=7.8 Hz, 1H), 7.36 (t, J=55.2 Hz, 1H), 7.05 (d, J=1.8 Hz, 1H), 3.02 (brs, 4H), 2.90 (brs, 4H); and $^{13}$C NMR (100 MHz, CDCl$_3$) δ (ppm): 148.7, 139.2, 136.0, 135.9, 134.7, 132.3, 130.9, 127.1, 125.4 (t, J=7.8 Hz), 125.1, 122.3 (t, J=4.4 Hz), 117.5 (t, J=24.2 Hz), 117.4, 110.8 (t, J=233.8 Hz), 110.3, 54.6, 46.3.

Example 29 1-((3-bromophenyl)sulfonyl)-6-chloro-3-(difluoromethyl)-4-(piperazin-1-yl)-1H-indole

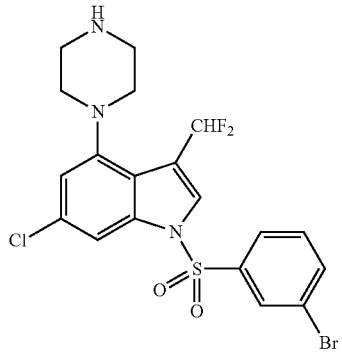 [SMILES: O=S(=O)(c1cccc(Br)c1)n1cc(C(F)F)c2c(N3CCNCC3)cc(Cl)cc21]

Step 1) 1-((3-bromophenyl)sulfonyl)-6-chloro-4-(4-(2,2,2-trifluoroacetyl)piperazin-1-yl)-1H-indole-3-carbaldehyde 6-Chloro-4-(4-(2,2,2-trifluoroacetyl)piperazin-1-yl)-1H-indole-3-carbaldehyde (300 mg, 0.83 mmol) was reacted with tetrabutylammonium hydrogen sulfate (15 mg, 0.043 mmol), potassium hydroxide (93 mg, 1.66 mmol) and 3-bromobenzenesulfonyl chloride (278 mg, 1.09 mmol) in DCM (15 mL) according to the procedure as described in step 4 of example 1, and the crude product was purified by silica gel column chromatography eluted with DCM/PE (v/v=2/1) to give the title compound as a brown solid (440 mg, 91.1%). The compound was characterized by the following spectroscopic data: MS (ESI, pos. ion) m/z: 577.7 [M+H]$^+$; and $^1$H NMR (400 MHz, CDCl$_3$) δ (ppm): 10.44 (s, 1H), 8.25 (s, 1H), 8.07 (t, J=1.6 Hz, 1H), 7.91 (d, J=8.0 Hz, 1H), 7.81-7.76 (m, 2H), 7.44 (t, J=8.0 Hz, 1H), 7.00 (d, J=1.6 Hz, 1H), 3.82 (brs, 4H), 3.09 (brs, 4H).

Step 2) 1-(4-(1-((3-bromophenyl)sulfonyl)-6-chloro-3-(difluoromethyl)-1H-indol-4-yl)piperazin-1-yl)-2,2,2-trifluoroethanone 1-((3-Bromophenyl)sulfonyl)-6-chloro-4-(4-(2,2,2-trifluoroacetyl)piperazin-1-yl)-1H-indole-3-carbaldehyde (435 mg, 0.75 mmol) was reacted with diethylaminosulphur trifluoride (0.30 mL, 2.29 mmol) in DCM (10 mL) according to the procedure as described in step 5 of example 1, and the crude product was purified by silica gel column chromatography eluted with PE/EtOAc (v/v=4/1) to give the title compound as a yellow solid (410 mg, 90.8%). The compound was characterized by the following spectroscopic data: MS (ESI, pos. ion) m/z: 600.1 [M+H]$^+$; and $^1$H NMR (400 MHz, CDCl$_3$) δ (ppm): 8.06 (s, 1H), 7.87 (d, J=8.4 Hz, 1H), 7.84 (d, J=1.2 Hz, 2H), 7.76 (d, J=8.4 Hz, 1H), 7.44-7.41 (m, 1H), 7.27 (t, J=55.2 Hz, 1H), 7.07 (d, J=1.6 Hz, 1H), 3.60-2.80 (m, 8H).

Step 3) 1-((3-bromophenyl)sulfonyl)-6-chloro-3-(difluoromethyl)-4-(piperazin-1-yl)-1H-indole 1-(4-(1-((3-Bromophenyl)sulfonyl)-6-chloro-3-(difluoromethyl)-1H-indol-4-yl) piperazin-1-yl)-2,2,2-trifluoroethanone (410 mg, 0.68 mmol) was reacted with potassium hydroxide (77 mg, 1.37 mmol, dissolved in water (1 mL)) in THF (10 mL) according to the procedure as described in step 6 of example 1, and the crude product was purified by silica gel column chromatography eluted with DCM/MeOH (v/v=30/1) to give the title compound as a white solid (180 mg, 52.3%). The compound was characterized by the following spectroscopic data: MS (ESI, pos. ion) m/z: 503.8 [M+H]$^+$; $^1$H NMR (600 MHz, CDCl$_3$) δ (ppm): 8.05 (s, 1H), 7.85 (d, J=8.4 Hz, 1H), 7.83 (s, 1H), 7.77 (d, J=1.2 Hz, 1H), 7.73 (d, J=8.4 Hz, 1H), 7.40 (t, J=7.8 Hz, 1H), 7.36 (t, J=55.2 Hz, 1H), 7.05 (d, J=1.2 Hz, 1H), 3.02 (brs, 4H), 2.90 (brs, 4H); and $^{13}$C NMR (150 MHz, CDCl$_3$) δ (ppm): 148.7, 139.3, 137.7, 136.0, 132.3, 131.1, 129.9, 125.6, 125.4 (t, J=7.80 Hz), 123.6, 122.4 (t, J=4.35 Hz), 117.5, 117.4 (t, J=24.45 Hz), 110.8 (t, J=233.85 Hz), 110.3, 54.6, 46.3.

Example 30 6-chloro-3-(difluoromethyl)-1-((4-methoxyphenyl)sulfonyl)-4-(piperazin-1-yl)-1H-indole

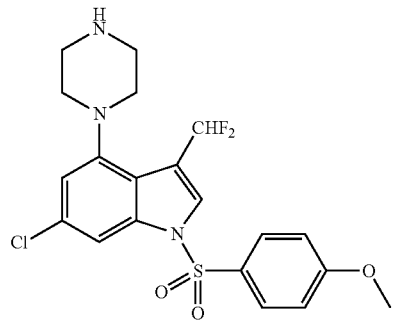 [SMILES: COc1ccc(S(=O)(=O)n2cc(C(F)F)c3c(N4CCNCC4)cc(Cl)cc32)cc1]

Step 1) 6-chloro-1-((4-methoxyphenyl)sulfonyl)-4-(4-(2,2,2-trifluoroacetyl)piperazin-1-yl)-1H-indole-3-carbaldehyde 6-Chloro-4-(4-(2,2,2-trifluoroacetyl)piperazin-1-yl)-1H-indole-3-carbaldehyde (330 mg, 0.97 mmol) was reacted with tetrabutylammonium hydrogen sulfate (15 mg, 0.045 mmol), potassium hydroxide (101 mg, 1.80 mmol) and 4-methoxybenzenesulfonyl chloride (248 mg, 1.2 mmol) in DCM (15 mL) according to the procedure as described in step 4 of example 1, and the crude product was purified by silica gel column chromatography eluted with DCM/PE (v/v=2/1) to give the title compound as a brown solid (400 mg, 82.3%). The compound was characterized by the following spectroscopic data: $^1$H NMR (400 MHz, CDCl$_3$) δ (ppm): 10.44 (s, 1H), 7.92-7.90 (m, 1H), 7.88 (s, 2H), 7.85 (d, J=1.6 Hz, 1H), 7.04 (d, J=1.2 Hz, 1H), 7.02-6.98 (m, 2H), 3.83 (brs, 4H), 3.79 (s, 3H), 3.09 (brs, 4H).

Step 2) 1-(4-(6-chloro-3-(difluoromethyl)-1-((4-methoxyphenyl)sulfonyl)-1H-indol-4-yl) piperazin-1-yl)-2,2,2-trifluoroethanone 6-Chloro-1-((4-methoxyphenyl)sulfonyl)-4-(4-(2,2,2-trifluoroacetyl)piperazin-1-yl)-1H-indole-3-carbaldehyde (250 mg, 0.44 mmol) was reacted with diethylaminosulphur trifluoride (0.20 mL, 1.53 mmol) in DCM (10 mL) according to the procedure as described in step 5 of example 1, and the crude product was purified by silica gel column chromatography eluted with PE/EtOAc (v/v=4/1) to give the title compound as a yellow solid (223 mg, 86.0%). The compound was characterized by the following spectroscopic data: MS (ESI, pos. ion) m/z: 551.8 [M+H]$^+$; and $^1$H NMR (400 MHz, CDCl$_3$) δ (ppm): 8.03 (d, J=1.2 Hz, 1H), 7.92-7.88 (m, 2H), 7.88-7.87 (m, 1H), 7.29 (t, J=55.2 Hz, 1H), 7.18 (d, J=1.2 Hz, 1H), 7.02-6.98 (m, 2H), 3.86 (s, 3H), 3.01 (br, 8H).

Step 3) 6-chloro-3-(difluoromethyl)-1-((4-methoxyphenyl)sulfonyl)-4-(piperazin-1-yl)-1H-indole 1-(4-(6-Chloro-3-(difluoromethyl)-1-((4-methoxyphenyl)sulfonyl)-1H-indol-4-yl) piperazin-1-yl)-2,2,2-trifluoroethanone (275 mg, 0.50 mmol) was reacted with potassium hydroxide (56 mg, 1.0 mmol, dissolved in water (1 mL)) in THF (10 mL) according to the procedure as described in step 6 of example 1, and the crude product was purified by silica gel column chromatography eluted with DCM/MeOH (v/v=30/1) to give the title compound as a white solid (175 mg, 77.0%). The compound was characterized by the following spectroscopic data: MS (ESI, pos. ion) m/z: 456.2 [M+H]$^+$; $^1$H NMR (600 MHz, CDCl$_3$) δ (ppm): 7.87-7.86 (m, 1H), 7.85 (s, 2H), 7.78 (d, J=1.2 Hz, 1H), 7.34 (t, J=55.2 Hz, 1H), 7.01 (d, J=1.8 Hz, 1H), 6.96-6.93 (m, 2H), 3.82 (s, 3H), 3.04 (brs, 4H), 2.92 (brs, 4H); and $^{13}$C NMR (150 MHz, CDCl$_3$) δ (ppm): 164.4, 148.2, 136.0, 131.8, 129.5, 128.9, 125.7 (t, J=7.65 Hz), 122.2 (t, J=4.35 Hz), 117.0, 116.5 (t, J=24.3 Hz), 114.9, 111.0 (t, J=233.4 Hz), 110.4, 55.8, 54.2, 46.1.

Example 31 6-bromo-3-(difluoromethyl)-4-(piperazin-1-yl)-1-((2-(trifluoromethyl)phenyl) sulfonyl)-1H-indole

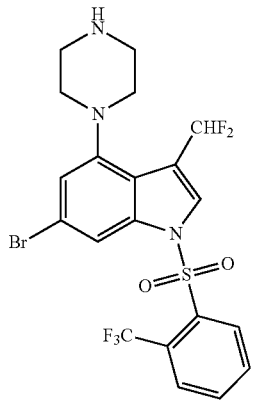

Step 1) 6-bromo-4-(piperazin-1-yl)-1H-indole

To 50 mL of isopropanol were added 6-bromo-4-aminoindole (4.5 g, 21.0 mmol), bis(2-chloroethyl)amine hydrochloride (5.71 g, 32.0 mmol) and potassium carbonate (6.48 g, 46.9 mmol). The mixture was stirred for 48 hours at 90° C., then to the mixture were added dichloromethane (50 mL) and methanol (50 mL). The resulting mixture was filtered and the filtrate was concentrated in vacuo. The residue was purified by silica gel column chromatography eluted with DCM/MeOH (v/v=10/1) to give the title compound as a brown solid (2.5 g, 42.0%). The compound was characterized by the following spectroscopic data: MS (ESI, pos. ion) m/z: 280.0 [M+H]$^+$; and $^1$H NMR (400 MHz, CD$_3$OD) δ (ppm): 7.27 (s, 1H), 7.20 (d, J=3.2 Hz, 1H), 6.66 (d, J=1.6 Hz, 1H), 6.47 (dd, J=3.2, 0.8 Hz, 1H), 3.34-3.30 (m, 8H).

Step 2) 1-(4-(6-bromo-1H-indol-4-yl)piperazin-1-yl)-2,2,2-trifluoroethanone

To a solution of 6-bromo-4-(piperazin-1-yl)-1H-indole (2.5 g, 8.9 mmol) and triethylamine (3.7 mL, 27.0 mmol) in dichloromethane (20 mL) was added a solution of trifluoroacetic anhydride (1.9 mL, 13.0 mmol) in dichloromethane (20 mL) at 0° C. in an low temperature bath. The mixture was stirred at rt for 4 hours, then diluted with dichloromethane (50 mL) and the resulting mixture washed with saturated aqueous sodium bicarbonate (60 mL). The organic layer was dried over anhydrous sodium sulfate and filtered. The filtrate was concentrated in vacuo and the residue was purified by silica gel column chromatography eluted with PE/EtOAc (v/v=10/1) to give the title compound as a yellow solid (3.0 g, 89%). The compound was characterized by the following spectroscopic data: MS (ESI, pos. ion) m/z: 376.0 [M+H]$^+$; and $^1$H NMR (400 MHz, CDCl$_3$) δ (ppm): 8.27 (s, 1H), 7.29 (s, 1H), 7.17 (t, J=2.4 Hz, 1H), 6.68 (d, J=1.2 Hz, 1H), 6.49 (t, J=2.4 Hz, 1H), 3.92 (t, J=4.8 Hz, 2H), 3.84 (t, J=4.8 Hz, 2H), 3.28 (t, J=4.8 Hz, 4H).

Step 3) 6-bromo-4-(4-(2,2,2-trifluoroacetyl)piperazin-1-yl)-1H-indole-3-carbaldehyde To a solution of 1-(4-(6-bromo-1H-indol-4-yl)piperazin-1-yl)-2,2,2-trifluoroethanone (3.0 g, 7.97 mmol) in N,N-dimethylformamide (15 mL) was added dropwise slowly phosphorus oxychloride (0.95 mL, 10.3 mmol) at 0° C. The mixture was warmed to 25° C. and stirred for 24 hours. The reaction mixture was quenched with water (30 mL) and the resulting mixture was neutralized with sodium carbonate solid to pH about 8-9. The mixture was filtered and the filtrate was dried in vacuo to give the title compound as a claybank solid (1.95 g, 60.5%). The compound was characterized by the following spectroscopic data: MS (ESI, pos. ion) m/z: 403.9 [M+H]$^+$; and $^1$H NMR (400 MHz, CDCl$_3$) δ (ppm): 10.32 (s, 1H), 9.43 (s, 1H), 7.93 (d, J=2.8 Hz, 1H), 7.38 (d, J=1.2 Hz, 1H), 6.99 (d, J=1.2 Hz, 1H), 3.87 (brs, 4H), 3.16 (brs, 4H).

Step 4) 6-bromo-4-(4-(2,2,2-trifluoroacetyl)piperazin-1-yl)-1-((2-(trifluoromethyl)phenyl) sulfonyl)-1H-indole-3-carbaldehyde 6-Bromo-4-(4-(2,2,2-trifluoroacetyl)piperazin-1-yl)-1H-indole-3-carbaldehyde (290 mg, 0.72 mmol) was reacted with tetrabutylammonium hydrogen sulfate (12 mg, 0.035 mmol), potassium hydroxide (80.5 mg, 1.43 mmol) and 2-trifluoromethylbenzenesulfonyl chloride (228 mg, 0.93 mmol) in DCM (15 mL) according to the procedure as described in step 4 of example 1, and the crude product was purified by silica gel column chromatography eluted with DCM/PE (v/v=2/1) to give the title compound as a white solid (330 mg, 75.1%). The compound was characterized by the following spectroscopic data: MS (ESI, pos. ion) m/z: 612.1 [M+H]$^+$; and $^1$H NMR (400 MHz, CDCl$_3$) δ (ppm): 10.45 (s, 1H), 8.30 (d, J=1.2 Hz, 1H), 8.15-8.09 (m, 1H), 7.99-7.97 (m, 1H), 7.89-7.80 (m, 2H), 7.72 (d, J=1.2 Hz, 1H), 7.13 (d, J=1.2 Hz, 1H), 3.87 (brs, 4H), 3.13 (brs, 4H).

Step 5) 1-(4-(6-bromo-3-(difluoromethyl)-1-((2-(trifluoromethyl)phenyl)sulfonyl)-1H-indol-4-yl) piperazin-1-yl)-2,2,2-trifluoroethanone 6-Bromo-4-(4-(2,2,2-trifluoroacetyl)piperazin-1-yl)-1-((2-(trifluoromethyl)phenyl) sulfonyl)-1H-indole-3-carbaldehyde (324 mg, 0.53 mmol) was reacted with diethylaminosulphur trifluoride (0.21 mL, 1.59 mmol) in DCM (10 mL) according to the procedure as described in step 5 of example 1, and the crude product was purified by silica gel column chromatography eluted with PE/EtOAc (v/v=4/1) to give the title compound as a yellow solid (300 mg, 89.4%). The compound was characterized by the following spectroscopic data: MS (ESI, pos. ion) m/z: 634.1 [M+H]$^+$; and $^1$H NMR (400 MHz, CDCl$_3$) δ (ppm): 7.97-7.92 (m, 2H), 7.89 (s, 1H), 7.83-7.73 (m, 3H), 7.30 (t, J=55.2 Hz, 1H), 7.20 (d, J=1.2 Hz, 1H), 3.53-3.02 (m, 8H).

Step 6) 6-bromo-3-(difluoromethyl)-4-(piperazin-1-yl)-1-((2-(trifluoromethyl)phenyl)sulfonyl)-1H-indole 1-(4-(6-Bromo-3-(difluoromethyl)-1-((2-(trifluoromethyl)phenyl)sulfonyl)-1H-indol-4-yl)piperazin-1-yl)-2,2,2-trifluoroethanone (295 mg, 0.47 mmol) was reacted with potassium hydroxide (52 mg, 0.93 mmol, dissolved in water (1 mL)) in THF (10 mL) according to the procedure as described in step 6 of example 1, and the crude product was purified by silica gel column chromatography eluted with DCM/MeOH (v/v=30/1) to give the title compound as a white solid (120 mg, 47.9%). The compound was characterized by the following spectroscopic data: MS (ESI, pos. ion) m/z: 538.1 [M+H]$^+$; $^1$H NMR (600 MHz, CDCl$_3$) δ (ppm): 7.93 (d, J=7.8 Hz, 1H), 7.88 (s, 1H), 7.81 (d, J=8.4 Hz, 1H), 7.78 (t, J=7.8 Hz, 1H), 7.72 (m, 2H), 7.40 (t, J=55.2 Hz, 1H), 7.19 (d, J=1.2 Hz, 1H), 3.04 (brs, 4H), 2.93 (brs, 4H); and $^{13}$C NMR (150 MHz, CDCl$_3$) δ (ppm): 148.8, 137.0, 136.5, 134.4, 133.0, 130.4, 129.1 (q, J=6.0 Hz), 128.5 (q, J=33.6 Hz), 126.5 (t, J=7.65 Hz), 122.5 (t, J=4.5 Hz), 122.1 (q, J=272.55 Hz), 120.2, 119.6, 116.5 (t, J=24.3 Hz), 113.2, 110.8 (t, J=233.85 Hz), 54.6, 46.3.

Example 32 6-bromo-3-(difluoromethyl)-1-((2-fluorophenyl)sulfonyl)-4-(piperazin-1-yl)-1H-indole

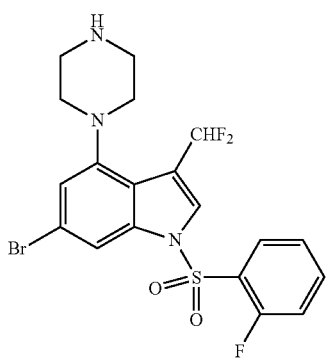 [SMILES: O=S(=O)(c1ccccc1F)n1cc(C(F)F)c2c(N3CCNCC3)cc(Br)cc21]

Step 1) 6-bromo-1-((2-fluorophenyl)sulfonyl)-4-(4-(2,2,2-trifluoroacetyl)piperazin-1-yl)-1H-indole-3-carbaldehyde 6-Bromo-4-(4-(2,2,2-trifluoroacetyl)piperazin-1-yl)-1H-indole-3-carbaldehyde (300 mg, 0.74 mmol) was reacted with tetrabutylammonium hydrogen sulfate (15 mg, 0.043 mmol), potassium hydroxide (93 mg, 1.66 mmol) and 2-fluorobenzenesulfonyl chloride (189 mg, 0.97 mmol) in DCM (15 mL) according to the procedure as described in step 4 of example 1, and the crude product was purified by silica gel column chromatography eluted with DCM/PE (v/v=2/1) to give the title compound as a brown solid (400 mg, 95.8%). The compound was characterized by the following spectroscopic data: MS (ESI, pos. ion) m/z: 562.1 [M+H]$^+$; and $^1$H NMR (600 MHz, CDCl$_3$) δ (ppm): 10.41 (s, 1H), 8.35 (d, J=2.4 Hz, 1H), 8.17 (td, J=7.8, 1.2 Hz, 1H), 7.77 (d, J=1.2 Hz, 1H), 7.72-7.67 (m, 1H), 7.42 (td, J=7.8, 1.2 Hz, 1H), 7.18 (td, J=8.4, 0.6 Hz, 1H), 7.09 (d, J=1.2 Hz, 1H), 3.84 (brs, 4H), 3.09 (brs, 4H).

Step 2) 1-(4-(6-bromo-3-(difluoromethyl)-1-((2-fluorophenyl)sulfonyl)-1H-indol-4-yl) piperazin-1-yl)-2,2,2-trifluoroethanone 6-Bromo-1-((2-fluorophenyl)sulfonyl)-4-(4-(2,2,2-trifluoroacetyl)piperazin-1-yl)-1H-indole-3-carbaldehyde (400 mg, 0.71 mmol) was reacted with diethylaminosulphur trifluoride (0.28 mL, 2.14 mmol) in DCM (10 mL) according to the procedure as described in step 5 of example 1, and the crude product was purified by silica gel column chromatography eluted with PE/EtOAc (v/v=4/1) to give the title compound as a yellow solid (400 mg, 96.2%). The compound was characterized by the following spectroscopic data: MS (ESI, pos. ion) m/z: 584.2 [M+H]$^+$; and $^1$H NMR (600 MHz, CDCl$_3$) δ (ppm): 8.15-8.11 (m, 1H), 7.94 (d, J=1.8 Hz, 1H), 7.86 (d, J=1.2 Hz, 1H), 7.69-7.64 (m, 1H), 7.39 (t, J=7.8 Hz, 1H), 7.28 (t, J=55.2 Hz, 1H), 7.20-7.16 (m, 2H), 3.68-2.69 (m, 8H).

Step 3) 6-bromo-3-(difluoromethyl)-1-((2-fluorophenyl)sulfonyl)-4-(piperazin-1-yl)-1H-indole 1-(4-(6-Bromo-3-(difluoromethyl)-1-((2-fluorophenyl)sulfonyl)-1H-indol-4-yl) piperazin-1-yl)-2,2,2-trifluoroethanone (400 mg, 0.69 mmol) was reacted with potassium hydroxide (77 mg, 1.37 mmol, dissolved in water (1 mL)) in THF (10 mL) according to the procedure as described in step 6 of example 1, and the crude product was purified by silica gel column chromatography eluted with DCM/MeOH (v/v=30/1) to give the title compound as a white solid (120 mg, 35.9%). The compound was characterized by the following spectroscopic data: MS (ESI, pos. ion) m/z: 487.8 [M+H]$^+$; $^1$H NMR (600 MHz, CDCl$_3$) δ (ppm): 8.13-8.09 (m, 1H), 7.93 (d, J=1.8 Hz, 1H), 7.79 (d, J=1.2 Hz, 1H), 7.66-7.62 (m, 1H), 7.38 (dd, J=14.4, 1.2 Hz, 1H), 7.27 (t, J=55.2 Hz, 1H), 7.18-7.14 (m, 2H), 3.03 (brs, 4H), 2.92 (brs, 4H); and $^{13}$C NMR (150 MHz, CDCl$_3$) δ (ppm): 159.2 (d, J=258.45 Hz), 148.6, 137.2 (d, J=8.55 Hz), 136.1, 130.4, 126.3 (td, J=7.35, 2.25 Hz), 125.6 (d, J=13.35 Hz), 125.0 (d, J=3.7 Hz), 122.7 (t, J=4.5 Hz), 120.0, 119.3, 117.8 (d, J=20.55 Hz), 116.4 (t, J=24.15 Hz), 113.2, 110.9 (t, J=233.7 Hz), 54.5, 46.2.

Example 33 6-bromo-1-((2-chlorophenyl)sulfonyl)-3-(difluoromethyl)-4-(piperazin-1-yl)-1H-indole

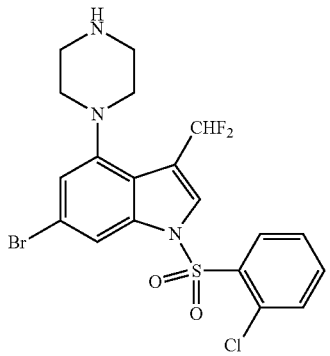 [SMILES: O=S(=O)(c1ccccc1Cl)n1cc(C(F)F)c2c(N3CCNCC3)cc(Br)cc21]

Step 1) 6-bromo-1-((2-chlorophenyl)sulfonyl)-4-(4-(2,2,2-trifluoroacetyl)piperazin-1-yl)-1H-indole-3-carbaldehyde 6-Bromo-4-(4-(2,2,2-trifluoroacetyl)piperazin-1-yl)-1H-indole-3-carbaldehyde (300 mg, 0.74 mmol) was reacted with tetrabutylammonium hydrogen sulfate (13 mg, 0.038 mmol), potassium hydroxide (83 mg, 1.49 mmol) and 2-chlorobenzenesulfonyl chloride (204 mg, 0.97 mmol) in DCM (15 mL) according to the procedure as described in step 4 of example 1, and the crude product was purified by silica gel column chromatography eluted with DCM/PE (v/v=2/1) to give the title compound as a brown solid (320 mg, 74.5%). The compound was characterized by the following spectroscopic data: MS (ESI, pos. ion) m/z: 578.1 [M+H]$^+$; and $^1$H NMR (400 MHz, CDCl$_3$) δ (ppm): 10.46 (s, 1H), 8.26 (s, 1H), 7.96 (d, J=1.6 Hz, 1H), 7.94 (t, J=2.0 Hz, 1H), 7.89 (d, J=8.0 Hz, 1H), 7.65 (dd, J=8.0, 0.8 Hz, 1H), 7.53 (t, J=8.0 Hz, 1H), 7.15 (d, J=1.2 Hz, 1H), 3.84 (brs, 4H), 3.11 (brs, 4H).

Step 2) 1-(4-(6-bromo-1-((2-chlorophenyl)sulfonyl)-3-(difluoromethyl)-1H-indol-4-yl) piperazin-1-yl)-2,2,2-trifluoroethanone 6-Bromo-1-((2-chlorophenyl)sulfonyl)-4-(4-(2,2,2-trifluoroacetyl)piperazin-1-yl)-1H-indole-3-carbaldehyde (350 mg, 0.61 mmol) was reacted with diethylaminosulphur trifluoride (0.24 mL, 1.83 mmol) in DCM (10 mL) according to the procedure as described in step 5 of example 1, and the crude product was purified by silica gel column chromatography eluted with PE/EtOAc (v/v=4/1) to give the title compound as a yellow solid (320 mg, 88.1%). The compound was characterized by the following spectroscopic data: MS (ESI, pos. ion) m/z: 599.7 [M+H]$^+$; and $^1$H NMR (400 MHz, CDCl$_3$) δ (ppm): 8.34 (dd, J=8.0, 1.6 Hz, 1H), 8.06 (t, J=1.6 Hz, 1H), 7.70 (d, J=1.6 Hz, 1H), 7.66-7.55 (m, 2H), 7.52 (dd, J=7.6, 1.2 Hz, 1H), 7.31 (t, J=55.2 Hz, 1H), 7.18 (d, J=1.2 Hz, 1H), 3.56-3.04 (m, 8H).

Step 3) 6-bromo-1-((2-chlorophenyl)sulfonyl)-3-(difluoromethyl)-4-(piperazin-1-yl)-1H-indole 1-(4-(6-Bromo-1-((2-chlorophenyl)sulfonyl)-3-(difluoromethyl)-1H-indol-4-yl) piperazin-1-yl)-2,2,2-trifluoroethanone (310 mg, 0.52 mmol) was reacted with potassium hydroxide (59 mg, 1.05 mmol, dissolved in water (1 mL)) in THF (10 mL) according to the procedure as described in step 6 of example 1, and the crude product was purified by silica gel column chromatography eluted with DCM/MeOH (v/v=30/1) to give the title compound as a white solid (180 mg, 59.1%). The compound was characterized by the following spectroscopic data: MS (ESI, pos. ion) m/z: 503.8 [M+H]$^+$; $^1$H NMR (600 MHz, CDCl$_3$) δ (ppm): 8.26 (dd, J=7.8, 1.2 Hz, 1H), 8.01 (s, 1H), 7.60 (d, J=1.2 Hz, 1H), 7.57 (td, J=7.8, 1.2 Hz, 1H), 7.53-7.51 (m, 1H), 7.47 (s, 1H), 7.38 (t, J=55.2 Hz, 1H), 7.14 (d, J=1.2 Hz, 1H), 3.03 (brs, 4H), 2.91 (brs, 4H); and $^{13}$C NMR (150 MHz, CDCl$_3$) δ (ppm): 148.7, 136.1, 135.7, 135.2, 133.1, 132.7, 131.7, 127.6, 127.4 (t, J=7.65 Hz), 122.6 (t, J=4.5 Hz), 119.9, 119.2, 115.5 (t, J=24.3 Hz), 112.9, 110.9 (t, J=233.7 Hz), 54.5, 46.2.

Example 34 6-bromo-1-((2-bromophenyl)sulfonyl)-3-(difluoromethyl)-4-(piperazin-1-yl)-1H-indole

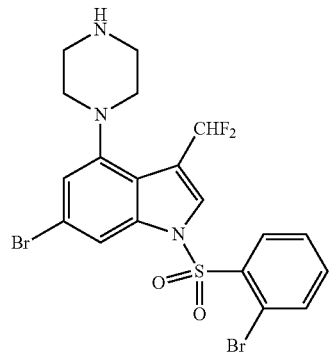

Step 1) 6-bromo-1-((2-bromophenyl)sulfonyl)-4-(4-(2,2,2-trifluoroacetyl)piperazin-1-yl)-1H-indole-3-carbaldehyde 6-Bromo-4-(4-(2,2,2-trifluoroacetyl)piperazin-1-yl)-1H-indole-3-carbaldehyde (300 mg, 0.74 mmol) was reacted with tetrabutylammonium hydrogen sulfate (12 mg, 0.037 mmol), potassium hydroxide (83 mg, 1.49 mmol) and 2-bromobenzenesulfonyl chloride (247 mg, 0.97 mmol) in DCM (15 mL) according to the procedure as described in step 4 of example 1, and the crude product was purified by silica gel column chromatography eluted with DCM/PE (v/v=2/1) to give the title compound as a brown solid (380 mg, 78.0%). The compound was characterized by the following spectroscopic data: MS (ESI, pos. ion) m/z: 621.8 [M+H]$^+$; and $^1$H NMR (400 MHz, CDCl$_3$) δ (ppm): 10.43 (s, 1H), 8.49 (s, 1H), 8.40 (dd, J=8.0, 1.6 Hz, 1H), 7.72 (dd, J=8.0, 1.2 Hz, 1H), 7.64 (td, J=7.6, 0.8 Hz, 1H), 7.54-7.52 (m, 2H), 7.08 (d, J=1.2 Hz, 1H), 3.84 (brs, 4H), 3.10 (brs, 4H).

Step 2) 1-(4-(6-bromo-1-((2-bromophenyl)sulfonyl)-3-(difluoromethyl)-1H-indol-4-yl) piperazin-1-yl)-2,2,2-trifluoroethanone 6-Bromo-1-((2-bromophenyl)sulfonyl)-4-(4-(2,2,2-trifluoroacetyl)piperazin-1-yl)-1H-indole-3-carbaldehyde (360 mg, 0.58 mmol) was reacted with diethylaminosulphur trifluoride (0.23 mL, 1.73 mmol) in DCM (10 mL) according to the procedure as described in step 5 of example 1, and the crude product was purified by silica gel column chromatography eluted with PE/EtOAc (v/v=4/1) to give the title compound as a yellow solid (326 mg, 87.2%). The compound was characterized by the following spectroscopic data: $^1$H NMR (400 MHz, CDCl$_3$) δ (ppm): 8.34 (dd, J=8.0, 1.6 Hz, 1H), 8.10 (s, 1H), 7.75 (dd, J=8.0, 0.8 Hz, 1H), 7.68 (d, J=1.2 Hz, 1H), 7.63 (td, J=8.0, 1.2 Hz, 1H), 7.53 (td, J=7.6, 1.6 Hz, 1H), 7.33 (t, J=55.2 Hz, 1H), 7.18 (d, J=1.2 Hz, 1H), 3.57-3.05 (m, 8H).

Step 3) 6-bromo-1-((2-bromophenyl)sulfonyl)-3-(difluoromethyl)-4-(piperazin-1-yl)-1H-indole 1-(4-(6-Bromo-1-((2-bromophenyl)sulfonyl)-3-(difluoromethyl)-1H-indol-4-yl) piperazin-1-yl)-2,2,2-trifluoroethanone (320 mg, 0.50 mmol) was reacted with potassium hydroxide (56 mg, 1.0 mmol, dissolved in water (1 mL)) in THF (10 mL) according to the procedure as described in step 6 of example 1, and the crude product was purified by silica gel column chromatography eluted with DCM/MeOH (v/v=30/1) to give the title compound as a white solid (150 mg, 55.0%). The compound was characterized by the following spectroscopic data: MS (ESI, pos. ion) m/z: 547.9 [M+H]$^+$; $^1$H NMR (600 MHz, CDCl$_3$) δ (ppm): 8.27 (d, J=7.8 Hz, 1H), 8.06 (s, 1H), 7.71 (d, J=7.8 Hz, 1H), 7.61-7.54 (m, 2H), 7.50-7.47 (m, 1H), 7.39 (t, J=55.2 Hz, 1H), 7.15 (s, 1H), 3.04 (brs, 4H), 2.92 (brs, 4H); and $^{13}$C NMR (150 MHz, CDCl$_3$) δ (ppm): 148.7, 137.0, 136.3, 136.1, 135.5, 131.9, 128.2, 127.7 (t, J=7.8 Hz), 122.6 (t, J=7.8 Hz), 121.0, 119.9, 119.2, 115.4 (t, J=24.6 Hz), 113.0, 110.9 (t, J=233.7 Hz), 54.6, 46.3.

Example 35 6-bromo-3-(difluoromethyl)-1-((3-fluorophenyl)sulfonyl)-4-(piperazin-1-yl)-1H-indole

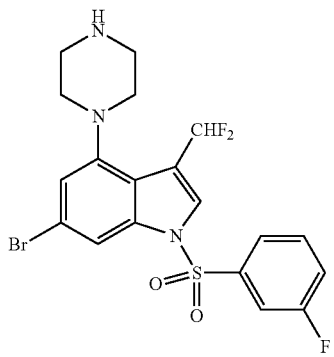

Step 1) 6-bromo-1-((3-fluorophenyl)sulfonyl)-4-(4-(2,2,2-trifluoroacetyl)piperazin-1-yl)-1H-indole-3-carbaldehyde 6-Bromo-4-(4-(2,2,2-trifluoroacetyl)piperazin-1-yl)-1H-indole-3-carbaldehyde (310 mg, 0.77 mmol) was reacted with tetrabutylammonium hydrogen sulfate (14 mg, 0.04 mmol), potassium hydroxide (86 mg, 1.53 mmol) and 3-fluorobenzenesulfonyl chloride (194 mg, 1.0 mmol) in DCM (15 mL) according to the procedure as described in step 4 of example 1, and the crude product was purified by silica gel column chromatography eluted with DCM/PE (v/v=2/1) to give the title compound as a brown solid (400 mg, 92.8%). The compound was characterized by the following spectroscopic data: MS (ESI, pos. ion) m/z: 562.1 [M+H]$^+$; and $^1$H NMR (600 MHz, CDCl$_3$) δ (ppm): 10.43 (s, 1H), 8.24 (s, 1H), 7.94 (d, J=1.2 Hz, 1H), 7.78 (d, J=7.8 Hz, 1H), 7.64 (dt, J=7.2, 1.8 Hz, 1H), 7.57 (td, J=8.4, 5.4 Hz, 1H), 7.37 (td, J=8.4, 2.4 Hz, 1H), 7.13 (d, J=1.2 Hz, 1H), 3.82 (brs, 4H), 3.09 (brs, 4H).

Step 2) 1-(4-(6-bromo-3-(difluoromethyl)-1-((3-fluorophenyl)sulfonyl)-1H-indol-4-yl) piperazin-1-yl)-2,2,2-trifluoroethanone 6-Bromo-1-((3-fluorophenyl)sulfonyl)-4-(4-(2,2,2-trifluoroacetyl)piperazin-1-yl)-1H-indole-3-carbaldehyde (400 mg, 0.71 mmol) was reacted with diethylaminosulphur trifluoride (0.28 mL, 2.14 mmol) in DCM (10 mL) according to the procedure as described in step 5 of example 1, and the crude product was purified by silica gel column chromatography eluted with PE/EtOAc (v/v=4/1) to give the title compound as a yellow solid (380 mg, 91.4%). The compound was characterized by the following spectroscopic data: MS (ESI, pos. ion) m/z: 584.1 [M+H]$^+$; and $^1$H NMR (600 MHz, CDCl$_3$) δ (ppm): 8.01 (d, J=1.2 Hz, 1H), 7.84 (s, 1H), 7.75 (dd, J=8.4, 0.6 Hz, 1H), 7.61 (dt, J=7.2, 2.4 Hz, 1H), 7.55 (td, J=7.8, 5.4 Hz, 1H), 7.36-7.32 (m, 1H), 7.27 (t, J=55.2 Hz, 1H), 7.19 (d, J=1.2 Hz, 1H), 3.50-2.90 (m, 8H).

Step 3) 6-bromo-3-(difluoromethyl)-1-((3-fluorophenyl)sulfonyl)-4-(piperazin-1-yl)-1H-indole 1-(4-(6-Bromo-3-(difluoromethyl)-1-((3-fluorophenyl)sulfonyl)-1H-indol-4-yl) piperazin-1-yl)-2,2,2-trifluoroethanone (380 mg, 0.65 mmol) was reacted with potassium hydroxide (73 mg, 1.3 mmol, dissolved in water (1 mL)) in THF (10 mL) according to the procedure as described in step 6 of example 1, and the crude product was purified by silica gel column chromatography eluted with DCM/MeOH (v/v=30/1) to give the title compound as a white solid (180 mg, 56.7%). The compound was characterized by the following spectroscopic data: MS (ESI, pos. ion) m/z: 487.8 [M+H]$^+$; $^1$H NMR (600 MHz, CDCl$_3$) δ (ppm): 7.83 (s, 1H), 7.78 (d, J=1.2 Hz, 1H), 7.73 (d, J=7.8 Hz, 1H), 7.61 (dt, J=7.8, 1.8 Hz, 1H), 7.52 (td, J=7.8, 4.8 Hz, 1H), 7.36 (t, J=55.2 Hz, 1H), 7.32 (td, J=8.4, 2.4 Hz, 1H), 7.05 (d, J=1.8 Hz, 1H), 3.02 (brs, 4H), 2.91 (brs, 4H); and $^{13}$C NMR (100 MHz, CDCl$_3$) δ (ppm): 162.4 (d, J=251.4 Hz), 148.6, 139.4 (d, J=6.3 Hz), 136.1, 132.3, 131.6 (d, J=7.8 Hz), 125.4 (t, J=7.7 Hz), 122.9 (d, J=3.4 Hz), 122.3 (t, J=4.6 Hz), 121.9 (d, J=21.1 Hz), 117.5 (t, J=24.3 Hz), 117.4, 114.5 (d, J=24.8 Hz), 110.8 (d, J=233.9 Hz), 110.3, 54.6, 46.2.

Example 36 6-bromo-1-((3-chlorophenyl)sulfonyl)-3-(difluoromethyl)-4-(piperazin-1-yl)-1H-indole

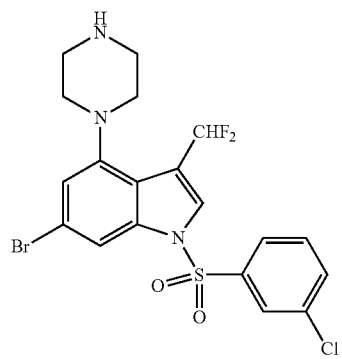 [SMILES: O=S(=O)(c1cccc(Br)c1)n1cc(C(F)F)c2c(N3CCNCC3)cc(Br)cc21]

Step 1) 6-bromo-1-((3-chlorophenyl)sulfonyl)-4-(4-(2,2,2-trifluoroacetyl)piperazin-1-yl)-1H-indole-3-carbaldehyde 6-Bromo-4-(4-(2,2,2-trifluoroacetyl)piperazin-1-yl)-1H-indole-3-carbaldehyde (300 mg, 0.74 mmol) was reacted with tetrabutylammonium hydrogen sulfate (13 mg, 0.038 mmol), potassium hydroxide (83 mg, 1.49 mmol) and 3-chlorobenzenesulfonyl chloride (204 mg, 0.97 mmol) in DCM (15 mL) according to the procedure as described in step 4 of example 1, and the crude product was purified by silica gel column chromatography eluted with DCM/PE (v/v=2/1) to give the title compound as a brown solid (300 mg, 69.8%). The compound was characterized by the following spectroscopic data: MS (ESI, pos. ion) m/z: 578.1 [M+H]$^+$; and $^1$H NMR (400 MHz, CDCl$_3$) δ (ppm): 10.45 (s, 1H), 8.46 (s, 1H), 8.40 (dd, J=8.0, 1.6 Hz, 1H), 7.69-7.58 (m, 3H), 7.53 (dd, J=7.6, 1.2 Hz, 1H), 7.10 (d, J=1.6 Hz, 1H), 3.86 (brs, 4H), 3.12 (brs, 4H).

Step 2) 1-(4-(6-bromo-1-((3-chlorophenyl)sulfonyl)-3-(difluoromethyl)-1H-indol-4-yl) piperazin-1-yl)-2,2,2-trifluoroethanone 6-Bromo-1-((3-chlorophenyl)sulfonyl)-4-(4-(2,2,2-trifluoroacetyl)piperazin-1-yl)-1H-indole-3-carbaldehyde (350 mg, 0.61 mmol) was reacted with diethylaminosulphur trifluoride (0.24 mL, 1.83 mmol) in DCM (10 mL) according to the procedure as described in step 5 of example 1, and the crude product was purified by silica gel column chromatography eluted with PE/EtOAc (v/v=4/1) to give the title compound as a yellow solid (300 mg, 82.6%). The compound was characterized by the following spectroscopic data: $^1$H NMR (400 MHz, CDCl$_3$) δ (ppm): 8.00 (d, J=1.2 Hz, 1H), 7.90 (t, J=1.8 Hz, 1H), 7.84-7.82 (m, 2H), 7.61 (ddd, J=8.0, 1.6, 0.8 Hz, 1H), 7.49 (t, J=8.0 Hz, 1H), 7.27 (t, J=55.2 Hz, 1H), 7.20 (d, J=1.6 Hz, 1H), 3.53-3.01 (m, 8H).

Step 3) 6-bromo-1-((3-chlorophenyl)sulfonyl)-3-(difluoromethyl)-4-(piperazin-1-yl)-1H-indole 1-(4-(6-Bromo-1-((3-chlorophenyl)sulfonyl)-3-(difluoromethyl)-1H-indol-4-yl) piperazin-1-yl)-2,2,2-trifluoroethanone (300 mg, 0.5 mmol) was reacted with potassium hydroxide (56 mg, 1.0 mmol, dissolved in water (1 mL)) in THF (10 mL) according to the procedure as described in step 6 of example 1, and the crude product was purified by silica gel column chromatography eluted with DCM/MeOH (v/v=30/1) to give the title compound as a white solid (120 mg, 47.6%). The compound was characterized by the following spectroscopic data: MS (ESI, pos. ion) m/z: 503.8 [M+H]$^+$; $^1$H NMR (600 MHz, CDCl$_3$) δ (ppm): 7.92 (d, J=1.2 Hz, 1H), 7.89 (t, J=1.8 Hz, 1H), 7.83-7.78 (m, 2H), 7.57 (dd, J=8.4, 1.2 Hz, 1H), 7.46 (t, J=8.4 Hz, 1H), 7.35 (t, J=55.2 Hz, 1H), 7.18 (d, J=1.2 Hz, 1H), 3.02 (brs, 4H), 2.90 (brs, 4H); and $^{13}$C NMR (150 MHz, CDCl$_3$) δ (ppm): 148.8, 139.1, 136.3, 136.0, 134.8, 131.0, 127.0, 125.3 (t, J=7.65 Hz), 125.1, 122.8 (t, J=4.5 Hz), 120.2, 119.8, 117.5 (t, J=24.3 Hz), 113.2, 110.8 (t, J=233.7 Hz), 54.6, 46.2.

Example 37 6-bromo-1-((3-bromophenyl)sulfonyl)-3-(difluoromethyl)-4-(piperazin-1-yl)-1H-indole

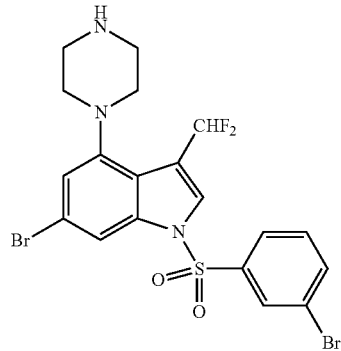

Step 1) 6-bromo-1-((3-bromophenyl)sulfonyl)-4-(4-(2,2,2-trifluoroacetyl)piperazin-1-yl)-1H-indole-3-carbaldehyde 6-Bromo-4-(4-(2,2,2-trifluoroacetyl)piperazin-1-yl)-1H-indole-3-carbaldehyde (300 mg, 0.74 mmol) was reacted with tetrabutylammonium hydrogen sulfate (13 mg, 0.037 mmol), potassium hydroxide (83 mg, 1.48 mmol) and 3-bromobenzenesulfonyl chloride (247 mg, 0.97 mmol) in DCM (15 mL) according to the procedure as described in step 4 of example 1, and the crude product was purified by silica gel column chromatography eluted with DCM/PE (v/v=2/1) to give the title compound as a brown solid (400 mg, 90.0%). The compound was characterized by the following spectroscopic data: MS (ESI, pos. ion) m/z: 621.8 [M+H]$^+$; and $^1$H NMR (400 MHz, CDCl$_3$) δ (ppm): 10.46 (s, 1H), 8.26 (s, 1H), 8.09 (t, J=2.0 Hz, 1H), 7.96 (d, J=1.2 Hz, 1H), 7.93 (dd, J=8.0, 0.8 Hz, 1H), 7.81 (dd, J=8.0, 0.8 Hz, 1H), 7.46 (t, J=8.0 Hz, 1H), 7.15 (d, J=1.6 Hz, 1H), 3.85 (brs, 4H), 3.11 (brs, 4H).

Step 2) 1-(4-(6-bromo-1-((3-bromophenyl)sulfonyl)-3-(difluoromethyl)-1H-indol-4-yl) piperazin-1-yl)-2,2,2-trifluoroethanone 6-Bromo-1-((3-bromophenyl)sulfonyl)-4-(4-(2,2,2-trifluoroacetyl)piperazin-1-yl)-1H-indole-3-carbaldehyde (400 mg, 0.64 mmol) was reacted with diethylaminosulphur trifluoride (0.25 mL, 1.92 mmol) in DCM (10 mL) according to the procedure as described in step 5 of example 1, and the crude product was purified by silica gel column chromatography eluted with PE/EtOAc (v/v=4/1) to give the title compound as a yellow solid (361 mg, 87.2%). The compound was characterized by the following spectroscopic data: $^1$H NMR (400 MHz, CDCl$_3$) δ (ppm): 8.08 (t, J=1.6 Hz, 1H), 8.02 (d, J=1.2 Hz, 1H), 7.89 (dd, J=8.0, 0.4 Hz, 1H), 7.86 (s, 1H), 7.79 (dd, J=8.0, 0.8 Hz, 1H), 7.45 (t, J=8.0 Hz, 1H), 7.30 (t, J=55.2 Hz, 1H), 7.22 (d, J=1.2 Hz, 1H), 3.55-3.03 (m 8H).

Step 3 6-bromo-1-((3-bromophenyl)sulfonyl)-3-(difluoromethyl)-4-(piperazin-1-yl)-1H-indole 1-(4-(6-Bromo-1-((3-bromophenyl)sulfonyl)-3-(difluoromethyl)-1H-indol-4-yl) piperazin-1-yl)-2,2,2-trifluoroethanone (355 mg, 0.55 mmol) was reacted with potassium hydroxide (62 mg, 1.10 mmol, dissolved in water (1 mL)) in THF (10 mL) according to the procedure as described in step 6 of example 1, and the crude product was purified by silica gel column chromatography eluted with DCM/MeOH (v/v=30/1) to give the title compound as a white solid (183 mg, 60.6%). The compound was characterized by the following spectroscopic data: MS (ESI, pos. ion) m/z: 547.9 [M+H]$^+$; $^1$H NMR (600 MHz, CDCl$_3$) δ (ppm): 8.05 (t, J=1.8 Hz, 1H), 7.93 (d, J=1.2 Hz, 1H), 7.85 (d, J=8.4 Hz, 1H), 7.82 (s, 1H), 7.73 (dd, J=7.8, 0.6 Hz, 1H), 7.40 (t, J=8.4 Hz, 1H), 7.36 (t, J=55.2 Hz, 1H), 7.18 (d, J=1.2 Hz, 1H), 3.04 (brs, 4H), 2.93 (brs, 4H); and $^{13}$C NMR (150 MHz, CDCl$_3$) δ (ppm): 148.8, 139.3, 137.7, 136.3, 131.1, 129.9, 125.6, 125.3 (t, J=7.5 Hz), 123.6, 122.8 (t, J=4.35 Hz), 120.2, 119.8, 117.4 (t, J=24.3 Hz), 113.2, 110.8 (t, J=233.85 Hz), 54.6, 46.2.

Example 38 6-bromo-3-(difluoromethyl)-1-((4-methoxyphenyl)sulfonyl)-4-(piperazin-1-yl)-1H-indole

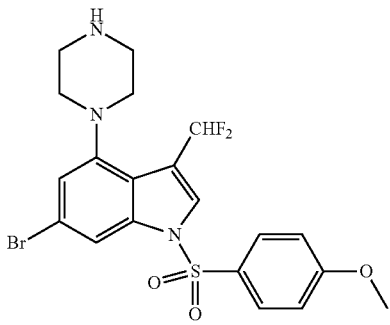 [SMILES: COc1ccc(S(=O)(=O)n2cc(C(F)F)c3c(N4CCNCC4)cc(Br)cc32)cc1]

Step 1) 6-bromo-1-((4-methoxyphenyl)sulfonyl)-4-(4-(2,2,2-trifluoroacetyl)piperazin-1-yl)-1H-indole-3-carbaldehyde 6-Bromo-4-(4-(2,2,2-trifluoroacetyl)piperazin-1-yl)-1H-indole-3-carbaldehyde (240 mg, 0.59 mmol) was reacted with tetrabutylammonium hydrogen sulfate (11 mg, 0.032 mmol), potassium hydroxide (69 mg, 1.23 mmol) and 4-methoxybenzenesulfonyl chloride (160 mg, 0.77 mmol) in DCM (15 mL) according to the procedure as described in step 4 of example 1, and the crude product was purified by silica gel column chromatography eluted with DCM/PE (v/v=2/1) to give the title compound as a brown solid (250 mg, 73.3%). The compound was characterized by the following spectroscopic data: $^1$H NMR (400 MHz, CDCl$_3$) δ (ppm): 10.42 (s, 1H), 7.93-7.90 (m, 1H), 7.88 (s, 2H), 7.84 (d, J=1.6 Hz, 1H), 7.05 (d, J=1.2 Hz, 1H), 7.03-6.97 (m, 2H), 3.84 (brs, 4H), 3.10 (brs, 4H).

Step 2) 1-(4-(6-bromo-3-(difluoromethyl)-1-((4-methoxyphenyl)sulfonyl)-1H-indol-4-yl) piperazin-1-yl)-2,2,2-trifluoroethanone 6-Bromo-1-((4-methoxyphenyl)sulfonyl)-4-(4-(2,2,2-trifluoroacetyl)piperazin-1-yl)-1H-indole-3-carbaldehyde (250 mg, 0.44 mmol) was reacted with diethylaminosulphur trifluoride (0.20 mL, 1.53 mmol) in DCM (10 mL) according to the procedure as described in step 5 of example 1, and the crude product was purified by silica gel column chromatography eluted with PE/EtOAc (v/v=4/1) to give the title compound as a yellow solid (223 mg, 86.0%). The compound was characterized by the following spectroscopic data: MS (ESI, pos. ion) m/z: 595.8 [M+H]$^+$; and $^1$H NMR (400 MHz, CDCl$_3$) δ (ppm): 8.03 (d, J=1.2 Hz, 1H), 7.92-7.88 (m, 2H), 7.88-7.87 (m, 1H), 7.29 (t, J=55.2 Hz, 1H), 7.18 (d, J=1.2 Hz, 1H), 7.02-6.98 (m, 2H), 3.86 (s, 3H), 3.01 (br, 8H).

Step 3) 6-bromo-3-(difluoromethyl)-1-((4-methoxyphenyl)sulfonyl)-4-(piperazin-1-yl)-1H-indole 1-(4-(6-Bromo-3-(difluoromethyl)-1-((4-methoxyphenyl)sulfonyl)-1H-indol-4-yl) piperazin-1-yl)-2,2,2-trifluoroethanone (220 mg, 0.37 mmol) was reacted with potassium hydroxide (42 mg, 0.74 mmol, dissolved in water (1 mL)) in THF (10 mL) according to the procedure as described in step 6 of example 1, and the crude product was purified by silica gel column chromatography eluted with DCM/MeOH (v/v=30/1) to give the title compound as a white solid (148 mg, 80.2%). The compound was characterized by the following spectroscopic data: MS (ESI, pos. ion) m/z: 499.9 [M+H]$^+$; $^1$H NMR (600 MHz, CDCl$_3$) δ (ppm): 7.94 (d, J=1.8 Hz, 1H), 7.88-7.85 (m, 2H), 7.84 (s, 1H), 7.34 (t, J=55.2 Hz, 1H), 7.14 (d, J=1.2 Hz, 1H), 6.98-6.94 (m, 2H), 3.83 (s, 3H), 3.02 (brs, 4H), 2.91 (brs, 4H); and $^{13}$C NMR (150 MHz, CDCl$_3$) δ (ppm): 164.4, 148.5, 136.3, 129.5, 128.9, 125.5 (t, J=7.5 Hz), 122.7 (t, J=4.5 Hz), 119.7, 119.3, 116.5 (t, J=24.3 Hz), 114.9, 113.3, 111.0 (t, J=233.55 Hz), 55.8, 54.4, 46.2.

Example 39 1-((3-chlorophenyl)sulfonyl)-3-(difluoromethyl)-4-(piperidin-4-yl)-1H-indole

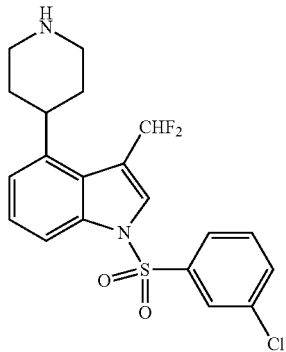 [SMILES: O=S(=O)(c1cccc(Cl)c1)n1cc(C(F)F)c2c(C3CCNCC3)cccc21]

Step 1) tert-butyl 4-(1H-indol-4-yl)-5,6-dihydropyridine-1(2H)-carboxylate

To a mixture of N,N-dimethylformamide (40 mL) and water (3 mL) were added 4-bromoindole (3.6 g, 16 mmol), PdCl$_2$(dppf) (650 mg, 0.9 mmol), potassium acetate (2.36 g, 24 mmol) and N-Boc-1,2,5,6-tetrahydropyridine-4-boronic acid pinacol ester (5.47 g, 17.6 mmol). The mixture was stirred for 24 hours at 95° C., then diluted with dichloromethane (50 mL) and the resulting mixture was washed with saturated aqueous sodium chloride (40 mL×2). The organic layer was dried over anhydrous sodium sulfate and filtered. The filtrate was concentrated in vacuo and the residue was purified by silica gel column chromatography eluted with PE/EtOAc (v/v=10/1) to give the title compound as a white solid (3.28 g, 68.9%). The compound was characterized by the following spectroscopic data: MS (ESI, neg. ion) m/z: 297.2 [M−H]⁻.

Step 2) tert-butyl 4-(1H-indol-4-yl)piperidine-1-carboxylate

To 15 mL of methanol were added tert-butyl 4-(1H-indol-4-yl)-5,6-dihydropyridine-1(2H)-carboxylate (2.98 g, 10 mmol) and Pd/C (298 mg). The mixture was stirred at rt for 24 hours under hydrogen atmosphere (1 atm), then filtered. The filtrate was concentrated in vacuo and the residue was purified by silica gel column chromatography eluted with PE/DCM (v/v=1/1) to give the title compound as a white solid (2.12 g, 70.9%). The compound was characterized by the following spectroscopic data: $^1$H NMR (400 MHz, CDCl$_3$) δ (ppm): 8.28 (s, 1H), 7.30 (d, J=8.4 Hz, 1H), 7.24 (t, J=2.8 Hz, 1H), 7.19 (t, J=8.07 Hz, 1H), 6.97 (d, J=7.2 Hz, 1H), 6.64 (t, J=2.0 Hz, 1H), 4.30 (s, 2H), 3.13 (tt, J=12.0, 3.6 Hz, 1H), 2.92 (t, J=12.0 Hz, 2H), 1.98 (d, J=12.8 Hz, 2H), 1.84 (qd, J=12.8, 4.4 Hz, 2H), 1.53 (s, 9H).

Step 3) tert-butyl 4-(3-formyl-1H-indol-4-yl)piperidine-1-carboxylate

To 5 mL of N,N-dimethylformamide was added tert-butyl 4-(1H-indol-4-yl)piperidine-1-carboxylate (600 mg, 2.0 mmol) at 0° C., and phosphorus oxychloride (210 μL, 2.2 mmol) was added dropwise slowly. The mixture was warmed to 25° C. and stirred for 24 hours. The reaction mixture was quenched with water (30 mL) and the resulting mixture was neutralized with sodium carbonate solid to pH about 8~9. The mixture was filtered and the filter cake was dried in vacuo to give the title compound as a claybank solid (543 mg, 82.8%). The compound was characterized by the following spectroscopic data: MS (ESI, pos. ion) m/z: 229.0 [M+H−Boc]⁺; and $^1$H NMR (400 MHz, CDCl$_3$) δ (ppm): 9.98 (s, 1H), 9.37 (s, 1H), 7.93 (d, J=3.2 Hz, 1H), 7.34-7.31 (m, 2H), 7.17 (dd, J=6.0, 2.4 Hz, 1H), 4.28 (s, 2H), 4.17 (tt, J=12.0, 3.2 Hz, 1H), 3.07 (s, 2H), 1.95 (d, J=12.8 Hz, 2H), 1.72-1.68 (m, 2H), 1.52 (s, 9H).

Step 4) tert-butyl 4-(1-((3-chlorophenyl)sulfonyl)-3-formyl-1H-indol-4-yl)piperidine-1-carboxylate tert-Butyl 4-(3-formyl-1H-indol-4-yl)piperidine-1-carboxylate (400 mg, 1.22 mmol) was reacted with tetrabutylammonium hydrogen sulfate (21 mg, 0.061 mmol), potassium hydroxide (137 mg, 2.44 mmol) and 3-chlorobenzenesulfonyl chloride (422 mg, 1.58 mmol) in DCM (15 mL) according to the procedure as described in step 4 of example 1, and the crude product was purified by silica gel column chromatography eluted with DCM/PE (v/v=2/1) to give the title compound as a white solid (490 mg, 79.9%). The compound was characterized by the following spectroscopic data: MS (ESI, pos. ion) m/z: 403.2 [M+H−Boc]⁺; and $^1$H NMR (400 MHz, DMSO-d$_6$) δ (ppm): 10.00 (s, 1H), 8.99 (s, 1H), 8.28 (t, J=1.6 Hz, 1H), 8.15 (d, J=8.0 Hz, 1H), 7.88 (d, J=8.4 Hz, 2H), 7.72-7.68 (m, 2H), 7.44 (t, J=8.0 Hz, 1H), 7.30 (d, J=7.6 Hz, 1H), 4.08 (d, J=11.6 Hz, 2H), 3.96 (t, J=11.6 Hz, 1H), 2.88 (s, 2H), 1.72 (d, J=11.6 Hz, 2H), 1.55-1.47 (m, 2H), 1.41 (s, 9H).

Step 5) tert-butyl 4-(1-((3-chlorophenyl)sulfonyl)-3-(difluoromethyl)-1H-indol-4-yl)piperidine-1-carboxylate tert-Butyl 4-(1-((3-chlorophenyl)sulfonyl)-3-formyl-1H-indol-4-yl)piperidine-1-carboxylate (490 mg, 0.97 mmol) was reacted with diethylaminosulphur trifluoride (0.51 mL, 3.88 mmol) in DCM (10 mL) according to the procedure as described in step 5 of example 1, and the crude product was purified by silica gel column chromatography eluted with PE/EtOAc (v/v=4/1) to give the title compound as a yellow solid (354 mg, 69.3%). The compound was characterized by the following spectroscopic data: MS (ESI, pos. ion) m/z: 524.7 [M+H]⁺; and $^1$H NMR (400 MHz, DMSO-d$_6$) δ (ppm): 8.35 (s, 1H), 8.22 (t, J=2.0 Hz, 1H), 8.08 (d, J=8.0 Hz, 1H), 7.90 (d, J=8.4 Hz, 1H), 7.85 (dd, J=8.0, 1.2 Hz, 1H), 7.68 (t, J=8.4 Hz, 1H), 7.43 (t, J=8.0 Hz, 1H), 7.38 (t, J=54.8 Hz, 1H), 7.31 (d, J=7.6 Hz, 1H), 4.09 (d, J=12.0 Hz, 2H), 3.16 (t, J=11.6 Hz, 1H), 2.75 (s, 2H), 1.71 (d, J=12.4 Hz, 2H), 1.60-1.54 (m, 2H), 1.42 (s, 9H).

Step 6) 1-((3-chlorophenyl)sulfonyl)-3-(difluoromethyl)-4-(piperidin-4-yl)-1H-indole tert-Butyl 4-(1-((3-chlorophenyl)sulfonyl)-3-(difluoromethyl)-1H-indol-4-yl)piperidine-1-carboxylate (354 mg, 0.67 mmol) was reacted with a solution of hydrogen chloride in ethyl acetate (4 mL, 2 M) in dichloromethane (5 mL) according to the procedure as described in step 5 of example 17 to give the title compound as a white solid (250 mg, 87.4%). The compound was characterized by the following spectroscopic data: MS (ESI, pos. ion) m/z: 425.0 [M+H]⁺; $^1$H NMR (400 MHz, DMSO-d$_6$) δ (ppm): 8.33 (s, 1H), 8.20 (s, 1H), 8.07 (d, J=7.6 Hz, 1H), 7.87 (d, J=8.4 Hz, 1H), 7.83 (d, J=8.4 Hz, 1H), 7.69-7.65 (m, 1H), 7.42 (d, J=8.0 Hz, 1H), 7.33 (t, J=50.8 Hz, 1H), 7.29 (d, J=7.6 Hz, 1H), 3.10 (s, 1H), 3.03 (d, J=11.6 Hz, 2H), 2.58 (t, J=10.8 Hz, 2H), 1.68-1.54 (m, 4H); and $^{13}$C NMR (150 MHz, DMSO-d$_6$) δ (ppm): 141.3, 138.7, 135.7, 135.3, 135.1, 132.6, 129.1 (t, J=12.75 Hz), 127.1, 126.8, 126.4, 124.6, 122.5, 116.5 (t, J=24.9 Hz), 112.8 (t, J=220.85 Hz), 111.4, 47.1, 39.3, 34.3.

Example 40 1-((3-bromophenyl)sulfonyl)-3-(difluoromethyl)-4-(piperidin-4-yl)-1H-indole

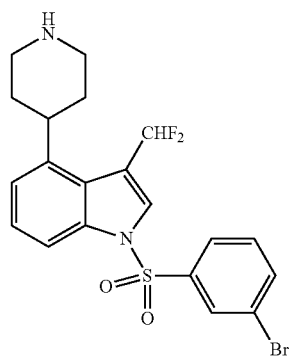 [SMILES: O=S(=O)(c1cccc(Br)c1)n1cc(C(F)F)c2c(C3CCNCC3)cccc21]

Step 1) tert-butyl 4-(1-((3-bromophenyl)sulfonyl)-3-formyl-1H-indol-4-yl)piperidine-1-carboxylate tert-Butyl 4-(3-formyl-1H-indol-4-yl)piperidine-1-carboxylate (400 mg, 1.22 mmol) was reacted with tetrabutylammonium hydrogen sulfate (21 mg, 0.061 mmol), potassium hydroxide (137 mg, 2.44 mmol) and 3-bromobenzenesulfonyl chloride (410 mg, 1.58 mmol) in DCM (15 mL) according to the procedure as described in step 4 of example 1, and the crude product was purified by silica gel column chromatography eluted with DCM/PE (v/v=2/1) to give the title compound as a white solid (620 mg, 93.0%). The compound was characterized by the following spectroscopic data: MS (ESI, neg. ion) m/z: 545.0 [M−H]−; and ¹H NMR (400 MHz, DMSO-d₆) δ (ppm): 10.00 (s, 1H), 8.99 (s, 1H), 8.38 (t, J=2.0 Hz, 1H), 8.19 (dd, J=8.0, 1.8 Hz, 1H), 8.00 (dd, J=8.0, 1.8 Hz, 1H), 7.88 (d, J=8.4 Hz, 1H), 7.63 (t, J=8.0 Hz, 1H), 7.44 (t, J=7.6 Hz, 1H), 7.30 (d, J=7.6 Hz, 1H), 4.08 (d, J=12.0 Hz, 2H), 3.99-3.92 (m, 1H), 2.88 (s, 2H), 1.72 (d, J=12.4 Hz, 2H), 1.54-1.48 (m, 2H), 1.42 (s, 9H).

Step 2) tert-butyl 4-(1-((3-bromophenyl)sulfonyl)-3-(difluoromethyl)-1H-indol-4-yl)piperidine-1-carboxylate tert-Butyl 4-(1-((3-bromophenyl)sulfonyl)-3-formyl-1H-indol-4-yl)piperidine-1-carboxylate (620 mg, 1.13 mmol) was reacted with diethylaminosulphur trifluoride (0.59 mL, 4.51 mmol) in dichloromethane (10 mL) according to the procedure as described in step 5 of example 1, and the crude product was purified by silica gel column chromatography eluted with PE/EtOAc (v/v=4/1) to give the title compound as a yellow solid (570 mg, 89.0%). The compound was characterized by the following spectroscopic data: ¹H NMR (400 MHz, DMSO-d₆) δ (ppm): 8.35 (s, 1H), 8.22 (t, J=2.0 Hz, 1H), 8.08 (dd, J=8.0, 0.8 Hz, 1H), 7.90 (d, J=8.0 Hz, 1H), 7.85 (dd, J=8.0, 1.2 Hz, 1H), 7.68 (t, J=8.0 Hz, 1H), 7.43 (t, J=8.0 Hz, 1H), 7.38 (t, J=54.4 Hz, 1H), 7.31 (d, J=7.6 Hz, 1H), 4.15-4.08 (m, 2H), 3.16 (t, J=11.2 Hz, 1H), 2.77 (s, 2H), 1.71 (d, J=12.8 Hz, 2H), 1.62-1.54 (m, 2H), 1.42 (s, 9H).

Step 3) 1-((3-bromophenyl)sulfonyl)-3-(difluoromethyl)-4-(piperidin-4-yl)-1H-indole tert-Butyl 4-(1-((3-bromophenyl)sulfonyl)-3-(difluoromethyl)-1H-indol-4-yl)piperidine-1-carboxylate (570 mg, 0.67 mmol) was reacted with a solution of hydrogen chloride in ethyl acetate (4 mL, 2 M) in dichloromethane (5 mL) according to the procedure as described in step 5 of example 17 to give the title compound as a white solid (444 mg, 94.7%). The compound was characterized by the following spectroscopic data: MS (ESI, pos. ion) m/z: 469.0 [M+H]+; ¹H NMR (600 MHz, DMSO-d₆) δ (ppm): 8.35 (s, 1H), 8.31 (s, 1H), 8.12 (d, J=8.4 Hz, 1H), 7.97 (dd, J=7.8, 0.8 Hz, 1H), 7.88 (d, J=8.4 Hz, 1H), 7.60 (t, J=7.8 Hz, 1H), 7.44 (d, J=7.8 Hz, 1H), 7.34 (t, J=54.6 Hz, 1H), 7.29 (d, J=7.8 Hz, 1H), 3.11 (t, J=11.4 Hz, 1H), 3.06 (d, J=12.0 Hz, 2H), 2.61 (t, J=10.8 Hz, 2H), 1.70-1.60 (m, 4H); and ¹³C NMR (150 MHz, DMSO-d₆) δ (ppm): 141.2, 138.8, 138.6, 135.3, 132.7, 129.8, 129.2 (t, J=11.85 Hz), 126.8, 126.7, 124.6, 123.3, 122.4, 116.5 (t, J=25.2 Hz), 112.8 (t, J=231.45 Hz), 111.5, 46.9, 39.1, 34.1.

Example 41 3-(difluoromethyl)-4-(piperidin-4-yl)-1-((2-(trifluoromethyl)phenyl)sulfonyl)-1H-indole

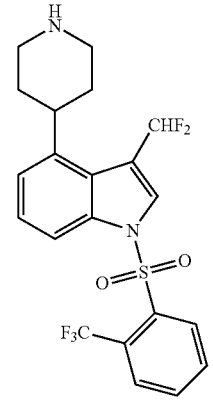 [SMILES: O=S(=O)(c1ccccc1C(F)(F)F)n1cc(C(F)F)c2c(C3CCNCC3)cccc21]

Step 1) tert-butyl 4-(3-formyl-1-((2-(trifluoromethyl)phenyl)sulfonyl)-1H-indol-4-yl)piperidine-1-carboxylate tert-Butyl 4-(3-formyl-1H-indol-4-yl)piperidine-1-carboxylate (400 mg, 1.22 mmol) was reacted with tetrabutylammonium hydrogen sulfate (21 mg, 0.061 mmol), potassium hydroxide (137 mg, 2.44 mmol) and 2-trifluoromethylbenzenesulfonyl chloride (388 mg, 1.58 mmol) in DCM (15 mL) according to the procedure as described in step 4 of example 1, and the crude product was purified by silica gel column chromatography eluted with DCM/PE (v/v=2/1) to give the title compound as a white solid (574 mg, 87.8%). The compound was characterized by the following spectroscopic data: MS (ESI, pos. ion) m/z: 437.1 [M+H-Boc]+; and ¹H NMR (400 MHz, DMSO-d₆) δ (ppm): 10.06 (s, 1H), 8.94 (s, 1H), 8.16 (d, J=7.2 Hz, 1H), 8.08 (d, J=7.6 Hz, 1H), 8.02 (t, J=7.6 Hz, 1H), 7.97 (t, J=7.2 Hz, 1H), 7.56 (d, J=8.0 Hz, 1H), 7.39 (t, J=8.0 Hz, 1H), 7.31 (d, J=7.6 Hz, 1H), 4.10 (d, J=12.4 Hz, 2H), 4.02 (tt, J=11.6, 3.2 Hz, 1H), 2.91 (s, 2H), 1.76 (d, J=12.4 Hz, 2H), 1.53 (td, J=12.4, 3.6 Hz, 2H), 1.42 (s, 9H).

Step 2) tert-butyl 4-(3-(difluoromethyl)-1-((2-(trifluoromethyl)phenyl)sulfonyl)-1H-indol-4-yl) piperidine-1-carboxylate tert-Butyl 4-(3-formyl-1-((2-(trifluoromethyl)phenyl)sulfonyl)-1H-indol-4-yl)piperidine-1-carboxylate (574 mg, 1.07 mmol) was reacted with diethylaminosulphur trifluoride (0.56 mL, 4.28 mmol) in DCM (10 mL) according to the procedure as described in step 5 of example 1, and the crude product was purified by silica gel column chromatography eluted with PE/EtOAc (v/v=4/1) to give the title compound as a yellow solid (520 mg, 87.0%). The compound was characterized by the following spectroscopic data: MS (ESI, neg. ion) m/z: 557.3 [M−H]−; and ¹H NMR (400 MHz, DMSO-d₆) δ (ppm): 8.28 (s, 1H), 8.13 (d, J=8.0 Hz, 1H), 8.03-7.94 (m, 3H), 7.59 (d, J=8.2 Hz, 1H), 7.44 (t, J=54.8 Hz, 1H), 7.38 (t, J=8.0 Hz, 1H), 7.33 (d, J=7.2 Hz, 1H), 4.17-4.10 (m, 2H), 3.24 (t, J=12.0 Hz, 1H), 2.81 (s, 2H), 1.75 (d, J=12.0 Hz, 2H), 1.64-1.54 (m, 2H), 1.43 (s, 9H).

Step 3) 3-(difluoromethyl)-4-(piperidin-4-yl)-1-((2-(trifluoromethyl)phenyl)sulfonyl)-1H-indole tert-Butyl 4-(3-(difluoromethyl)-1-((2-(trifluoromethyl)phenyl)sulfonyl)-1H-indol-4-yl) piperidine-1-carboxylate (520 mg, 0.93 mmol) was reacted with a solution of hydrogen chloride in ethyl acetate (4 mL, 2 M) in dichloromethane (5 mL) according to the procedure as described in step 5 of example 17 to give the title compound as a white solid (385 mg, 90.2%). The compound was characterized by the following spectroscopic data: MS (ESI, pos. ion) m/z: 459.1 [M+H]$^+$; $^1$H NMR (600 MHz, DMSO-d$_6$) δ (ppm): 8.26 (s, 1H), 8.11 (d, J=7.8 Hz, 1H), 8.01-7.95 (m, 3H), 7.57 (d, J=8.4 Hz, 1H), 7.39 (d, J=7.8 Hz, 1H), 7.37 (t, J=54.6 Hz, 1H), 7.30 (d, J=7.6 Hz, 1H), 3.18 (t, J=10.8 Hz, 1H), 3.05 (d, J=9.6 Hz, 2H), 2.61 (t, J=10.2 Hz, 2H), 1.69-1.60 (m, 4H); and $^{13}$C NMR (150 MHz, DMSO-d$_6$) δ (ppm): 141.5, 136.2, 135.8, 135.5, 134.8, 131.6, 129.9 (q, J=6.15 Hz), 129.8 (t, J=11.7 Hz), 129.1, 126.7 (q, J=33.15 Hz), 126.6, 124.0, 122.8 (q, J=272.25 Hz), 115.8 (t, J=25.5 Hz), 112.9 (t, J=230.4 Hz), 111.2, 47.1, 39.3, 34.4.

Example 42 3-(difluoromethyl)-1-((3-fluorophenyl)sulfonyl)-4-(4-methylpiperazin-1-yl)-1H-indole

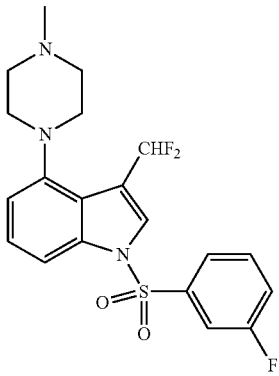 [SMILES: CN1CCN(c2cccc3c2c(C(F)F)cn3S(=O)(=O)c2cccc(F)c2)CC1]

To a solution of 3-(difluoromethyl)-1-((3-fluorophenyl)sulfonyl)-4-(piperazin-1-yl)-1H-indole (200 mg, 0.49 mmol) in methanol (10 mL) was added two drops of acetic acid. Then sodium cyanoborohydride (90 mg, 1.42 mmol) and formaldehyde (40%, 0.11 mL, 1.6 mmol) were added at 0° C. The mixture was stirred at 0° C. for 10 minutes, then warmed to 25° C. and stirred for 5 hours. The reaction mixture was quenched with water (10 mL) and potassium carbonate (212 mg, 2.0 mmol), and the resulting mixture was extracted with dichloromethane (20 mL×2). The combined organic layers were dried over anhydrous sodium sulfate, and filtered. The filtrate was concentrated in vacuo and the residue was purified by silica gel column chromatography (DCM/MeOH (v/v)=15/1) to give the title compound as a brown solid (90 mg, 43.5%). The compound was characterized by the following spectroscopic data: MS (ESI, pos. ion) m/z: 424.0 [M+H]$^+$; $^1$H NMR (400 MHz, DMSO-d$_6$) δ (ppm): 8.14 (s, 1H), 8.05 (dt, J=8.4, 1.6 Hz, 1H), 7.93 (d, J=7.6 Hz, 1H), 7.76 (d, J=8.0 Hz, 1H), 7.67 (td, J=8.0, 5.6 Hz, 1H), 7.59 (td, J=8.4, 2.4 Hz, 1H), 7.39 (t, J=55.2 Hz, 1H), 7.36 (t, J=8.0 Hz, 1H), 7.15 (d, J=7.6 Hz, 1H), 2.83 (t, J=4.8 Hz, 4H), 2.46 (brs, 4H), 2.20 (s, 3H); and $^{13}$C NMR (100 MHz, CDCl$_3$) δ (ppm): 162.3 (d, J=251.8 Hz), 147.7, 139.6 (d, J=6.9 Hz), 135.9, 131.3 (d, J=7.8 Hz), 126.4, 125.0 (t, J=7.8 Hz), 123.9 (t, J=4.5 Hz), 122.8 (d, J=3.5 Hz), 121.6 (d, J=21.1 Hz), 117.7 (t, J=24.0 Hz), 116.2, 114.4 (d, J=24.7 Hz), 111.1 (t, J=233.5 Hz), 110.2, 55.5, 53.3, 46.0.

Example 43 3-(difluoromethyl)-4-(4-ethylpiperazin-1-yl)-1-((3-fluorophenyl)sulfonyl)-1H-indole

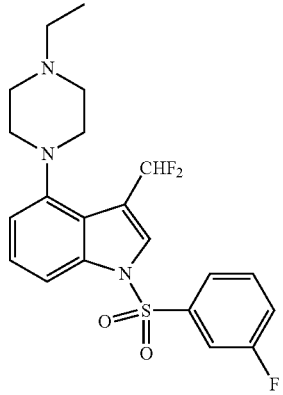 [SMILES: CCN1CCN(c2cccc3c2c(C(F)F)cn3S(=O)(=O)c2cccc(F)c2)CC1]

To atetone (10 mL) were added 3-(difluoromethyl)-1-((3-fluorophenyl)sulfonyl)-4-(piperazin-1-yl)-1H-indole (200 mg, 0.49 mmol), K$_2$CO$_3$ (135 mg, 0.98 mmol) and bromoethane (110 μL, 1.47 mmol). The mixture was stirred at 25° C. for 20 hours, then 40 mL of dichloromethane was added. The mixture was washed with 40 mL of saturated aqueous sodium bicarbonate. The organic layer was dried over anhydrous sodium sulfate, and filtered. The filtrate was concentrated in vacuo and the residue was purified by silica gel column chromatography (PE/EtOAc (v/v)=1/1) to give the title compound as colourless oil (70 mg, 32.8%). The compound was characterized by the following spectroscopic data: MS (ESI, pos. ion) m/z: 438.0 [M+H]$^+$; $^1$H NMR (400 MHz, DMSO-d$_6$) δ (ppm): 8.15 (s, 1H), 8.06 (dt, J=8.0, 2.0 Hz, 1H), 7.95 (d, J=7.6 Hz, 1H), 7.77 (d, J=8.4 Hz, 1H), 7.68 (td, J=8.0, 5.2 Hz, 1H), 7.60 (td, J=8.4, 2.0 Hz, 1H), 7.40 (t, J=55.2 Hz, 1H), 7.37 (t, J=8.0 Hz, 1H), 7.17 (d, J=7.6 Hz, 1H), 2.85 (t, J=4.4 Hz, 4H), 2.52 (brs, 4H), 2.36 (q, J=7.2 Hz, 2H), 1.00 (t, J=7.2 Hz, 3H); and $^{13}$C NMR (100 MHz, CDCl$_3$) δ (ppm): 162.3 (d, J=251.8 Hz), 147.8, 139.7 (d, J=6.9 Hz), 135.9, 131.3 (d, J=7.8 Hz), 126.4, 125.0 (t, J=7.6 Hz), 123.9 (t, J=4.6 Hz), 122.8 (d, J=3.5 Hz), 121.6 (d, J=21.1 Hz), 117.7 (t, J=24.0 Hz), 116.2, 114.5 (d, J=24.7 Hz), 111.1 (t, J=233.5 Hz), 110.1, 53.4, 53.2, 52.4, 12.0.

Example 44 3-(difluoromethyl)-1-((3-fluorophenyl)sulfonyl)-4-(4-isopropylpiperazin-1-yl)-1H-indole

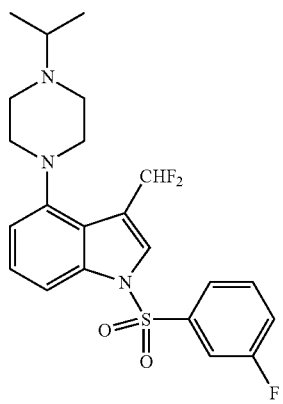 [SMILES: CC(C)N1CCN(c2cccc3c2c(C(F)F)cn3S(=O)(=O)c2cccc(F)c2)CC1]

3-(Difluoromethyl)-1-((3-fluorophenyl)sulfonyl)-4-(piperazin-1-yl)-1H-indole (170 mg, 0.42 mmol) was reacted with sodium cyanoborohydride (80 mg, 1.27 mmol), acetic acid (60 μL, 1.0 mmol) and acetone (0.1 mL, 1.36 mmol) in methanol (10 mL) according to the procedure as described in example 42, and the crude product was purified by silica gel column chromatography (DCM/MeOH (v/v)=50/1) to give the title compound as a light yellow solid (130 mg, 69.3%). The compound was characterized by the following spectroscopic data: MS (ESI, pos. ion) m/z: 452.2 [M+H]$^+$; $^1$H NMR (600 MHz, DMSO-d$_6$) δ (ppm): 8.18 (s, 1H), 8.09 (dt, J=8.4, 1.8 Hz, 1H), 7.98 (ddd, J=7.8, 1.8, 0.8 Hz, 1H), 7.81-7.77 (m, 1H), 7.70 (td, J=8.4, 5.4 Hz, 1H), 7.64-7.61 (m, 1H), 7.44 (t, J=55.2 Hz, 1H), 7.39 (t, J=7.8 Hz, 1H), 7.19 (d, J=7.2 Hz, 1H), 3.35 (brs, 4H), 2.67 (m, 1H), 2.58 (brs, 4H), 1.00 (d, J=6.6 Hz, 6H); and $^{13}$C NMR (150 MHz, DMSO-d$_6$) δ (ppm): 162.3 (d, J=248.8 Hz), 148.2, 138.8 (d, J=7.4 Hz), 135.6, 133.0 (d, J=7.9 Hz), 127.1, 126.0 (t, J=7.7 Hz), 123.9 (d, J=3.0 Hz), 123.3 (t, J=4.0 Hz), 122.9 (d, J=21.2 Hz), 117.2 (t, J=24.0 Hz), 116.7, 115.9 (d, J=25.2 Hz), 111.7 (t, J=232.6 Hz), 110.1, 54.2, 53.8, 48.8, 18.8.

Example 45 4-(4-cyclopropylpiperazin-1-yl)-3-(difluoromethyl)-1-((3-fluorophenyl)sulfonyl)-1H-indole

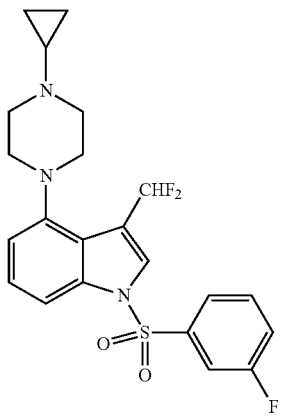 [SMILES: O=S(=O)(c1cccc(F)c1)n1cc(C(F)F)c2c(N3CCN(C4CC4)CC3)cccc21]

3-(Difluoromethyl)-1-((3-fluorophenyl)sulfonyl)-4-(piperazin-1-yl)-1H-indole (300 mg, 0.73 mmol) was reacted with sodium cyanoborohydride (140 mg, 2.2 mmol), acetic acid (120 μL, 2.0 mmol) and (1-ethoxycyclopropoxy)trimethylsilane (1.94 mmol, 420 μL) in methanol (10 mL) according to the procedure as described in example 42, and the crude product was purified by silica gel column chromatography (DCM/MeOH (v/v)=3/1) to give the title compound as light yellow oil (120 mg, 36.4%). The compound was characterized by the following spectroscopic data: MS (ESI, pos. ion) m/z: 450.2 [M+H]$^+$; $^1$H NMR (600 MHz, DMSO-d$_6$) δ (ppm): 8.18 (s, 1H), 8.09 (dd, J=8.4, 1.8 Hz, 1H), 7.97 (d, J=7.8 Hz, 1H), 7.79 (dd, J=8.4, 1.8 Hz, 1H), 7.72-7.69 (m, 1H), 7.63 (t, J=8.4 Hz, 1H), 7.46 (t, J=55.2 Hz, 1H), 7.41-7.36 (m, 1H), 7.17 (dd, J=7.8, 1.2 Hz, 1H), 2.83 (brs, 4H), 2.69 (brs, 4H), 1.20-1.15 (m, 1H), 0.43 (d, J=6.6 Hz, 2H), 0.32 (s, 2H); and $^{13}$C NMR (150 MHz, DMSO-d$_6$) δ (ppm): 162.3 (d, J=248.7 Hz), 148.2, 138.8 (d, J=7.4 Hz), 135.6, 133.0 (d, J=8.1 Hz), 127.1, 126.1 (t, J=7.8 Hz), 124.0 (d, J=3.0 Hz), 123.3 (t, J=4.0 Hz), 122.9 (d, J=21.1 Hz), 117.3 (t, J=24.2 Hz), 116.8, 114.9 (d, J=25.0 Hz), 111.8 (t, J=232.5 Hz), 110.2, 53.4, 38.4, 6.1.

Example 46 4-(4-cyclobutylpiperazin-1-yl)-3-(difluoromethyl)-1-((3-fluorophenyl)sulfonyl)-1H-indole

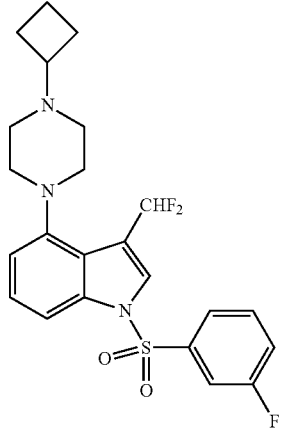 [SMILES: O=S(=O)(c1cccc(F)c1)n1cc(C(F)F)c2c(N3CCN(C4CCC4)CC3)cccc21]

3-(Difluoromethyl)-1-((3-fluorophenyl)sulfonyl)-4-(piperazin-1-yl)-1H-indole (300 mg, 0.73 mmol) was reacted with sodium cyanoborohydride (134 mg, 2.12 mmol), acetic acid (120 μL, 2.0 mmol) and cyclobutanone (162 μL, 2.2 mmol) in methanol (10 mL) according to the procedure as described in example 42, and the crude product was purified by silica gel column chromatography (DCM/MeOH (v/v)=50/1) to give the title compound as a white solid (310 mg, 91.2%). The compound was characterized by the following spectroscopic data: MS (ESI, pos. ion) m/z: 464.2 [M+H]$^+$; $^1$H NMR (600 MHz, DMSO-d$_6$) δ (ppm): 8.11 (s, 1H), 8.02 (dt, J=8.4, 1.8 Hz, 1H), 7.91 (dd, J=7.6, 0.6 Hz, 1H), 7.73 (d, J=8.4 Hz, 1H), 7.63 (td, J=8.4, 5.4 Hz, 1H), 7.56 (td, J=8.4, 1.8 Hz, 1H), 7.34 (t, J=55.2 Hz, 1H), 7.33 (t, J=8.4 Hz, 1H), 7.12 (d, J=7.8 Hz, 1H), 2.79 (brs, 4H), 2.74-2.67 (m, 1H), 2.35 (brs, 4H), 1.94-1.85 (m, 2H), 1.77-1.67 (m, 2H), 1.60-1.52 (m, 2H); and $^{13}$C NMR (150 MHz, DMSO-d$_6$) δ (ppm): 162.3 (d, J=248.8 Hz), 148.1, 138.8 (d, J=7.4 Hz), 135.6, 133.0 (d, J=8.1 Hz), 127.1, 126.1 (t, J=7.8 Hz), 124.0 (d, J=2.8 Hz), 123.3 (t, J=3.9 Hz), 122.9 (d, J=21.0 Hz), 117.2 (t, J=24.2 Hz), 116.8, 114.9 (d, J=25.0 Hz), 111.7 (t, J=232.5 Hz), 110.2, 60.1, 53.2, 49.6, 27.0, 14.4.

Example 47 3-(difluoromethyl)-1-((3-fluorophenyl)sulfonyl)-4-(4-(oxetan-3-yl)piperazin-1-yl)-1H-indole

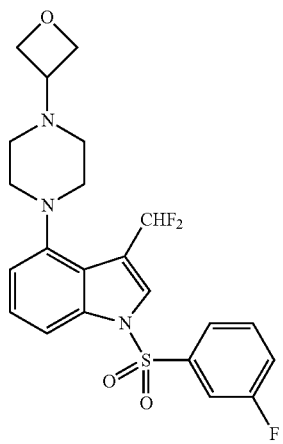 [SMILES: O=S(=O)(c1cccc(F)c1)n1cc(C(F)F)c2c(N3CCN(C4COC4)CC3)cccc21]

3-(Difluoromethyl)-1-((3-fluorophenyl)sulfonyl)-4-(piperazin-1-yl)-1H-indole (200 mg, 0.49 mmol) was reacted with sodium cyanoborohydride (94 mg, 1.49 mmol), acetic acid (90 μL, 1.5 mmol) and 3-oxetanone (108 mg, 1.5 mmol) in methanol (10 mL) according to the procedure as described in example 42, and the crude product was purified by silica gel column chromatography (DCM/MeOH (v/v)=50/1) to give the title compound as a white solid (190 mg, 83.5%). The compound was characterized by the following spectroscopic data: MS (ESI, pos. ion) m/z: 466.1 [M+H]$^+$; $^1$H NMR (600 MHz, DMSO-d$_6$) δ (ppm): 8.18 (s, 1H), 8.09 (dt, J=8.4, 1.8 Hz, 1H), 7.97 (ddd, J=7.8, 1.6, 0.8 Hz, 1H), 7.81 (d, J=8.4 Hz, 1H), 7.71 (td, J=8.4, 5.4 Hz, 1H), 7.63 (m, 1H), 7.42 (t, J=55.2 Hz, 1H), 7.41 (t, J=7.8 Hz, 1H), 7.22 (d, J=7.8 Hz, 1H), 4.56 (t, J=6.6 Hz, 2H), 4.46 (t, J=6.6 Hz, 2H), 3.49 (p, J=6.6 Hz, 1H), 2.91 (t, J=4.2 Hz, 4H), 2.41 (brs, 4H); and $^{13}$C NMR (150 MHz, DMSO-d$_6$) δ (ppm): 162.3 (d, J=248.8 Hz), 148.0, 138.8 (d, J=7.4 Hz), 135.6, 133.0 (d, J=7.9 Hz), 127.2, 126.1 (t, J=8.1 Hz), 124.0 (d, J=3.0 Hz), 123.4 (t, J=4.2 Hz), 122.9 (d, J=21.0 Hz), 117.2 (t, J=24.0 Hz), 116.9, 114.9 (d, J=25.0 Hz), 111.8 (t, J=232.4 Hz), 110.3, 74.0, 59.0, 53.1, 49.8.

Example 48 3-(difluoromethyl)-N-(piperidin-4-yl)-1-((2-(trifluoromethyl)phenyl)sulfonyl)-1H-indol-4-amine

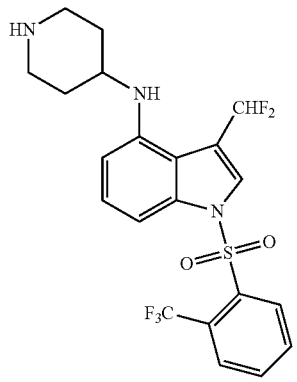 [SMILES: O=S(=O)(c1ccccc1C(F)(F)F)n1cc(C(F)F)c2c(NC3CCNCC3)cccc21]

Step 1) 4-nitro-1H-indole-3-carbaldehyde

4-Nitroindole (2.0 g, 12.3 mmol) was reacted with phosphorus oxychloride (1.5 mL, 16 mmol) in DMF (12 mL) according to the procedure as described in step 3 of example 1 to give the title compound as a yellow solid (1.95 g, 83%). The compound was characterized by the following spectroscopic data: MS (ESI, pos. ion) m/z: 191.0 [M+H]$^+$; and $^1$H NMR (400 MHz, DMSO-d$_6$) δ (ppm): 12.84 (s, 1H), 10.10 (s, 1H), 8.51 (s, 1H), 7.92 (d, J=8.1 Hz, 1H), 7.88 (d, J=7.8 Hz, 1H), 7.44 (t, J=8.0 Hz, 1H).

Step 2) 4-nitro-1-((2-(trifluoromethyl)phenyl)sulfonyl)-1H-indole-3-carbaldehyde 4-Nitro-1H-indole-3-carbaldehyde (800 mg, 4.2 mmol) was reacted with benzyltriethylammonium chloride (192 mg, 0.84 mmol), potassium hydroxide (470 mg, 8.4 mmol) and 2-(trifluoromethyl)benzenesulfonyl chloride (0.78 mL, 5.1 mmol) in DCM (15 mL) according to the procedure as described in step 4 of example 1, and the crude product was purified by silica gel column chromatography eluted with PE/EtOAc (v/v=2/1) to give the title compound as a light yellow solid (1.32 g, 90%). The compound was characterized by the following spectroscopic data: MS (ESI, pos. ion) m/z: 399.1 [M+H]$^+$; and $^1$H NMR (400 MHz, CDCl$_3$) δ (ppm): 10.34 (s, 1H), 8.47 (s, 1H), 8.16 (d, J=8.4 Hz, 1H), 8.10 (t, J=7.6 Hz, 2H), 7.97 (d, J=7.6 Hz, 1H), 7.86 (t, J=7.5 Hz, 1H), 7.82-7.79 (m, 1H), 7.50 (t, J=8.2 Hz, 1H).

Step 3) 3-(difluoromethyl)-4-nitro-1-((2-(trifluoromethyl)phenyl)sulfonyl)-1H-indole 4-Nitro-1-((2-(trifluoromethyl)phenyl)sulfonyl)-1H-indole-3-carbaldehyde (1.49 g, 3.74 mmol) was reacted with diethylaminosulphur trifluoride (1.5 mL, 11 mmol) in DCM (10 mL) according to the procedure as described in step 5 of example 1, and the crude product was purified by silica gel column chromatography eluted with PE/EtOAc (v/v=4/1) to give the title compound as a white solid (1.16 g, 73.8%). The compound was characterized by the following spectroscopic data: MS (ESI, pos. ion) m/z: 443.0 [M+Na]$^+$; and $^1$H NMR (400 MHz, CDCl$_3$) δ (ppm): 8.18-8.16 (m, 2H), 8.11 (d, J=8.0 Hz, 1H), 7.95 (d, J=13.8 Hz, 1H), 7.93 (d, J=14.0 Hz, 1H), 7.82 (t, J=7.5 Hz, 1H), 7.76 (t, J=7.7 Hz, 1H), 7.47 (t, J=8.2 Hz, 1H), 7.29 (t, J=56.0 Hz, 1H).

Step 4) 3-(difluoromethyl)-1-((2-(trifluoromethyl)phenyl)sulfonyl)-1H-indol-4-amine To a mixed solvent of tertrahydrofuran (10 mL), ethanol (5 mL) and water (5 mL) was added 3-(difluoromethyl)-4-nitro-1-((2-(trifluoromethyl)phenyl)sulfonyl)-1H-indole (1.15 g, 2.74 mmol), then iron powder (0.76 g, 13.6 mmol), acetic acid (0.1 mL) and concentrated hydrochloric acid (0.1 mL) were added to the resulting mixture. The mixture was stirred at 90° C. for 30 minutes, then cooled to rt and concentrated in vacuo to remove most of the solvent. To the residue was added water (20 mL), and the mixture was neutralized with sodium carbonate solid to pH about 9~10. The resulting mixture was extracted with dichloromethane (50 mL). The organic layer was dried over anhydrous sodium sulfate, and filtered. The filtrate was concentrated in vacuo and the residue was purified by silica gel column chromatography (PE/EtOAc (v/v)=3/1) to give the title compound as colourless oil (968 mg, 90.6%). The compound was characterized by the following spectroscopic data: MS (ESI, pos. ion) m/z: 391.1 [M+H]$^+$; and $^1$H NMR (400 MHz, CDCl$_3$) δ (ppm): 7.90 (d, J=7.7 Hz, 1H), 7.77 (s, 1H), 7.73 (t, J=8.9 Hz, 2H), 7.65 (t, J=7.7 Hz, 1H), 7.17-7.09 (m, 2H), 6.93 (t, J=55.2 Hz, 1H), 6.58 (dd, J=6.9, 1.4 Hz, 1H).

Step 5) tert-butyl 4-((3-(difluoromethyl)-1-((2-(trifluoromethyl)phenyl)sulfonyl)-1H-indol-4-yl) amino) piperidine-1-carboxylate 3-(Difluoromethyl)-1-((2-(trifluoromethyl)phenyl)sulfonyl)-1H-indol-4-amine (500 mg, 1.3 mmol) was reacted with sodium cyanoborohydride (484 mg, 7.68 mmol), acetic acid (150 μL, 2.6 mmol) and tert-butyl 4-oxopiperidine-1-carboxylate (0.76 g, 3.8 mmol) in methanol (10 mL) according to the procedure as described in example 42, and the crude product was purified by silica gel column chromatography (PE/EtOAc (v/v)=1/1) to give the title compound as light yellow oil (439 mg, 59%). The compound was characterized by the following spectroscopic data: $^1$H NMR (400 MHz, CDCl$_3$) δ (ppm): 7.90 (d, J=7.6 Hz, 1H), 7.78 (d, J=8.0 Hz, 1H), 7.75 (s, 1H), 7.71 (d, J=7.6 Hz, 1H), 7.66 (t, J=7.7 Hz, 1H), 7.17 (t, J=8.2 Hz, 1H), 7.06 (d, J=8.2 Hz, 1H), 6.87 (t, J=55.0 Hz, 1H), 6.50 (d, J=8.0 Hz, 1H), 4.66 (d, J=5.1 Hz, 1H), 3.91 (d, J=12.8 Hz, 2H), 3.61 (brs, 1H), 3.11 (t, J=10.4 Hz, 2H), 2.05-2.03 (m, 2H), 1.66-1.65 (m, 2H), 1.49 (s, 9H).

Step 6) 3-(difluoromethyl)-N-(piperidin-4-yl)-1-((2-(trifluoromethyl)phenyl)sulfonyl)-1H-indol-4-amine tert-Butyl 4-((3-(difluoromethyl)-1-((2-(trifluoromethyl)phenyl)sulfonyl)-1H-indol-4-yl) amino)piperidine-1-carboxylate (420 mg, 0.74 mmol) was dissolved in dichloromethane (10 mL) at 25° C., then a solution of hydrogen chloride in ethyl acetate (1 mL, 2 M) was added to the solution. The mixture was stirred for 1 hour, then concentrated in vacuo to remove most of the solvent. To the residue was added water (20 mL), and the mixture was neutralized with sodium carbonate solid to pH about 8-9. The resulting mixture was extracted with dichloromethane (30 mL). The organic layer was dried over anhydrous sodium sulfate, and filtered. The filtrate was concentrated in vacuo and the residue was purified by silica gel column chromatography (DCM/MeOH (v/v)=10/1) to give the title compound as light yellow oil (161 mg, 46%). The compound was characterized by the following spectroscopic data: MS (ESI, pos. ion) m/z: 473.8 [M+H]$^+$; $^1$H NMR (600 MHz, CDCl$_3$) δ (ppm): 7.89 (d, J=7.7 Hz, 1H), 7.77 (d, J=8.1 Hz, 1H), 7.76 (s, 1H), 7.72 (t, J=7.5 Hz, 1H), 7.65 (t, J=7.6 Hz, 1H), 7.18 (t, J=8.1 Hz, 1H), 7.08 (d, J=8.3 Hz, 1H), 6.88 (t, J=55.0 Hz, 1H), 6.49 (d, J=8.0 Hz, 1H), 4.66 (s, 1H), 3.63 (brs, 1H), 3.32-3.18 (m, 2H), 2.91 (t, J=9.9 Hz, 2H), 2.23-2.14 (m, 2H), 1.74-1.61 (m, 2H); and $^{13}$C NMR (150 MHz, CDCl$_3$) δ (ppm): 140.6, 137.2, 137.1, 134.1, 132.7, 130.5, 128.9 (t, J=6.1 Hz), 127.4, 126.5 (t, J=13.2 Hz), 122.2 (q, J=274.4 Hz), 114.5 (t, J=26.1 Hz), 114.1, 112.6 (t, J=231.9 Hz), 105.1, 102.3, 48.4, 43.4, 31.2.

Example 49 3-(difluoromethyl)-1-((2-fluorophenyl)sulfonyl)-N-(piperidin-4-yl)-1H-indol-4-amine

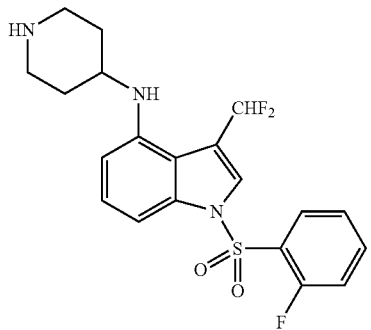 [SMILES: O=S(=O)(c1ccccc1Cl)n1cc(C(F)F)c2c(NC3CCNCC3)cccc21]

Step 1) 1-((2-fluorophenyl)sulfonyl)-4-nitro-1H-indole-3-carbaldehyde

4-Nitro-1H-indole-3-carbaldehyde (800 mg, 4.2 mmol) was reacted with benzyltriethylammonium chloride (192 mg, 0.84 mmol), potassium hydroxide (470 mg, 8.4 mmol) and 2-fluorobenzenesulfonyl chloride (0.67 mL, 5.1 mmol) in DCM (15 mL) according to the procedure as described in step 4 of example 1, and the crude product was purified by silica gel column chromatography eluted with PE/EtOAc (v/v)=2/1 to give the title compound as a light yellow solid (1.34 g, 92%). The compound was characterized by the following spectroscopic data: MS (ESI, pos. ion) m/z: 349.1 [M+H]$^+$; and $^1$H NMR (400 MHz, CDCl$_3$) δ (ppm): 10.32 (s, 1H), 8.55 (d, J=2.1 Hz, 1H), 8.22 (d, J=8.4 Hz, 1H), 8.19-8.15 (m, 1H), 8.08 (d, J=8.0 Hz, 1H), 7.73-7.66 (m, 1H), 7.49 (t, J=8.2 Hz, 1H), 7.41 (t, J=7.7 Hz, 1H), 7.19 (t, J=9.5 Hz, 1H).

Step 2) 3-(difluoromethyl)-1-((2-fluorophenyl)sulfonyl)-4-nitro-1H-indole 1-((2-Fluorophenyl)sulfonyl)-4-nitro-1H-indole-3-carbaldehyde (1.32 g, 3.79 mmol) was reacted with diethylaminosulphur trifluoride (1.5 mL, 11 mmol) in DCM (10 mL) according to the procedure as described in step 5 of example 1, and the crude product was purified by silica gel column chromatography eluted with PE/EtOAc (v/v)=4/1 to give the title compound as a light yellow solid (1.0 g, 71.3%). The compound was characterized by the following spectroscopic data: $^1$H NMR (400 MHz, CDCl$_3$) δ (ppm): 8.24 (d, J=8.4 Hz, 1H), 8.21 (d, J=0.7 Hz, 1H), 8.17-8.12 (m, 1H), 8.09 (d, J=8.1 Hz, 1H), 7.71-7.64 (m, 1H), 7.46 (t, J=8.2 Hz, 1H), 7.38 (d, J=7.5 Hz, 1H), 7.27 (d, J=56.5 Hz, 1H), 7.18 (t, J=9.7 Hz, 1H).

Step 3) 3-(difluoromethyl)-1-((2-fluorophenyl)sulfonyl)-1H-indol-4-amine 3-(Difluoromethyl)-1-((2-fluorophenyl)sulfonyl)-4-nitro-1H-indole (1.0 g, 2.7 mmol) was reacted with iron powder (0.76 g, 13.5 mmol), acetic acid (0.1 mL) and concentrated hydrochloric acid (0.1 mL) in a mixture of tetrahydrofuran (10 mL), ethanol (5 mL) and water (5 mL) according to the procedure as described in step 4 of example 48, and the crude product was purified by silica gel column chromatography (PE/EtOAc (v/v)=3/1) to give the title compound as a brown solid (0.66 g, 72%). The compound was characterized by the following spectroscopic data: MS (ESI, pos. ion) m/z: 341.1 [M+H]$^+$; and $^1$H NMR (400 MHz, CDCl$_3$) δ (ppm): 8.15-8.06 (m, 1H), 7.82 (q, J=2.9 Hz, 1H), 7.62-7.56 (m, 1H), 7.32 (t, J=7.7 Hz, 1H), 7.18 (d, J=8.3 Hz, 1H), 7.12 (t, J=9.4 Hz, 1H), 7.11 (t, J=7.8 Hz, 1H), 6.92 (t, J=55.2 Hz, 1H), 6.55 (d, J=7.7 Hz, 1H).

Step 4) tert-butyl 4-((3-(difluoromethyl)-1-((2-fluorophenyl)sulfonyl)-1H-indol-4-yl)amino) piperidine-1-carboxylate 3-(Difluoromethyl)-1-((2-fluorophenyl)sulfonyl)-1H-indol-4-amine (779 mg, 2.3 mmol) was reacted with sodium cyanoborohydride (866 mg, 13.5 mmol), acetic acid (260 µL, 4.5 mmol) and tert-butyl 4-oxopiperidine-1-carboxylate (0.91 g, 4.6 mmol) in methanol (10 mL) according to the procedure as described in example 42, and the crude product was purified by silica gel chromatography (PE/EtOAc (v/v) =1/1) to give the title compound as light yellow oil (526 mg, 43.9%). The compound was characterized by the following spectroscopic data: MS (ESI, pos. ion) m/z: 524.2 [M+H]$^+$; and $^1$H NMR (400 MHz, CDCl$_3$) δ (ppm): 8.13-8.06 (m, 1H), 7.80 (d, J=2.8 Hz, 1H), 7.62-7.54 (m, 1H), 7.31 (t, J=7.7 Hz, 1H), 7.18-7.13 (m, 1H), 7.11 (s, 1H), 7.09 (s, 1H), 6.86 (t, J=55.1 Hz, 1H), 6.47 (d, J=7.8 Hz, 1H), 4.63 (s, 1H), 3.89-3.88 (m, 2H), 3.57 (brs, 1H), 3.14-3.05 (m, 2H), 2.02-2.01 (m, 2H), 1.66-1.64 (m, 2H), 1.46 (s, 9H).

Step 5) 3-(difluoromethyl)-1-((2-fluorophenyl)sulfonyl)-N-(piperidin-4-yl)-1H-indol-4-amine tert-Butyl 4-((3-(difluoromethyl)-1-((2-fluorophenyl)sulfonyl)-1H-indol-4-yl)amino) piperidine-1-carboxylate (500 mg, 0.95 mmol) was reacted with a solution of hydrogen chloride in ethyl acetate (1 mL, 2 M) in dichloromethane (10 mL) according to the procedure as described in step 6 of example 48, and the crude product was purified by silica gel chromatography (DCM/MeOH (v/v)=10/1) to give the title compound as light yellow oil (141 mg, 35%). The compound was characterized by the following spectroscopic data: MS (ESI, pos. ion) m/z: 424.2 [M+H]$^+$; and $^1$H NMR (400 MHz, CDCl$_3$) δ (ppm): 8.11-8.07 (m, 1H), 7.81 (d, J=2.8 Hz, 1H), 7.63-7.54 (m, 1H), 7.31 (t, J=7.8 Hz, 1H), 7.17-7.12 (m, 2H), 7.09 (s, 1H), 6.87 (t, J=55.2 Hz, 1H), 6.48 (d, J=7.8 Hz, 1H), 4.63 (s, 1H), 3.65 (brs, 1H), 3.35-3.33 (m, 2H), 3.12-3.07 (m, 2H), 2.30-2.28 (m, 2H), 1.89-1.87 (m, 2H).

Example 50 1-((2-chlorophenyl)sulfonyl)-3-(difluoromethyl)-N-(piperidin-4-yl)-1H-indol-4-amine

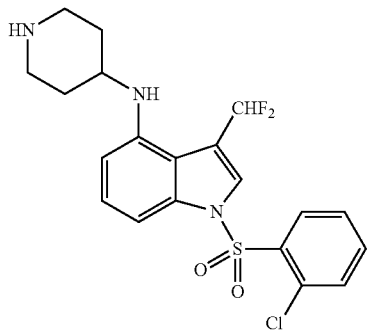

Step 1) 1-((2-chlorophenyl)sulfonyl)-4-nitro-1H-indole-3-carbaldehyde

4-Nitro-1H-indole-3-carbaldehyde (940 mg, 4.96 mmol) was reacted with benzyltriethylammonium chloride (226 mg, 0.99 mmol), potassium hydroxide (560 mg, 9.9 mmol) and 2-chlorobenzenesulfonyl chloride (0.81 mL, 5.9 mmol) in DCM (15 mL) according to the procedure as described in step 4 of example 1, and the crude product was purified by silica gel column chromatography eluted with PE/EtOAc (v/v=2/1) to give the title compound as a light yellow solid (1.34 g, 89.6%). The compound was characterized by the following spectroscopic data: MS (ESI, pos. ion) m/z: 364.8 [M+H]$^+$; and $^1$H NMR (400 MHz, CDCl$_3$) δ (ppm): 10.34 (s, 1H), 8.64 (s, 1H), 8.40 (dd, J=7.9, 1.6 Hz, 1H), 8.07 (d, J=8.0 Hz, 1H), 8.04 (d, J=8.4 Hz, 1H), 7.64 (td, J=7.7, 1.7 Hz, 1H), 7.58 (td, J=7.7, 1.3 Hz, 1H), 7.51 (dd, J=7.8, 1.1 Hz, 1H), 7.44 (t, J=8.2 Hz, 1H).

Step 2) 1-((2-chlorophenyl)sulfonyl)-3-(difluoromethyl)-4-nitro-1H-indole 1-((2-Chlorophenyl)sulfonyl)-4-nitro-1H-indole-3-carbaldehyde (1.6 g, 4.4 mmol) was reacted with diethylaminosulphur trifluoride (1.7 mL, 13 mmol) in DCM (10 mL) according to the procedure as described in step 5 of example 1, and the crude product was purified by silica gel column chromatography eluted with PE/EtOAc (v/v=4/1) to give the title compound as a light brown solid (1.09 g, 64%). The compound was characterized by the following spectroscopic data: MS (ESI, pos. ion) m/z: 408.6 [M+Na]$^+$; and $^1$H NMR (400 MHz, CDCl$_3$) δ (ppm): 8.35 (dd, J=7.9, 1.6 Hz, 1H), 8.30 (s, 1H), 8.07 (t, J=8.2 Hz, 2H), 7.61 (td, J=7.7, 1.7 Hz, 1H), 7.55 (td, J=7.8, 1.3 Hz, 1H), 7.50 (dd, J=7.8, 1.1 Hz, 1H), 7.44-7.42 (m, 1H), 7.29 (t, J=56.2 Hz, 1H).

Step 3) 1-((2-chlorophenyl)sulfonyl)-3-(difluoromethyl)-1H-indol-4-amine 1-((2-Chlorophenyl)sulfonyl)-3-(difluoromethyl)-4-nitro-1H-indole (0.35 g, 0.9 mmol) was reacted with iron powder (0.25 g, 4.5 mmol), acetic acid (0.1 mL) and concentrated hydrochloric acid (0.1 mL) in a mixture of tetrahydrofuran (5 mL), ethanol (2 mL) and water (2 mL) according to the procedure as described in step 4 of example 48, and the crude product was purified by silica gel column chromatography (PE/EtOAc (v/v)=3/1) to give the title compound as brown oil (138 mg, 43%). The compound was characterized by the following spectroscopic data: MS (ESI, pos. ion) m/z: 357.1 [M+H]$^+$; and $^1$H NMR (400 MHz, CDCl$_3$) δ (ppm): 8.26 (dd, J=7.8, 1.6 Hz, 1H), 7.91 (t, J=3.1 Hz, 1H), 7.53 (td, J=7.6, 1.6 Hz, 1H), 7.48 (dd, J=7.7, 1.2 Hz, 1H), 7.44 (d, J=7.7 Hz, 1H), 7.06 (d, J=8.1 Hz, 1H), 7.00 (d, J=8.2 Hz, 1H), 6.93 (t, J=55.3 Hz, 1H), 6.54 (d, J=7.6 Hz, 1H).

Step 4) tert-butyl 4-((1-((2-chlorophenyl)sulfonyl)-3-(difluoromethyl)-1H-indol-4-yl)amino) piperidine-1-carboxylate 1-((2-Chlorophenyl)sulfonyl)-3-(difluoromethyl)-1H-indol-4-amine (0.4 g, 1.2 mmol) was reacted with sodium cyanoborohydride (424 mg, 6.6 mmol), acetic acid (130 μL, 2.3 mmol) and tert-butyl 4-oxopiperidine-1-carboxylate (0.67 g, 3.4 mmol) in methanol (10 mL) according to the procedure as described in example 42, and the crude product was purified by silica gel column chromatography (PE/EtOAc (v/v)=1/1) to give the title compound as light yellow oil (427 mg, 66%). The compound was characterized by the following spectroscopic data: MS (ESI, pos. ion) m/z: 539.7 [M+H]$^+$; and $^1$H NMR (400 MHz, CDCl$_3$) δ (ppm): 8.27 (dd, J=7.8, 1.6 Hz, 1H), 7.89 (t, J=3.3 Hz, 1H), 7.54 (td, J=7.6, 1.6 Hz, 1H), 7.48 (td, J=7.7, 1.4 Hz, 1H), 7.44 (dd, J=7.7, 1.1 Hz, 1H), 7.12 (t, J=8.2 Hz, 1H), 6.93 (d, J=8.3 Hz, 1H), 6.87 (t, J=55.1 Hz, 1H), 6.47 (d, J=8.1 Hz, 1H), 4.65 (s, 1H), 3.90 (d, J=12.4 Hz, 2H), 3.58 (brs, 1H), 3.14-3.07 (m, 2H), 2.06-2.02 (m, 2H), 1.66-1.61 (m, 2H), 1.46 (s, 9H).

Step 5) 1-((2-chlorophenyl)sulfonyl)-3-(difluoromethyl)-N-(piperidin-4-yl)-1H-indol-4-amine tert-Butyl 4-((1-((2-chlorophenyl)sulfonyl)-3-(difluoromethyl)-1H-indol-4-yl)amino) piperidine-1-carboxylate (385 mg, 0.71 mmol) was reacted with a solution of hydrogen chloride in ethyl acetate (1 mL, 2 M) in dichloromethane (10 mL) according to the procedure as described in step 6 of example 48, and the crude product was purified by silica gel column chromatography (DCM/MeOH (v/v)=10/1) to give the title compound as light yellow oil (100 mg, 32%). The compound was characterized by the following spectroscopic data: MS (ESI, pos. ion) m/z: 440.2 [M+H]$^+$; $^1$H NMR (400 MHz, CDCl$_3$) δ (ppm): 8.27 (d, J=7.6 Hz, 1H), 7.90 (s, 1H), 7.55-7.50 (m, 1H), 7.48 (d, J=7.3 Hz, 1H), 7.43 (t, J=8.0 Hz, 1H), 7.13 (t, J=8.1 Hz, 1H), 6.97 (d, J=8.3 Hz, 1H), 6.87 (t, J=55.0 Hz, 1H), 6.43 (d, J=8.0 Hz, 1H), 4.63-4.62 (d, J=7.6 Hz, 1H), 3.70 (brs, 1H), 3.35-3.34 (m, 2H), 3.11-3.06 (m, 2H), 2.30-2.27 (m, 2H), 1.87-1.86 (m, 2H); and $^{13}$C NMR (100 MHz, CDCl$_3$) δ (ppm): 140.2, 136.5, 135.3, 135.2, 132.9, 132.5, 131.9, 127.6 (t, J=13.2 Hz), 127.3, 127.1, 114.3, 113.4 (t, J=26.0 Hz), 112.7 (t, J=232.3 Hz), 105.0, 102.5, 47.0, 42.2, 29.1.

Example 51 1-((2-bromophenyl)sulfonyl)-3-(difluoromethyl)-N-(piperidin-4-yl)-1H-indol-4-amine

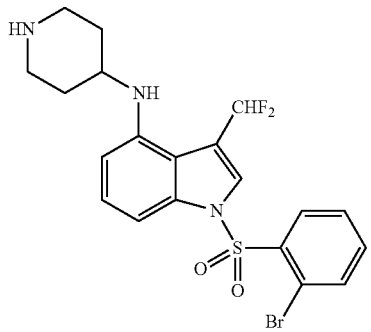

Step 1) 1-((2-bromophenyl)sulfonyl)-4-nitro-1H-indole-3-carbaldehyde

4-Nitro-1H-indole-3-carbaldehyde (940 mg, 4.96 mmol) was reacted with benzyltriethylammonium chloride (226 mg, 0.99 mmol), potassium hydroxide (560 mg, 9.9 mmol) and 2-bromobenzenesulfonyl chloride (1.5 g, 5.9 mmol) in DCM (15 mL) according to the procedure as described in step 4 of example 1, and the crude product was purified by silica gel column chromatography eluted with PE/EtOAc (v/v=2/1) to give the title compound as a light yellow solid (1.36 g, 67%). The compound was characterized by the following spectroscopic data: MS (ESI, pos. ion) m/z: 408.6 [M+H]$^+$; and $^1$H NMR (400 MHz, CDCl$_3$) δ (ppm): 10.35 (s, 1H), 8.69 (s, 1H), 8.42 (dd, J=8.0, 1.4 Hz, 1H), 8.08 (d, J=8.0 Hz, 1H), 8.01 (d, J=8.4 Hz, 1H), 7.73 (dd, J=7.9, 0.7 Hz, 1H), 7.65-7.61 (m, 1H), 7.54 (td, J=7.7, 1.5 Hz, 1H), 7.44 (t, J=8.2 Hz, 1H).

Step 2) 1-((2-bromophenyl)sulfonyl)-3-(difluoromethyl)-4-nitro-1H-indole 1-((2-Bromophenyl)sulfonyl)-4-nitro-1H-indole-3-carbaldehyde (1.29 g, 3.15 mmol) was reacted with diethylaminosulphur trifluoride (1.2 mL, 8.9 mmol) in DCM (10 mL) according to the procedure as described in step 5 of example 1, and the crude product was purified by silica gel column chromatography eluted with PE/EtOAc (v/v=4/1) to give the title compound as a white solid (983 mg, 72.6%). The compound was characterized by the following spectroscopic data: MS (ESI, pos. ion) m/z: 452.6 [M+Na]$^+$; and $^1$H NMR (400 MHz, CDCl$_3$) δ (ppm): 8.39-8.33 (m, 2H), 8.09 (d, J=8.0 Hz, 1H), 8.03 (d, J=8.4 Hz, 1H), 7.73 (dd, J=7.9, 0.9 Hz, 1H), 7.60 (td, J=7.9, 1.1 Hz, 1H), 7.51 (td, J=7.8, 1.6 Hz, 1H), 7.42 (d, J=8.4 Hz, 1H), 7.30 (t, J=56.3 Hz, 1H).

Step 3) 1-((2-bromophenyl)sulfonyl)-3-(difluoromethyl)-1H-indol-4-amine 1-((2-Bromophenyl)sulfonyl)-3-(difluoromethyl)-4-nitro-1H-indole (0.7 g, 1.63 mmol) was reacted with iron powder (0.45 g, 8.1 mmol), acetic acid (0.1 mL) and concentrated hydrochloric acid (0.1 mL) in a mixture of tetrahydrofuran (10 mL), ethanol (5 mL) and water (5 mL) according to the procedure as described in step 4 of example 48, and the crude product was purified by silica gel column chromatography (PE/EtOAc (v/v)=3/1) to give the title compound as brown oil (326 mg, 50%). The compound was characterized by the following spectroscopic data: MS (ESI, pos. ion) m/z: 401.0 [M+H]$^+$; and $^1$H NMR (400 MHz, CDCl$_3$) δ (ppm): 8.24 (dd, J=8.0, 1.5 Hz, 1H), 7.96 (t, J=3.1 Hz, 1H), 7.67 (dd, J=7.9, 1.0 Hz, 1H), 7.52 (td, J=7.9, 1.1 Hz, 1H), 7.43 (td, J=7.7, 1.6 Hz, 1H), 7.06 (d, J=8.0 Hz, 1H), 6.98 (d, J=8.3 Hz, 1H), 6.94 (t, J=55.2 Hz, 1H), 6.55 (d, J=7.7 Hz, 1H).

Step 4) tert-butyl 4-((1-((2-bromophenyl)sulfonyl)-3-(difluoromethyl)-1H-indol-4-yl)amino) piperidine-1-carboxylate 1-((2-Bromophenyl)sulfonyl)-3-(difluoromethyl)-1H-indol-4-amine (0.3 g, 0.75 mmol) was reacted with sodium cyanoborohydride (283 mg, 4.4 mmol), acetic acid (120 μL, 2.0 mmol) and tert-butyl 4-oxopiperidine-1-carboxylate (0.45 g, 2.2 mmol) in methanol (10 mL) according to the procedure as described in example 42, and the crude product was purified by silica gel chromatography (PE/EtOAc (v/v)=1/1) to give the title compound as light yellow oil (306 mg, 70%). The compound was characterized by the following spectroscopic data: MS (ESI, pos. ion) m/z: 583.6 [M+H]$^+$; and $^1$H NMR (400 MHz, CDCl$_3$) δ (ppm): 8.26 (dd, J=8.0, 1.4 Hz, 1H), 7.94 (t, J=3.3 Hz, 1H), 7.67 (d, J=7.9 Hz, 1H), 7.53 (t, J=7.7 Hz, 1H), 7.43 (td, J=7.8, 1.5 Hz, 1H), 7.12 (t, J=8.2 Hz, 1H), 6.90 (d, J=8.3 Hz, 1H), 6.88 (t, J=55.1 Hz, 1H), 6.47 (d, J=8.0 Hz, 1H), 4.64 (d, J=5.3 Hz, 1H), 3.90 (d, J=13.2 Hz, 2H), 3.59 (brs, 1H), 3.16-3.04 (m, 2H), 2.06-2.05 (m, 2H), 1.65-1.63 (m, 2H), 1.46 (s, 9H).

Step 5) 1-((2-bromophenyl)sulfonyl)-3-(difluoromethyl)-N-(piperidin-4-yl)-1H-indol-4-amine tert-Butyl 4-((1-((2-bromophenyl)sulfonyl)-3-(difluoromethyl)-1H-indol-4-yl)amino) piperidine-1-carboxylate (280 mg, 0.48 mmol) was reacted with a solution of hydrogen chloride in ethyl acetate (1 mL, 2 M) in dichloromethane (10 mL) according to the procedure as described in step 6 of example 48, and the crude product was purified by silica gel column chromatography (DCM/MeOH (v/v)=10/1) to give the title compound as light yellow oil (114 mg, 49%). The compound was characterized by the following spectroscopic data: MS (ESI, pos. ion) m/z: 484.1 [M+H]$^+$; and $^1$H NMR (400 MHz, CDCl$_3$) δ (ppm): 8.25 (d, J=7.5 Hz, 1H), 7.94 (s, 1H), 7.66 (d, J=7.6 Hz, 1H), 7.52 (t, J=7.3 Hz, 1H), 7.42 (t, J=7.0 Hz, 1H), 7.11 (t, J=7.9 Hz, 1H), 6.91 (d, J=8.2 Hz, 1H), 6.89 (t, J=54.8 Hz, 1H), 6.45 (d, J=7.8 Hz, 1H), 4.64 (s, 1H), 3.59 (brs, 1H), 3.21-3.18 (m, 2H), 2.86 (t, J=9.9 Hz, 2H), 2.17-2.14 (m, 2H), 1.62-1.60 (m, 2H).

Example 52 3-(difluoromethyl)-1-((3-fluorophenyl)sulfonyl)-N-(piperidin-4-yl)-1H-indol-4-amine

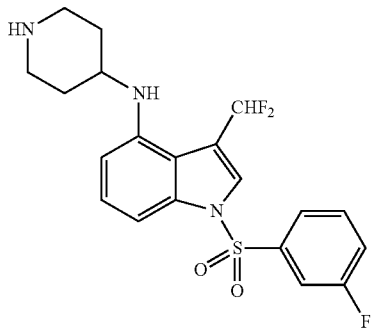 [SMILES: O=S(=O)(c1cccc(F)c1)n1cc(C(F)F)c2c(NC3CCNCC3)cccc21]

Step 1) tert-butyl 1H-indol-4-ylcarbamate

To dichloromethane (20 mL) were added 4-aminoindole (2.0 g, 15.1 mmol) and triethylamine (6.0 mL, 43 mmol) at 0° C., then Boc$_2$O (4.5 mL, 20 mmol) was added dropwise. The mixture was stirred for 13 hours, then concentrated in vacuo and the residue was purified by silica gel column chromatography (PE/EtOAc (v/v)=10/1) to give the title compound as a gray solid (998 mg, 28.5%). The compound was characterized by the following spectroscopic data: MS (ESI, pos. ion) m/z: 233.2 [M+H]$^+$; and $^1$H NMR (600 MHz, DMSO-d$_6$) δ (ppm): 11.01 (s, 1H), 8.95 (s, 1H), 7.34 (d, J=7.5 Hz, 1H), 7.21 (t, J=2.8 Hz, 1H), 7.07 (d, J=8.1 Hz, 1H), 6.97 (t, J=7.9 Hz, 1H), 6.73 (t, J=2.1 Hz, 1H), 1.50 (s, 9H).

Step 2) tert-butyl (3-formyl-1H-indol-4-yl)carbamate tert-Butyl 1H-indol-4-ylcarbamate (2.0 g, 8.6 mmol) was reacted with phosphorus oxychloride (1.0 mL, 10.6 mmol) in DMF (10 mL) according to the procedure as described in step 3 of example 1 to give the title compound as a light red solid (1.12 g, 50%). The compound was characterized by the following spectroscopic data: MS (ESI, pos. ion) m/z: 161.2 [M+H−100]$^+$; and $^1$H NMR (400 MHz, CDCl$_3$) δ (ppm): 10.85 (s, 1H), 10.05 (s, 1H), 9.64 (s, 1H), 8.07 (d, J=7.9 Hz, 1H), 7.80 (s, 1H), 7.22 (t, J=8.1 Hz, 1H), 7.03 (d, J=8.1 Hz, 1H), 1.56 (s, 9H).

Step 3) tert-butyl (1-((3-fluorophenyl)sulfonyl)-3-formyl-1H-indol-4-yl)carbamate tert-Butyl (3-formyl-1H-indol-4-yl)carbamate (500 mg, 1.9 mmol) was reacted with benzyltriethylammonium chloride (88 mg, 0.38 mmol), potassium hydroxide (215 mg, 3.8 mmol) and 3-fluorobenzenesulfonyl chloride (0.3 mL, 2.3 mmol) in DCM (10 mL) according to the procedure as described in step 4 of example 1, and the crude product was purified by silica gel column chromatography eluted with PE/EtOAc (v/v=2/1) to give the title compound as a light yellow solid (786 mg, 99%). The compound was characterized by the following spectroscopic data: MS (ESI, pos. ion) m/z: 318.9 [M+H−100]$^+$; and $^1$H NMR (400 MHz, CDCl$_3$) δ (ppm): 10.38 (s, 1H), 9.80 (s, 1H), 8.25 (s, 1H), 8.22 (d, J=8.2 Hz, 1H), 7.76 (dd, J=7.9, 0.7 Hz, 1H), 7.65 (dt, J=7.6, 2.0 Hz, 1H), 7.55-7.50 (m, 2H), 7.38 (t, J=8.3 Hz, 1H), 7.33 (dd, J=7.9, 2.2 Hz, 1H), 1.54 (s, 9H).

Step 4) tert-butyl (3-(difluoromethyl)-1-((3-fluorophenyl)sulfonyl)-1H-indol-4-yl)carbamate tert-Butyl (1-((3-fluorophenyl)sulfonyl)-3-formyl-1H-indol-4-yl)carbamate (0.8 g, 1.9 mmol) was reacted with diethylaminosulphur trifluoride (0.75 mL, 7.5 mmol) in DCM (10 mL) according to the procedure as described in step 5 of example 1, and the crude product was purified by silica gel column chromatography eluted with PE/EtOAc (v/v=10/1) to give the title compound as a white solid (251 mg, 30%). The compound was characterized by the following spectroscopic data: MS (ESI, neg. ion) m/z: 439.1 [M−H]$^−$; and $^1$H NMR (400 MHz, CDCl$_3$) δ (ppm): 7.79 (d, J=4.9 Hz, 1H), 7.78 (s, 1H), 7.70 (t, J=8.1 Hz, 2H), 7.60 (dt, J=7.7, 2.1 Hz, 1H), 7.48 (td, J=8.1, 5.2 Hz, 1H), 7.39 (t, J=8.2 Hz, 1H), 7.30 (td, J=8.2, 1.8 Hz, 1H), 7.05 (s, 1H), 6.90 (t, J=55.1 Hz, 1H), 1.51 (s, 9H).

Step 5) 3-(difluoromethyl)-1-((3-fluorophenyl)sulfonyl)-1H-indol-4-amine tert-Butyl (3-(difluoromethyl)-1-((3-fluorophenyl)sulfonyl)-1H-indol-4-yl)carbamate (260 mg, 0.6 mmol) was reacted with a solution of hydrogen chloride in ethyl acetate (1 mL, 2 M) in dichloromethane (5 mL) according to the procedure as described in step 6 of example 48, and the crude product was purified by silica gel column chromatography (DCM/MeOH (v/v)=10/1) to give the title compound as a brown solid (177 mg, 87%). The compound was characterized by the following spectroscopic data: MS (ESI, pos. ion) m/z: 340.9 [M+H]$^+$; and $^1$H NMR (400 MHz, CDCl$_3$) δ (ppm): 7.70-7.69 (m, 2H), 7.60 (dt, J=7.8, 2.0 Hz, 1H), 7.46 (td, J=8.1, 5.2 Hz, 1H), 7.37 (d, J=8.3 Hz, 1H), 7.28 (dd, J=8.3, 2.3 Hz, 1H), 7.18 (t, J=8.1 Hz, 1H), 6.90 (t, J=55.2 Hz, 1H), 6.57 (d, J=7.8 Hz, 1H).

Step 6) tert-butyl 4-((3-(difluoromethyl)-1-((3-fluorophenyl)sulfonyl)-1H-indol-4-yl)amino) piperidine-1-carboxylate 3-(Difluoromethyl)-1-((3-fluorophenyl)sulfonyl)-1H-indol-4-amine (0.16 g, 0.47 mmol) was reacted with sodium cyanoborohydride (90 mg, 1.3 mmol), acetic acid (50 μL, 0.9 mmol) and tert-butyl 4-oxopiperidine-1-carboxylate (281 mg, 1.41 mmol) in methanol (5 mL) according to the procedure as described in example 42, and the crude product was purified by silica gel column chromatography (PE/EtOAc (v/v)=1/1) to give the title compound as a white solid (197 mg, 80%). The compound was characterized by the following spectroscopic data: $^1$H NMR (400 MHz, DMSO-d$_6$) δ (ppm): 8.17 (t, J=2.9 Hz, 1H), 7.95 (d, J=8.1 Hz, 1H), 7.87 (d, J=7.8 Hz, 1H), 7.70 (td, J=8.1, 5.5 Hz, 1H), 7.62 (td, J=8.5, 1.8 Hz, 1H), 7.33 (t, J=54.6 Hz, 1H), 7.27-7.23 (m, 2H), 6.60 (dd, J=5.8, 3.0 Hz, 1H), 4.58 (s, 1H), 3.78-3.75 (m, 2H), 3.68-3.55 (m, 2H), 2.94 (brs, 1H), 1.95-1.92 (m, 2H), 1.55-1.50 (m, 2H), 1.39 (s, 9H).

Step 7) 3-(difluoromethyl)-1-((3-fluorophenyl)sulfonyl)-N-(piperidin-4-yl)-1H-indol-4-amine tert-Butyl 4-((3-(difluoromethyl)-1-((3-fluorophenyl)sulfonyl)-1H-indol-4-yl)amino) piperidine-1-carboxylate (195 mg, 0.37 mmol) was reacted with a solution of hydrogen chloride in ethyl acetate (1 mL, 2 M) in dichloromethane (5 mL) according to the procedure as described in step 6 of example 48, and the crude product was purified by silica gel column chromatography (DCM/MeOH (v/v)=10/1) to give the title compound as a light yellow solid (50 mg, 32%). The compound was characterized by the following spectroscopic data: MS (ESI, pos. ion) m/z: 424.0 [M+H]$^+$; $^1$H NMR (600 MHz, DMSO-d$_6$) δ (ppm): 8.19 (s, 1H), 7.95 (dt, J=8.2, 1.9 Hz, 1H), 7.87 (d, J=7.9 Hz, 1H), 7.71 (td, J=8.1, 5.5 Hz, 1H), 7.63 (td, J=8.5, 2.0 Hz, 1H), 7.33 (t, J=54.7 Hz, 1H), 7.24 (d, J=4.2 Hz, 2H), 6.58 (t, J=4.4 Hz, 1H), 4.64-4.56 (m, 1H), 2.99-2.97 (m, 2H), 2.70-2.67 (m, 2H), 1.97-1.95 (m, 2H), 1.34-1.30 (m, 2H); and $^{13}$C NMR (150 MHz, DMSO-d$_6$) δ (ppm): 162.2 (d, J=250.6 Hz), 141.0, 138.7 (d, J=27.3 Hz), 136.6, 133.0 (d, J=8.1 Hz), 128.0, 127.5 (t, J=12.9 Hz), 123.9 (d, J=2.9 Hz), 122.9 (d, J=21.1 Hz), 115.5 (t, J=26.0 Hz), 114.7 (d, J=25.3 Hz), 113.8, 113.2 (t, J=229.6 Hz), 105.6, 101.9, 49.0, 44.2, 32.3.

Example 53 1-((3-chlorophenyl)sulfonyl)-3-(difluoromethyl)-N-(piperidin-4-yl)-1H-indol-4-amine

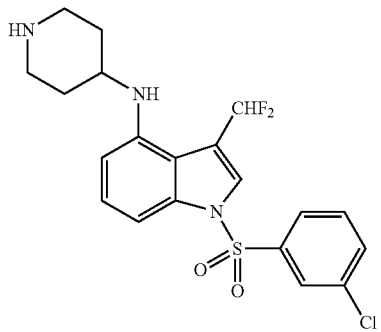 [SMILES: O=S(=O)(c1cccc(Cl)c1)n1cc(C(F)F)c2c(NC3CCNCC3)cccc21]

Step 1) 1-((3-chlorophenyl)sulfonyl)-4-nitro-1H-indole-3-carbaldehyde

4-Nitro-1H-indole-3-carbaldehyde (800 mg, 4.2 mmol) was reacted with benzyltriethylammonium chloride (192 mg, 0.84 mmol), potassium hydroxide (470 mg, 8.4 mmol) and 3-chlorobenzenesulfonyl chloride (0.71 mL, 5.0 mmol) in DCM (15 mL) according to the procedure as described in step 4 of example 1, and the crude product was purified by silica gel column chromatography eluted with PE/EtOAc (v/v)=2/1) to give the title compound as a yellow solid (1.37 g, 90%). The compound was characterized by the following spectroscopic data: MS (ESI, pos. ion) m/z: 364.7 [M+H]$^+$; and $^1$H NMR (400 MHz, CDCl$_3$) δ (ppm): 10.33 (s, 1H), 8.48 (s, 1H), 8.35 (d, J=8.4 Hz, 1H), 8.13 (d, J=8.0 Hz, 1H), 7.95 (t, J=1.6 Hz, 1H), 7.85 (d, J=8.0 Hz, 1H), 7.63 (dd, J=8.1, 0.9 Hz, 1H), 7.57 (t, J=8.2 Hz, 1H), 7.51 (t, J=8.0 Hz, 1H).

Step 2) 1-((3-chlorophenyl)sulfonyl)-3-(difluoromethyl)-4-nitro-1H-indole 1-((3-Chlorophenyl)sulfonyl)-4-nitro-1H-indole-3-carbaldehyde (1.38 g, 3.78 mmol) was reacted with diethylaminosulphur trifluoride (1.45 mL, 11.1 mmol) in DCM (10 mL) according to the procedure as described in step 5 of example 1, and the crude product was purified by silica gel column chromatography eluted with PE/EtOAc (v/v)=4/1) to give the title compound as a white solid (1.05 g, 72.4%). The compound was characterized by the following spectroscopic data: $^1$H NMR (400 MHz, CDCl$_3$) δ (ppm): 8.36 (d, J=8.4 Hz, 1H), 8.13 (s, 1H), 8.11 (d, J=8.2 Hz, 1H), 7.93 (t, J=1.8 Hz, 1H), 7.82 (d, J=7.9 Hz, 1H), 7.63-7.60 (m, 1H), 7.54 (t, J=8.2 Hz, 1H), 7.49 (t, J=8.0 Hz, 1H), 7.25 (t, J=56.0 Hz, 1H).

Step 3) 1-((3-chlorophenyl)sulfonyl)-3-(difluoromethyl)-1H-indol-4-amine 1-((3-Chlorophenyl)sulfonyl)-3-(difluoromethyl)-4-nitro-1H-indole (1.05 g, 2.71 mmol) was reacted with iron powder (0.76 g, 13.5 mmol), acetic acid (0.1 mL) and concentrated hydrochloric acid (0.1 mL) in a mixture of tetrahydrofuran (10 mL), ethanol (5 mL) and water (5 mL) according to the procedure as described in step 4 of example 48, and the crude product was purified by silica gel column chromatography (PE/EtOAc (v/v)=3/1) to give the title compound as a light yellow solid (874 mg, 90.6%). The compound was characterized by the following spectroscopic data: MS (ESI, pos. ion) m/z: 357.1 [M+H]$^+$; and $^1$H NMR (400 MHz, CDCl$_3$) δ (ppm): 7.89 (s, 1H), 7.78 (d, J=7.6 Hz, 1H), 7.70 (s, 1H), 7.53 (d, J=7.6 Hz, 1H), 7.41 (d, J=7.9 Hz, 1H), 7.37 (d, J=8.4 Hz, 1H), 7.19 (t, J=7.9 Hz, 1H), 6.91 (t, J=55.2 Hz, 1H), 6.57 (d, J=7.6 Hz, 1H).

Step 4) tert-butyl 4-((1-((3-chlorophenyl)sulfonyl)-3-(difluoromethyl)-1H-indol-4-yl)amino) piperidine-1-carboxylate 1-((3-Chlorophenyl)sulfonyl)-3-(difluoromethyl)-1H-indol-4-amine (0.4 g, 1.12 mmol) was reacted with sodium cyanoborohydride (280 mg, 4.4 mmol), acetic acid (120 μL, 2.0 mmol) and tert-butyl 4-oxopiperidine-1-carboxylate (0.67 g, 3.36 mmol) in methanol (10 mL) according to the procedure as described in example 42, and the crude product was purified by silica gel column chromatography (PE/EtOAc (v/v)=1/1) to give the title compound as light yellow oil (211 mg, 35%). The compound was characterized by the following spectroscopic data: $^1$H NMR (400 MHz, CDCl$_3$) δ (ppm): 7.89-7.88 (m, 1H), 7.78 (d, J=7.9 Hz, 1H), 7.68 (t, J=3.1 Hz, 1H), 7.54 (d, J=8.1 Hz, 1H), 7.41 (t, J=8.0 Hz, 1H), 7.29 (d, J=8.1 Hz, 1H), 7.23 (d, J=8.2 Hz, 1H), 6.84 (t, J=55.1 Hz, 1H), 6.50 (d, J=7.7 Hz, 1H), 4.59 (d, J=4.6 Hz, 1H), 3.90-3.88 (m, 2H), 3.59 (brs, 1H), 3.15-3.03 (m, 2H), 2.06-2.01 (m, 2H), 1.63 (brs, 2H), 1.46 (s, 9H).

Step 5) 1-((3-chlorophenyl)sulfonyl)-3-(difluoromethyl)-N-(piperidin-4-yl)-1H-indol-4-amine tert-Butyl 4-((1-((3-chlorophenyl)sulfonyl)-3-(difluoromethyl)-1H-indol-4-yl)amino) piperidine-1-carboxylate (240 mg, 0.44 mmol) was reacted with a solution of hydrogen chloride in ethyl acetate (1 mL, 2 M) in dichloromethane (10 mL) according to the procedure as described in step 6 of example 48, and the crude product was purified by silica gel column chromatography (DCM/MeOH (v/v)=10/1) to give the title compound as light yellow oil (79 mg, 41%). The compound was characterized by the following spectroscopic data: MS (ESI, pos. ion) m/z: 440.2 [M+H]$^+$; $^1$H NMR (400 MHz, CDCl$_3$) δ (ppm): 7.93 (t, J=1.7 Hz, 1H), 7.82 (d, J=7.9 Hz, 1H), 7.72 (t, J=3.0 Hz, 1H), 7.61-7.55 (m, 1H), 7.45 (t, J=8.0 Hz, 1H), 7.36-7.30 (m, 1H), 7.29 (d, J=8.0 Hz, 1H), 6.90 (t, J=55.0 Hz, 1H), 6.52 (d, J=7.8 Hz, 1H), 4.63 (d, J=5.4 Hz, 1H), 3.70 (brs, 1H), 3.29-3.24 (m, 2H), 3.01-2.89 (m, 2H), 2.23-2.20 (m, 2H), 1.70-1.66 (m, 2H); and $^{13}$C NMR (100 MHz, CDCl$_3$) δ (ppm): 140.6, 139.2, 137.0, 135.7, 134.4, 130.7, 127.6, 127.1, 125.2 (t, J=12.8 Hz), 125.1, 115.6 (t, J=26.1 Hz), 114.4 (t, J=233.1 Hz), 105.1, 102.4, 48.4, 43.6, 31.2.

Example 54 1-((3-bromophenyl)sulfonyl)-3-(difluoromethyl)-N-(piperidin-4-yl)-1H-indol 4-amine

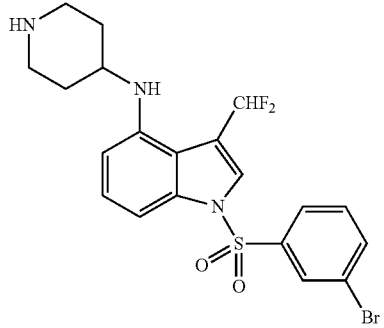 [SMILES: O=S(=O)(c1cccc(Br)c1)n1cc(C(F)F)c2c(NC3CCNCC3)cccc21]

Step 1) tert-butyl (1-((3-bromophenyl)sulfonyl)-3-formyl-1H-indol-4-yl)carbamate tert-Butyl (3-formyl-1H-indol-4-yl)carbamate (500 mg, 1.9 mmol) was reacted with benzyltriethylammonium chloride (88 mg, 0.38 mmol), potassium hydroxide (215 mg, 3.8 mmol) and 3-bromobenzenesulfonyl chloride (584 mg, 2.3 mmol) in DCM (10 mL) according to the procedure as described in step 4 of example 1, and the crude product was purified by silica gel column chromatography eluted with PE/EtOAc (v/v=2/1) to give the title compound as a light yellow solid (817 mg, 90%). The compound was characterized by the following spectroscopic data: MS (ESI, pos. ion) m/z: 378.9 [M+H−100]$^+$; and $^1$H NMR (400 MHz, CDCl$_3$) δ (ppm): 10.39 (s, 1H), 9.81 (s, 1H), 8.24 (s, 1H), 8.22 (d, J=8.3 Hz, 1H), 8.08 (t, J=1.7 Hz, 1H), 7.89 (dd, J=8.0, 0.8 Hz, 1H), 7.76 (dd, J=8.1, 0.8 Hz, 1H), 7.51 (d, J=8.3 Hz, 1H), 7.40 (td, J=8.1, 5.7 Hz, 2H), 1.55 (s, 9H).

Step 2) tert-butyl (1-((3-bromophenyl)sulfonyl)-3-(difluoromethyl)-1H-indol-4-yl)carbamate tert-Butyl (1-((3-bromophenyl)sulfonyl)-3-formyl-1H-indol-4-yl)carbamate (0.79 g, 1.7 mmol) was reacted with diethylaminosulphur trifluoride (0.65 mL, 5.1 mmol) in DCM (10 mL) according to the procedure as described in step 5 of example 1, and the crude product was purified by silica gel column chromatography eluted with PE/EtOAc (v/v=10/1) to give the title compound as a light brown solid (281 mg, 34%). The compound was characterized by the following spectroscopic data: MS (ESI, neg. ion) m/z: 498.9 [M−H]$^-$; and $^1$H NMR (400 MHz, DMSO-d$_6$) δ (ppm): 8.59 (s, 1H), 8.33 (s, 1H), 8.24 (s, 1H), 8.13 (d, J=8.0 Hz, 1H), 7.95 (d, J=8.0 Hz, 1H), 7.86 (d, J=8.3 Hz, 1H), 7.59 (t, J=8.0 Hz, 1H), 7.42 (d, J=8.1 Hz, 1H), 7.31 (t, J=53.5 Hz, 1H), 7.29 (d, J=5.6 Hz, 1H), 1.43 (s, 9H).

Step 3) 1-((3-bromophenyl)sulfonyl)-3-(difluoromethyl)-1H-indol-4-amine tert-Butyl (1-((3-bromophenyl)sulfonyl)-3-(difluoromethyl)-1H-indol-4-yl)carbamate (268 mg, 0.53 mmol) was reacted with a solution of hydrogen chloride in ethyl acetate (1 mL, 2 M) in dichloromethane (5 mL) according to the procedure as described in step 6 of example 48, and the crude product was purified by silica gel column chromatography (DCM/MeOH (v/v)=10/1) to give the title compound as a brown solid (191 mg, 90%). The compound was characterized by the following spectroscopic data: MS (ESI, pos. ion) m/z: 401.1 [M+H]$^+$; and $^1$H NMR (400 MHz, DMSO-d$_6$) δ (ppm): 8.19 (t, J=1.7 Hz, 1H), 8.13 (t, J=3.0 Hz, 1H), 8.02 (d, J=8.0 Hz, 1H), 7.95 (dd, J=8.1, 0.9 Hz, 1H), 7.58 (t, J=8.0 Hz, 1H), 7.32 (t, J=54.7 Hz, 1H), 7.19-7.13 (m, 2H), 6.60 (d, J=7.5 Hz, 1H), 5.21 (s, 2H).

Step 4) tert-butyl 4-((1-((3-bromophenyl)sulfonyl)-3-(difluoromethyl)-1H-indol-4-yl)amino) piperidine-1-carboxylate 1-((3-Bromophenyl)sulfonyl)-3-(difluoromethyl)-1H-indol-4-amine (0.4 g, 1.0 mmol) was reacted with sodium cyanoborohydride (188 mg, 2.9 mmol), acetic acid (120 μL, 2.0 mmol) and tert-butyl 4-oxopiperidine-1-carboxylate (595 mg, 2.99 mmol) in methanol (5 mL) according to the procedure as described in example 42, and the crude product was purified by silica gel column chromatography (PE/EtOAc (v/v)=1/1) to give the title compound as a white solid (466 mg, 80%). The compound was characterized by the following spectroscopic data: $^1$H NMR (400 MHz, DMSO-d$_6$) δ (ppm): 8.21-8.18 (m, 2H), 8.03 (d, J=8.0 Hz, 1H), 7.96 (d, J=6.8 Hz, 1H), 7.60 (t, J=8.0 Hz, 1H), 7.34 (t, J=54.7 Hz, 1H), 7.26 (d, J=1.6 Hz, 1H), 7.25 (s, 1H), 6.64-6.58 (m, 1H), 4.59-4.58 (m, 1H), 3.79-3.75 (m, 2H), 3.63-3.59 (m, 2H), 1.95-1.93 (m, 2H), 1.55-1.54 (m, 2H), 1.40 (s, 9H).

Step 5) 1-((3-bromophenyl)sulfonyl)-3-(difluoromethyl)-N-(piperidin-4-yl)-1H-indol-4-amine tert-Butyl 4-((1-((3-bromophenyl)sulfonyl)-3-(difluoromethyl)-1H-indol-4-yl)amino) piperidine-1-carboxylate (440 mg, 0.75 mmol) was reacted with a solution of hydrogen chloride in ethyl acetate (1 mL, 2 M) in dichloromethane (10 mL) according to the procedure as described in step 6 of example 48, and the crude product was purified by silica gel column chromatography (DCM/MeOH (v/v)=10/1) to give the title compound as a light yellow solid (65 mg, 18%). The compound was characterized by the following spectroscopic data: MS (ESI, pos. ion) m/z: 483.7 [M+H]$^+$; $^1$H NMR (600 MHz, DMSO-d$_6$) δ (ppm): 8.20 (t, J=2.5 Hz, 1H), 8.19 (t, J=1.8 Hz, 1H), 8.02 (dd, J=8.0, 0.8 Hz, 1H), 7.95 (dd, J=8.1, 1.0 Hz, 1H), 7.59 (t, J=8.0 Hz, 1H), 7.32 (t, J=54.7 Hz, 1H), 7.24-7.21 (m, 2H), 6.57 (d, J=6.8 Hz, 1H), 4.65-4.56 (m, 1H), 3.63-3.61 (m, 1H), 2.99-2.91 (m, 2H), 2.66-2.63 (m, 2H), 1.94-1.93 (m, 2H), 1.33-1.26 (m, 2H); and $^{13}$C NMR (150 MHz, DMSO-d$_6$) δ (ppm): 141.0, 138.7, 138.4, 136.6, 132.6, 129.5, 128.0, 127.5 (t, J=13.1 Hz), 126.5, 123.2, 115.5 (t, J=26.0 Hz), 113.7, 113.1 (t, J=229.5 Hz), 105.6, 101.7, 49.2, 44.4, 32.6.

Example 55 3-(difluoromethyl)-1-(phenylsulfonyl)-N-(piperidin-4-yl)-1H-indol-4-amine

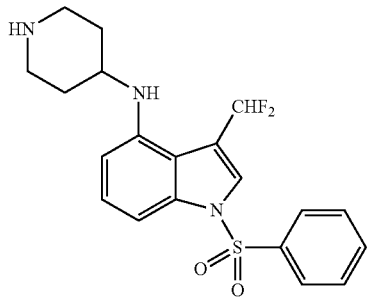 [SMILES: O=S(=O)(c1ccccc1)n1cc(C(F)F)c2c(NC3CCNCC3)cccc21]

Step 1) 4-nitro-1-(phenylsulfonyl)-1H-indole-3-carbaldehyde

4-Nitro-1H-indole-3-carbaldehyde (700 mg, 3.68 mmol) was reacted with benzyltriethylammonium chloride (168 mg, 0.73 mmol), potassium hydroxide (413 mg, 6.26 mmol) and benzenesulfonyl chloride (780 mg, 4.41 mmol) in DCM (15 mL) according to the procedure as described in step 4 of example 1, and the crude product was purified by silica gel column chromatography eluted with PE/EtOAc (v/v=2/1) to give the title compound as a yellow solid (607 mg, 50%). The compound was characterized by the following spectroscopic data: MS (ESI, pos. ion) m/z: 331.1 [M+H]$^+$; and $^1$H NMR (400 MHz, CDCl$_3$) δ (ppm): 10.35 (s, 1H), 8.53 (s, 1H), 8.39 (d, J=8.4 Hz, 1H), 8.13 (d, J=8.0 Hz, 1H), 8.00 (d, J=7.5 Hz, 2H), 7.70 (t, J=7.5 Hz, 1H), 7.60-7.53 (m, 3H).

Step 2) 3-(difluoromethyl)-4-nitro-1-(phenylsulfonyl)-1H-indole

4-Nitro-1-(phenylsulfonyl)-1H-indole-3-carbaldehyde (593 mg, 1.8 mmol) was reacted with diethylaminosulphur trifluoride (0.69 mL, 5.3 mmol) in DCM (10 mL) according to the procedure as described in step 5 of example 1, and the crude product was purified by silica gel column chromatography eluted with PE/EtOAc (v/v=4/1) to give the title compound as a white solid (0.57 g, 90.6%). The compound was characterized by the following spectroscopic data: $^1$H NMR (400 MHz, CDCl$_3$) δ (ppm): 8.40 (d, J=8.4 Hz, 1H), 8.19 (s, 1H), 8.11 (d, J=8.0 Hz, 1H), 7.97 (d, J=7.6 Hz, 2H), 7.68 (t, J=7.5 Hz, 1H), 7.60-7.50 (m, 3H), 7.28 (t, J=56.0 Hz, 1H).

Step 3) 3-(difluoromethyl)-1-(phenylsulfonyl)-1H-indol-4-amine 3-(Difluoromethyl)-4-nitro-1-(phenylsulfonyl)-1H-indole (560 mg, 1.59 mmol) was reacted with iron powder (445 mg, 7.97 mmol), acetic acid (0.1 mL) and concentrated hydrochloric acid (0.1 mL) in a mixture of tetrahydrofuran (10 mL), ethanol (5 mL) and water (5 mL) according to the procedure as described in step 4 of example 48, and the crude product was purified by silica gel column chromatography (PE/EtOAc (v/v)=3/1) to give the title compound as brown oil (353 mg, 68.9%). The compound was characterized by the following spectroscopic data: MS (ESI, pos. ion) m/z: 323.1 [M+H]$^+$; and $^1$H NMR (400 MHz, CDCl$_3$) δ (ppm): 7.93 (d, J=7.4 Hz, 2H), 7.75 (t, J=3.0 Hz, 1H), 7.60 (t, J=7.5 Hz, 1H), 7.50 (t, J=7.7 Hz, 2H), 7.41 (d, J=8.0 Hz, 1H), 7.19 (t, J=8.1 Hz, 1H), 6.92 (t, J=55.2 Hz, 1H), 6.58 (d, J=7.8 Hz, 1H).

Step 4) tert-butyl 4-((3-(difluoromethyl)-1-(phenylsulfonyl)-1H-indol-4-yl)amino) piperidine-1-carboxylate 3-(3-(Difluoromethyl)-1-(phenylsulfonyl)-1H-indol-4-amine (0.34 g, 1.05 mmol) was reacted with sodium cyanoborohydride (199 mg, 3.01 mmol), acetic acid (130 μL, 2.3 mmol) and tert-butyl 4-oxopiperidine-1-carboxylate (0.63 g, 3.17 mmol) in methanol (10 mL) according to the procedure as described in example 42, and the crude product was purified by silica gel column chromatography (PE/EtOAc (v/v)=1/1) to give the title compound as light yellow oil (196 mg, 37.1%). The compound was characterized by the following spectroscopic data: MS (ESI, pos. ion) m/z: 505.8 [M+H]$^+$; and $^1$H NMR (400 MHz, CDCl$_3$) δ (ppm): 7.93 (d, J=7.6 Hz, 2H), 7.73 (t, J=3.1 Hz, 1H), 7.60 (t, J=7.4 Hz, 1H), 7.50 (t, J=7.7 Hz, 2H), 7.33 (d, J=8.3 Hz, 1H), 7.24 (t, J=8.1 Hz, 1H), 6.86 (t, J=56.0 Hz, 1H), 6.50 (d, J=8.0 Hz, 1H), 4.18 (t, J=6.6 Hz, 1H), 4.11 (t, J=6.7 Hz, 2H), 3.91 (d, J=12.2 Hz, 2H), 3.59 (brs, 1H), 3.12 (t, J=10.4 Hz, 2H), 2.08 (brs, 2H), 1.48 (s, 9H).

Step 5) 3-(difluoromethyl)-1-(phenylsulfonyl)-N-(piperidin-4-yl)-1H-indol-4-amine tert-Butyl 4-((3-(difluoromethyl)-1-(phenylsulfonyl)-1H-indol-4-yl)amino)piperidine 1-carboxylate (198 mg, 0.39 mmol) was reacted with a solution of hydrogen chloride in ethyl acetate (1 mL, 2 M) in dichloromethane (5 mL) according to the procedure as described in step 6 of example 48, and the crude product was purified by silica gel column chromatography (DCM/MeOH (v/v)=10/1) to give the title compound as light yellow oil (46 mg, 29%). The compound was characterized by the following spectroscopic data: MS (ESI, pos. ion) m/z: 406.2 [M+H]$^+$; $^1$H NMR (600 MHz, CDCl$_3$) δ (ppm): 7.93 (d, J=7.8 Hz, 2H), 7.74 (s, 1H), 7.60 (t, J=7.3 Hz, 1H), 7.50 (t, J=7.7 Hz, 2H), 7.34 (d, J=8.3 Hz, 1H), 7.24 (t, J=8.1 Hz, 1H), 6.87 (t, J=54.0 Hz, 1H), 6.49 (d, J=8.0 Hz, 1H), 4.60 (s, 1H), 3.61 (brs, 1H), 3.22 (d, J=11.6 Hz, 2H), 2.91-2.87 (m, 2H), 2.17 (d, J=11.9 Hz, 2H), 1.63-1.60 (m, 2H); and $^{13}$C NMR (150 MHz, CDCl$_3$) δ (ppm): 140.6, 139.3, 137.8, 137.1, 134.2, 129.5, 127.3, 127.1, 125.4 (t, J=13.5 Hz), 114.4, 114.1, 112.6 (t, J=229.5 Hz), 104.9, 102.5, 53.4, 43.7, 31.9.

Example 56 3-(difluoromethyl)-N-(piperidin-4-yl)-1-tosyl-1H-indol-4-amine

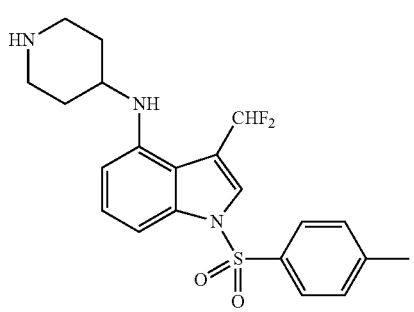 [SMILES: Cc1ccc(S(=O)(=O)n2cc(C(F)F)c3c(NC4CCNCC4)cccc32)cc1]

Step 1) 4-nitro-1-tosyl-1H-indole-3-carbaldehyde

4-Nitro-1H-indole-3-carbaldehyde (700 mg, 3.68 mmol) was reacted with benzyltriethylammonium chloride (168 mg, 0.73 mmol), potassium hydroxide (413 mg, 6.26 mmol) and p-methylbenzenesulfonyl chloride (1.2 g, 6.26 mmol) in DCM (15 mL) according to the procedure as described in step 4 of example 1, and the crude product was purified by silica gel column chromatography eluted with PE/EtOAc (v/v=2/1) to give the title compound as a light yellow solid (862 mg, 68.1%). The compound was characterized by the following spectroscopic data: MS (ESI, pos. ion) m/z: 345.1 [M+H]$^+$; and $^1$H NMR (400 MHz, CDCl$_3$) δ (ppm): 10.34 (s, 1H), 8.52 (s, 1H), 8.38 (d, J=8.3 Hz, 1H), 8.12 (d, J=8.0 Hz, 1H), 7.87 (d, J=8.4 Hz, 2H), 7.54 (t, J=8.2 Hz, 1H), 7.35 (d, J=8.2 Hz, 2H), 2.42 (s, 3H).

Step 2) 3-(difluoromethyl)-4-nitro-1-tosyl-1H-indole

4-Nitro-1-tosyl-1H-indole-3-carbaldehyde (863 mg, 2.51 mmol) was reacted with diethylaminosulphur trifluoride (0.97 mL, 7.4 mmol) in DCM (10 mL) according to the procedure as described in step 5 of example 1, and the crude product was purified by silica gel column chromatography eluted with PE/EtOAc (v/v=4/1) to give the title compound as a light yellow solid (694 mg, 75.5%). The compound was characterized by the following spectroscopic data: MS (ESI, pos. ion) m/z: 389.1 [M+Na]$^+$; and $^1$H NMR (400 MHz, CDCl$_3$) δ (ppm): 8.39 (d, J=8.4 Hz, 1H), 8.17 (s, 1H), 8.10 (d, J=8.0 Hz, 1H), 7.85 (d, J=8.4 Hz, 2H), 7.51 (t, J=8.2 Hz, 1H), 7.27 (t, J=56.0 Hz, 1H), 7.34 (d, J=8.2 Hz, 2H), 2.41 (s, 3H).

Step 3) 3-(difluoromethyl)-1-tosyl-1H-indol-4-amine 3-(Difluoromethyl)-4-nitro-1-tosyl-1H-indole (680 mg, 1.86 mmol) was reacted with iron powder (520 mg, 9.3 mmol), acetic acid (0.1 mL) and concentrated hydrochloric acid (0.1 mL) in a mixture of tetrahydrofuran (10 mL), ethanol (5 mL) and water (5 mL) according to the procedure as described in step 4 of example 48, and the crude product was purified by silica gel column chromatography (PE/EtOAc (v/v)=3/1) to give the title compound as brown oil (620 mg, 99.3%). The compound was characterized by the following spectroscopic data: MS (ESI, pos. ion) m/z: 336.9 [M+H]$^+$; and $^1$H NMR (400 MHz, CDCl$_3$) δ (ppm): 7.81 (d, J=8.3 Hz, 2H), 7.74 (t, J=3.0 Hz, 1H), 7.40 (d, J=8.3 Hz, 1H), 7.27 (d, J=6.6 Hz, 2H), 7.18 (t, J=8.1 Hz, 1H), 6.92 (t, J=55.2 Hz, 1H), 6.57 (d, J=7.8 Hz, 1H), 2.38 (s, 3H).

Step 4) tert-butyl 4-((3-(difluoromethyl)-1-tosyl-1H-indol-4-yl)amino)piperidine-1-carboxylate 3-(Difluoromethyl)-1-tosyl-1H-indol-4-amine (0.5 g, 1.5 mmol) was reacted with sodium cyanoborohydride (280 mg, 4.23 mmol), acetic acid (180 μL, 3.1 mmol) and tert-butyl 4-oxopiperidine-1-carboxylate (0.89 g, 4.46 mmol) in methanol (10 mL) according to the procedure as described in example 42, and the crude product was purified by silica gel column chromatography (PE/EtOAc (v/v)=1/1) to give the title compound as light yellow oil (528 mg, 67.8%). The compound was characterized by the following spectroscopic data: MS (ESI, pos. ion) m/z: 519.8 [M+H]$^+$; and $^1$H NMR (400 MHz, CDCl$_3$) δ (ppm): 7.81 (d, J=8.3 Hz, 2H), 7.72 (t, J=3.0 Hz, 1H), 7.32 (d, J=8.2 Hz, 2H), 7.28 (d, J=6.1 Hz, 2H), 7.23 (t, J=8.1 Hz, 1H), 6.86 (t, J=52.0 Hz, 1H), 6.49 (d, J=7.9 Hz, 1H), 4.60 (s, 1H), 3.91 (d, J=12.6 Hz, 2H), 3.59 (brs, 1H), 3.12 (t, J=10.4 Hz, 2H), 2.38 (s, 3H), 2.04 (d, J=9.9 Hz, 2H), 1.61 (brs, 2H), 1.49 (s, 9H).

Step 5) 3-(difluoromethyl)-N-(piperidin-4-yl)-1-tosyl-1H-indol-4-amine tert-Butyl 4-((3-(difluoromethyl)-1-tosyl-1H-indol-4-yl)amino)piperidine-1-carboxylate (510 mg, 0.98 mmol) was reacted with a solution of hydrogen chloride in ethyl acetate (1 mL, 2 M) in dichloromethane (5 mL) according to the procedure as described in step 6 of example 48, and the crude product was purified by silica gel column chromatography (DCM/MeOH (v/v)=10/1) to give the title compound as a light yellow solid (227 mg, 55.4%). The compound was characterized by the following spectroscopic data: MS (ESI, pos. ion) m/z: 420.2 [M+H]$^+$; $^1$H NMR (600 MHz, CDCl$_3$) δ (ppm): 7.80 (d, J=8.4 Hz, 2H), 7.72 (t, J=3.1 Hz, 1H), 7.32 (d, J=8.1 Hz, 1H), 7.27 (d, J=8.1 Hz, 2H), 7.22 (t, J=8.2 Hz, 1H), 6.86 (t, J=54.0 Hz, 1H), 6.48 (d, J=8.0 Hz, 1H), 4.59 (d, J=4.3 Hz, 1H), 3.61-3.55 (m, 1H), 3.20-3.17 (m, 2H), 2.85-2.82 (m, 2H), 2.37 (s, 3H), 2.19-2.09 (m, 2H), 1.62-1.53 (m, 2H); and $^{13}$C NMR (150 MHz, CDCl$_3$) δ (ppm): 145.5, 140.6, 137.1, 134.8, 130.1, 127.2, 127.1, 125.4 (t, J=13.5 Hz), 114.9 (t, J=25.5 Hz), 114.3, 112.7 (t, J=231.0 Hz), 104.7, 102.4, 48.9, 44.2, 32.2, 21.6.

Example 57 3-(difluoromethyl)-1-((4-methoxyphenyl)sulfonyl)-N-(piperidin-4-yl)-1H-indol 4-amine

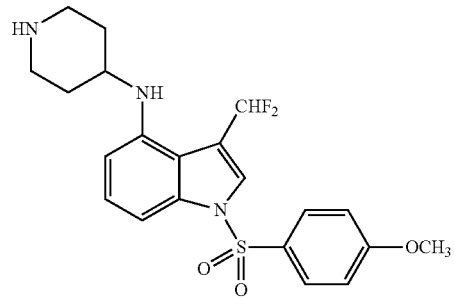 [SMILES: COc1ccc(S(=O)(=O)n2cc(C(F)F)c3c(NC4CCNCC4)cccc32)cc1]

Step 1) 1-((4-methoxyphenyl)sulfonyl)-4-nitro-1H-indole-3-carbaldehyde

4-Nitro-1H-indole-3-carbaldehyde (600 mg, 3.1 mmol) was reacted with benzyltriethylammonium chloride (144 mg, 0.63 mmol), potassium hydroxide (354 mg, 5.36 mmol) and p-methoxybenzenesulfonyl chloride (782 mg, 3.8 mmol) in DCM (15 mL) according to the procedure as described in step 4 of example 1, and the crude product was purified by silica gel column chromatography eluted with PE/EtOAc (v/v=2/1) to give the title compound as a light yellow solid (904 mg, 81.4%). The compound was characterized by the following spectroscopic data: MS (ESI, pos. ion) m/z: 361.1 [M+H]$^+$; and $^1$H NMR (400 MHz, CDCl$_3$) δ (ppm): 10.35 (s, 1H), 8.52 (s, 1H), 8.38 (d, J=8.4 Hz, 1H), 8.12 (d, J=8.0 Hz, 1H), 7.93 (d, J=9.1 Hz, 2H), 7.54 (t, J=8.2 Hz, 1H), 7.00 (d, J=9.1 Hz, 2H), 3.86 (s, 3H).

Step 2) 3-(difluoromethyl)-1-((4-methoxyphenyl)sulfonyl)-4-nitro-1H-indole 1-((4-Methoxyphenyl)sulfonyl)-4-nitro-1H-indole-3-carbaldehyde (840 mg, 2.33 mmol) was reacted with diethylaminosulphur trifluoride (0.89 mL, 6.53 mmol) in DCM (10 mL) according to the procedure as described in step 5 of example 1, and the crude product was purified by silica gel column chromatography eluted with PE/EtOAc (v/v=4/1) to give the title compound as a white solid (669 mg, 75.2%). The compound was characterized by the following spectroscopic data: MS (ESI, pos. ion) m/z: 404.8 [M+Na]$^+$; and $^1$H NMR (400 MHz, CDCl$_3$) δ (ppm): 8.38 (d, J=8.4 Hz, 1H), 8.17 (s, 1H), 8.10 (d, J=8.0 Hz, 1H), 7.90 (d, J=9.0 Hz, 2H), 7.51 (t, J=8.2 Hz, 1H), 7.27 (t, J=56.0 Hz, 1H), 6.99 (d, J=9.0 Hz, 2H), 3.85 (s, 3H).

Step 3) 3-(difluoromethyl)-1-((4-methoxyphenyl)sulfonyl)-1H-indol-4-amine 3-(Difluoromethyl)-1-((4-methoxyphenyl)sulfonyl)-4-nitro-1H-indole (650 mg, 1.7 mmol) was reacted with iron powder (475 mg, 8.5 mmol), acetic acid (0.1 mL) and concentrated hydrochloric acid (0.1 mL) in a mixture of tetrahydrofuran (10 mL), ethanol (5 mL) and water (5 mL) according to the procedure as described in step 4 of example 48, and the crude product was purified by silica gel column chromatography (PE/EtOAc (v/v)=3/1) to give the title compound as brown oil (478 mg, 79.8%). The compound was characterized by the following spectroscopic data: MS (ESI, pos. ion) m/z: 353.1 [M+H]$^+$; and $^1$H NMR (400 MHz, CDCl$_3$) δ (ppm): 7.86 (d, J=9.0 Hz, 2H), 7.74 (t, J=3.0 Hz, 1H), 7.39 (d, J=8.3 Hz, 1H), 7.18 (t, J=8.1 Hz, 1H), 6.93 (d, J=9.1 Hz, 2H), 6.92 (t, J=56.4 Hz, 1H), 6.57 (d, J=7.8 Hz, 1H), 3.83 (s, 3H).

Step 4) tert-butyl 4-((3-(difluoromethyl)-1-((4-methoxyphenyl)sulfonyl)-1H-indol-4-yl)amino) piperidine-1-carboxylate 3-(Difluoromethyl)-1-((4-methoxyphenyl)sulfonyl)-1H-indol-4-amine (340 mg, 0.96 mmol) was reacted with sodium cyanoborohydride (182 mg, 2.75 mmol), acetic acid (120 μL, 2.0 mmol) and tert-butyl 4-oxopiperidine-1-carboxylate (577 mg, 2.9 mmol) in methanol (10 mL) according to the procedure as described in example 42, and the crude product was purified by silica gel column chromatography (PE/EtOAc (v/v)=1/1) to give the title compound as light yellow oil (450 mg, 87.7%). The compound was characterized by the following spectroscopic data: MS (ESI, pos. ion) m/z: 536.2 [M+H]$^+$; and $^1$H NMR (400 MHz, CDCl$_3$) δ (ppm): 7.87 (d, J=9.0 Hz, 2H), 7.72 (t, J=3.2 Hz, 1H), 7.32 (d, J=8.2 Hz, 1H), 7.23 (t, J=8.1 Hz, 1H), 6.93 (d, J=9.0 Hz, 2H), 6.85 (t, J=52.0 Hz, 1H), 6.49 (d, J=7.9 Hz, 1H), 4.59 (s, 1H), 3.91 (d, J=13.1 Hz, 2H), 3.83 (s, 3H), 3.59 (brs, 1H), 3.12 (t, J=10.3 Hz, 2H), 2.07-2.04 (m, 2H), 1.66 (d, J=7.0 Hz, 2H), 1.48 (s, 9H).

Step 5) 3-(difluoromethyl)-1-((4-methoxyphenyl)sulfonyl)-N-(piperidin-4-yl)-1H-indol-4-amine tert-Butyl 4-((3-(difluoromethyl)-1-((4-methoxyphenyl)sulfonyl)-1H-indol-4-yl)amino) piperidine-1-carboxylate (453 mg, 0.85 mmol) was reacted with a solution of hydrogen chloride in ethyl acetate (1 mL, 2 M) in dichloromethane (10 mL) according to the procedure as described in step 6 of example 48, and the crude product was purified by silica gel column chromatography (DCM/MeOH (v/v)=10/1) to give the title compound as a light yellow solid (95 mg, 25.7%). The compound was characterized by the following spectroscopic data: MS (ESI, pos. ion) m/z: 436.2 [M+H]$^+$; $^1$H NMR (600 MHz, CDCl$_3$) δ (ppm): 7.86 (d, J=8.4 Hz, 2H), 7.72 (s, 1H), 7.34 (d, J=8.1 Hz, 1H), 7.23 (t, J=8.0 Hz, 1H), 6.92 (d, J=8.4 Hz, 2H), 6.86 (t, J=54.0 Hz, 1H), 6.46 (d, J=7.8 Hz, 1H), 4.59 (brs, 1H), 3.82 (s, 3H), 3.66 (brs, 1H), 3.28 (brs, 2H), 3.00 (brs, 2H), 2.23 (d, J=9.5 Hz, 2H), 1.75 (d, J=8.5 Hz, 2H); and $^{13}$C NMR (150 MHz, CDCl$_3$) δ (ppm): 164.2, 140.3, 137.0, 129.5, 129.0, 127.2, 125.7 (t, J=13.5 Hz), 114.7, 112.7 (t, J=231.0 Hz), 104.8, 102.8, 55.7, 47.8, 43.1, 30.5.

Example 58 1-((4-chlorophenyl)sulfonyl)-3-(difluoromethyl)-N-(piperidin-4-yl)-1H-indol 4-amine

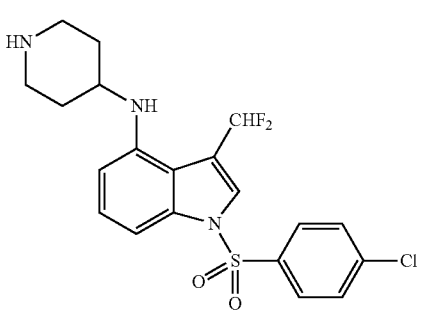 [SMILES: O=S(=O)(c1ccc(Br)cc1)n1cc(C(F)F)c2c(NC3CCNCC3)cccc21]

Step 1) 1-((4-chlorophenyl)sulfonyl)-4-nitro-1H-indole-3-carbaldehyde

4-Nitro-1H-indole-3-carbaldehyde (1.0 g, 5.26 mmol) was reacted with benzyltriethylammonium chloride (300 mg, 1.3 mmol), potassium hydroxide (354 mg, 5.36 mmol) and 4-chlorobenzenesulfonyl chloride (1.3 g, 6.16 mmol) in DCM (15 mL) according to the procedure as described in step 4 of example 1, and the crude product was purified by silica gel column chromatography eluted with PE/EtOAc (v/v=2/1) to give the title compound as a light yellow solid (751 mg, 39%). The compound was characterized by the following spectroscopic data: MS (ESI, pos. ion) m/z: 387.0 [M+Na]$^+$; and $^1$H NMR (400 MHz, CDCl$_3$) δ (ppm): 10.34 (s, 1H), 8.50 (s, 1H), 8.36-8.34 (m, 1H), 8.14 (d, J=8.0 Hz, 1H), 7.93 (d, J=8.8 Hz, 2H), 7.57-7.53 (m, 3H).

Step 2) 1-((4-chlorophenyl)sulfonyl)-3-(difluoromethyl)-4-nitro-1H-indole 1-((4-Chlorophenyl)sulfonyl)-4-nitro-1H-indole-3-carbaldehyde (1.03 g, 2.82 mmol) was reacted with diethylaminosulphur trifluoride (0.95 mL, 6.97 mmol) in DCM (10 mL) according to the procedure as described in step 5 of example 1, and the crude product was purified by silica gel column chromatography eluted with PE/EtOAc (v/v=4/1) to give the title compound as a light yellow solid (601 mg, 55%). The compound was characterized by the following spectroscopic data: $^1$H NMR (400 MHz, CDCl$_3$) δ (ppm): 8.37 (dd, J=8.4, 0.5 Hz, 1H), 8.15 (s, 1H), 8.11 (d, J=8.0 Hz, 1H), 7.90 (d, J=8.8 Hz, 2H), 7.65-7.48 (m, 3H), 7.28 (t, J=56.2 Hz, 1H).

Step 3) 1-((4-chlorophenyl)sulfonyl)-3-(difluoromethyl)-1H-indol-4-amine 1-((4-Chlorophenyl)sulfonyl)-3-(difluoromethyl)-4-nitro-1H-indole (534 mg, 1.38 mmol) was reacted with iron powder (400 mg, 7.14 mmol), acetic acid (0.1 mL) and concentrated hydrochloric acid (0.1 mL) in a mixture of tetrahydrofuran (10 mL), ethanol (5 mL) and water (5 mL) according to the procedure as described in step 4 of example 48, and the crude product was purified by silica gel column chromatography (PE/EtOAc (v/v)=3/1) to give the title compound as a light yellow solid (490 mg, 99.5%). The compound was characterized by the following spectroscopic data: MS (ESI, pos. ion) m/z: 357.1 [M+H]$^+$; and $^1$H NMR (400 MHz, CDCl$_3$) δ (ppm): 7.85 (d, J=8.7 Hz, 2H), 7.72 (t, J=3.0 Hz, 1H), 7.45 (d, J=8.7 Hz, 2H), 7.38 (d, J=8.3 Hz, 1H), 7.19 (t, J=8.1 Hz, 1H), 6.92 (t, J=55.3 Hz, 1H), 6.59 (d, J=7.8 Hz, 1H), 4.22 (s, 2H).

Step 4) tert-butyl 4-((1-((4-chlorophenyl)sulfonyl)-3-(difluoromethyl)-1H-indol-4-yl)amino) piperidine-1-carboxylate 1-((4-Chlorophenyl)sulfonyl)-3-(difluoromethyl)-1H-indol-4-amine (400 mg, 1.12 mmol) was reacted with sodium cyanoborohydride (212 mg, 3.37 mmol), acetic acid (120 µL, 2.0 mmol) and tert-butyl 4-oxopiperidine-1-carboxylate (670 mg, 3.36 mmol) in methanol (10 mL) according to the procedure as described in example 42, and the crude product was purified by silica gel column chromatography (PE/EtOAc (v/v)=1/1) to give the title compound as a light yellow solid (201 mg, 33%). The compound was characterized by the following spectroscopic data: MS (ESI, pos. ion) m/z: 484.1 [M+H−56]$^+$; and $^1$H NMR (400 MHz, CDCl$_3$) δ (ppm): 7.77 (d, J=8.6 Hz, 2H), 7.69 (t, J=3.1 Hz, 1H), 7.62 (d, J=8.6 Hz, 2H), 7.28-7.25 (m, 2H), 6.86 (t, J=55.1 Hz, 1H), 6.51 (d, J=7.7 Hz, 1H), 4.61 (s, 1H), 3.91 (d, J=12.7 Hz, 2H), 3.59 (brs, 1H), 3.14-3.11 (m, 2H), 2.04 (d, J=9.5 Hz, 2H), 1.65-1.63 (m, 2H), 1.48 (s, 9H).

Step 5) 1-((4-chlorophenyl)sulfonyl)-3-(difluoromethyl)-N-(piperidin-4-yl)-1H-indol-4-amine tert-Butyl 4-((1-((4-chlorophenyl)sulfonyl)-3-(difluoromethyl)-1H-indol-4-yl)amino) piperidine-1-carboxylate (390 mg, 0.72 mmol) was reacted with a solution of hydrogen chloride in ethyl acetate (1 mL, 2 M) in dichloromethane (5 mL) according to the procedure as described in step 6 of example 48, and the crude product was purified by silica gel column chromatography (DCM/MeOH (v/v)=10/1) to give the title compound as a light yellow solid (149 mg, 47.2%). The compound was characterized by the following spectroscopic data: MS (ESI, pos. ion) m/z: 440.2 [M+H]$^+$; $^1$H NMR (600 MHz, CDCl$_3$) δ (ppm): 7.90-7.74 (m, 2H), 7.68 (t, J=3.0 Hz, 1H), 7.49-7.39 (m, 2H), 7.28 (dd, J=5.0, 4.4 Hz, 1H), 7.23 (t, J=8.1 Hz, 1H), 6.86 (t, J=55.1 Hz, 1H), 6.51 (d, J=7.8 Hz, 1H), 4.60 (d, J=5.5 Hz, 1H), 3.62-3.49 (m, 1H), 3.12 (dt, J=12.7, 4.0 Hz, 2H), 2.82-2.69 (m, 2H), 2.16-2.00 (m, 2H), 1.50-1.41 (m, 2H); and $^{13}$C NMR (150 MHz, CDCl$_3$) δ (ppm): 141.1, 141.0, 137.0, 136.0, 129.8, 128.5, 127.5, 125.0 (t, J=12.0 Hz), 115.7 (t, J=25.5 Hz), 114.2, 112.5 (t, J=231 Hz), 105.0, 101.9, 49.6, 44.9, 33.3.

Example 59 1-((4-bromophenyl)sulfonyl)-3-(difluoromethyl)-N-(piperidin-4-yl)-1H-indol 4-amine

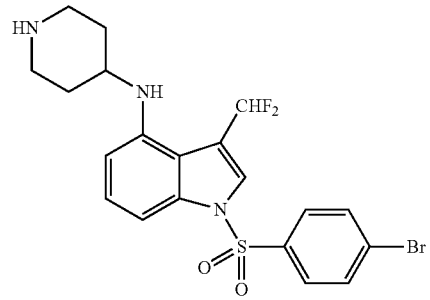

Step 1) 1-((4-bromophenyl)sulfonyl)-4-nitro-1H-indole-3-carbaldehyde 4-nitro-1H-indole-3-carbaldehyde (1.0 g, 5.26 mmol) was reacted with benzyltriethylammonium chloride (300 mg, 1.3 mmol), potassium hydroxide (354 mg, 5.36 mmol) and 4-bromobenzenesulfonyl chloride (1.6 g, 6.3 mmol) in DCM (15 mL) according to the procedure as described in step 4 of example 1, and the crude product was purified by silica gel column chromatography eluted with PE/EtOAc (v/v=2/1) to give the title compound as a light yellow solid (1.84 g, 85.6%). The compound was characterized by the following spectroscopic data: MS (ESI, pos. ion) m/z: 408.7 [M+H]$^+$; and $^1$H NMR (400 MHz, CDCl$_3$) δ (ppm): 10.35 (s, 1H), 8.50 (s, 1H), 8.36 (d, J=8.3 Hz, 1H), 8.15 (d, J=8.0 Hz, 1H), 7.85 (d, J=8.8 Hz, 2H), 7.71 (d, J=8.8 Hz, 2H), 7.57 (t, J=8.2 Hz, 1H).

Step 2) 1-((4-bromophenyl)sulfonyl)-3-(difluoromethyl)-4-nitro-1H-indole 1-((4-Bromophenyl)sulfonyl)-4-nitro-1H-indole-3-carbaldehyde (800 mg, 1.96 mmol) was reacted with diethylaminosulphur trifluoride (0.95 mL, 6.97 mmol) in DCM (10 mL) according to the procedure as described in step 5 of example 1, and the crude product was purified by silica gel column chromatography eluted with PE/EtOAc (v/v=4/1) to give the title compound as a light yellow solid (740 mg, 87.8%). The compound was characterized by the following spectroscopic data: $^1$H NMR (400 MHz, CDCl$_3$) δ (ppm): 8.36 (d, J=8.4 Hz, 1H), 8.15-8.12 (m, 2H), 7.82 (d, J=8.7 Hz, 2H), 7.69 (d, J=8.8 Hz, 2H), 7.54 (t, J=8.2 Hz, 1H), 7.26 (t, J=56.2 Hz, 1H).

Step 3) 1-((4-bromophenyl)sulfonyl)-3-(difluoromethyl)-1H-indol-4-amine 1-((4-Bromophenyl)sulfonyl)-3-(difluoromethyl)-4-nitro-1H-indole (740 mg, 1.72 mmol) was reacted with iron powder (480 mg, 8.57 mmol), acetic acid (0.1 mL) and concentrated hydrochloric acid (0.1 mL) in a mixture of tetrahydrofuran (10 mL), ethanol (5 mL) and water (5 mL) according to the procedure as described in step 4 of example 48, and the crude product was purified by silica gel column chromatography (PE/EtOAc (v/v)=3/1) to give the title compound as a light yellow solid (538 mg, 78.1%). The compound was characterized by the following spectroscopic data: MS (ESI, pos. ion) m/z: 401.0 [M+H]$^+$; and $^1$H NMR (400 MHz, CDCl$_3$) δ (ppm): 7.77 (d, J=8.8 Hz, 2H), 7.71 (t, J=3.0 Hz, 1H), 7.63 (d, J=8.8 Hz, 2H), 7.37 (d, J=8.3 Hz, 1H), 7.19 (t, J=8.1 Hz, 1H), 6.92 (t, J=55.3 Hz, 1H), 6.59 (d, J=7.8 Hz, 1H), 4.25 (s, 2H).

Step 4) tert-butyl 4-((1-((4-bromophenyl)sulfonyl)-3-(difluoromethyl)-1H-indol-4-yl)amino) piperidine-1-carboxylate 1-((4-Bromophenyl)sulfonyl)-3-(difluoromethyl)-1H-indol-4-amine (400 mg, 1.0 mmol) was reacted with sodium cyanoborohydride (227 mg, 3.6 mmol), acetic acid (120 μL, 2.0 mmol) and tert-butyl 4-oxopiperidine-1-carboxylate (600 mg, 3.01 mmol) in methanol (10 mL) according to the procedure as described in example 42, and the crude product was purified by silica gel column chromatography (PE/EtOAc (v/v)=1/1) to give the title compound as a light yellow solid (421 mg, 72.2%). The compound was characterized by the following spectroscopic data: MS (ESI, pos. ion) m/z: 528.1 [M+H−56]$^+$; and $^1$H NMR (400 MHz, CDCl$_3$) δ (ppm): 7.77 (d, J=8.6 Hz, 2H), 7.69 (t, J=3.1 Hz, 1H), 7.62 (d, J=8.6 Hz, 2H), 7.30-7.22 (m, 2H), 6.86 (t, J=55.1 Hz, 1H), 6.51 (d, J=7.7 Hz, 1H), 4.61 (s, 1H), 3.93-3.89 (m, 2H), 3.60 (brs, 1H), 3.14-3.11 (m, 2H), 2.04 (d, J=9.5 Hz, 2H), 1.67-1.61 (m, 2H), 1.48 (s, 9H).

Step 5) 1-((4-bromophenyl)sulfonyl)-3-(difluoromethyl)-N-(piperidin-4-yl)-1H-indol-4-amine tert-Butyl 4-((1-((4-bromophenyl)sulfonyl)-3-(difluoromethyl)-1H-indol-4-yl)amino) piperidine-1-carboxylate (370 mg, 0.63 mmol) was reacted with a solution of hydrogen chloride in ethyl acetate (1 mL, 2 M) in dichloromethane (5 mL) according to the procedure as described in step 6 of example 48, and the crude product was purified by silica gel column chromatography (DCM/MeOH (v/v)=10/1) to give the title compound as a light yellow solid (198 mg, 65.2%). The compound was characterized by the following spectroscopic data: MS (ESI, pos. ion) m/z: 483.7 [M+H]$^+$; $^1$H NMR (600 MHz, CDCl$_3$) δ (ppm): 7.77 (d, J=8.6 Hz, 2H), 7.68 (s, 1H), 7.62 (d, J=8.6 Hz, 2H), 7.28 (s, 1H), 7.24 (t, J=8.1 Hz, 1H), 6.87 (t, J=55.1 Hz, 1H), 6.51 (d, J=7.9 Hz, 1H), 4.60 (brs, 1H), 3.56 (brs, 1H), 3.16-3.14 (m, 2H), 2.80 (t, J=10.3 Hz, 2H), 2.12 (d, J=10.6 Hz, 2H), 1.53-1.48 (m, 2H); and $^{13}$C NMR (150 MHz, CDCl$_3$) δ (ppm): 140.9, 137.0, 136.6, 132.8, 129.7, 128.5, 127.5, 125.0 (t, J=13.5 Hz), 115.7 (t, J=25.5 Hz), 114.3, 112.5 (t, J=229.5 Hz), 105.1, 102.0, 49.4, 44.6, 32.8.

Biological Assays

LC/MS/MS analytical method used in the biological assays as follows:
the LC/MS/MS system for the analysis comprised an Agilent 1200 Series Vacuum Degasser, binary syringe pumps, a well-plate autosampler, a column oven and an Agilent G6430A Triple Quadrupole Mass Spectrometer equipped with an electrospray ionization (ESI) source. Quantitative analysis was performed in the MRM mode and the conversion parameters of MRM were listed in Table 2:

TABLE 2

| | |
|---|---|
| Fragmentor voltage | 30 V |
| Capillary voltage | 140 V |
| Dryer temperature | 350° C. |

TABLE 2-continued

| | |
|---|---|
| Nebulizer | 40 psi |
| Flow rate of dryer | 9 L/min |

Analysis was performed on waters XBridge C18 (2.1×50 mm, 3.5 μM column, and 5 μL of sample was injected). Conditions of the analysis comprised: a mobile phase consisting of mobile phase A (water, 2 mM ammonium formate and 0.1% formic acid) and mobile phase B (methanol, 2 mM ammonium formate and 0.1% formic acid), a flow rate of 0.4 mL/min, and conditions of gradient elution listed in Table 3:

TABLE 3

| Time | Gradient of mobile phase B |
|---|---|
| 1.1 min | 5% |
| 1.6 min | 95% |
| 2.6 min | 95% |
| 2.7 min | 5% |
| 3.7 min | final |

The invention provides the following methods for measuring biological activity of the compounds having Formula (I) to Formula (V) of this invention.

Example A: The Binding Affinities of the Compounds of this Invention to Human 5-HT$_6$ Receptor Expressed in CHO Cell were Evaluated by Radioligand Binding Assay as Follows 32 μg membrane proteins of CHO cell expressing human 5-HT$_6$ receptor, 2 nM of radioactive marker [3H]LSD, a compound of the present invention having different test concentrations, 100 μM 5-HT (5-HT was used to eliminate nonspecific binding sites) and a buffer solution were mixed uniformly. Then the resulting mixture was incubated at 37° C. for 120 min, in which the buffer solution comprised 50 mM Tris-HCl (pH 7.4), 10 mM MgCl$_2$, 0.5 mM EDTA, 10 μM pargyline and 20 mg/L protease inhibitor.

After incubation, the resulting mixture was filtered by a fiberglass filter (GF/B, Packard) in vacuo, and the filter membrane of the fiberglass filter was preimpregnated with 0.3% PEI before the filtering and washed with 50 mM of Tris-HCl for several times after the filtering. After the filter membrane was dried, and the radioactivity of filter membrane was determined by liquid scintillation counting by using a scintillometer (Topcount, Packard). The reference standard was 5-HT, and competitive inhibition curves were plotted based on several inhibition ratios and the corresponding compound concentrations. IC$_{50}$ values were calculated by non-linear regression analysis using Hill equation curves, and the Ki values were calculated from IC$_{50}$ by using the ChengPrusoff equation.

The Ki values of the compounds of the invention to human 5-HT$_6$ receptor expressed in CHO cell were summarized in table A:

TABLE A

Results of the affinity binding assays

| Example No. | Ki (nM) |
|---|---|
| Example 1 | 1.6 |
| Example 2 | 0.46 |
| Example 3 | 0.43 |
| Example 4 | 1.1 |

TABLE A-continued

Results of the affinity binding assays

| Example No. | Ki (nM) |
|---|---|
| Example 5 | 0.52 |
| Example 6 | 0.68 |
| Example 7 | 6.4 |
| Example 8 | 12 |
| Example 10 | 0.5 |
| Example 11 | 11 |
| Example 12 | 30 |
| Example 13 | 13 |
| Example 14 | 20 |
| Example 15 | 17 |
| Example 16 | 67 |
| Example 17 | 13 |
| Example 18 | 15 |
| Example 19 | 13 |
| Example 20 | 44 |
| Example 21 | 44 |
| Example 23 | 9.3 |
| Example 24 | 1.6 |
| Example 25 | 0.68 |
| Example 26 | 1.1 |
| Example 27 | 1.9 |
| Example 28 | 1.4 |
| Example 29 | 1.3 |
| Example 35 | 1.9 |
| Example 36 | 1.7 |
| Example 37 | 1.5 |
| Example 42 | 0.7 |
| Example 43 | 2.3 |
| Example 44 | 27 |
| Example 52 | 18 |
| Example 54 | 11 |
| Example 55 | 65 |

It was shown in table A that, the compounds of this invention generally showed good activities in the binding affinity test to human 5-HT$_6$ receptor.

Example B: Pharmacokinetic Evaluation after Administering a Certain Amount of the Compounds of the Invention Intravenously or by Gavage to Dogs and Monkeys 1) Experimental Animals Experimental animals were dogs and monkeys with features as shown in table 4:

TABLE 4

| genus | classification | gender | weight | age | source |
|---|---|---|---|---|---|
| Beagle dogs | clean grade | male | 8~10 kg | 6-7 weeks old | Hunan SJA Laboratory Animal Co., Ltd |
| cynomolgus monkey | SPF | male | 3~5 kg | 4 years old | Guangdong Landau Biotechnology Co., Ltd |

2) Experimental Method:

In vivo pharmacokinetic assays in dogs and cynomolgus monkeys of the compounds disclosed herein were performed by the following steps.

Experiments were divided into two groups, one group was administered through intravenous drug delivery, and the other group was administered by gavage. The compounds disclosed herein were administered in form of a saline solution containing 5% DMSO, 5% Kolliphor HS 15, 2% (2% HCl) and 88% Saline, or the solution containing 10% DMSO, 10% Kolliphor HS 15 and 80% physiological saline.

For intravenous administration, the animals were administered with a dose of 1 mg/kg, and 0.3 mL of vein blood was collected at the time points of 0.083, 0.25, 0.5, 1.0, 2.0, 4.0, 6.0, 8.0 and 24 h after drug administration (the time point of drug administration was set as 0 h), then each blood sample was processed to separate plasma by centrifugation at 3000 rpm or 4000 rpm for 10 minutes, and plasma was collected and stored at −20° C. or −70° C. until LC/MS/MS analysis described above. For gavage administration, the animals were administered with a dose of 2.5 mg/kg or 5 mg/kg, and 0.3 mL of vein blood was collected at the time points of 0.25, 0.5, 1.0, 2.0, 4.0, 6.0, 8.0 and 24 h after drug administration (the time point of drug administration was set as 0 h), then each blood sample was processed to separate plasma by centrifugation at 3000 rpm or 4000 rpm for 10 minutes, and plasma was collected and stored at −20° C. or −70° C. until LC/MS/MS analysis described above.

The above plasma was analyzed by the LC/MS/MS system. The analytic results showed that the compounds of the invention had good pharmacokinetic properties in dogs, and the pharmacokinetic parameters of compounds provided in example 2, example 3 and example 5 were listed in table B; Similarly, the compounds of the invention also had good pharmacokinetic properties in monkeys.

TABLE B

The pharmacokinetic parameters of compounds in dogs

| | Group | | | | | |
|---|---|---|---|---|---|---|
| | Intravenous drug delivery group | | | Gavage group | | |
| | Example No. | | | | | |
| | 2 | 3 | 5 | 2 | 3 | 5 |
| Dose (mg/kg) | 1 | 1 | 1 | 2.5 | 2.5 | 5 |
| AUC$_{INF}$ (h * ng/mL) | 926 | 2340 | 1190 | 3160 | 17600 | 8350 |
| AUC$_{last}$ (h * ng/mL) | 781 | 2660 | 1100 | 2400 | 9250 | 5680 |
| Cl (mL/min/kg) | 18.5 | 7.13 | 14 | — | — | — |
| C$_{max}$ (ng/mL) | 106 | 293 | 125 | 173 | 975 | 347 |
| MRT$_{INF}$ (h) | 8.73 | 8.77 | 8.77 | 16.8 | 17.9 | 15 |
| T$_{1/2}$ (h) | 6.43 | 6.26 | 6.49 | 11.4 | 14.7 | 10.1 |
| T$_{max}$ (h) | 0.194 | 8.06 | 0.389 | 3.33 | 4.67 | 6 |
| V$_{ss}$ (L/kg) | 9.86 | 3.77 | 7.36 | — | — | — |
| F (%) | — | — | — | 103.67 | 139 | 103.21 |

The test results showed that, the compounds of the invention had good pharmacokinetic properties in both dogs and monkeys.

Example C: Evaluation of the Stability of the Compounds of the Invention in Rat and Human Liver Microsomes The compound of the invention and rat liver microsome or human liver microsome were placed in 0.1 M potassium phosphate buffer (containing 1.0 mM EDTA, pH=7.4) at 37° C., and the mixture was incubated at 37° C. The concentrations of the compound at different incubation time points were determined, and the half-life of the compound was calculated by curve plotted based on the relative contents of the compound and the corresponding incubation times by using GraphPad Prism 5.01. Then the intrinsic clearance was calculated. The experimental system was shown in table 5:

TABLE 5

Experimental system

| Test sample | The compound of the invention (dissolved in DMSO, and diluted with acetonitrile) |
|---|---|
| Rat liver microsome (purchased from BD company) | A hybrid sample, with the test final concentration of 0.5 mg/mL |
| Human liver microsome (purchased from BD company) | A hybrid sample, with the test final concentration of 0.5 mg/mL |
| Buffer | 0.1M potassium phosphate buffer (containing 1.0 mM EDTA, pH = 7.4) |
| Final concentration of the test compound | 1 μM |
| Final content of the organic solvent | 0.2% |
| Final reaction system | 30 μL of buffer solution containing the compound of the invention and rat liver microsome or human liver microsome; 15 μL of NADPH buffer (concentration of 6 mM) |
| Test condition | Time points: 0 min, 15 min, 30 min, 60 min; Temperature: 37° C.; pH: 7.4 |
| Number of duplicate samples | 2 |
| Analytical method | LC/MS/MS, internal standard: propranolol |

The peak area ratio of sample to internal standard was analyzed by the LC/MS/MS system. The content of the compound at 0 min was 100%, and the relative contents of the compound at different time points were calculated. The half-life of the compound was calculated by curve plotted based on the relative contents of the compound and the corresponding incubation times, and the intrinsic clearance was calculated. The half-lifes and intrinsic clearances of the compounds of examples 2-6 were shown in table C:

TABLE C

The test results of half-lifes and intrinsic clearances of the compounds

| | Rat | | Human | |
|---|---|---|---|---|
| Example No. | Half-life (min) | Intrinsic clearance (mL/min/kg) | Half-life (min) | Intrinsic clearance (mL/min/kg) |
| Example 2 | 34.96 | 71.04 | 133.20 | 13.05 |
| Example 3 | 30.07 | 82.60 | 132.00 | 13.17 |
| Example 4 | 30.35 | 81.84 | 156.90 | 11.08 |
| Example 5 | 43.50 | 57.10 | 217.50 | 7.99 |
| Example 6 | 35.48 | 70.00 | N/A | — |

Note:
N/A refers that half-life can't be calculated because of the stability of the compound.

The test results showed that, the compounds of the invention had good stability in rat and humans liver microsomes. Especially, the compounds of example 5 and example 6 in human liver microsomes in vitro almost had no degradation in 60 minutes, which showed excellent stability.

Reference throughout this specification to "one embodiment", "an embodiment", "some embodiments", "explanatory embodiment", "an example", "a specific example" or "some examples", means that a particular feature, structure, material or characteristic described in connection with the embodiment or example is included in at least one embodiment or example of the present disclosure. Thus, the appearances of the phrases such as "in some embodiments", "in one embodiment", "in an embodiment", "in another example", "in an example", "in a specific examples", or "in some examples" in various places throughout this specification are not necessarily referring to the same embodiment or example of the present disclosure. Furthermore, the particular features, structures, materials or characteristics may be combined in any suitable manner in one or more embodiments or examples. In addition, those skilled in the art can integrate and combine different embodiments, examples or the features of them as long as they are not contradictory to one another.

Although explanatory embodiments have been shown and described, it would be appreciated by those skilled in the art that the above embodiments can not be construed to limit the present disclosure, and changes, alternatives, and modifications can be made in the embodiments without departing from spirit, principles and scope of the present disclosure.

The invention claimed is:
1. A compound having Formula (I), or a stereoisomer, an N-oxide, or a pharmaceutically acceptable salt thereof,

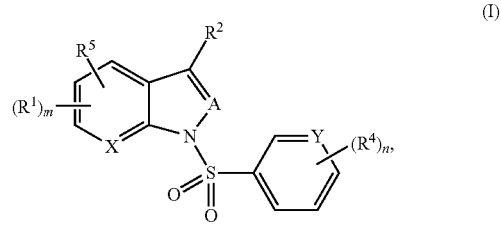

(I)

wherein
m is 0, 1 or 2;
n is 0, 1, 2, 3 or 4;
A is $CR^3$ or N;
X is $CR^1$;
Y is $CR^4$ or N;
each $R^1$ is independently H, D, F, Cl, Br, I, —CN, —NO$_2$, —OH, —NH$_2$, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$ alkylthio, —C(=O)NR$^6$R$^{6a}$, —C(=O)R$^{6b}$, —C(=O)OR$^{6c}$, R$^6$R$^{6a}$N—S(=O)$_2$—, R$^{6b}$S(=O)$_2$—, $C_{3-8}$ cycloalkyl, 3- to 12-membered heterocyclyl, $C_{6-10}$ aryl or 5- to 12-membered heteroaryl;
$R^2$ is —CN, —OH, —NR$^6$R$^{6a}$, —C(=O)—($C_{1-6}$ alkyl), —C(=O)NR$^6$R$^{6a}$, R$^6$R$^{6a}$N—S(=O)$_2$—, hydroxy-substituted $C_{1-6}$ alkyl, $C_{1-6}$ haloalkyl, $C_{2-6}$ alkoxy or ($C_{6-10}$ aryl)-($C_{1-6}$ alkylene)-;
$R^3$ is H, D, F, Cl, Br, I, —CN, —NO$_2$, —OH, —NH$_2$, $C_{1-6}$ alkyl, $C_{2-6}$ alkenyl, $C_{2-6}$ alkynyl, carboxy-substituted $C_{1-6}$ alkyl, $C_{1-6}$ haloalkyl, $C_{1-6}$ haloalkoxy, —C(=O)NR$^6$R$^{6a}$, —C(=O)R$^{6b}$, $C_{3-8}$ cycloalkyl or $C_{6-10}$ aryl;
each $R^4$ is independently H, D, F, Cl, Br, I, —CN, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{3-8}$ cycloalkyl or $C_{6-10}$ aryl;
$R^5$ is 3- to 12-membered heterocyclyl, $C_{5-8}$ cycloalkyl, 5- to 12-membered heteroaryl, (3- to 12-membered heterocyclyl)-NH—, (3- to 12-membered heterocyclyl)-($C_{1-3}$ alkylene)-, (3- to 12-membered heterocyclyl)-O— or (3- to 12-membered heterocyclyl)-S—, and wherein optionally each of 3- to 12-membered heterocyclyl, $C_{5-8}$ cycloalkyl, 5- to 12-membered heteroaryl, (3- to 12-membered heterocyclyl)-NH—, (3- to 12-membered heterocyclyl)-($C_{1-3}$ alkylene)-, (3- to 12-membered heterocyclyl)-O— and (3- to 12-membered heterocyclyl)-S— is independently substituted with 1, 2, 3 or 4 R$^7$;

each R$^6$, R$^{6a}$, R$^{6b}$ and R$^{6c}$ is independently H, D, —OH, C$_{1-6}$ alkyl, C$_{1-6}$ haloalkyl, C$_{1-6}$ alkoxy, C$_{3-8}$ cycloalkyl, 3- to 12-membered heterocyclyl, C$_{6-10}$ aryl or 5- to 12-membered heteroaryl; or R$^6$ and R$^{6a}$, together with the nitrogen atom to which they are attached, form a substituted or unsubstituted 3- to 8-membered ring; and each R$^7$ is independently H, D, F, Cl, Br, I, —CN, —C(=O)NR$^6$R$^{6a}$, —C(=O)R$^{6b}$, —C(=O)OR$^{6c}$, C$_{1-6}$ alkyl, C$_{1-6}$ haloalkyl, C$_{1-6}$ alkoxy, C$_{1-6}$ haloalkoxy, C$_{3-8}$ cycloalkyl, 3- to 12-membered heterocyclyl or (5- to 12-membered heteroaryl)-(C$_{1-6}$ alkylene)-.

2. The compound according to claim 1, wherein R$^5$ is 5- to 6-membered heterocyclyl, (5- to 6-membered heterocyclyl)-NH—, (5- to 6-membered heterocyclyl)-CH$_2$—, (5- to 6-membered heterocyclyl)-CH(CH$_3$)—, (5- to 6-membered heterocyclyl)-O— or (5- to 6-membered heterocyclyl)-S—, and wherein optionally each of 5- to 6-membered heterocyclyl, (5- to 6-membered heterocyclyl)-NH—, (5- to 6-membered heterocyclyl)-CH$_2$—, (5- to 6-membered heterocyclyl)-CH(CH$_3$)—, (5- to 6-membered heterocyclyl)-O— and (5- to 6-membered heterocyclyl)-S— is independently substituted with 1, 2, 3 or 4 R$^7$.

3. The compound according to claim 1 having Formula (II), or a stereoisomer, an N-oxide, or a pharmaceutically acceptable salt thereof,

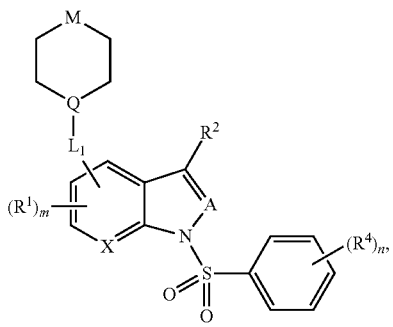

(II)

wherein
Q is CH or N;
M is —NR$^7$— or —O—; and
L$_1$ is a bond, —NH—, —CH$_2$—, —O— or —S—.

4. The compound according to claim 1, wherein each R$^1$ is independently H, D, F, Cl, Br, I, —CN, —NO$_2$, —OH, —NH$_2$, methyl, ethyl, —CHF$_2$ or —CF$_3$.

5. The compound according to claim 1, wherein R$^2$ is —CN, —OH, —NH$_2$, —C(=O)—(C$_{1-4}$ alkyl), hydroxy-substituted C$_{1-4}$ alkyl, C$_{1-4}$ haloalkyl, C$_{2-4}$ alkoxy or phenyl-(C$_{1-4}$ alkylene)-.

6. The compound according to claim 5, wherein R$^2$ is —CN, —OH, —NH$_2$, —C(=O)CH$_3$, —C(=O)CH$_2$CH$_3$, —C(=O)CH$_2$CH$_2$CH$_3$, —C(=O)CH$_2$(CH$_3$)$_2$, —CH$_2$F, —CHF$_2$, —CF$_3$, —CH$_2$Cl, —CHCl$_2$, —CCl$_3$, —CH$_2$Br, —CHBr$_2$, —CBr$_3$, —CH$_2$CHF$_2$, —CH$_2$CF$_3$, —CHFCF$_3$, —CF$_2$CHF$_2$, —CF$_2$CF$_3$, —CH$_2$CH$_2$CF$_3$, —CH$_2$CF$_2$CHF$_2$ or ethoxy.

7. The compound according to claim 1, wherein each R$^4$ is independently H, D, F, Cl, Br, I, —CN, C$_{1-4}$ alkyl, C$_{2-4}$ alkenyl, C$_{2-4}$ alkynyl, C$_{1-4}$ haloalkyl, C$_{1-4}$ alkoxy, C$_{1-4}$ haloalkoxy, C$_{3-6}$ cycloalkyl or C$_{6-10}$ aryl.

8. The compound according to claim 7, wherein each R$^4$ is independently H, D, F, Cl, Br, I, —CN, methyl, ethyl, n-propyl, i-propyl, n-butyl, i-butyl, t-butyl, —CH$_2$F, —CHF$_2$, —CF$_3$, —CH$_2$CHF$_2$, —CH$_2$CF$_3$, —CHFCF$_3$, —CF$_2$CHF$_2$, —CF$_2$CF$_3$, methoxy, ethoxy, n-propoxy, i-propoxy, n-butoxy, i-butoxy, t-butoxy, —OCHF$_2$, —OCF$_3$ or —OCH$_2$CF$_3$.

9. The compound according to claim 1, wherein each R$^7$ is independently H, D, F, Cl, Br, I, —CN, C$_{1-4}$ alkyl, C$_{1-4}$ haloalkyl, C$_{3-6}$ cycloalkyl or 3- to 6-membered heterocyclyl.

10. The compound according to claim 9, wherein each R$^7$ is independently H, D, methyl, ethyl, n-propyl, i-propyl, n-butyl, i-butyl, t-butyl, cyclopropyl, cyclobutyl, cyclopentyl, azetidinyl, oxetanyl, thietanyl, pyrrolidyl or tetrahydrofuryl.

11. The compound according to claim 1 having one of the following structures, or a stereoisomer, an N-oxide, or a pharmaceutically acceptable salt thereof,

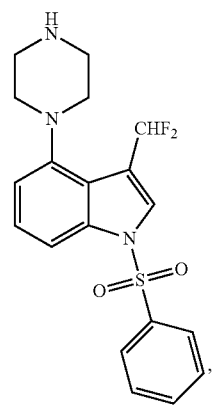

(1)

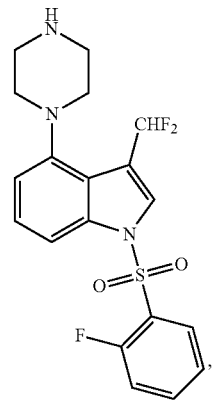

(2)

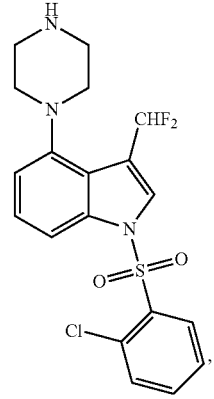

(3)

-continued
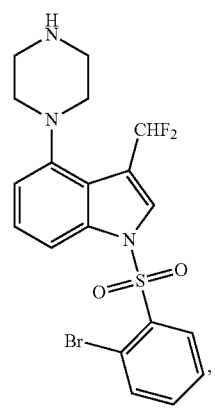 (4)
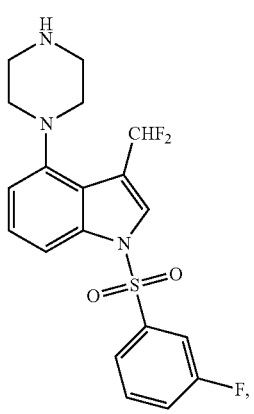 (5)
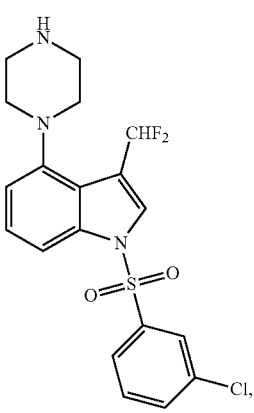 (6)
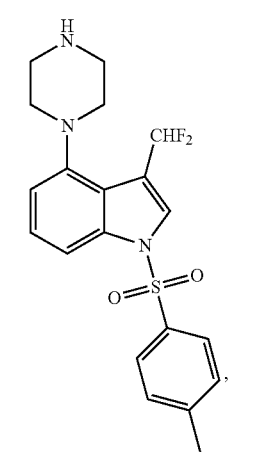 (7)
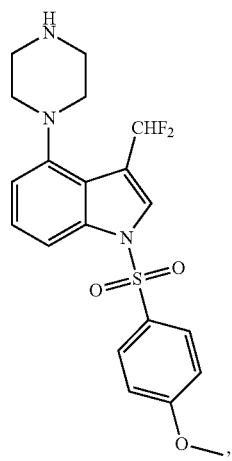 (8)
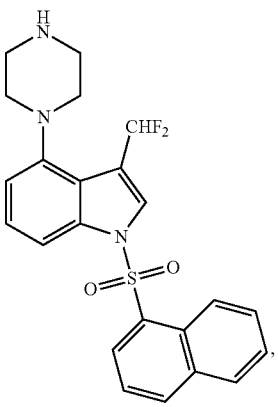 (9)
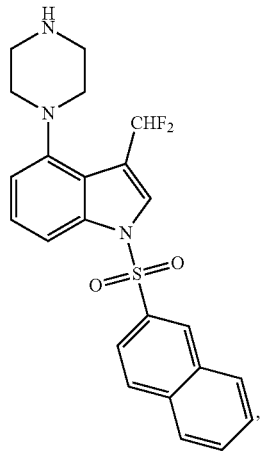 (10)

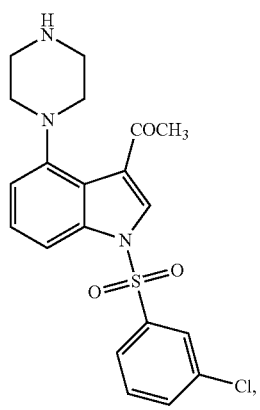 (11)
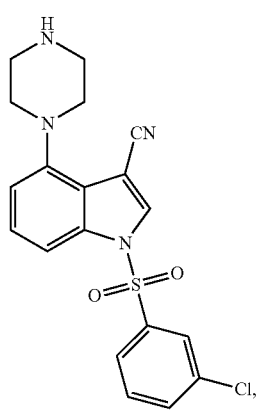 (12)
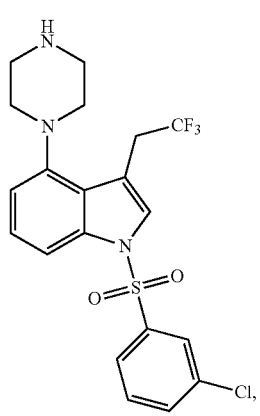 (13)
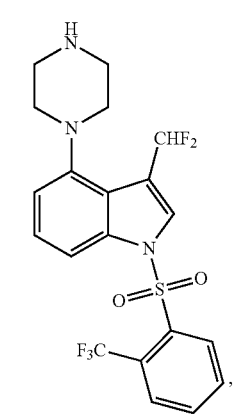 (14)
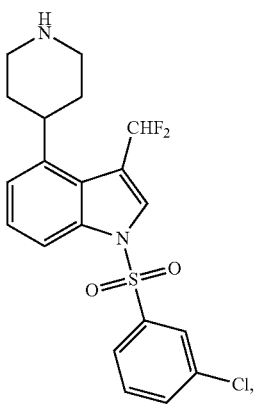 (15)
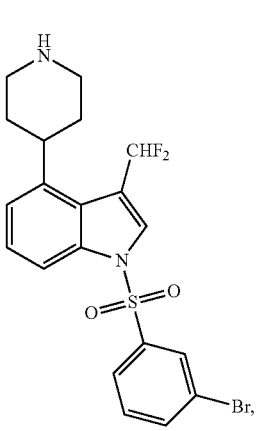 (16)
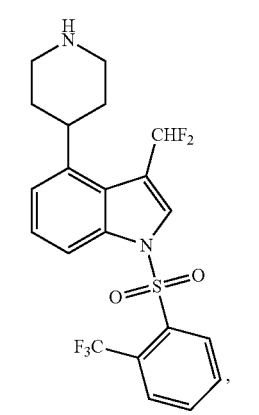 (17)
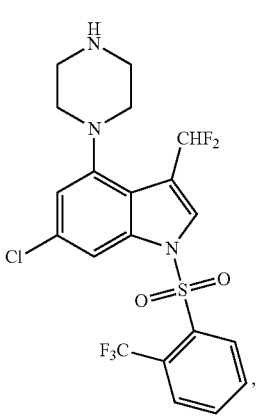 (18)

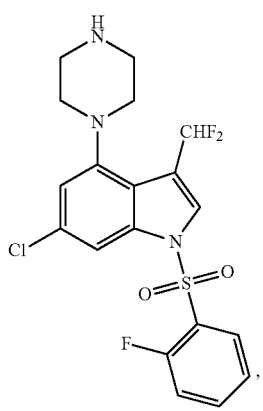
(19)
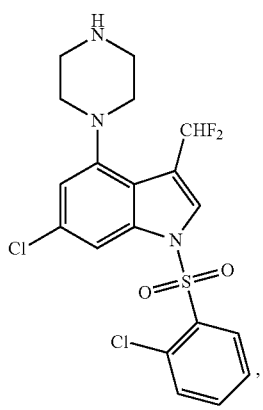
(20)
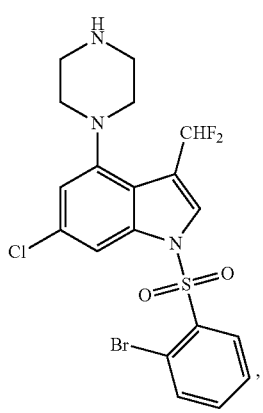
(21)
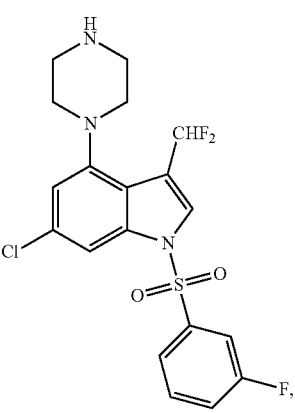
(22)
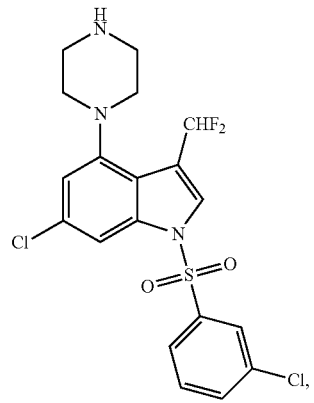
(23)
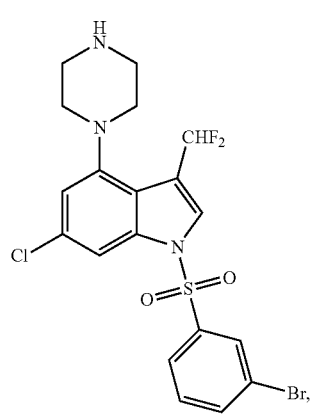
(24)
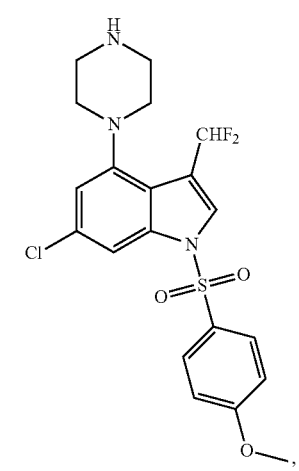
(25)

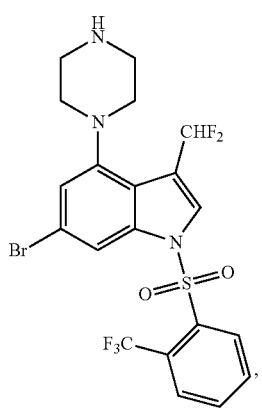
(26)
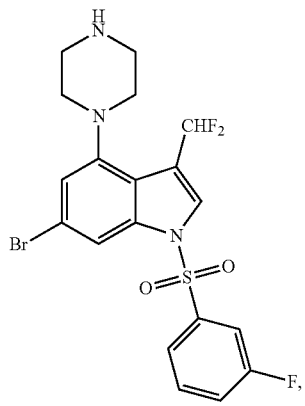
(30)
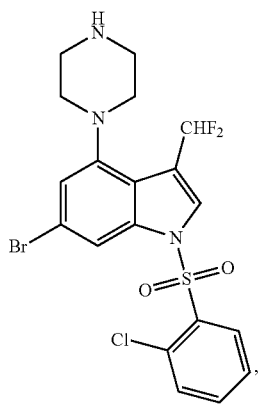
(27)
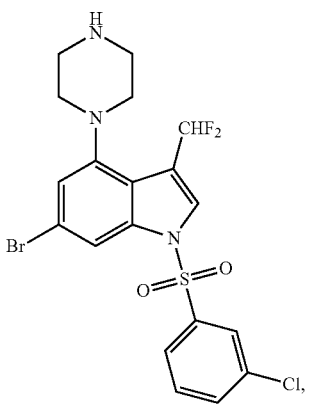
(31)
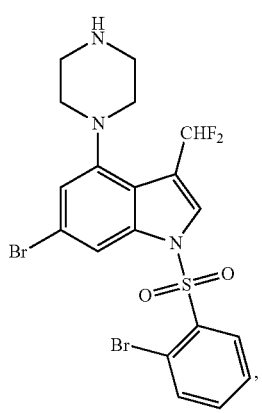
(28)
(29)
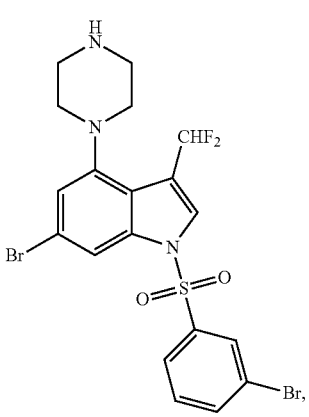
(32)

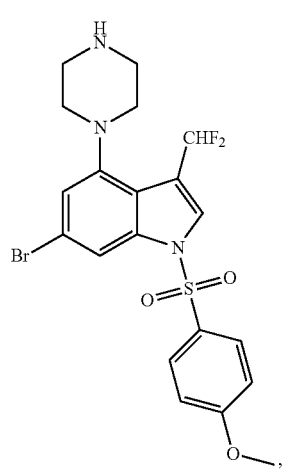
(33)
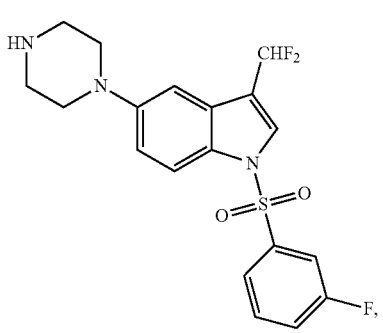
(37)
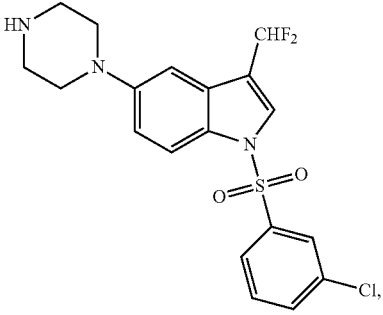
(38)
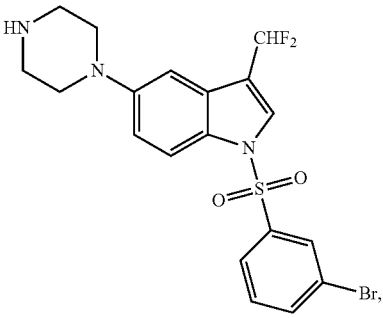
(39)
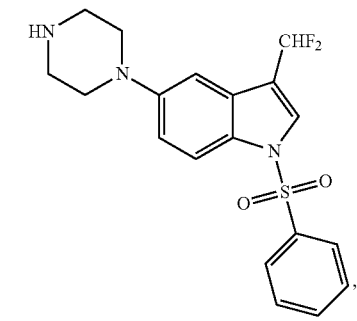
(40)
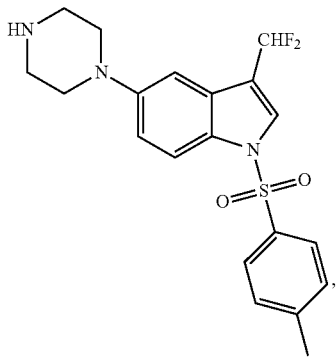
(41)

-continued (42), (43), (44), (45), (46), (47), (48), (49)

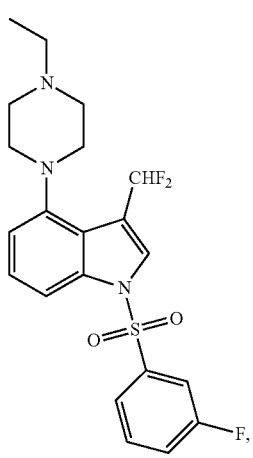
(50)
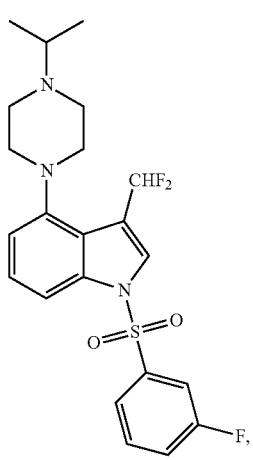
(51)
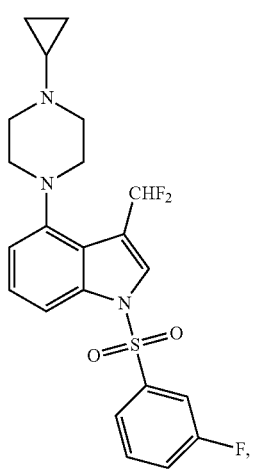
(52)
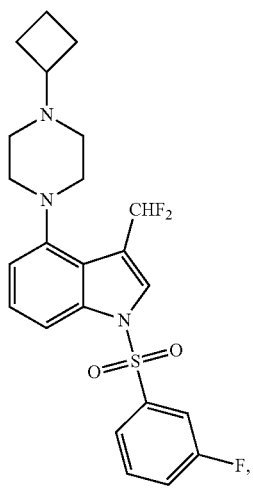
(53)
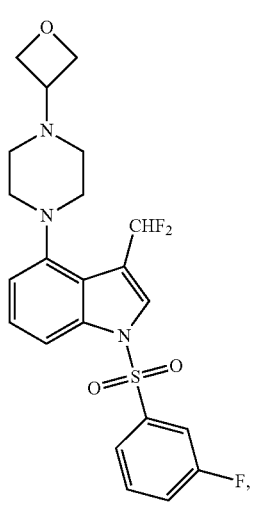
(54)
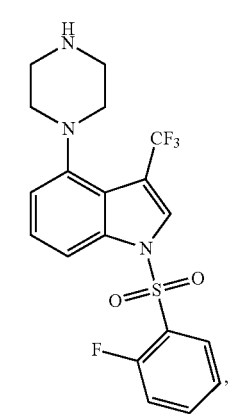
(55)

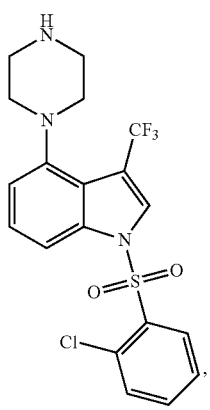
(56)
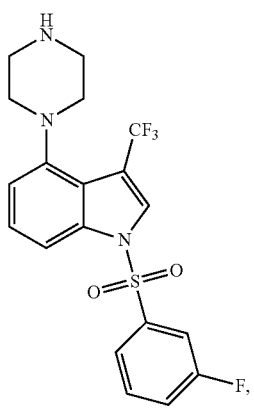
(57)
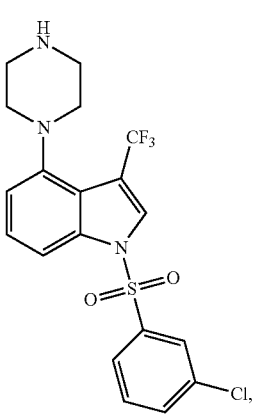
(58)
(59)
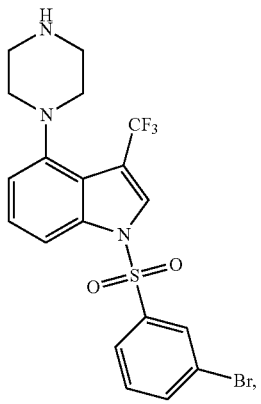
(60)
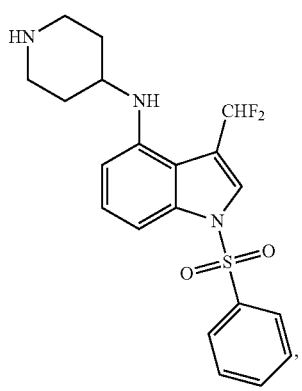
(61)
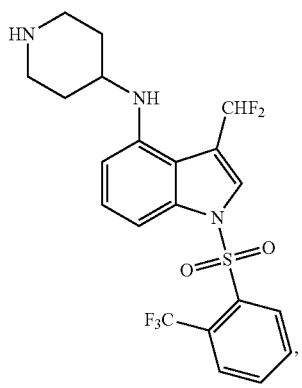
(62)
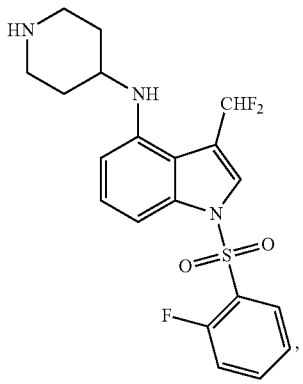
(63)

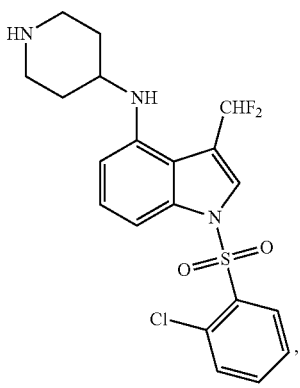
(64)
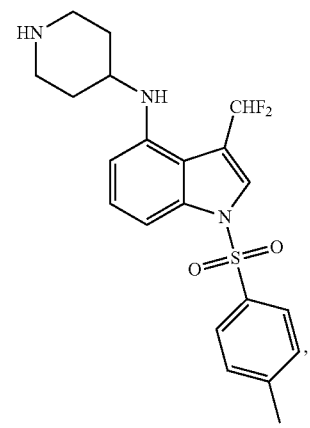
(65)
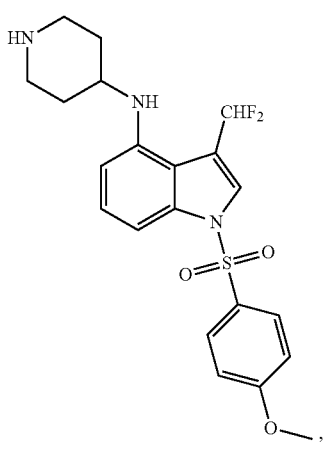
(66)
(67)
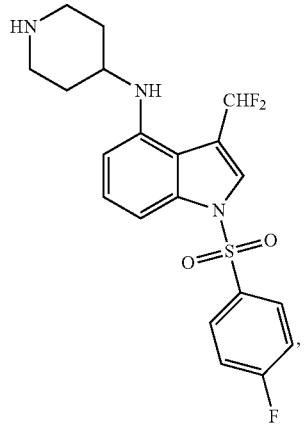
(68)
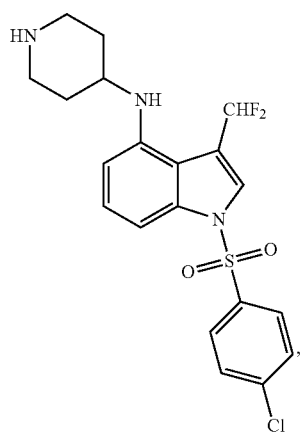
(69)
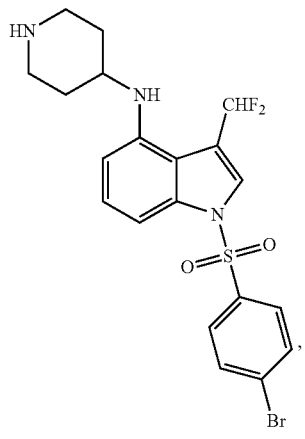
(70)

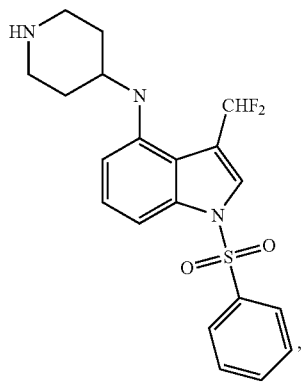

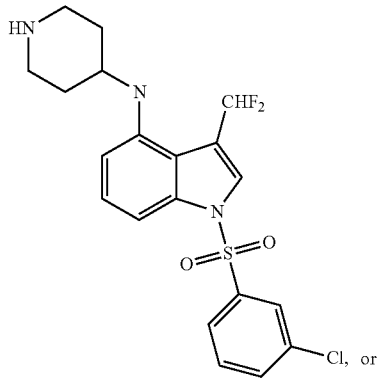

12. A pharmaceutical composition comprising the compound according to claim 1, and a pharmaceutically acceptable carrier, excipient, diluent, adjuvant, vehicle or a combination thereof.

13. The pharmaceutical composition according to claim 12 further comprising an additional therapeutic agent used for treating Alzheimer's disease, neuropathy or a combination thereof.

14. The pharmaceutical composition according to claim 13, wherein the additional therapeutic agent is donepezil, nalmefene, risperidone, Vitamin E, SAM-760, AVN-211, AVN-101, RP-5063, tozadenant, PRX-3140, PRX-8066, RVT-101, naluzaton, idalopirdine, tacrine, rivastigmine, galantamine, memantine, mirtazapine, venlafaxine, desipramine, nortriptyline, zolpidem, zopiclone, nicergoline, piracetam, selegiline, pentoxifylline or a combination thereof.

15. A method for treating or lessening a 5-HT$_6$ receptor-mediated disease in a subject, comprising administering to the subject in need of such treatment a therapeutically effective amount of the compound according to claim 1, wherein the 5-HT$_6$ receptor-mediated disease is obesity, anxiety, manic depression, attention deficit disorder (ADD), attention deficit hyperactivity disorder (ADHD), and Alzheimer's disease.

16. A method for treating or lessening a 5-HT$_6$ receptor-mediated disease in a subject, comprising administering to the subject in need of such treatment a therapeutically effective amount of the pharmaceutical composition according to claim 12, wherein the 5-HT$_6$ receptor-mediated disease is obesity, anxiety, manic depression, attention deficit disorder (ADD), attention deficit hyperactivity disorder (ADHD), and Alzheimer's disease.

* * * * *